US009905785B2

(12) United States Patent
Brooks et al.

(10) Patent No.: US 9,905,785 B2
(45) Date of Patent: Feb. 27, 2018

(54) ORGANIC ELECTROLUMINESCENT MATERIALS AND DEVICES

(71) Applicant: Universal Display Corporation, Ewing, NJ (US)

(72) Inventors: Jason Brooks, Ewing, NJ (US); Geza Szigethy, Ewing, NJ (US); Scott Beers, Ewing, NJ (US); Hsiao-Fan Chen, Ewing, NJ (US)

(73) Assignee: Universal Display Corporation, Ewing, NJ (US)

( * ) Notice: Subject to any disclaimer, the term of this patent is extended or adjusted under 35 U.S.C. 154(b) by 271 days.

(21) Appl. No.: 14/671,075

(22) Filed: Mar. 27, 2015

(65) Prior Publication Data
US 2015/0295189 A1 Oct. 15, 2015

Related U.S. Application Data

(60) Provisional application No. 61/979,103, filed on Apr. 14, 2014, provisional application No. 61/991,720, filed on May 12, 2014.

(51) Int. Cl.
H01L 51/00 (2006.01)
C07F 15/00 (2006.01)
C09K 11/06 (2006.01)
H01L 51/50 (2006.01)
H01L 51/52 (2006.01)

(52) U.S. Cl.
CPC ...... H01L 51/0085 (2013.01); C07F 15/0033 (2013.01); C07F 15/0086 (2013.01); C09K 11/06 (2013.01); H01L 51/0087 (2013.01); H01L 51/0094 (2013.01); C09K 2211/1007 (2013.01); C09K 2211/1029 (2013.01); C09K 2211/1044 (2013.01); C09K 2211/185 (2013.01); H01L 51/0052 (2013.01); H01L 51/0054 (2013.01); H01L 51/0067 (2013.01); H01L 51/0072 (2013.01); H01L 51/0074 (2013.01); H01L 51/5016 (2013.01); H01L 51/5096 (2013.01); H01L 51/5206 (2013.01); H01L 51/5221 (2013.01)

(58) Field of Classification Search
CPC ............ H01L 51/0085; H01L 51/0087; H01L 51/0094; C07F 15/0086; C07F 15/0033; C09K 11/06
USPC ........................ 428/690; 252/514, 500, 519.2
See application file for complete search history.

(56) References Cited

U.S. PATENT DOCUMENTS

| 4,769,292 | A | 9/1988 | Tang et al. |
|---|---|---|---|
| 5,061,569 | A | 10/1991 | VanSlyke et al. |
| 5,247,190 | A | 9/1993 | Friend et al. |
| 5,703,436 | A | 12/1997 | Forrest et al. |
| 5,707,745 | A | 1/1998 | Forrest et al. |
| 5,834,893 | A | 11/1998 | Bulovic et al. |
| 5,844,363 | A | 12/1998 | Gu et al. |
| 6,013,982 | A | 1/2000 | Thompson et al. |
| 6,087,196 | A | 7/2000 | Sturm et al. |
| 6,091,195 | A | 7/2000 | Forrest et al. |
| 6,097,147 | A | 8/2000 | Baldo et al. |
| 6,294,398 | B1 | 9/2001 | Kim et al. |
| 6,303,238 | B1 | 10/2001 | Thompson et al. |
| 6,337,102 | B1 | 1/2002 | Forrest et al. |
| 6,468,819 | B1 | 10/2002 | Kim et al. |
| 6,528,187 | B1 | 3/2003 | Okada |
| 6,687,266 | B1 | 2/2004 | Ma et al. |
| 6,835,469 | B2 | 12/2004 | Kwong et al. |
| 6,921,915 | B2 | 7/2005 | Takiguchi et al. |
| 7,087,321 | B2 | 8/2006 | Kwong et al. |
| 7,090,928 | B2 | 8/2006 | Thompson et al. |
| 7,154,114 | B2 | 12/2006 | Brooks et al. |
| 7,250,226 | B2 | 7/2007 | Tokito et al. |
| 7,279,704 | B2 | 10/2007 | Walters et al. |
| 7,332,232 | B2 | 2/2008 | Ma et al. |
| 7,338,722 | B2 | 3/2008 | Thompson et al. |
| 7,393,599 | B2 | 7/2008 | Thompson et al. |
| 7,396,598 | B2 | 7/2008 | Takeuchi et al. |
| 7,431,968 | B1 | 10/2008 | Shtein et al. |
| 7,445,855 | B2 | 11/2008 | Mackenzie et al. |
| 7,534,505 | B2 | 5/2009 | Lin et al. |
| 7,968,146 | B2 | 6/2011 | Wanger et al. |
| 9,472,762 | B2 * | 10/2016 | Murer ................ C07F 15/0033 |
| 9,502,669 | B2 * | 11/2016 | Huh ................... H01L 51/0072 |
| 2002/0034656 | A1 | 3/2002 | Thompson et al. |
| 2002/0134984 | A1 | 9/2002 | Igarashi |
| 2002/0158242 | A1 | 10/2002 | Son et al. |
| 2003/0138657 | A1 | 7/2003 | Li et al. |
| 2003/0152802 | A1 | 8/2003 | Tsuboyama et al. |

(Continued)

FOREIGN PATENT DOCUMENTS

| CN | 101827834 | 9/2010 |
|---|---|---|
| EP | 650955 | 5/1995 |

(Continued)

OTHER PUBLICATIONS

Baldo et al., "Highly Efficient Phosphorescent Emission from Organic Electroluminescent Devices," Nature, vol. 395, 151-154, (1998).
Baldo et al., "Very high-efficiency green organic light-emitting devices based on electrophosphorescence," Appl. Phys. Lett., vol. 75, No. 3, 4-6 (1999).
U.S. Appl. No. 13/193,221, filed Jul. 28, 2011.
U.S. Appl. No. 13/296,806, filed Nov. 15, 2011.
Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino)triphenylamine (Continued)

Primary Examiner — Douglas McGinty
(74) Attorney, Agent, or Firm — Riverside Law LLP

(57) ABSTRACT

This invention discloses novel metal complexes for phosphorescent OLEDs. The incorporation of a specific nitrogen substitution in the benzimidazole phenanthridine ligand system is shown to provide desirable color.

21 Claims, 12 Drawing Sheets

(56) References Cited

U.S. PATENT DOCUMENTS

| | | |
|---|---|---|
| 2003/0162053 A1 | 8/2003 | Marks et al. |
| 2003/0175553 A1 | 9/2003 | Thompson et al. |
| 2003/0230980 A1 | 12/2003 | Forrest et al. |
| 2004/0036077 A1 | 2/2004 | Ise |
| 2004/0137267 A1 | 7/2004 | Igarashi et al. |
| 2004/0137268 A1 | 7/2004 | Igarashi et al. |
| 2004/0174116 A1 | 9/2004 | Lu et al. |
| 2005/0025993 A1 | 2/2005 | Thompson et al. |
| 2005/0112407 A1 | 5/2005 | Ogasawara et al. |
| 2005/0238919 A1 | 10/2005 | Ogasawara |
| 2005/0244673 A1 | 11/2005 | Satoh et al. |
| 2005/0260441 A1 | 11/2005 | Thompson et al. |
| 2005/0260449 A1 | 11/2005 | Walters et al. |
| 2006/0008670 A1 | 1/2006 | Lin et al. |
| 2006/0202194 A1 | 9/2006 | Jeong et al. |
| 2006/0240279 A1 | 10/2006 | Adamovich et al. |
| 2006/0251923 A1 | 11/2006 | Lin et al. |
| 2006/0263635 A1 | 11/2006 | Ise |
| 2006/0280965 A1 | 12/2006 | Kwong et al. |
| 2007/0190359 A1 | 8/2007 | Knowles et al. |
| 2007/0278938 A1 | 12/2007 | Yabunouchi et al. |
| 2008/0015355 A1 | 1/2008 | Schafer et al. |
| 2008/0018221 A1 | 1/2008 | Egen et al. |
| 2008/0106190 A1 | 5/2008 | Yabunouchi et al. |
| 2008/0124572 A1 | 5/2008 | Mizuki et al. |
| 2008/0220265 A1 | 9/2008 | Xia et al. |
| 2008/0297033 A1* | 12/2008 | Knowles ............ C07F 15/0033 313/504 |
| 2009/0008605 A1 | 1/2009 | Kawamura et al. |
| 2009/0009065 A1 | 1/2009 | Nishimura et al. |
| 2009/0017330 A1 | 1/2009 | Iwakuma et al. |
| 2009/0030202 A1 | 1/2009 | Iwakuma et al. |
| 2009/0039776 A1 | 2/2009 | Yamada et al. |
| 2009/0045730 A1 | 2/2009 | Nishimura et al. |
| 2009/0045731 A1 | 2/2009 | Nishimura et al. |
| 2009/0101870 A1 | 4/2009 | Prakash et al. |
| 2009/0108737 A1 | 4/2009 | Kwong et al. |
| 2009/0115316 A1 | 5/2009 | Zheng et al. |
| 2009/0165846 A1 | 7/2009 | Johannes et al. |
| 2009/0167162 A1 | 7/2009 | Lin et al. |
| 2009/0179554 A1 | 7/2009 | Kuma et al. |
| 2012/0007069 A1* | 1/2012 | Lee ..................... C07D 401/04 257/40 |
| 2013/0026452 A1 | 1/2013 | Kottas et al. |
| 2013/0048963 A1* | 2/2013 | Beers ................. C07F 15/0086 257/40 |
| 2013/0082245 A1* | 4/2013 | Kottas ................ C07F 15/0086 257/40 |
| 2013/0119354 A1 | 5/2013 | Ma et al. |
| 2013/0181190 A1 | 7/2013 | Ma et al. |
| 2013/0181196 A1* | 7/2013 | Lee ..................... C07D 471/04 257/40 |
| 2017/0084851 A1* | 3/2017 | Knowles ............ C07F 15/0033 |

FOREIGN PATENT DOCUMENTS

| | | | |
|---|---|---|---|
| EP | 1238981 | 9/2002 | |
| EP | 1725079 | 11/2006 | |
| EP | 2034538 | 3/2009 | |
| EP | 2551274 | 1/2013 | |
| EP | 2565249 | 3/2013 | |
| EP | 2574613 | 4/2013 | |
| EP | 2933259 A1 * | 10/2015 | ......... H01L 51/0085 |
| JP | 200511610 | 1/2005 | |
| JP | 2007123392 | 5/2007 | |
| JP | 2007254297 | 10/2007 | |
| JP | 2008074939 | 4/2008 | |
| JP | 2009102533 | 5/2009 | |
| JP | 2010118591 | 5/2010 | |
| JP | 2010/135467 | 6/2010 | |
| JP | 2013191804 | 9/2013 | |
| WO | 2001/039234 | 5/2001 | |
| WO | 2002/002714 | 1/2002 | |
| WO | 2002/15645 | 2/2002 | |
| WO | 2003/040257 | 5/2003 | |
| WO | 2003/060956 | 7/2003 | |
| WO | 2004/093207 | 10/2004 | |
| WO | 2004/107822 | 12/2004 | |
| WO | 2004/111066 | 12/2004 | |
| WO | 2005/014551 | 2/2005 | |
| WO | 2005/019373 | 3/2005 | |
| WO | 2005/030900 | 4/2005 | |
| WO | 2005/089025 | 9/2005 | |
| WO | 2005/123873 | 12/2005 | |
| WO | 2006/009024 | 1/2006 | |
| WO | 2006/056418 | 6/2006 | |
| WO | 2006/072002 | 7/2006 | |
| WO | 2006/082742 | 8/2006 | |
| WO | 2006/098120 | 9/2006 | |
| WO | 2006/100298 | 9/2006 | |
| WO | 2006/103874 | 10/2006 | |
| WO | 2006/114966 | 11/2006 | |
| WO | 2006/132173 | 12/2006 | |
| WO | 2007/002683 | 1/2007 | |
| WO | 2007/004380 | 1/2007 | |
| WO | 2007/063754 | 6/2007 | |
| WO | 2007/063796 | 6/2007 | |
| WO | 2008/044723 | 4/2008 | |
| WO | 2008057394 | 5/2008 | |
| WO | 2008/101842 | 8/2008 | |
| WO | 2008/132085 | 11/2008 | |
| WO | 2008/156879 | 12/2008 | |
| WO | 2009/000673 | 12/2008 | |
| WO | 2008156879 | 12/2008 | |
| WO | 2009/003898 | 1/2009 | |
| WO | 2009/008311 | 1/2009 | |
| WO | 2009/018009 | 2/2009 | |
| WO | 2009/050290 | 4/2009 | |
| WO | 2008/056746 | 5/2009 | |
| WO | 2009/021126 | 5/2009 | |
| WO | 2009/062578 | 5/2009 | |
| WO | 2009/063833 | 5/2009 | |
| WO | 2009/066778 | 5/2009 | |
| WO | 2009/066779 | 5/2009 | |
| WO | 2009/086028 | 7/2009 | |
| WO | 2009/100991 | 8/2009 | |
| WO | 2010011390 | 1/2010 | |
| WO | 2010/111175 | 9/2010 | |
| WO | 2011025068 | 3/2011 | |

OTHER PUBLICATIONS (m-MTDATA), as Hole-Transport Materials," *Adv. Mater.*, 6(9):677-679 (1994).

Paulose, Betty Marie Jennifer S. et al., "First Examples of Alkenyl Pyridines as Organic Ligands for Phosphorescent Iridium Complexes," *Adv. Mater.*, 16(22):2003-2007 (2004).

Tung, Yung-Liang et al., "Organic Light-Emitting Diodes Based on Charge-Neutral Ru$^{II}$ PHosphorescent Emitters," Adv. Mater., 17(8):1059-1064 (2005).

Huang, Jinsong et al., "Highly Efficient Red-Emission Polymer Phosphorescent Light-Emitting Diodes Based on Two Novel Tris(1-phenylisoquinolinato-C2,N)iridium(III) Derivatives," *Adv. Mater.*, 19:739-743 (2007).

Wong, Wai-Yeung, "Multifunctional Iridium Complexes Based on Carbazole Modules as Highly Efficient Electrophosphors," *Angew. Chem. Int. Ed.*, 45:7800-7803 (2006).

Tang, C.W. and VanSlyke, S.A., "Organic Electroluminescent Diodes," *Appl. Phys. Lett.*, 51(12):913-915 (1987).

Adachi, Chihaya et al., "Organic Electroluminescent Device Having a Hole Conductor as an Emitting Layer," *Appl. Phys. Lett.*, 55(15):1489-1491 (1989).

Ma, Yuguang et al., "Triplet Luminescent Dinuclear-Gold(/) Complex-Based Light-Emitting Diodes with Low Turn-On voltage," *Appl. Phys. Lett.*, 74(10):1361-1363 (1999).

Gao, Zhiqiang et al., "Bright-Blue Electroluminescence From a Silyl-Substituted ter-(phenylene-vinylene) derivative," *Appl. Phys. Lett.*, 74(6):865-867 (1999).

Lee, Chang-Lyoul et al., "Polymer Phosphorescent Light-Emitting Devices Doped with Tris(2-phenylpyridine) Iridium as a Triplet Emitter," *Appl. Phys. Lett.*, 77(15):2280-2282 (2000).

(56) References Cited

OTHER PUBLICATIONS

Hung, L.S. et al., "Anode Modification in Organic Light-Emitting Diodes by Low-Frequency Plasma Polymerization of $CHF_3$," *Appl. Phys. Lett.*, 78(5):673-675 (2001).

Ikai, Masamichi and Tokito, Shizuo, "Highly Efficient Phosphorescence From Organic Light-Emitting Devices with an Exciton-Block Layer," *Appl. Phys. Lett.*, 79(2):156-158 (2001).

Wang, Y. et al., "Highly Efficient Electroluminescent Materials Based on Fluorinated Organometallic Iridium Compounds," *Appl. Phys. Lett.*, 79(4):449-451 (2001).

Kwong, Raymond C. et al., "High Operational Stability of Electrophosphorescent Devices," *Appl. Phys. Lett.*, 81(1):162-164 (2002).

Holmes, R.J. et al., "Blue Organic Electrophosphorescence Using Exothermic Host-Guest Energy Transfer," *Appl. Phys. Lett.*, 82(15):2422-2424 (2003).

Sotoyama, Wataru et al., "Efficient Organic Light-Emitting Diodes with Phosphorescent Platinum Complexes Containing NCN-Coordinating Tridentate Ligand," *Appl. Phys. Lett.*, 86:153505-1-153505-3 (2005).

Okumoto, Kenji et al., "Green Fluorescent Organic Light-Emitting Device with External Quantum Efficiency of Nearly 10%," *Appl. Phys. Lett.*, 89:063504-1-063504-3 (2006).

Kanno, Hiroshi et al., "Highly Efficient and Stable Red Phosphorescent Organic Light-Emitting Device Using bis[2-(2-benzothiazoyl)phenolato]zinc(II) as host material," *Appl. Phys. Lett.*, 90:123509-1-123509-3 (2007).

Aonuma, Masaki et al., "Material Design of Hole Transport Materials Capable of Thick-Film Formation in Organic Light Emitting Diodes," *Appl. Phys. Lett.*, 90:183503-1-183503-3 (2007).

Sun, Yiru and Forrest, Stephen R., "High-Efficiency White Organic Light Emitting Devices with Three Separate Phosphorescent Emission Layers," *Appl. Phys. Lett.*, 91:263503-1-263503-3 (2007).

Adachi, Chihaya et al., "High-Efficiency Red Electrophosphorescence Devices," *Appl. Phys. Lett.*, 78(11):1622-1624 (2001).

Wong, Keith Man-Chung et al., A Novel Class of Phosphorescent Gold(III) Alkynyl-Based Organic Light-Emitting Devices with Tunable Colour, *Chem. Commun.*, 2906-2908 (2005).

Hamada, Yuji et al., "High Luminance in Organic Electroluminescent Devices with Bis(10-hydroxybenzo[h]quinolinato)beryllium as an Emitter," *Chem. Lett.*, 905-906 (1993).

Nishida, Jun-ichi et al., "Preparation, Characterization, and Electroluminescence Characteristics of α-Diimine-type Platinum(II) Complexes with Perfluorinated Phenyl Groups as Ligands," *Chem. Lett.*, 34(4):592-593 (2005).

Mi, Bao-Xiu et al., "Thermally Stable Hole-Transporting Material for Organic Light-Emitting Diode: an Isoindole Derivative," *Chem. Mater.*, 15(16):3148-3151 (2003).

Huang, Wei-Sheng et al., "Highly Phosphorescent Bis-Cyclometalated Iridium Complexes Containing Benzoimidazole-Based Ligands," *Chem. Mater.*, 16(12):2480-2488 (2004).

Niu, Yu-Hua et al., "Highly Efficient Electrophosphorescent Devices with Saturated Red Emission from a Neutral Osmium Complex," *Chem. Mater.*, 17(13):3532-3536 (2005).

Lo, Shih-Chun et al., "Blue Phosphorescence from Iridium(III) Complexes at Room Temperature," *Chem. Mater.*, 18(21):5119-5129 (2006).

Takizawa, Shin-ya et al., "Phosphorescent Iridium Complexes Based on 2-Phenylimidazo[1,2-α]pyridine Ligands: Tuning of Emission Color toward the Blue Region and Application to Polymer Light-Emitting Devices," *Inorg. Chem.*, 46(10):4308-4319 (2007).

Lamansky, Sergey et al., "Synthesis and Characterization of Phosphorescent Cyclometalated Iridium Complexes," *Inorg. Chem.*, 40(7):1704-1711 (2001).

Ranjan, Sudhir et al., "Realizing Green Phosphorescent Light-Emitting Materials from Rhenium(I) Pyrazolato Diimine Complexes," *Inorg. Chem.*, 42(4):1248-1255 (2003).

Noda, Tetsuya and Shirota,Yasuhiko, "5,5'-Bis(dimesitylboryl)-2,2'-bithiophene and 5,5''-Bis(dimesitylboryl)-2,2':5',2''-terthiophene as a Novel Family of Electron-Transporting Amorphous Molecular Materials," *J. Am. Chem. Soc.*, 120 (37):9714-9715 (1998).

Sakamoto, Youichi et al., "Synthesis, Characterization, and Electron-Transport Property of Perfluorinated Phenylene Dendrimers," *J. Am. Chem. Soc.*, 122(8):1832-1833 (2000).

Adachi, Chihaya et al., "Nearly 100% Internal Phosphorescence Efficiency in an Organic Light Emitting Device," *J. Appl. Phys.*, 90(10):5048-5051 (2001).

Shirota, Yasuhiko et al., "Starburst Molecules Based on p-Electron Systems as Materials for Organic Electroluminescent Devices," *Journal of Luminescence*, 72-74:985-991 (1997).

Inada, Hiroshi and Shirota, Yasuhiko, "1,3,5-Tris[4-(diphenylamino)phenyl]benzene and its Methylsubstituted Derivatives as a Novel Class of Amorphous Molecular Materials," *J. Mater. Chem.*, 3(3):319-320 (1993).

Kido, Junji et al., 1,2,4-Triazole Derivative as an Electron Transport Layer in Organic Electroluminescent Devices, *Jpn. J. Appl. Phys.*, 32:L917-L920 (1993).

Van Slyke, S. A. et al., "Organic Electroluminescent Devices with Improved Stability," *Appl. Phys. Lett.*, 69(15 ):2160-2162 (1996).

Guo, Tzung-Fang et al., "Highly Efficient Electrophosphorescent Polymer Light-Emitting Devices," *Organic Electronics*, 1:15-20 (2000).

Palilis, Leonidas C., "High Efficiency Molecular Organic Light-Emitting Diodes Based on Silole Derivatives and Their Exciplexes," *Organic Electronics*, 4:113-121 (2003).

Ikeda, Hisao et al., "P-185: Low-Drive-Voltage OLEDs with a Buffer Layer Having Molybdenum Oxide," *SID Symposium Digest*, 37:923-926 (2006).

T. Östergård et al., "Langmuir-Blodgett Light-Emitting Diodes of Poly(3-Hexylthiophene): Electro-Optical Characteristics Related to Structure," *Synthetic Metals*, 87:171-177 (1997).

Hu, Nan-Xing et al., "Novel High $T_g$ Hole-Transport Molecules Based on Indolo[3,2-b]carbazoles for Organic Light-Emitting Devices," *Synthetic Metals*, 111-112:421-424 (2000).

Salbeck, J. et al., "Low Molecular Organic Glasses for Blue Electroluminescence," *Synthetic Metals*, 91:209-215 (1997).

Elangannan Arunan et al, "Definition of the hydrogen bond (IUPAC Recommendations 2011)" Pure and Applied Chemistry, Vo. 83, No. 8, Jan. 2011; ISSN: 0033-4545, DOI: 10.1351/PAC-REC-10-01-02.

* cited by examiner

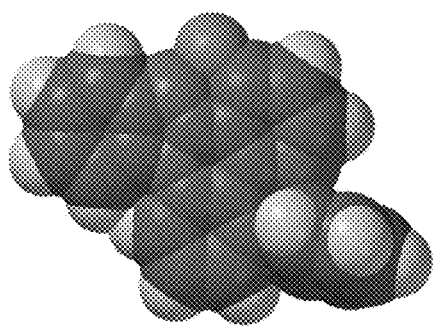
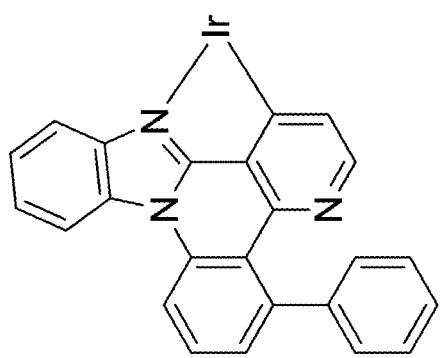
Figure 4

ORGANIC ELECTROLUMINESCENT MATERIALS AND DEVICES

CROSS-REFERENCE TO RELATED APPLICATIONS

This application claims priority from U.S. Provisional Patent Application Ser. Nos. 61/979,103, filed Apr. 14, 2014, and 61/991,720, filed May 12, 2014, the entire contents of each of which is incorporated herein by reference.

PARTIES TO A JOINT RESEARCH AGREEMENT

The claimed invention was made by, on behalf of, and/or in connection with one or more of the following parties to a joint university corporation research agreement: Regents of the University of Michigan, Princeton University, University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to compounds for use as emitters and devices, such as organic light emitting diodes, including the same.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted Ir(ppy)$_3$, which has the following structure:

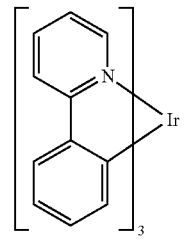

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher"

3

HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

Substitution of nitrogen in a specific position in the polycyclic benzimidazole phenanthridine ligand system can lead to a profound blue shifting effect. However, the uncoordinated nitrogen presents a stability issue as it may be susceptible to protonation in the excited state. There is a need in the art to prevent protonation of the uncoordinated nitrogen in the polycyclic benzimidazole phenanthridine ligand system while maintaining the blue shifting effect. The present invention addresses this unmet need.

SUMMARY OF THE INVENTION

According to an embodiment, a compound is provided that comprises a ligand $L_A$ of Formula I:

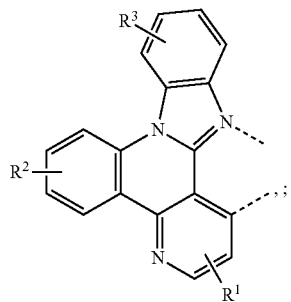

Formula I wherein $R^1$ represents mono, or di-substitution, or no substitution;
wherein $R^2$ and $R^3$ each independently represent mono, di, tri, or tetra-substitution, or no substitution;
wherein any adjacent substitutions in $R^1$, $R^2$ and $R^3$ are optionally linked together to form a ring;
wherein $R^1$, $R^2$ and $R^3$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;
wherein the ligand $L_A$ is coordinated to a metal M; and
wherein the ligand $L_A$ is optionally linked with other ligands to comprise a tridentate, tetradentate, pentadentate or hexadentate ligand.

In one embodiment, the compound has the formula $M(L_A)_m(L_B)_n$, having the structure:

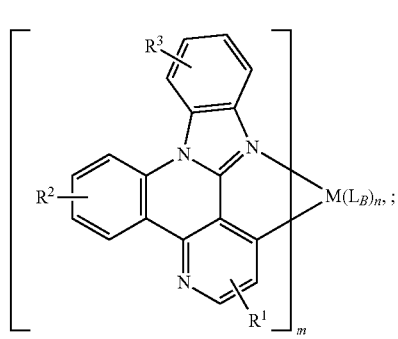

Formula II wherein $L_B$ is a different ligand from $L_A$; and
wherein m is an integer from 1 to the maximum number of ligands that may be coordinated to the metal M; m+n is the maximum number of ligands that may be coordinated to the metal M.

In one embodiment, M is selected from the group consisting of Ir, Rh, Re, Ru, Os, Pt, Au, and Cu. In another embodiment, M is Ir.

In one embodiment, the ligand $L_A$ has the structure of:

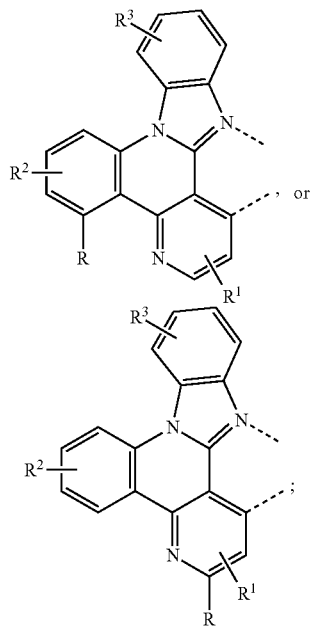

wherein R is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one embodiment, R is selected from the group consisting of alkyl, cycloalkyl, silyl, aryl, heteroaryl, and combinations thereof. In one embodiment, R is selected from the group consisting of methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, cyclopentyl, cyclohexyl, phenyl, 2,6-dimethylphenyl, 3,5-dimethylphenyl, 2,4,6-trimethylphenyl, 2,6-diisopropylphenyl, 4-isobutylphenyl, and combinations thereof.

In one embodiment, the compound has the structure:

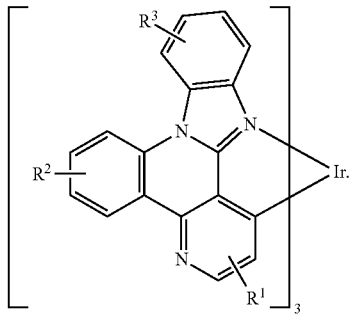

In one embodiment, the compound has the structure:

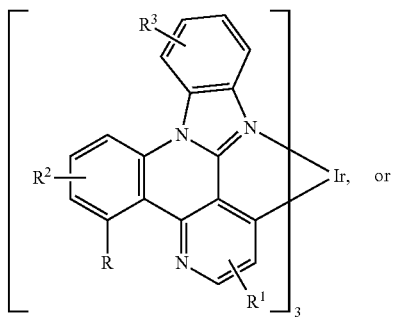

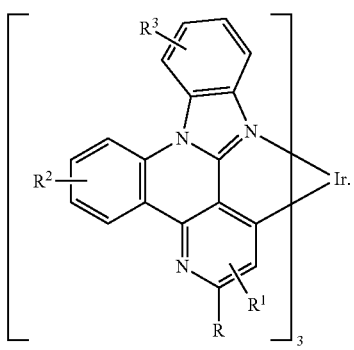

In one embodiment, the ligand $L_A$ is selected from the group consisting of $L_{A1}$ through $L_{A316}$.

In one embodiment, the compound is selected from the group consisting of Compound 1 through Compound 316; wherein each Compound x has the formula $Ir(L_{Ai})_3$; and wherein x=i; i is an integer from 1 to 316.

In one embodiment, the compound has the formula $Ir(L_A)_m(L_B)_{3-m}$, having the structure:

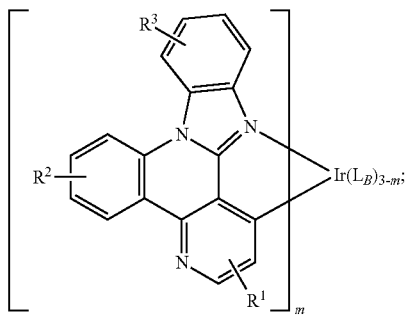

wherein $L_B$ is a different ligand from $L_A$;
wherein m is 1 or 2;
wherein $L_B$ is selected from the group consisting of:

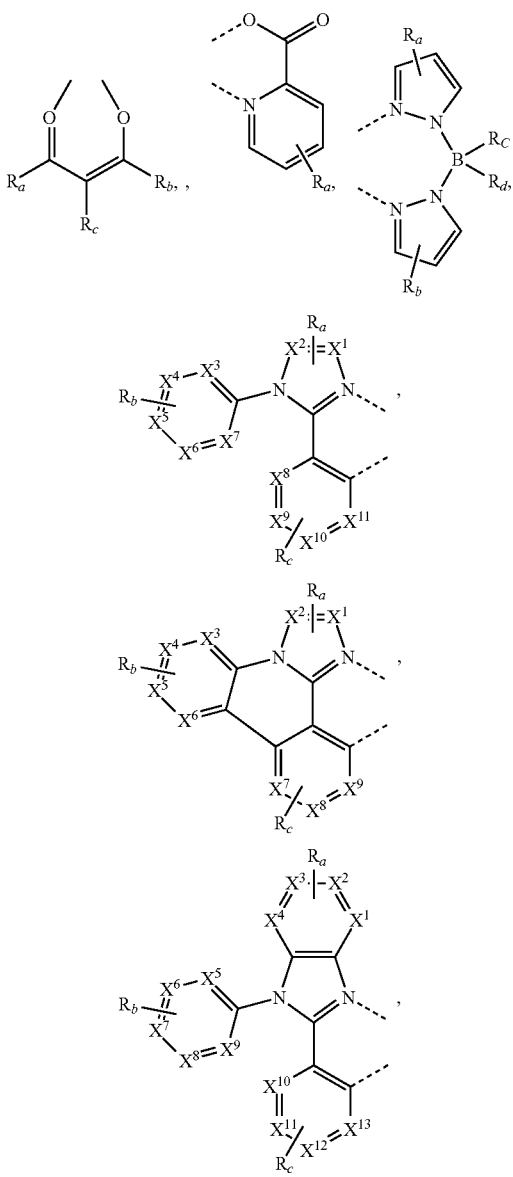

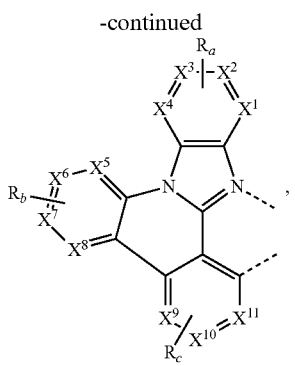
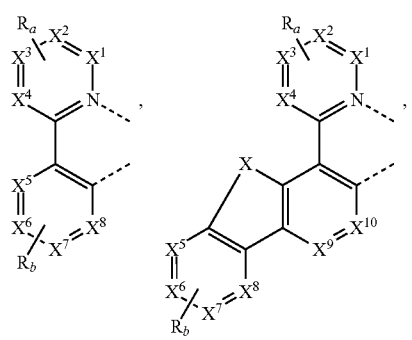
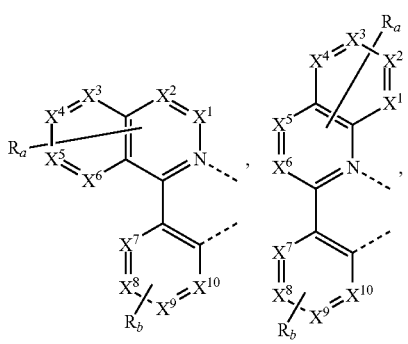
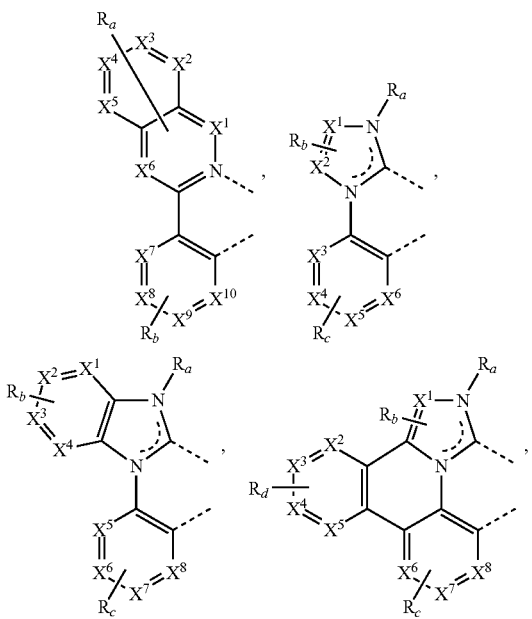

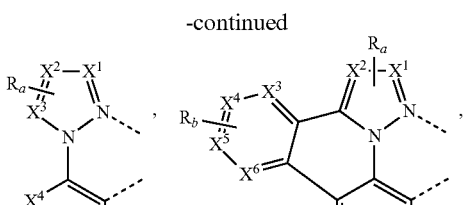
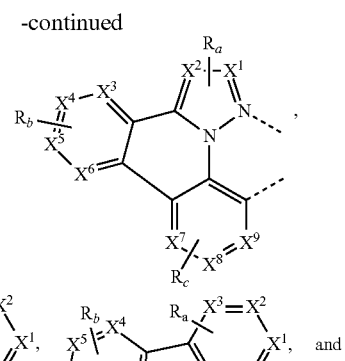
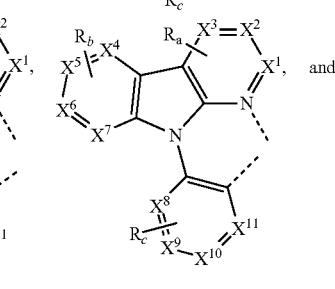
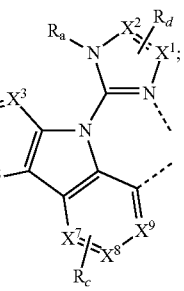

wherein each $X^1$ to $X^{13}$ is independently selected from the group consisting of carbon and nitrogen;

wherein X is selected from the group consisting of BR', NR', PR', O, S, Se, C=O, S=O, SO$_2$, CR'R", SiR'R", and GeR'R";

wherein R' and R" are optionally fused or joined to form a ring;

wherein each $R_a$, $R_b$, $R_c$, and $R_d$ may represent from mono substitution to the possible maximum number of substitution, or no substitution;

wherein $R_a$, $R_b$, $R_c$, and $R_d$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein when $R_a$, $R_b$, $R_c$, and $R_d$ represent at least di substitution, each of the two adjacent $R_a$, two adjacent $R_b$, two adjacent $R_c$, and two adjacent $R_d$ are optionally fused or joined to form a ring or form a multidentate ligand.

In one embodiment, $L_B$ is selected from the group consisting of $L_{B1}$ through $L_{B267}$.

In one embodiment, the compound is selected from the group consisting of Compound 317 through Compound 84,688; wherein each Compound x has the formula Ir($L_{Ai}$)($L_{Bj}$)$_2$;

wherein $L_{Bi}$ is selected from the group consisting of $L_{B1}$ through $L_{B267}$; and wherein x=316j+i; i is an integer from 1 to 316, and j is an integer from 1 to 267.

In one embodiment, the $L_B$ is chosen such that the HOMO energy in Ir($L_B$)$_3$ is deeper than that in Ir($L_A$)$_3$.

In one embodiment, the compound is selected from the group consisting of:
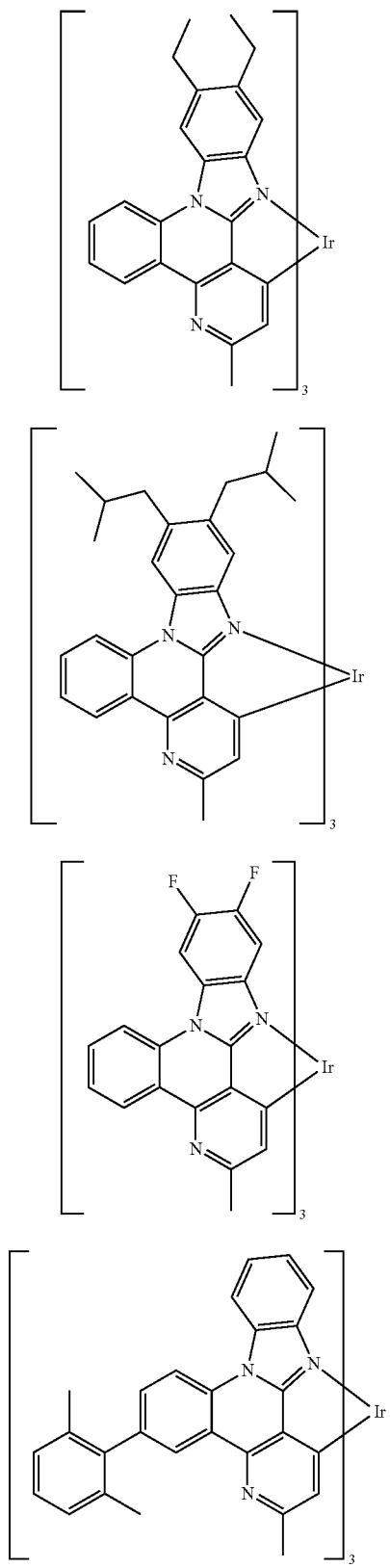
Compound 306
Compound 307
Compound 308
Compound 110
-continued
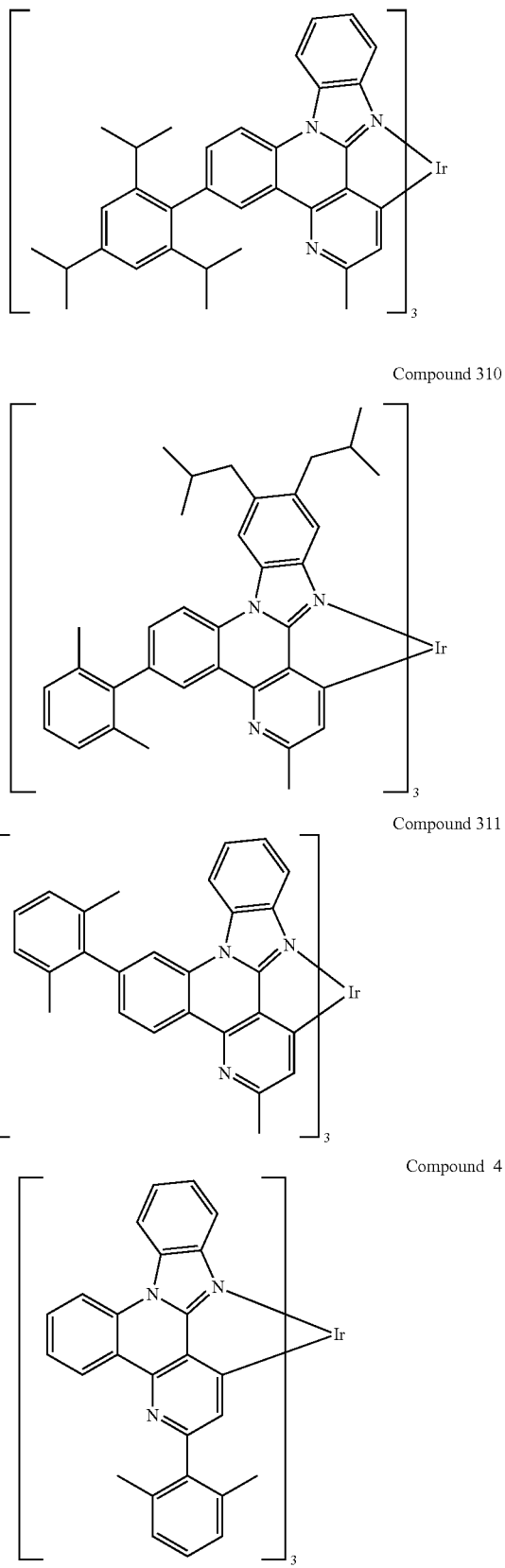
Compound 309
Compound 310
Compound 311
Compound 4

-continued

Compound 7

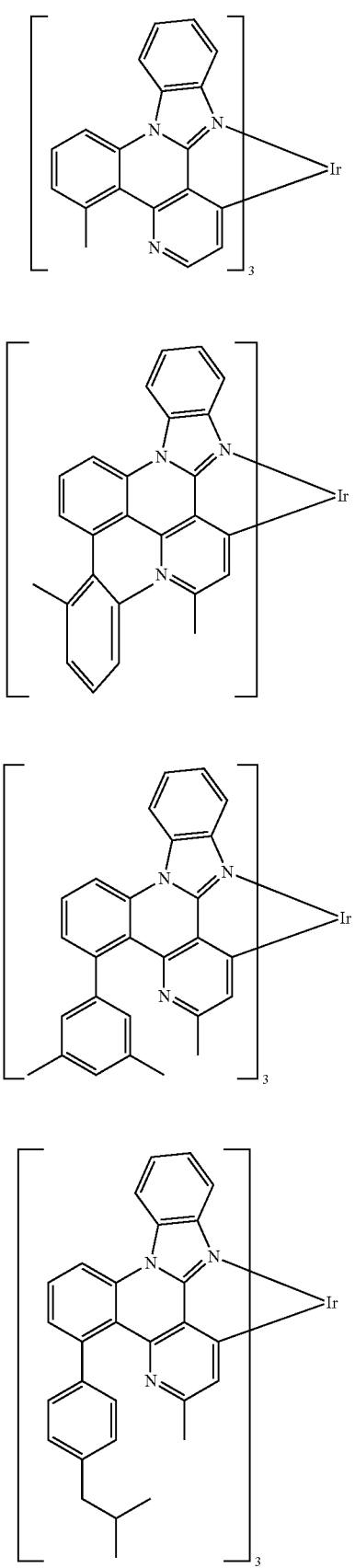

Compound 312

Compound 313

Compound 314

-continued

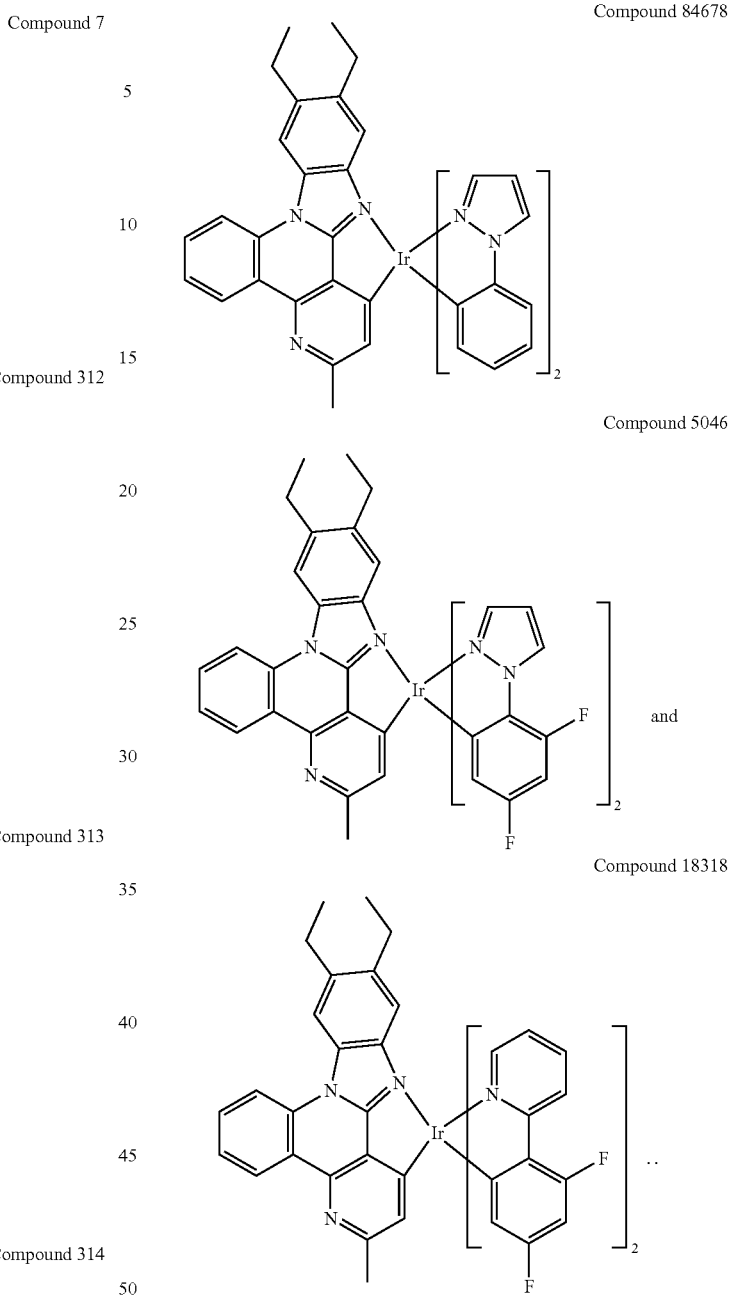

Compound 84678

Compound 5046 and

Compound 18318

According to another embodiment, a first device comprising a first organic light emitting device is also provided. The first organic light emitting device can include an anode, a cathode, and an organic layer, disposed between the anode and the cathode. The organic layer can include a compound of Formula I. The first device can be a consumer product, an organic light-emitting device, and/or a lighting panel.

In one embodiment, the first device comprises a first organic light emitting device, the first organic light emitting device comprising:
an anode;
a cathode; and
an organic layer, disposed between the anode and the cathode, comprising a compound comprising a ligand $L_A$ of Formula I:

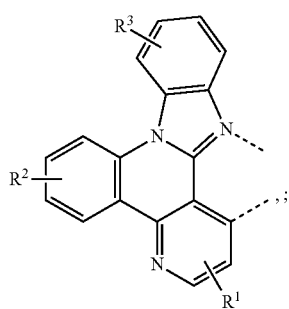

Formula I wherein $R^1$ represents mono, or di-substitution, or no substitution;

wherein $R^2$ and $R^3$ each independently represent mono, di, tri, or tetra-substitution, or no substitution;

wherein any adjacent substitutions in $R^1$, $R^2$ and $R^3$ are optionally linked together to form a ring;

wherein $R^1$, $R^2$ and $R^3$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

wherein the ligand $L_A$ is coordinated to a metal M; and wherein the ligand $L_A$ is optionally linked with other ligands to comprise a tridentate, tetradentate, pentadentate or hexadentate ligand.

In one embodiment, the first device is selected from the group consisting of a consumer product, an electronic component module, an organic light-emitting device, and a lighting panel. In another embodiment, the organic layer is an emissive layer and the compound is an emissive dopant or a non-emissive dopant. In another embodiment, the organic layer is a charge transporting layer and the compound is a charge transporting material in the organic layer. In another embodiment, the organic layer is a blocking layer and the compound is a blocking material in the organic layer.

In one embodiment, the organic layer further comprises a host; wherein the host comprises a triphenylene containing benzo-fused thiophene or benzo-fused furan;

wherein any substituent in the host is an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, $CH=CH-C_nH_{2n+1}$, $C\equiv CC_nH_{2n+1}$, $Ar_1$, $Ar_1-Ar_2$, $C_nH_{2n}Ar_1$, or no substitution;

wherein n is from 1 to 10; and wherein $Ar_1$ and $Ar_2$ are independently selected from the group consisting of benzene, biphenyl, naphthalene, triphenylene, carbazole, and heteroaromatic analogs thereof.

In one embodiment, the organic layer further comprises a host, wherein the host comprises at least one chemical group selected from the group consisting of triphenylene, carbazole, dibenzothiphene, dibenzofuran, dibenzoselenophene, azatriphenylene, azacarbazole, aza-dibenzothiophene, aza-dibenzofuran, and aza-dibenzoselenophene.

In one embodiment, the organic layer further comprises a host and the host is selected from the group consisting of:

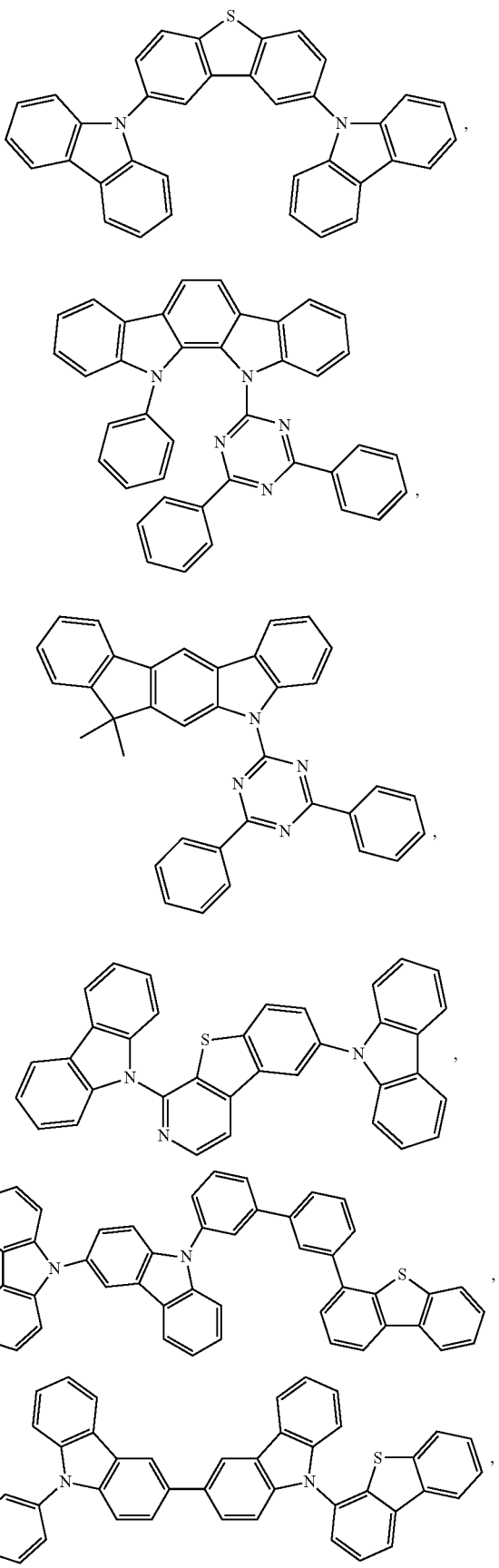

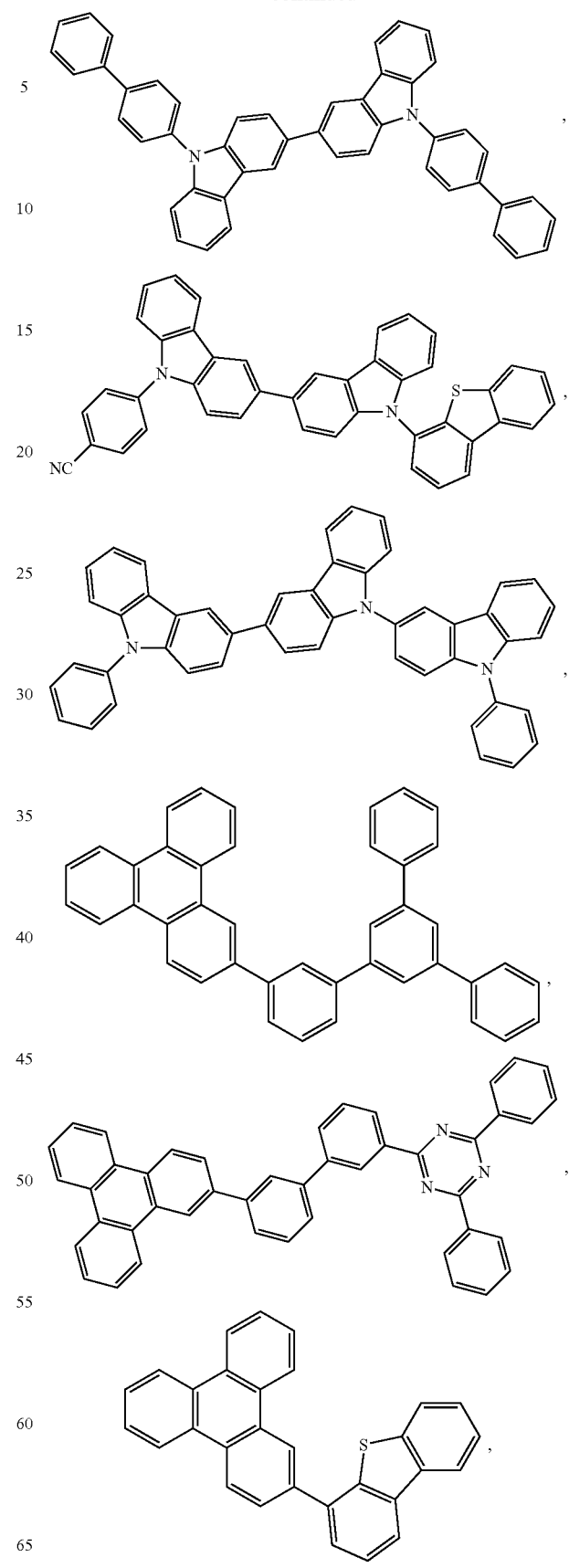

-continued

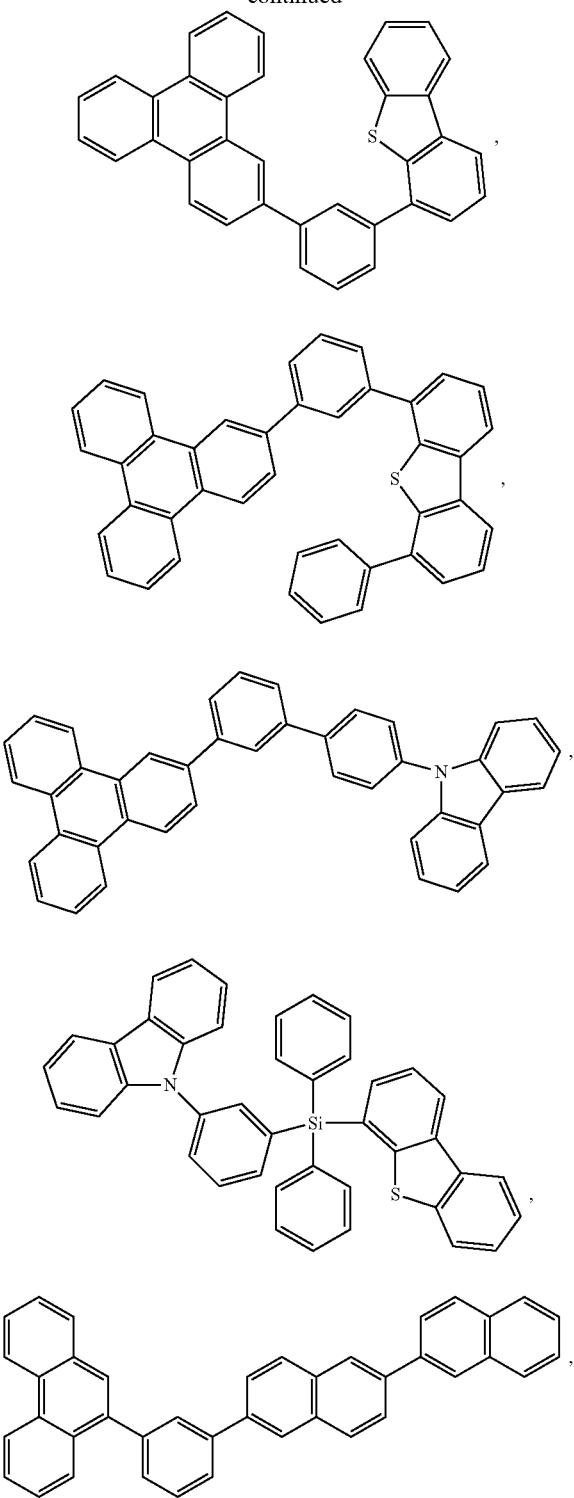

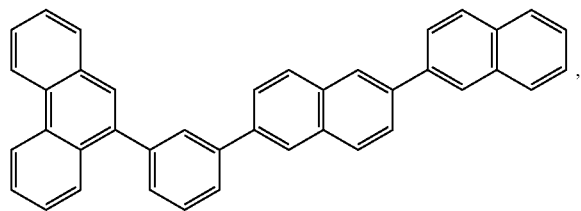

and combinations thereof.

In one embodiment, the organic layer further comprises a host and the host comprises a metal complex.

According to another embodiment, a formulation comprising the above compound is also provided. In one embodiment, the formulation comprises a compound comprising a ligand $L_A$ of Formula I:

Formula I wherein $R^1$ represents mono, or di-substitution, or no substitution;

wherein $R^2$ and $R^3$ each independently represent mono, di, tri, or tetra-substitution, or no substitution;

wherein any adjacent substitutions in $R^1$, $R^2$ and $R^3$ are optionally linked together to form a ring;

wherein $R^1$, $R^2$ and $R^3$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

wherein the ligand $L_A$ is coordinated to a metal M; and wherein the ligand $L_A$ is optionally linked with other ligands to comprise a tridentate, tetradentate, pentadentate or hexadentate ligand.

BRIEF DESCRIPTION OF THE DRAWINGS

FIG. 4 shows a minimized space filling model of Compound 315. The uncoordinated nitrogen atom is completely shielded by the plane of the phenyl substituent. Two of the ligands have been hidden for clarity.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 which is incorporated by reference in its entirety.

Figure 1:
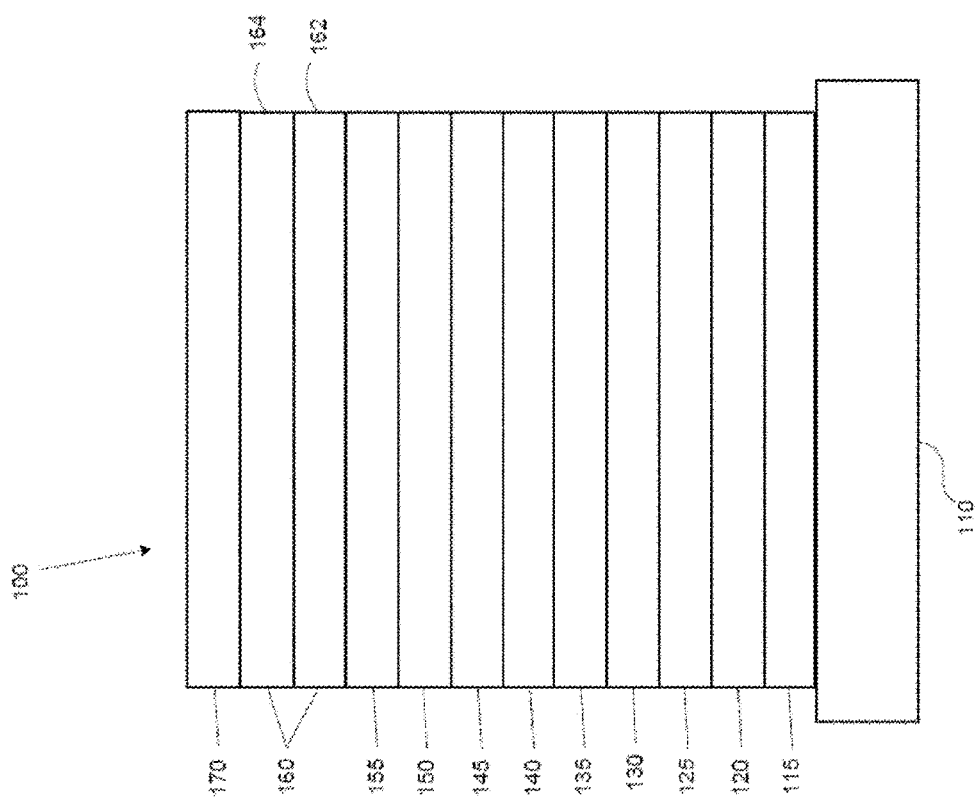
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 which is incorporated by reference in its entirety.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
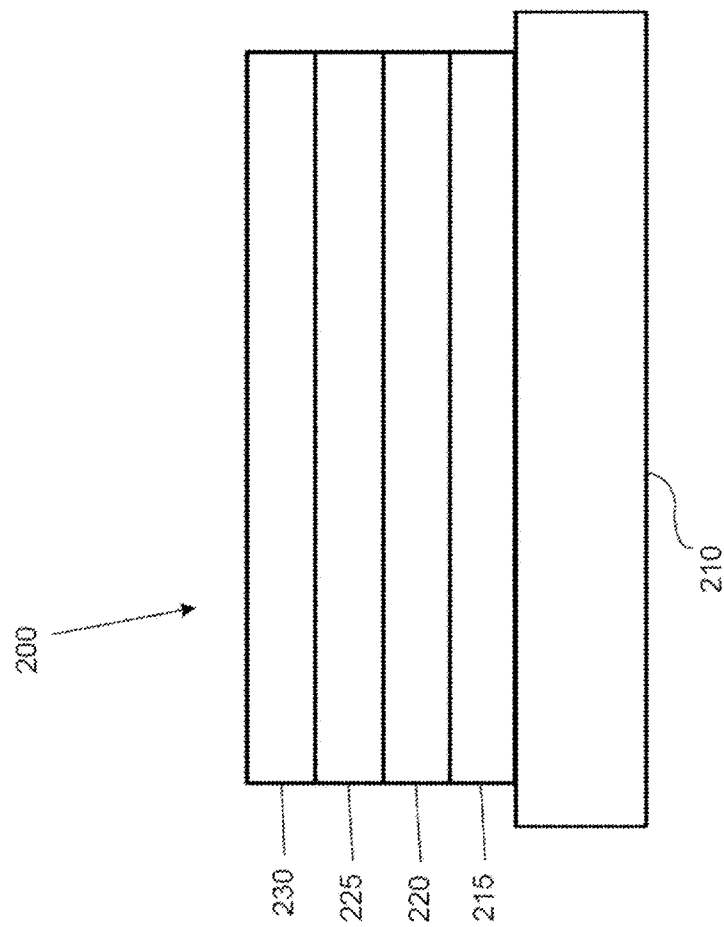
FIG. 2 shows an inverted organic light emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the invention can be incorporated into a wide variety of electronic component modules (or units) that can be incorporated into a variety of electronic products or intermediate components. Examples of such electronic products or intermediate components include display screens, lighting devices such as discrete light source devices or lighting panels, etc. that can be utilized by the end-user product manufacturers. Such electronic component modules can optionally include the driving electronics and/or power source(s). Devices fabricated in accordance with embodiments of the invention can be incorporated into a wide variety of consumer products that have one or more of the electronic component modules (or units) incorporated therein. Such consumer products would include any kind of products that include one or more light source(s) and/or one or more of some type of visual displays. Some examples of such consumer products include flat panel displays, computer monitors, medical monitors, televisions, billboards, lights for interior or exterior illumination and/or signaling, heads-up displays, fully or partially transparent displays, flexible displays, laser printers, telephones, cell phones, tablets, phablets, personal digital assistants (PDAs), laptop computers, digital cameras, camcorders, viewfinders, microdisplays, 3-D displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.), but could be used outside this temperature range, for example, from −40 degree C. to +80 degree C.

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The term "halo," "halogen," or "halide" as used herein includes fluorine, chlorine, bromine, and iodine.

The term "alkyl" as used herein contemplates both straight and branched chain alkyl radicals. Preferred alkyl groups are those containing from one to fifteen carbon atoms and includes methyl, ethyl, propyl, isopropyl, butyl, isobutyl, tert-butyl, and the like. Additionally, the alkyl group may be optionally substituted.

The term "cycloalkyl" as used herein contemplates cyclic alkyl radicals. Preferred cycloalkyl groups are those containing 3 to 7 carbon atoms and includes cyclopropyl, cyclopentyl, cyclohexyl, and the like. Additionally, the cycloalkyl group may be optionally substituted.

The term "alkenyl" as used herein contemplates both straight and branched chain alkene radicals. Preferred alkenyl groups are those containing two to fifteen carbon atoms. Additionally, the alkenyl group may be optionally substituted.

The term "alkynyl" as used herein contemplates both straight and branched chain alkyne radicals. Preferred alkynyl groups are those containing two to fifteen carbon atoms. Additionally, the alkynyl group may be optionally substituted.

The terms "aralkyl" or "arylalkyl" as used herein are used interchangeably and contemplate an alkyl group that has as a substituent an aromatic group. Additionally, the aralkyl group may be optionally substituted.

The term "heterocyclic group" as used herein contemplates aromatic and non-aromatic cyclic radicals. Heteroaromatic cyclic radicals also means heteroaryl. Preferred hetero-non-aromatic cyclic groups are those containing 3 or 7 ring atoms which includes at least one hetero atom, and includes cyclic amines such as morpholino, piperdino, pyrrolidino, and the like, and cyclic ethers, such as tetrahydrofuran, tetrahydropyran, and the like. Additionally, the heterocyclic group may be optionally substituted.

The term "aryl" or "aromatic group" as used herein contemplates single-ring groups and polycyclic ring systems. The polycyclic rings may have two or more rings in which two carbons are common to two adjoining rings (the rings are "fused") wherein at least one of the rings is aromatic, e.g., the other rings can be cycloalkyls, cycloalkenyls, aryl, heterocycles, and/or heteroaryls. Additionally, the aryl group may be optionally substituted.

The term "heteroaryl" as used herein contemplates single-ring hetero-aromatic groups that may include from one to three heteroatoms, for example, pyrrole, furan, thiophene, imidazole, oxazole, thiazole, triazole, pyrazole, pyridine, pyrazine and pyrimidine, and the like. The term heteroaryl also includes polycyclic hetero-aromatic systems having two or more rings in which two atoms are common to two adjoining rings (the rings are "fused") wherein at least one of the rings is a heteroaryl, e.g., the other rings can be cycloalkyls, cycloalkenyls, aryl, heterocycles, and/or heteroaryls. Additionally, the heteroaryl group may be optionally substituted.

The alkyl, cycloalkyl, alkenyl, alkynyl, aralkyl, heterocyclic group, aryl, and heteroaryl may be optionally substituted with one or more substituents selected from the group consisting of hydrogen, deuterium, halogen, alkyl, cycloalkyl, heteroalkyl, arylalkyl, alkoxy, aryloxy, amino, cyclic amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof.

As used herein, "substituted" indicates that a substituent other than H is bonded to the relevant position, such as carbon. Thus, for example, where $R^1$ is mono-substituted, then one $R^1$ must be other than H. Similarly, where $R^1$ is di-substituted, then two of $R^1$ must be other than H. Similarly, where $R^1$ is unsubstituted, $R^1$ is hydrogen for all available positions.

The "aza" designation in the fragments described herein, i.e. aza-dibenzofuran, aza-dibenzothiophene, etc. means that one or more of the C—H groups in the respective fragment can be replaced by a nitrogen atom, for example, and without any limitation, azatriphenylene encompasses both dibenzo[f,h]quinoxaline and dibenzo[f,h]quinoline. One of ordinary skill in the art can readily envision other nitrogen analogs of the aza-derivatives described above, and all such analogs are intended to be encompassed by the terms as set forth herein.

It is to be understood that when a molecular fragment is described as being a substituent or otherwise attached to another moiety, its name may be written as if it were a fragment (e.g. phenyl, phenylene, naphthyl, dibenzofuryl) or as if it were the whole molecule (e.g. benzene, naphthalene, dibenzofuran). As used herein, these different ways of designating a substituent or attached fragment are considered to be equivalent.

Substitution of nitrogen in a specific position in the polycyclic benzimidazole phenanthridine ligand system can lead to a profound blue shifting effect. However, the uncoordinated nitrogen presents a stability issue as it may be susceptible to protonation in the excited state. The three ring structure of benzimidazole phenanthridine has a site that, when substituted with a bulky group, such as an aryl ring, shields the uncoordinated nitrogen from the protons of neighboring molecules. Therefore, this type of substitution in this position is useful for improving stability by preventing the uncoordinated nitrogen from being protonated. In addition, substituting a conjugating aryl ring at this position requires that the ring is fully twisted out of plane; therefore, aryl substitution at this site does not lower the triplet energy of the complex.

Compounds of the Invention:

The compounds of the present invention may be synthesized using techniques well-known in the art of organic synthesis. The starting materials and intermediates required for the synthesis may be obtained from commercial sources or synthesized according to methods known to those skilled in the art.

In one aspect, the compound of the invention is a compound comprising a ligand $L_A$ of Formula I:

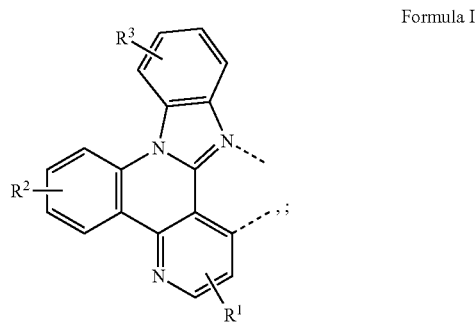

Formula I wherein $R^1$ represents mono, or di-substitution, or no substitution;

wherein $R^2$ and $R^3$ each independently represent mono, di, tri, or tetra-substitution, or no substitution;

wherein any adjacent substitutions in $R^1$, $R^2$ and $R^3$ are optionally linked together to form a ring;

wherein $R^1$, $R^2$ and $R^3$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

wherein the ligand $L_A$ is coordinated to a metal M; and wherein the ligand $L_A$ is optionally linked with other ligands to comprise a tridentate, tetradentate, pentadentate or hexadentate ligand.

The metal M is not particularly limited. Examples of metals useful in the compounds of the present invention include, but are not limited to, transition metals such as Ir, Pt, Au, Re, Ru, W, Rh, Ru, Os, Pd, Ag, Cu, Co, Zn, Ni, Pb, Al, and Ga. In one embodiment, M is selected from the group consisting of Ir, Rh, Re, Ru, Os, Pt, Au, and Cu. In another embodiment, M is Ir.

In one embodiment, the ligand $L_A$ has the structure of:

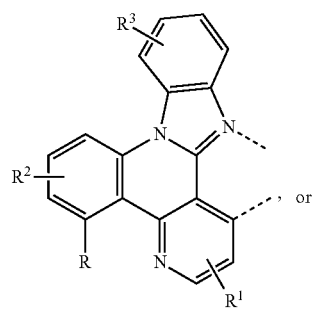

, or

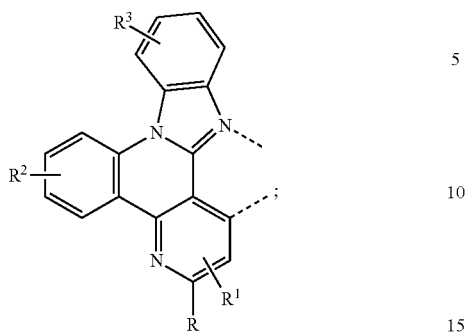

wherein R is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one embodiment, R is selected from the group consisting of alkyl, cycloalkyl, silyl, aryl, heteroaryl, and combinations thereof. In another embodiment, R is selected from the group consisting of methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, cyclopentyl, cyclohexyl, phenyl, 2,6-dimethylphenyl, 3,5-dimethylphenyl, 2,4,6-trimethylphenyl, 2,6-diisopropylphenyl, 4-isobutylphenyl, and combinations thereof.

In one embodiment, the ligand $L_A$ is selected from the group consisting of:

$L_{A1}$

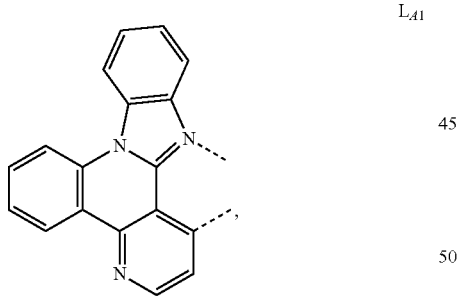

$L_{A2}$

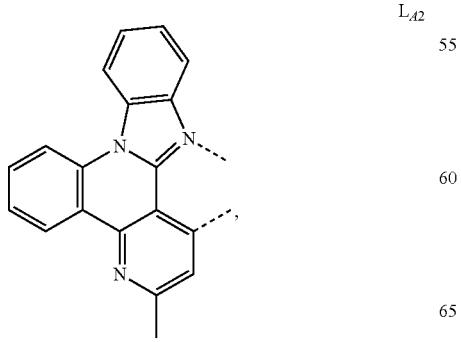

$L_{A3}$

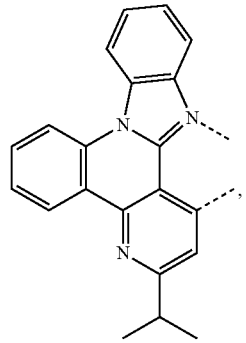

$L_{A4}$

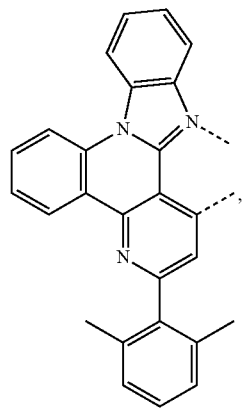

$L_{A5}$

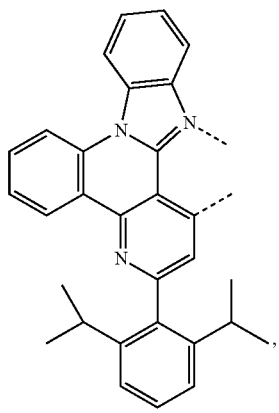

$L_{A6}$

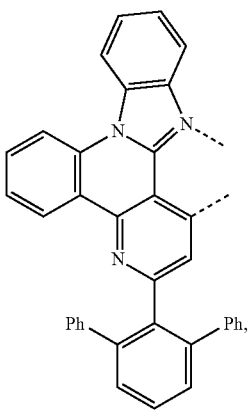

L_{A7}
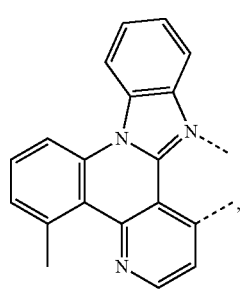
L_{A8}
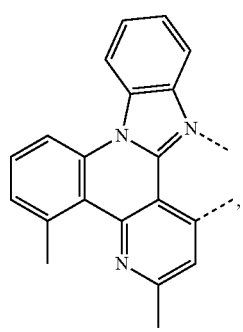
L_{A9}
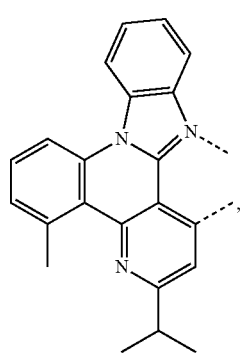
L_{A10}
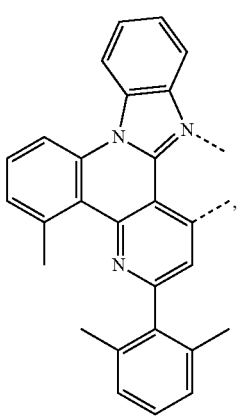
L_{A11}
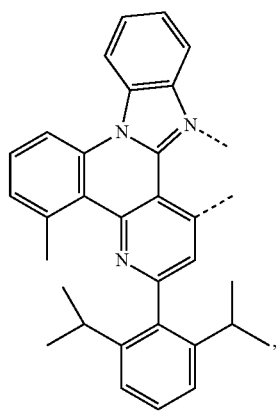
L_{A12}
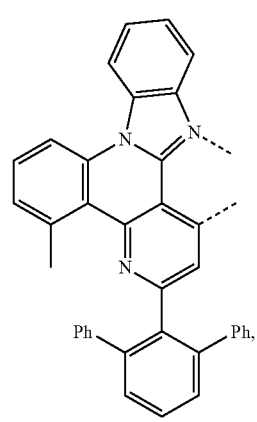
L_{A13}
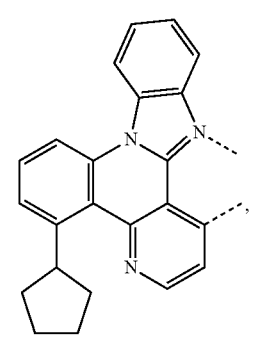
L_{A14}
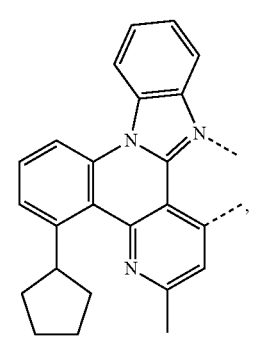

-continued
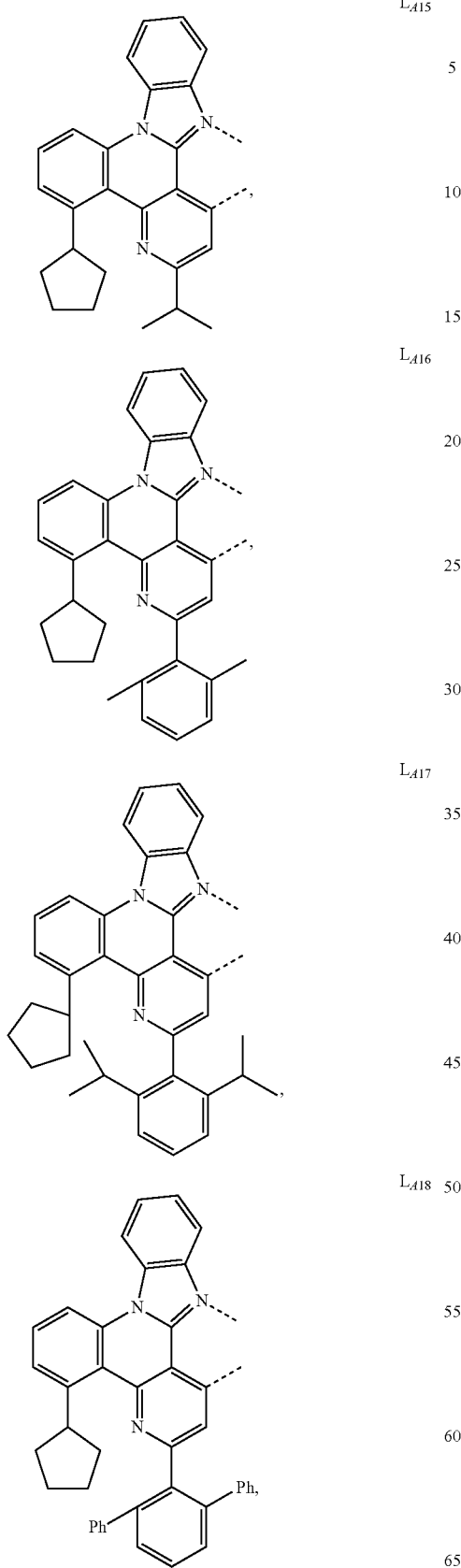
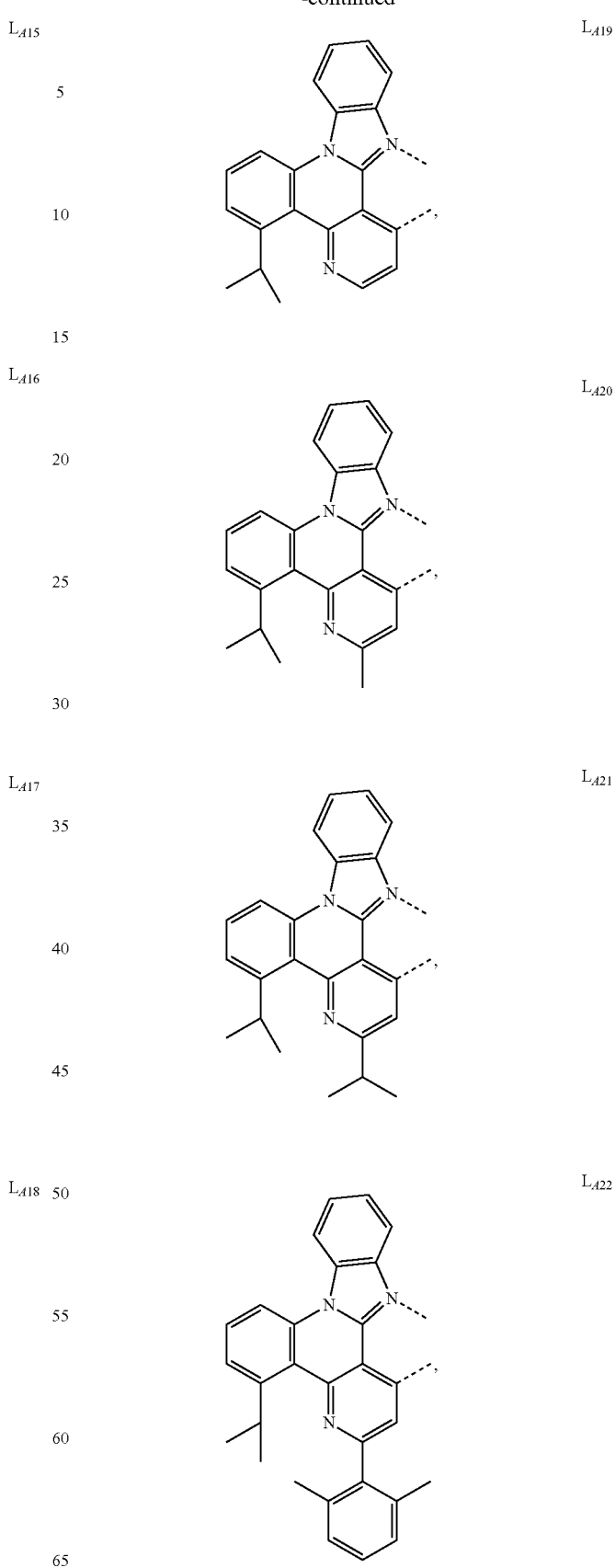

| | |
|---|---|
| 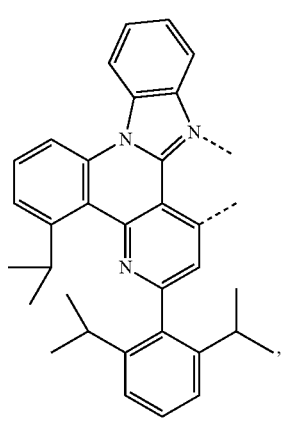 L_{A23} 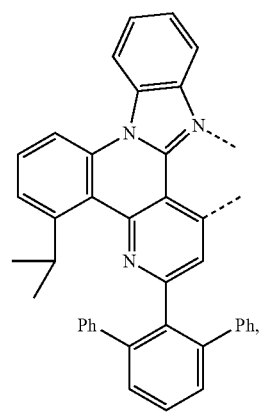 L_{A24} 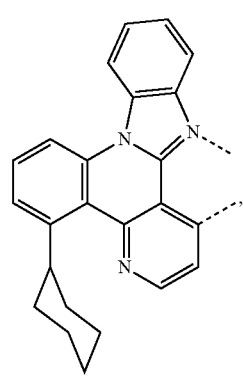 L_{A25} 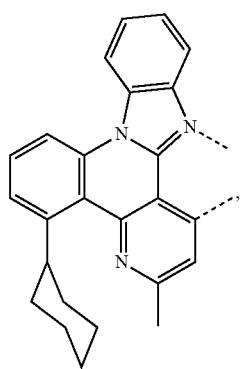 L_{A26} | 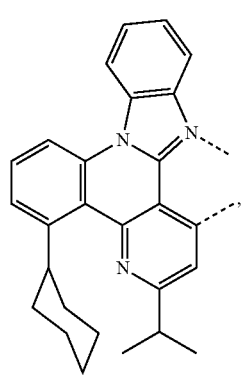 L_{A27} 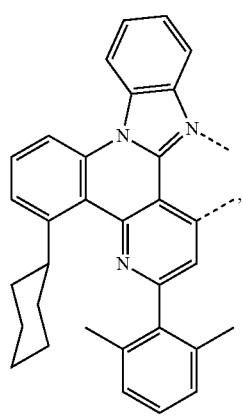 L_{A28} 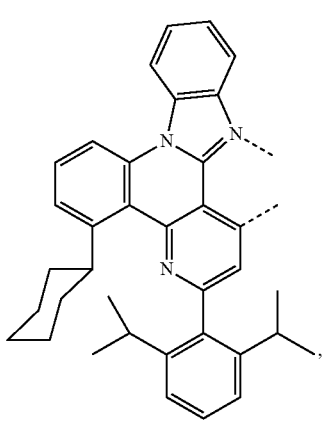 L_{A29} 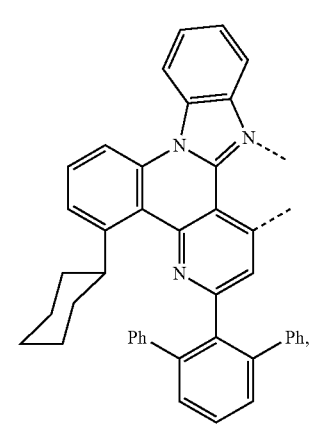 L_{A30} |

L_{A31}
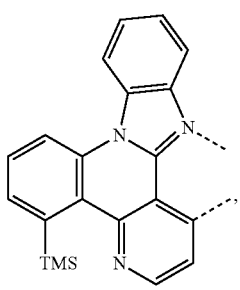
L_{A32}
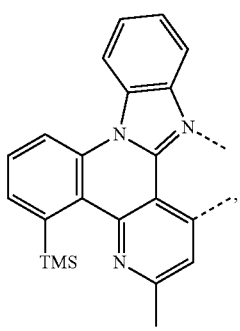
L_{A33}
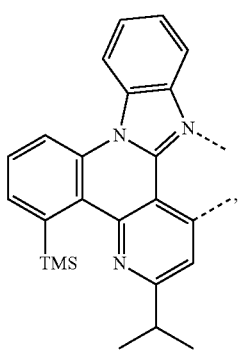
L_{A34}
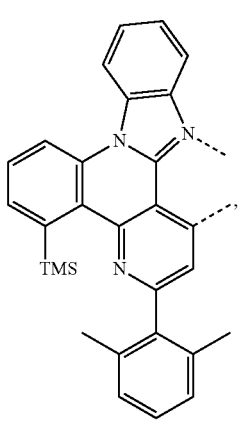
L_{A35}
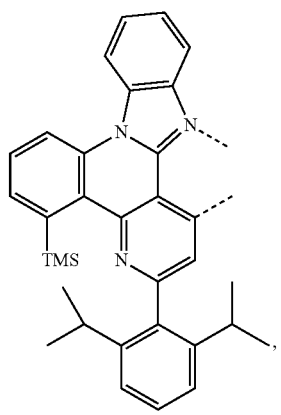
L_{A36}
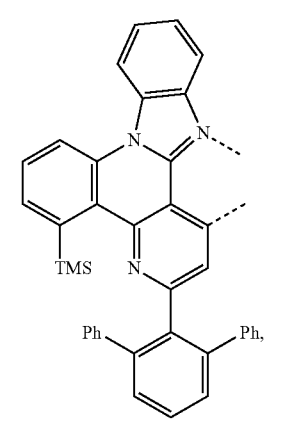
L_{A37}
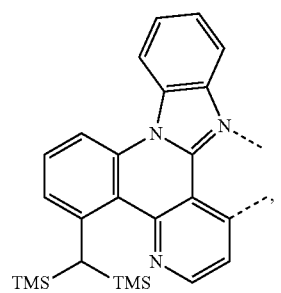
L_{A38}
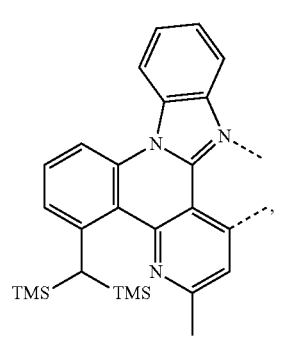

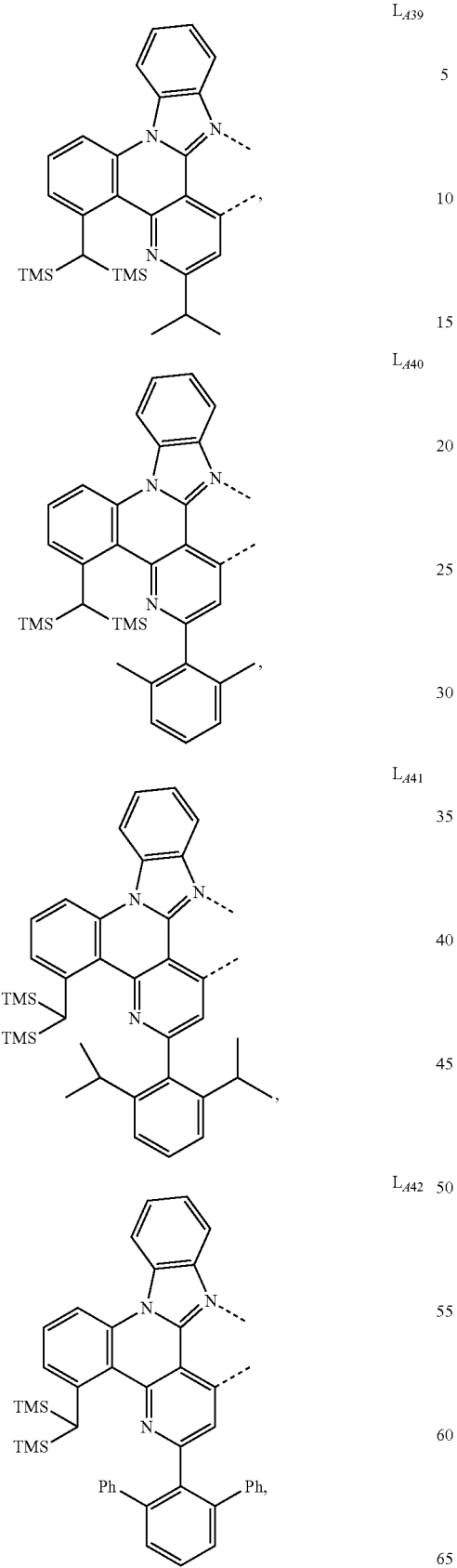
$L_{A39}$, $L_{A40}$, $L_{A41}$, $L_{A42}$
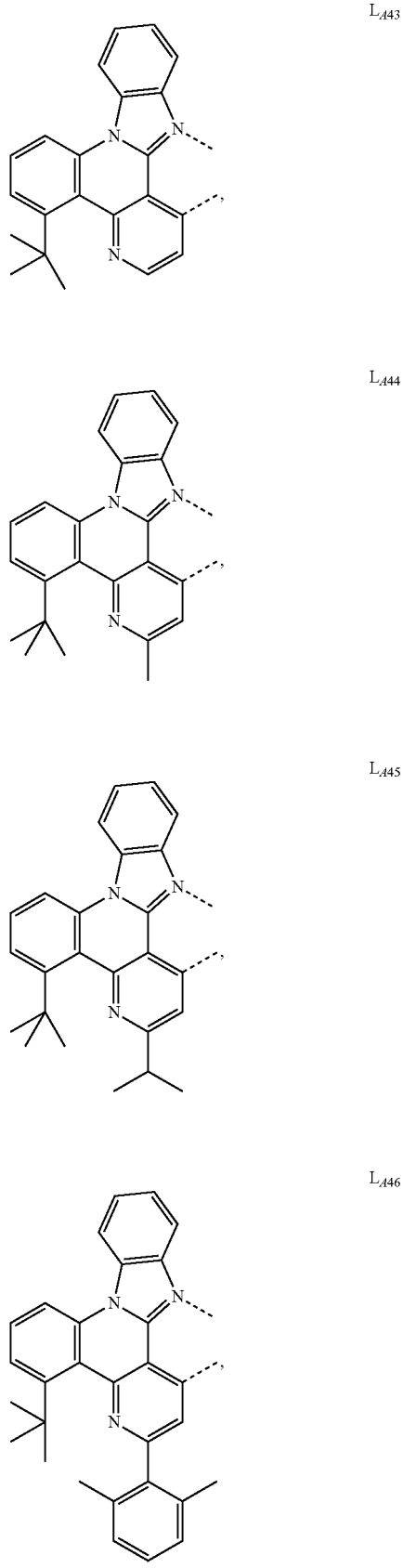
$L_{A43}$, $L_{A44}$, $L_{A45}$, $L_{A46}$

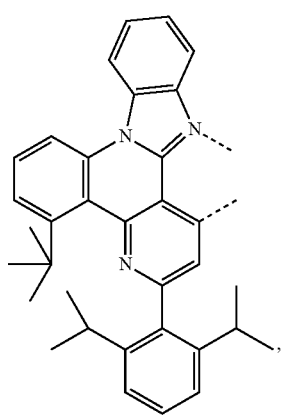 L_{A47}
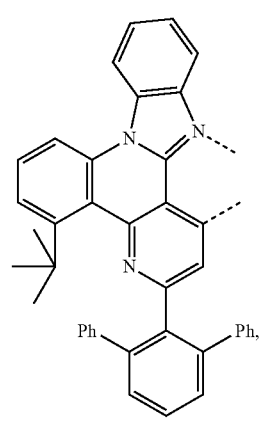 L_{A48}
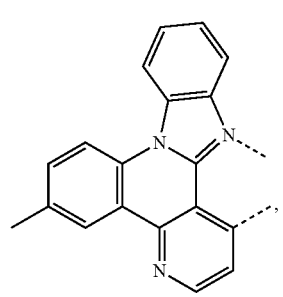 L_{A49}
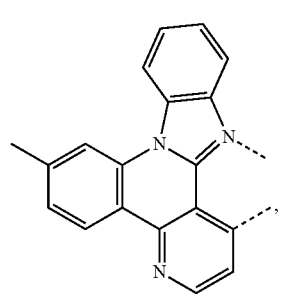 L_{A50}
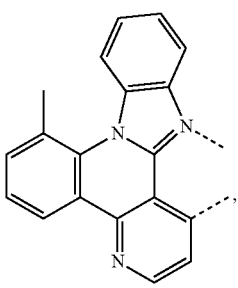 L_{A51}
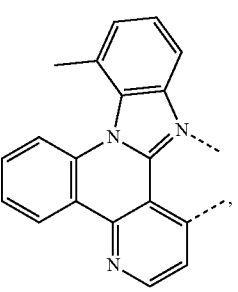 L_{A51A}
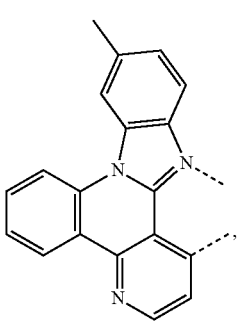 L_{A52}
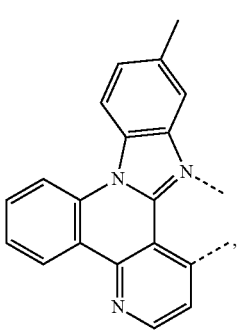 L_{A53}
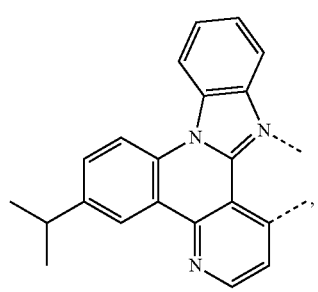 L_{A54}

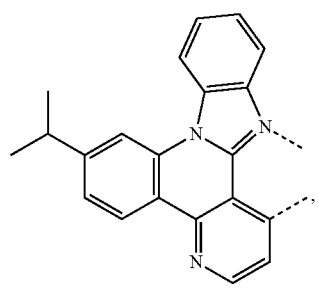 L_{A55}
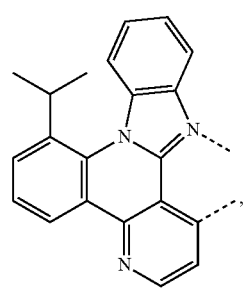 L_{A56}
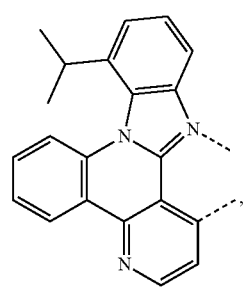 L_{A57}
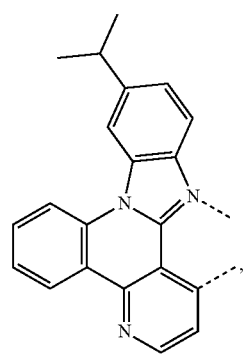 L_{A58}
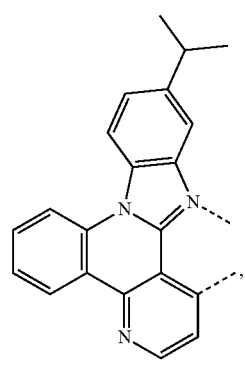 L_{A59}
 L_{A60}
 L_{A61}
 L_{A62}
 L_{A63}
 L_{A64}

L<sub>A65</sub>
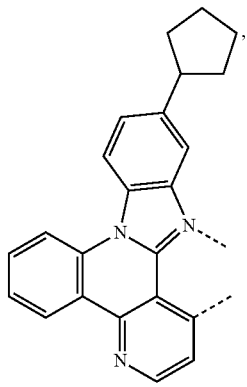
L<sub>A66</sub>
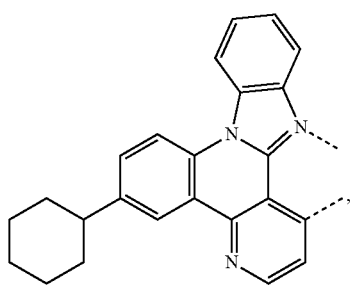
L<sub>A67</sub>
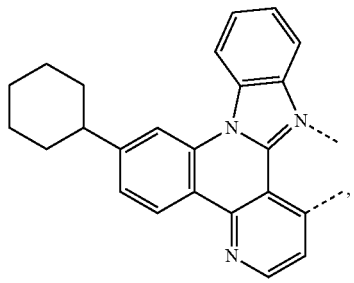
L<sub>A68</sub>
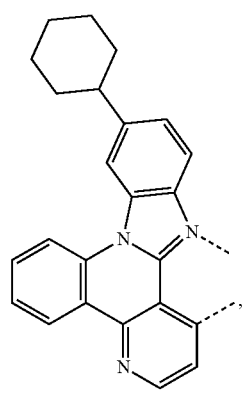
L<sub>A69</sub>
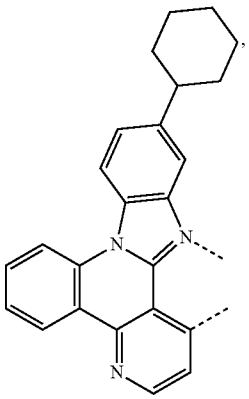
L<sub>A70</sub>
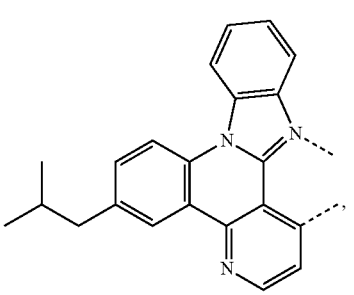
L<sub>A71</sub>
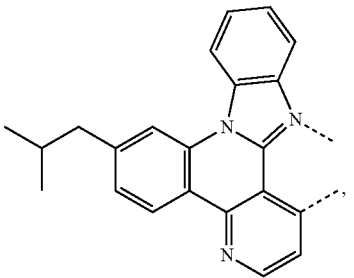
L<sub>A72</sub>
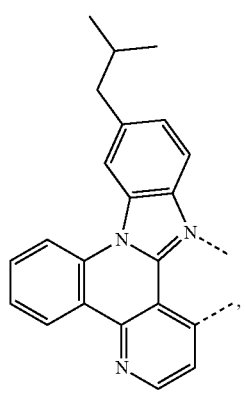

L_{A73} 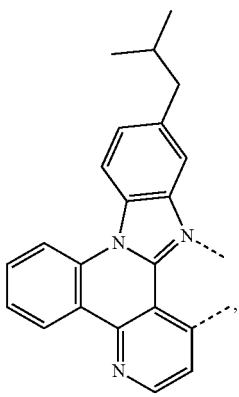
L_{A74} 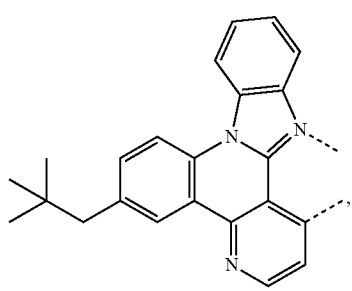
L_{A75} 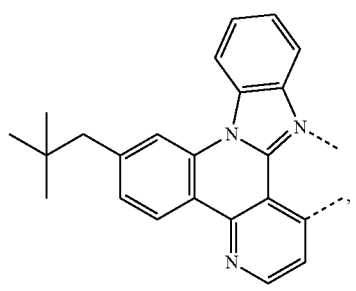
L_{A76} 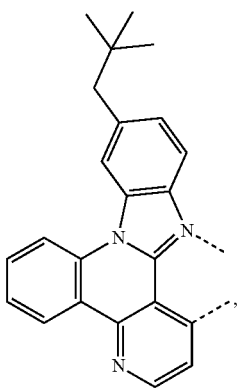
L_{A77} 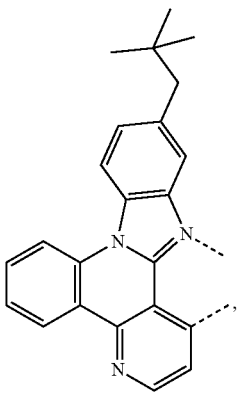
L_{A78} 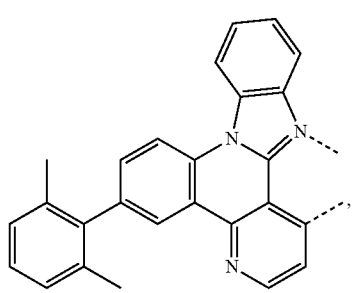
L_{A79} 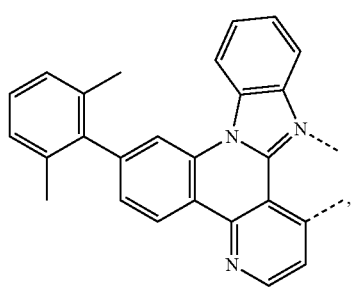
L_{A80} 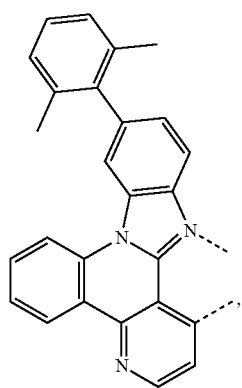

| | |
|---|---|
| L_{A81} 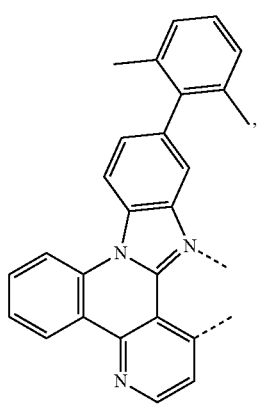 | L_{A85} 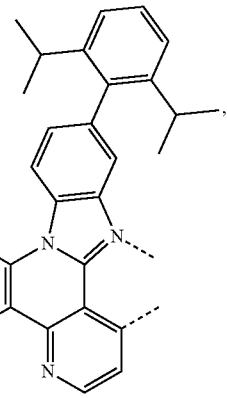 |
| L_{A82} 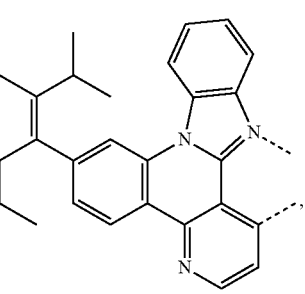 | L_{A86} 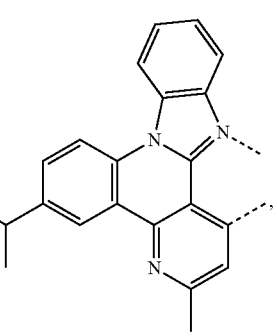 |
| L_{A83} | L_{A87} 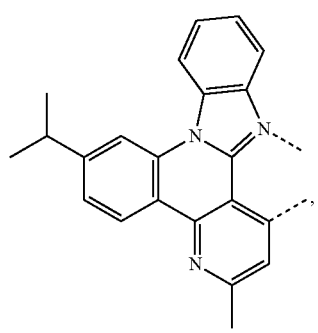 |
| L_{A84} | L_{A88} 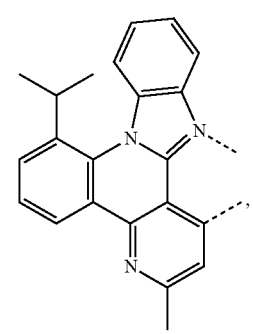 |

L<sub>A89</sub>
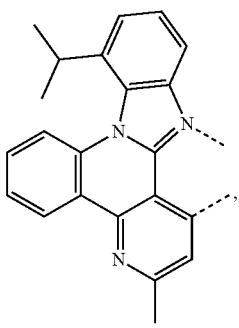
L<sub>A90</sub>
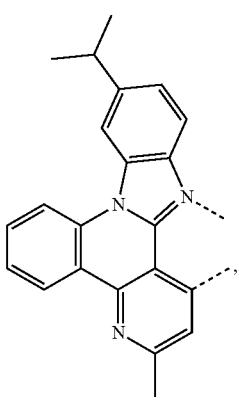
L<sub>A91</sub>
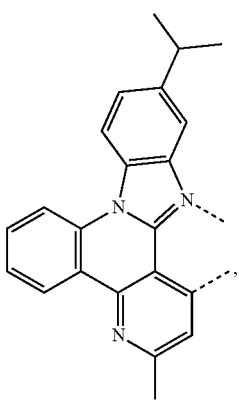
L<sub>A92</sub>
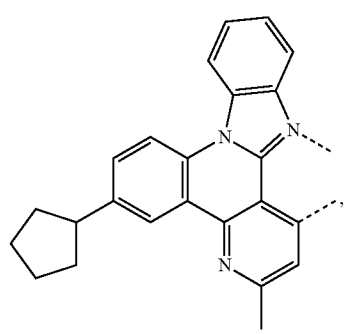
L<sub>A93</sub>
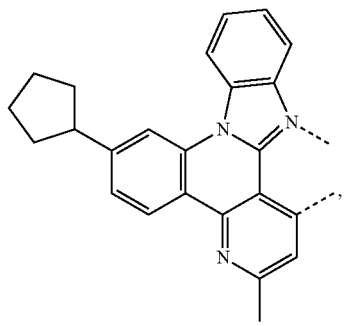
L<sub>A94</sub>
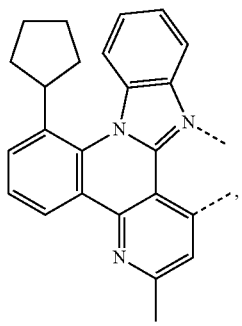
L<sub>A95</sub>
L<sub>A96</sub>

L_{A97}
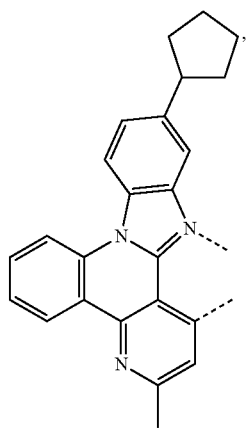
L_{A98}
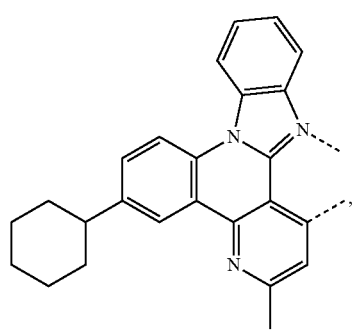
L_{A99}
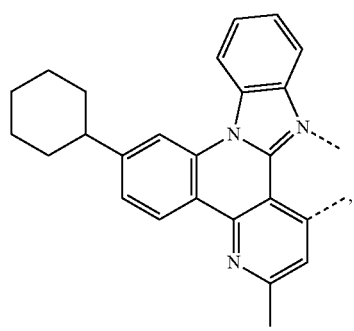
L_{A100}
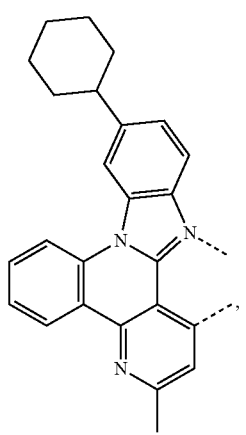
L_{A101}
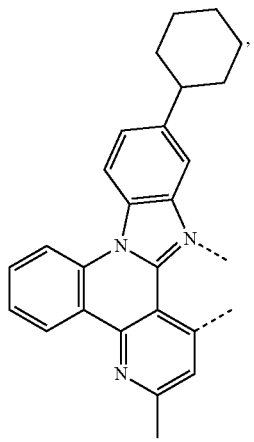
L_{A102}
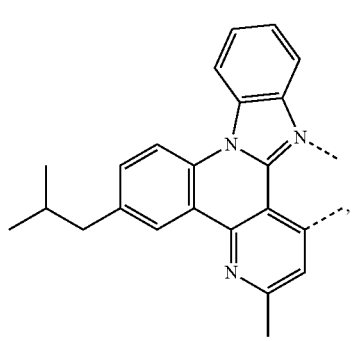
L_{A103}
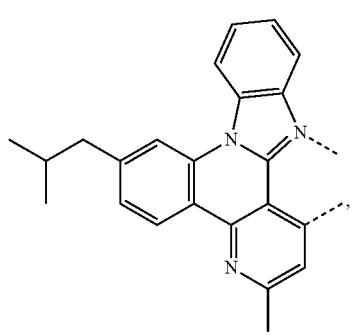
L_{A104}
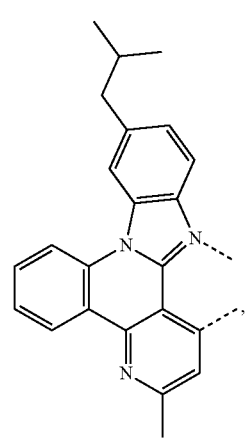

$L_{A105}$
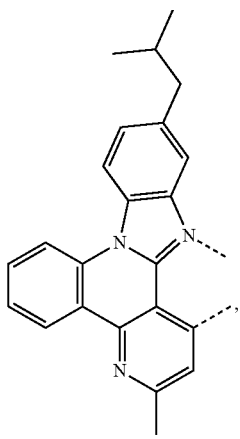
$L_{A106}$
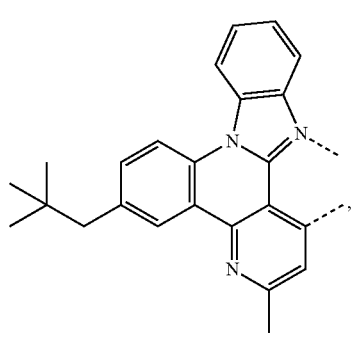
$L_{A107}$
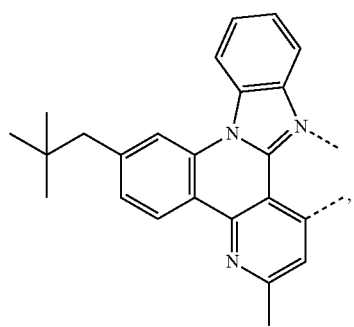
$L_{A108}$
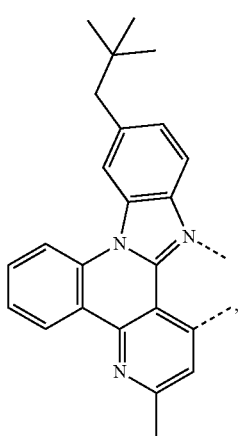
$L_{A109}$
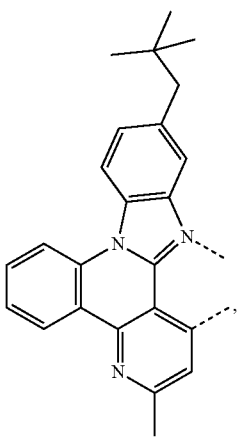
$L_{A110}$
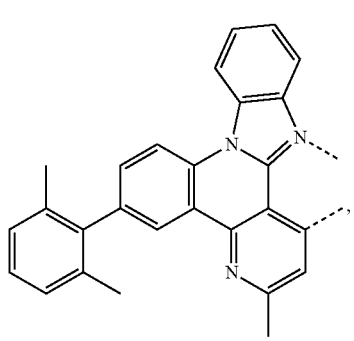
$L_{A111}$
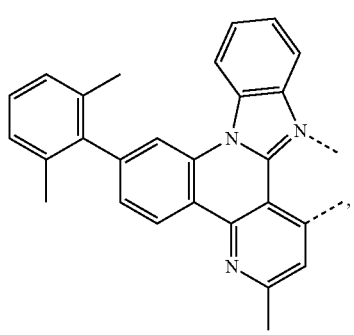
$L_{A112}$
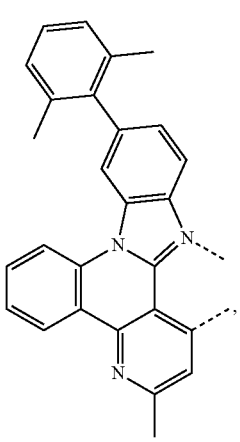

-continued
L_{A113}
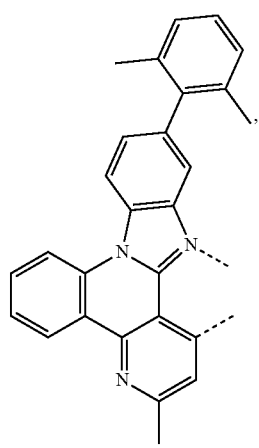
L_{A114}
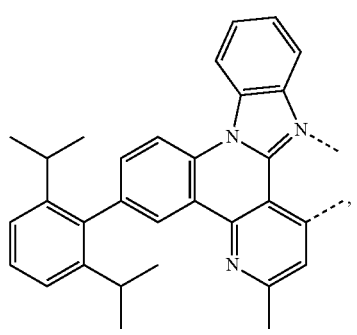
L_{A115}
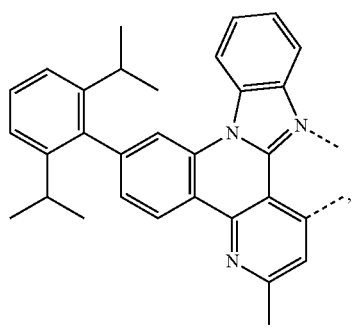
L_{A116}
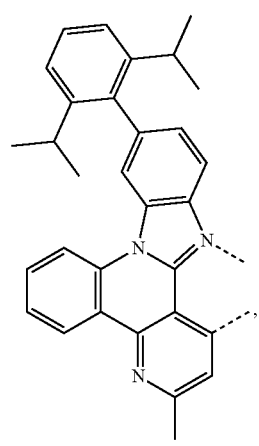
-continued
L_{A117}
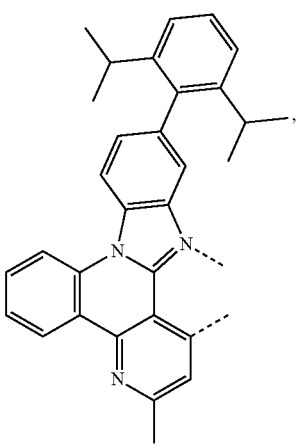
L_{A118}
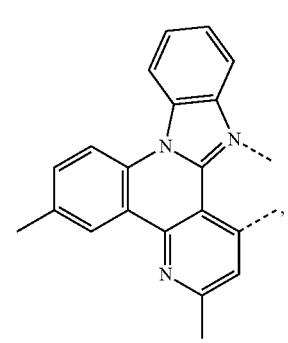
L_{A119}
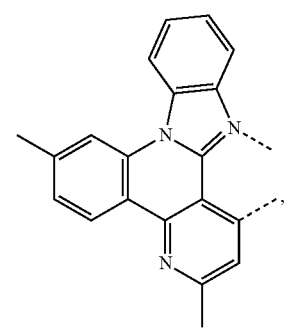
L_{A120}
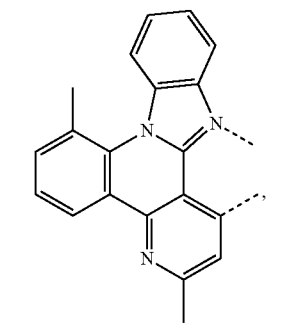

L<sub>A121</sub>
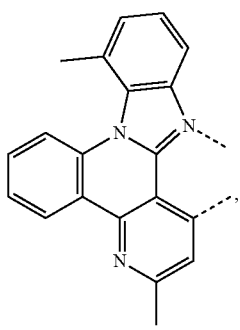
L<sub>A122</sub>
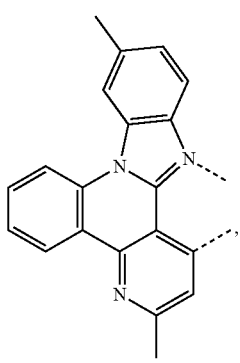
L<sub>A123</sub>
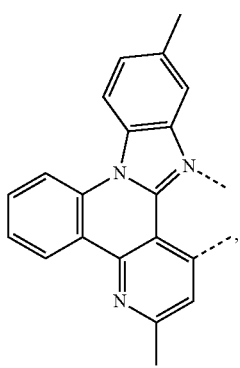
L<sub>A124</sub>
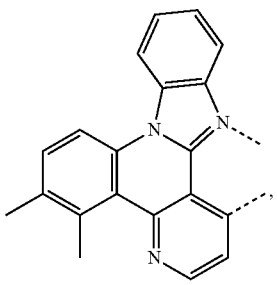
L<sub>A125</sub>
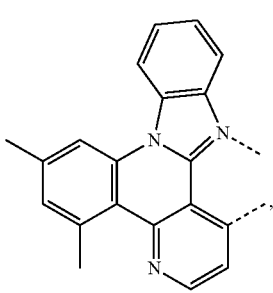
L<sub>A126</sub>
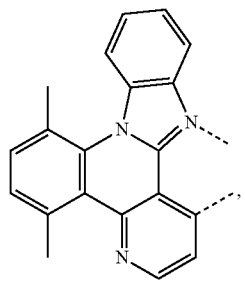
L<sub>A127</sub>
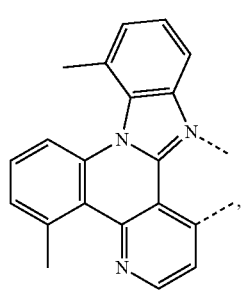
L<sub>A128</sub>
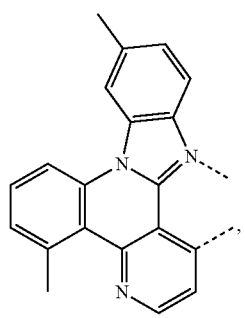
L<sub>A129</sub>
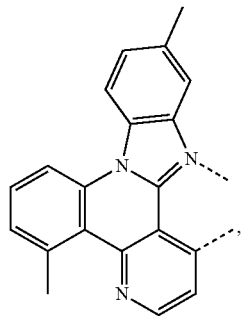
L<sub>A130</sub>
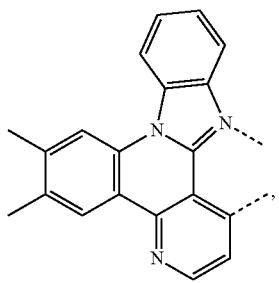

L<sub>A131</sub>
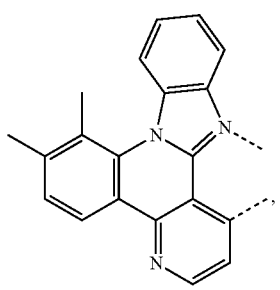
L<sub>A132</sub>
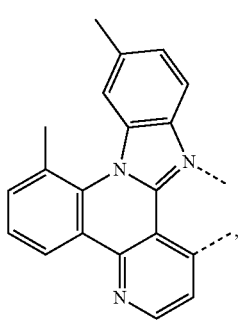
L<sub>A133</sub>
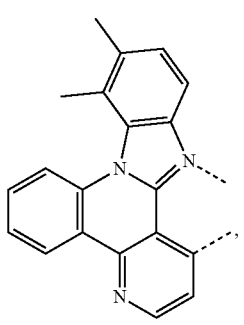
L<sub>A134</sub>
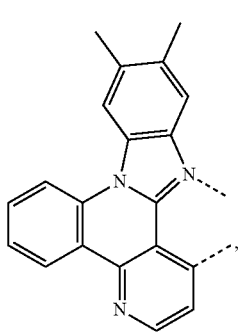
L<sub>A135</sub>
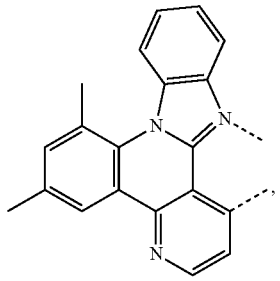
L<sub>A136</sub>
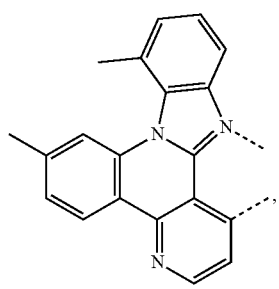
L<sub>A137</sub>
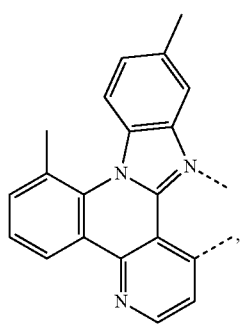
L<sub>A138</sub>
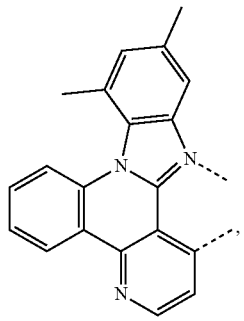
L<sub>A139</sub>
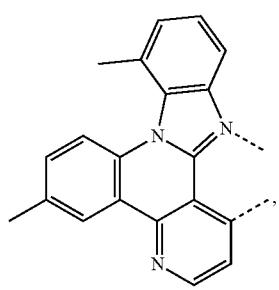
L<sub>A140</sub>
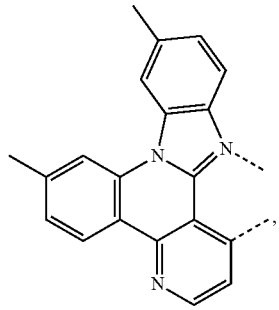

L<sub>A</sub>141 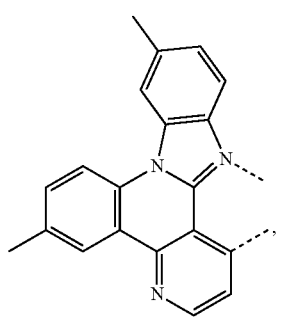
L<sub>A</sub>145 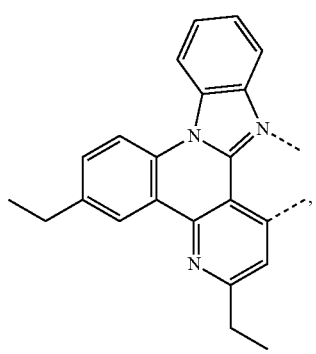
L<sub>A</sub>142 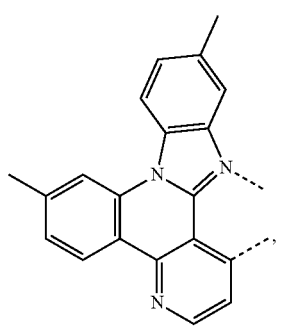
L<sub>A</sub>146 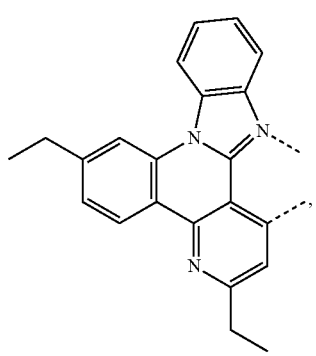
L<sub>A</sub>143 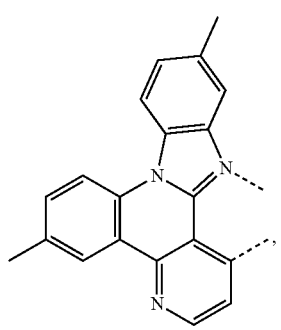
L<sub>A</sub>147 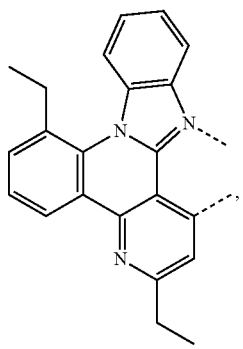
L<sub>A</sub>144 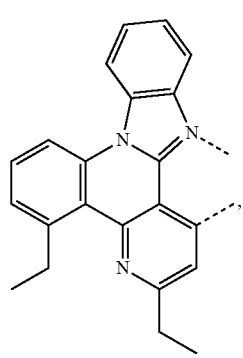
L<sub>A</sub>148 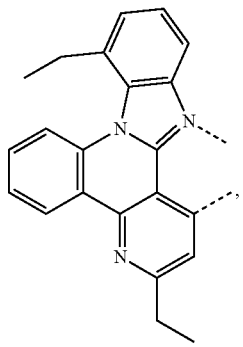

-continued
L<sub>A149</sub>
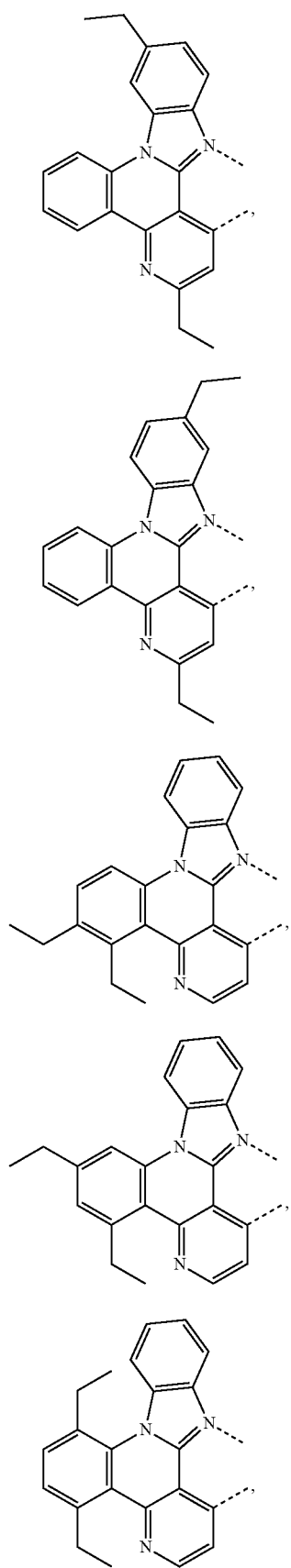
L<sub>A150</sub>
L<sub>A151</sub>
L<sub>A152</sub>
L<sub>A153</sub>
-continued
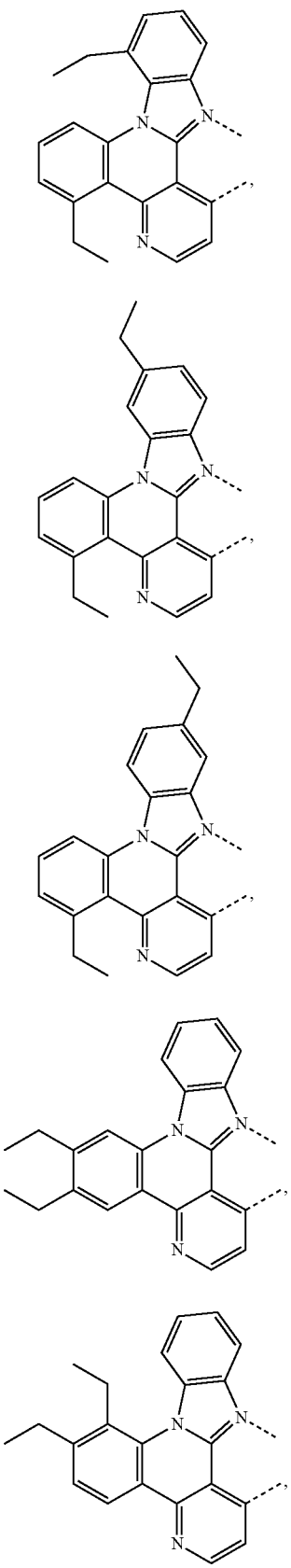
L<sub>A154</sub>
L<sub>A155</sub>
L<sub>A156</sub>
L<sub>A157</sub>
L<sub>A158</sub>

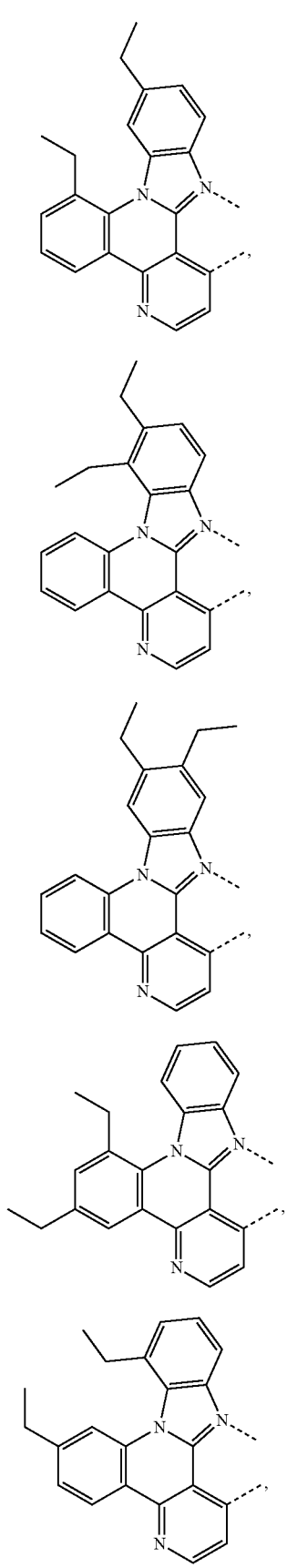
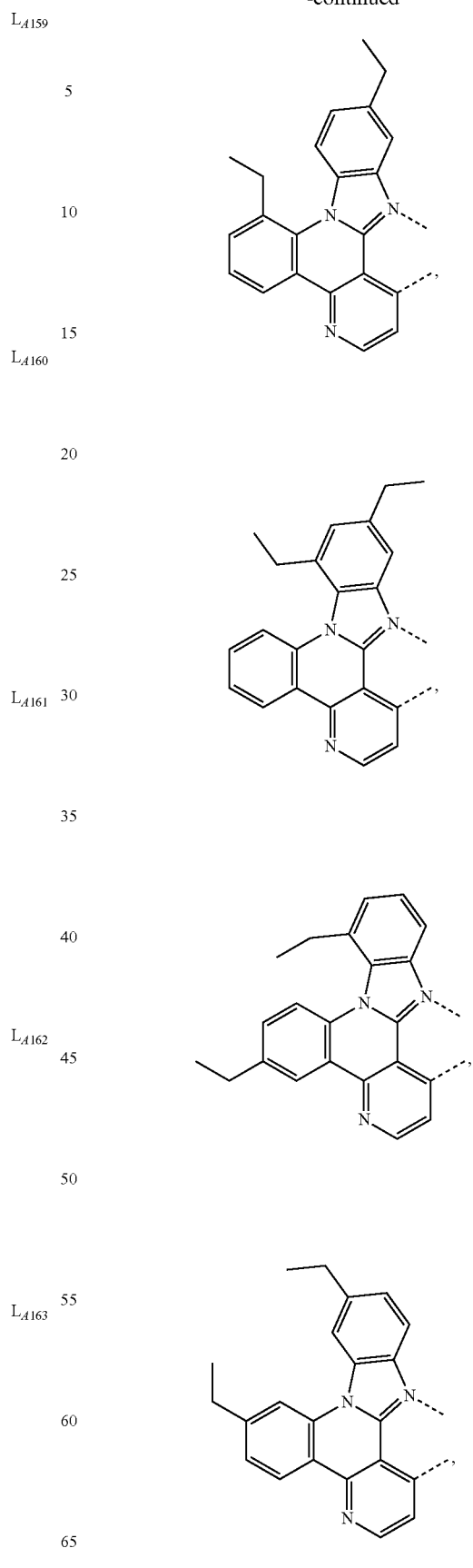

L_A168 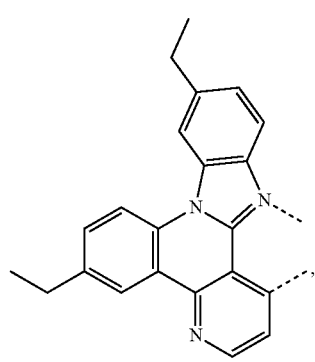
L_A169 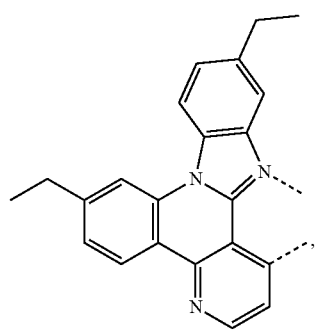
L_A170 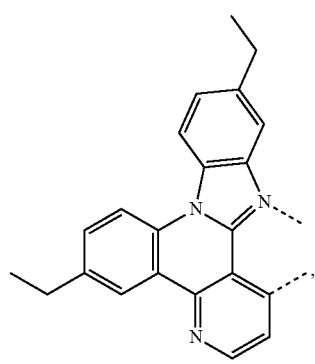
L_A171 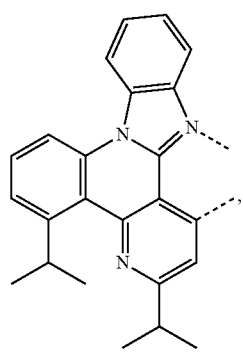
L_A172 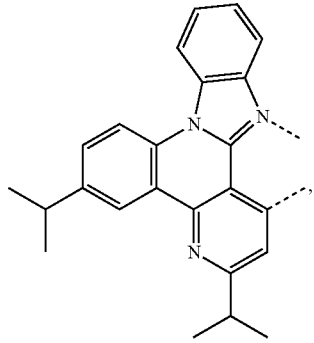
L_A173 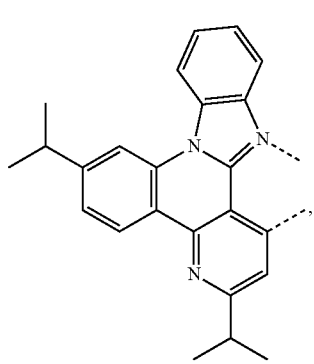
L_A174 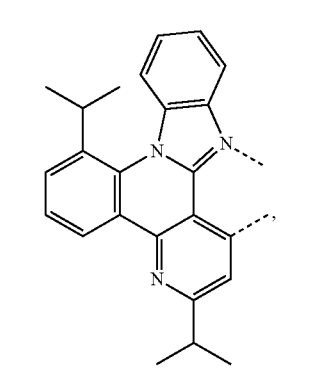
L_A175 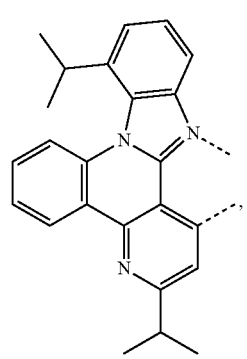

L_{A176}
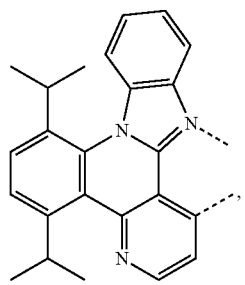
L_{A177}
L_{A178}
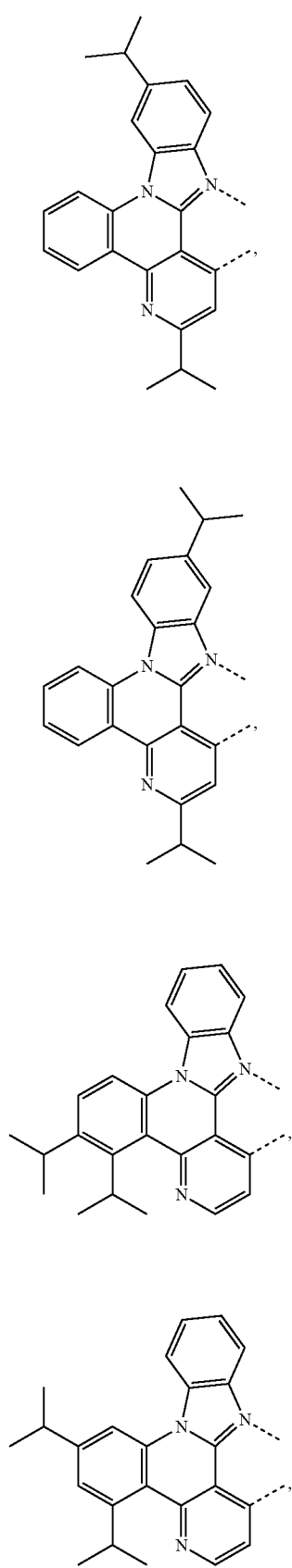
L_{A179}
L_{A180}
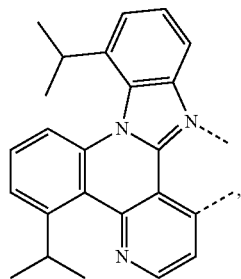
L_{A181}
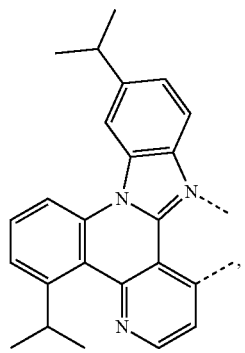
L_{A182}
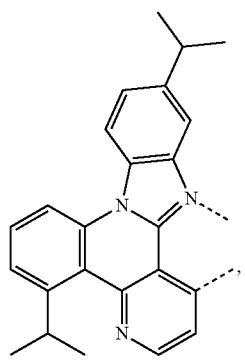
L_{A183}
L_{A184}
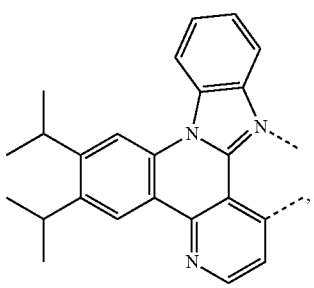

-continued
L<sub>A185</sub> 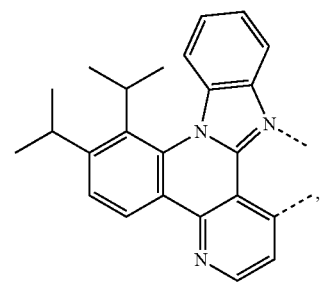
L<sub>A186</sub> 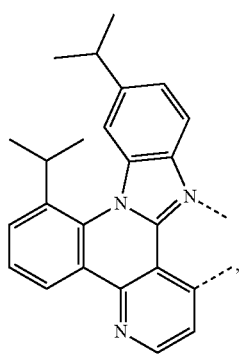
L<sub>A187</sub> 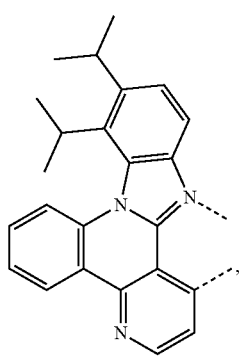
L<sub>A188</sub> 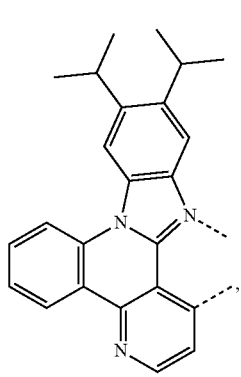
L<sub>A189</sub> 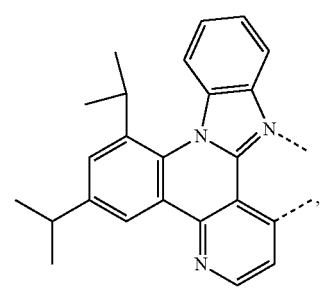
-continued
L<sub>A190</sub> 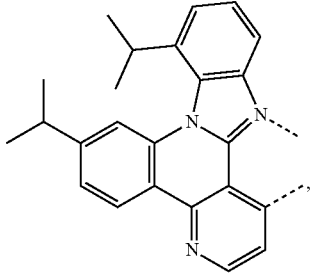
L<sub>A191</sub> 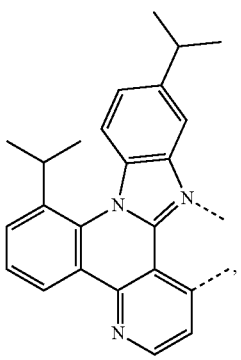
L<sub>A192</sub> 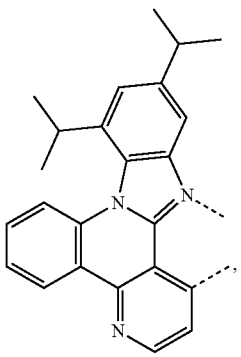
L<sub>A193</sub> 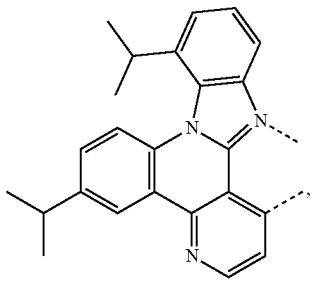

L_{A194}
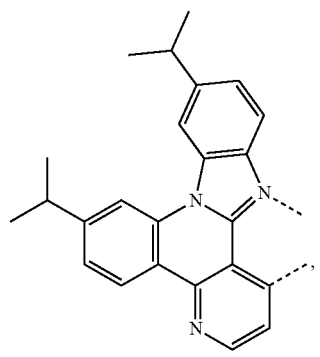
L_{A195}
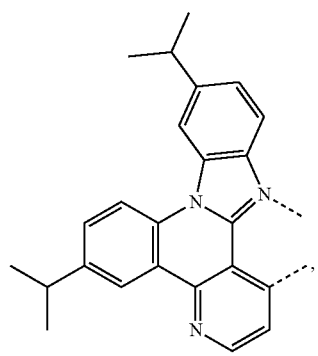
L_{A196}
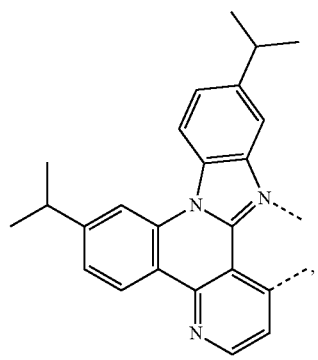
L_{A197}
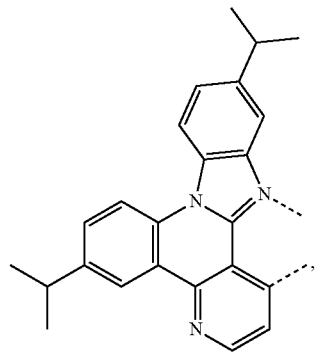
L_{A198}
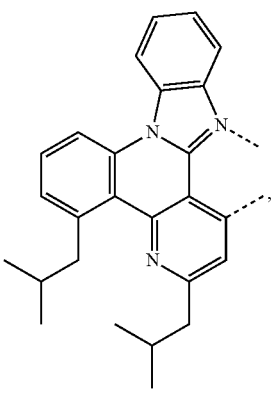
L_{A199}
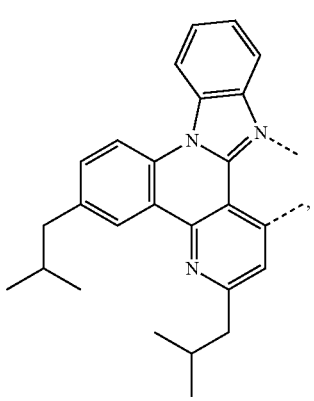
L_{A200}
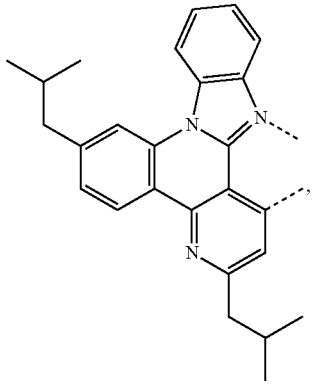
L_{A201}
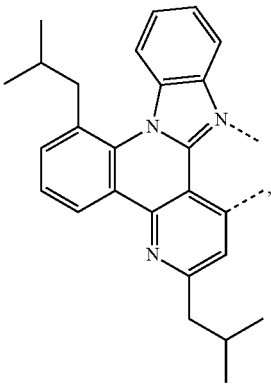

L_{A202}
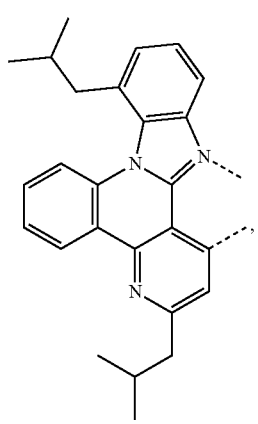
L_{A203}
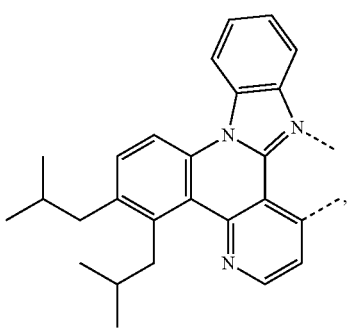
L_{A205}
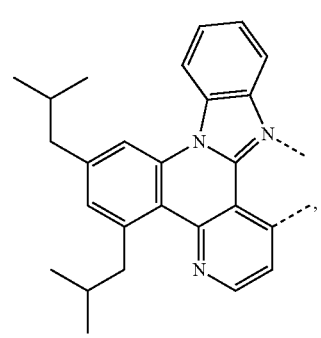
L_{A206}
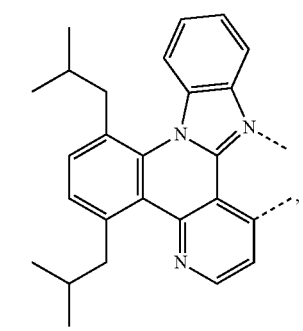
L_{A207}
L_{A204}
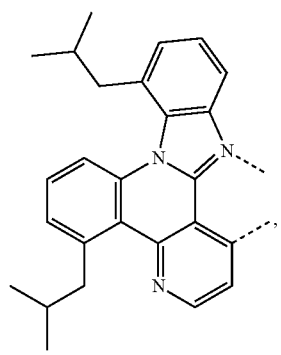
L_{A208}

L_{A209}
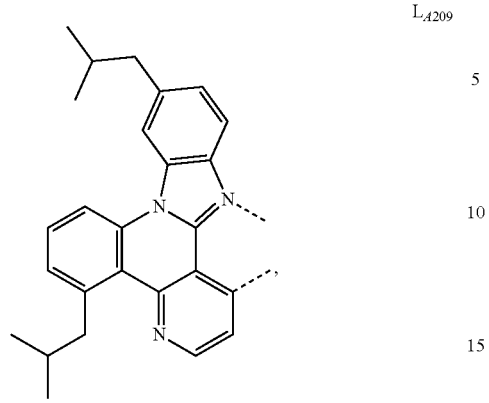
L_{A210}
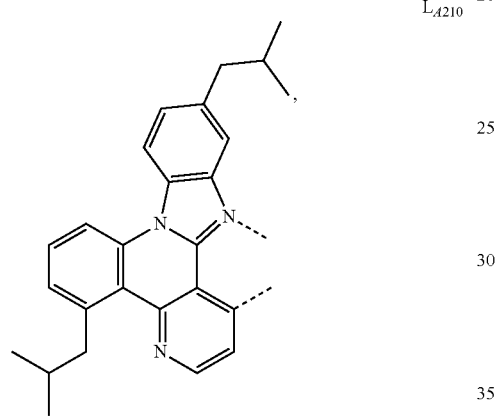
L_{A211}
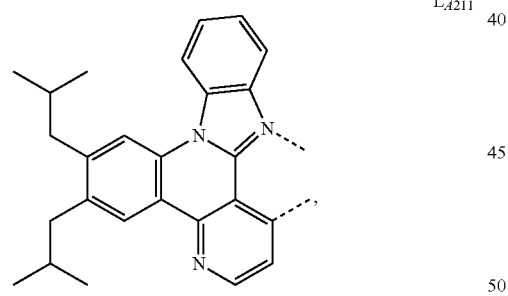
L_{A212}
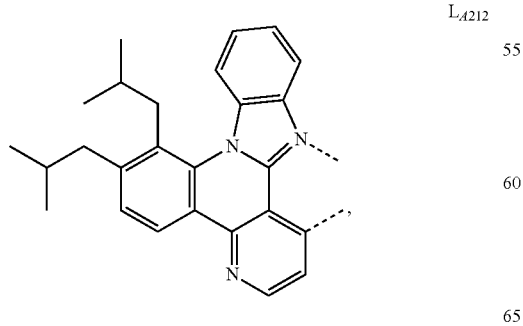
L_{A213}
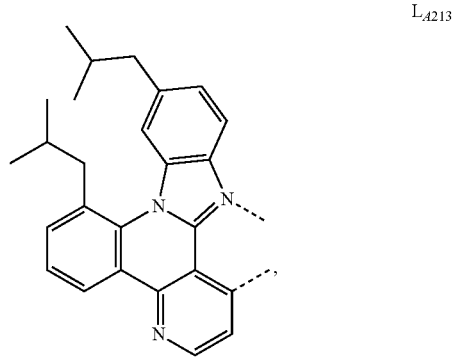
L_{A214}
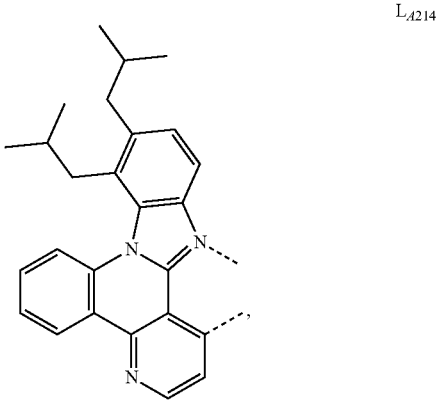
L_{A215}
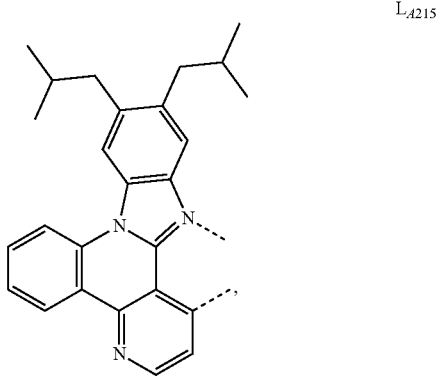
L_{A216}
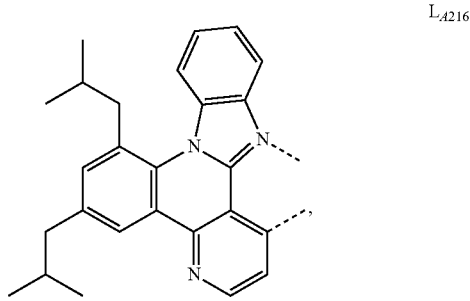

-continued
L<sub>A217</sub>
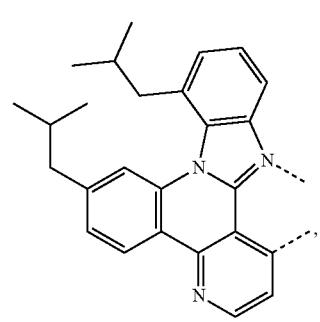
L<sub>A218</sub>
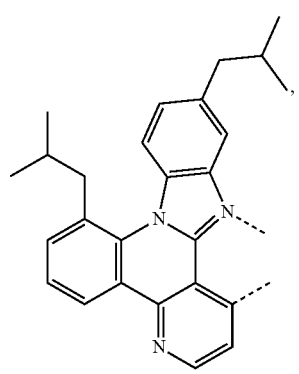
L<sub>A219</sub>
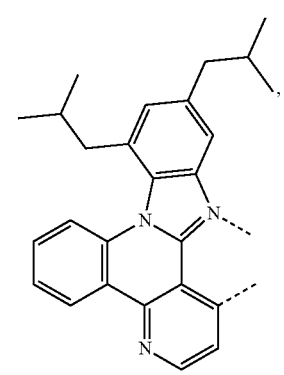
L<sub>A220</sub>
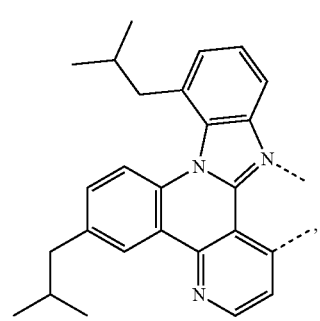
-continued
L<sub>A221</sub>
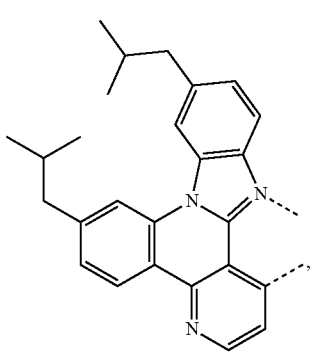
L<sub>A222</sub>
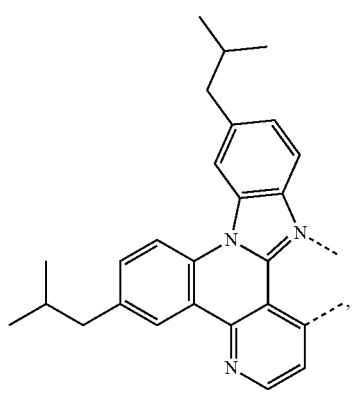
L<sub>A223</sub>
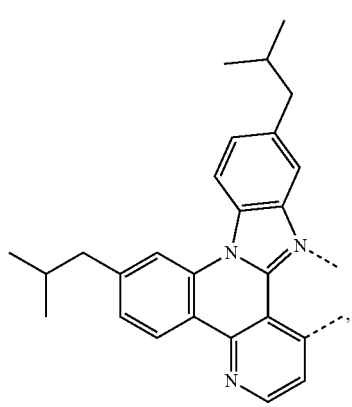
L<sub>A224</sub>
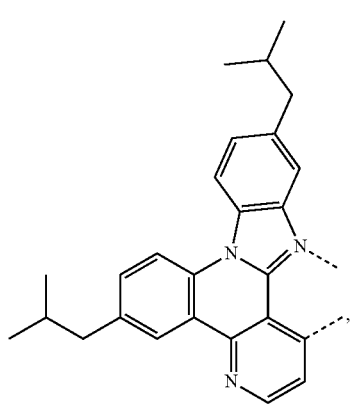

-continued
L<sub>A225</sub>
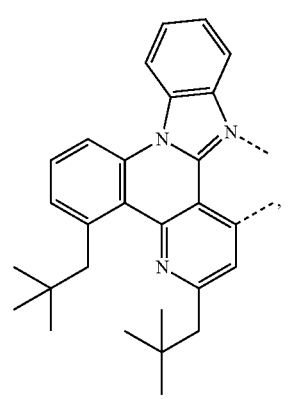
L<sub>A226</sub>
L<sub>A227</sub>
L<sub>A228</sub>
-continued
L<sub>A229</sub>
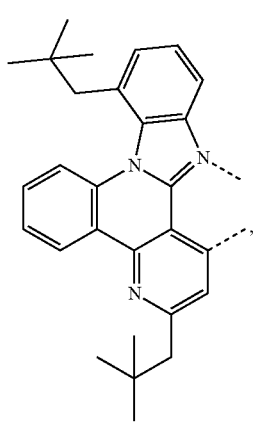
L<sub>A230</sub>
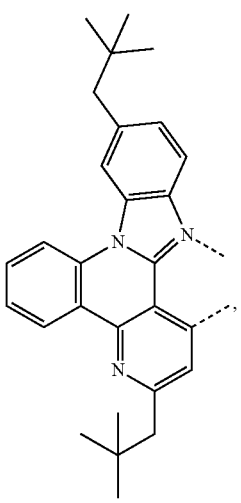
L<sub>A231</sub>
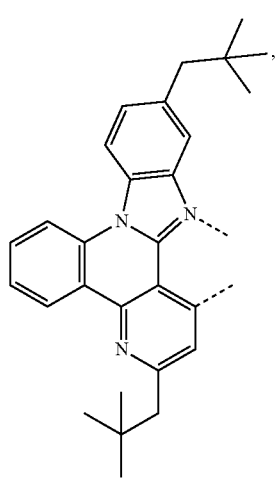

L_{A232} 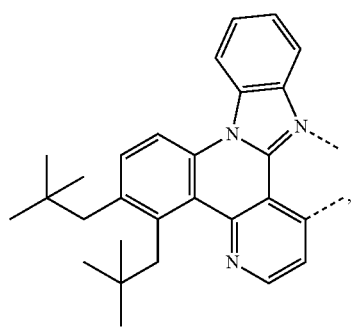
L_{A233} 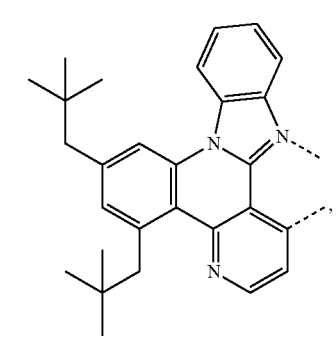
L_{A234} 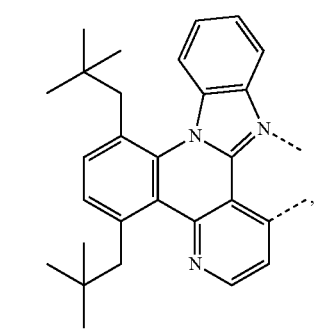
L_{A235} 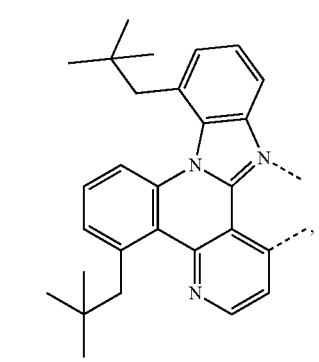
L_{A236} 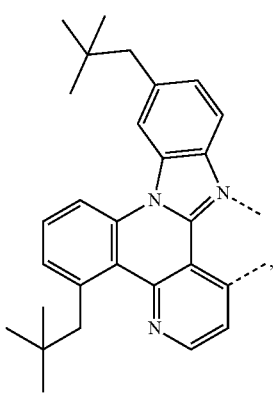
L_{A237} 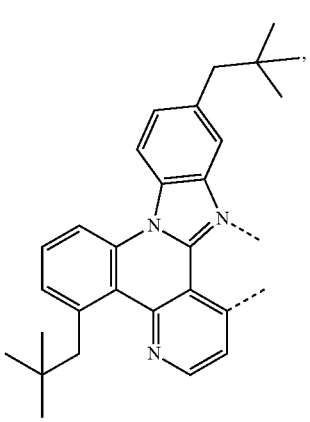
L_{A238} 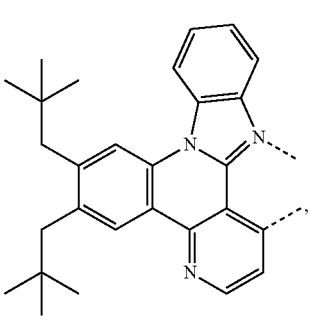
L_{A239} 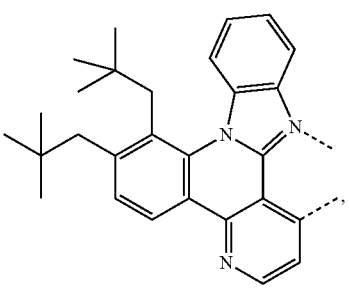

-continued
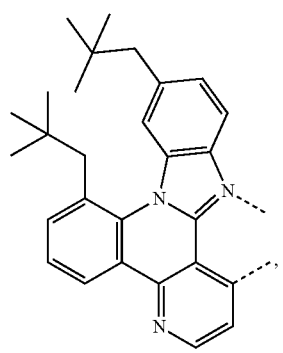
L_{A240}
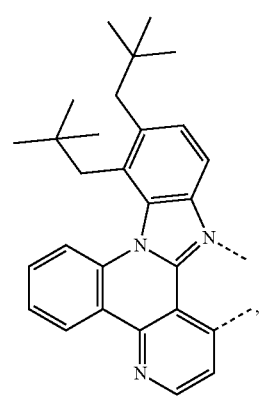
L_{A241}
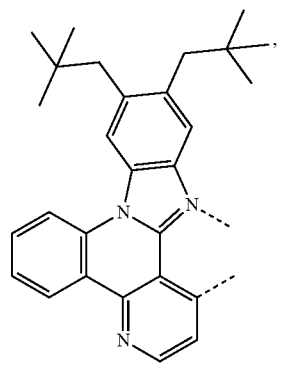
L_{A242}
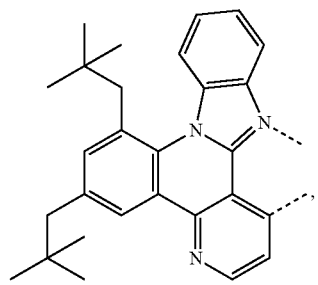
L_{A243}
-continued
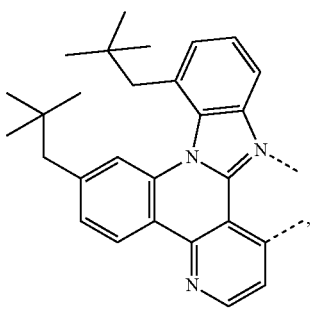
L_{A244}
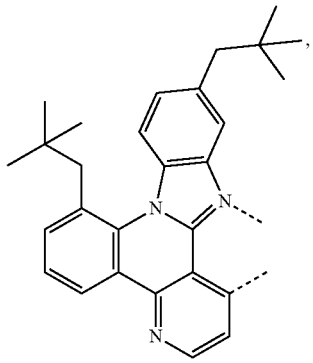
L_{A245}
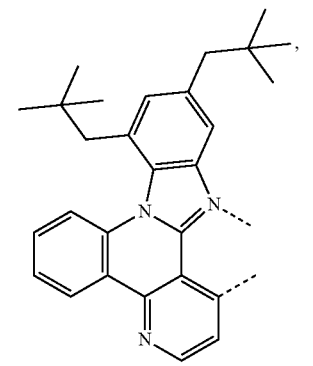
L_{A246}
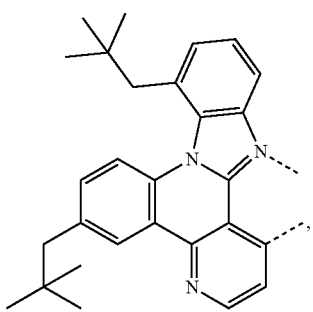
L_{A247}

-continued
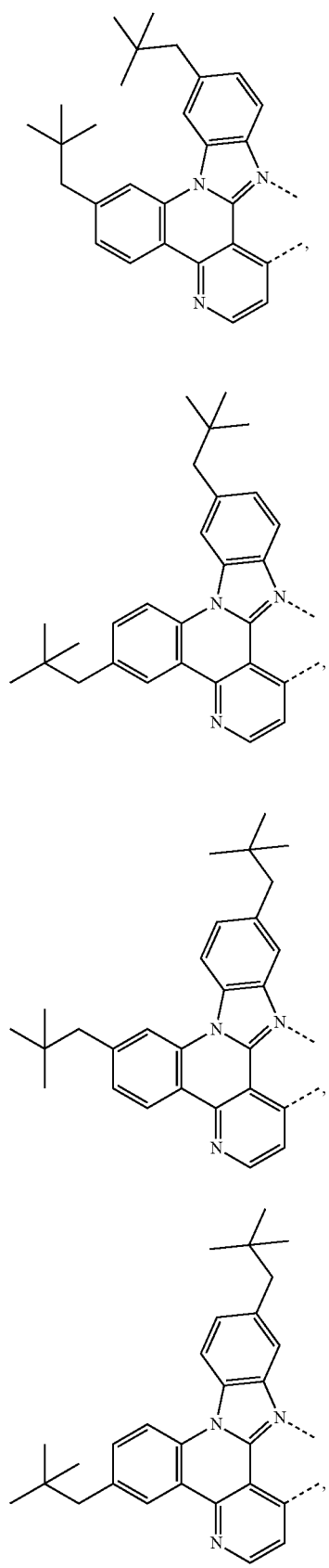
L_{A248}
L_{A249}
L_{A250}
L_{A251}
-continued
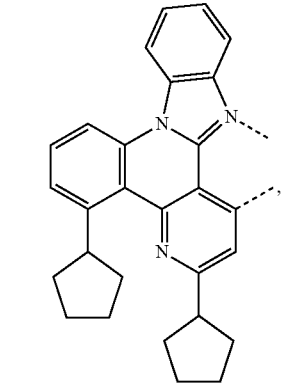
L_{A252}
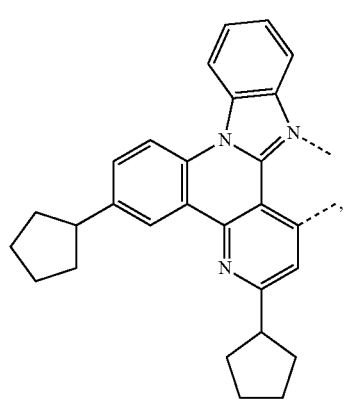
L_{A253}
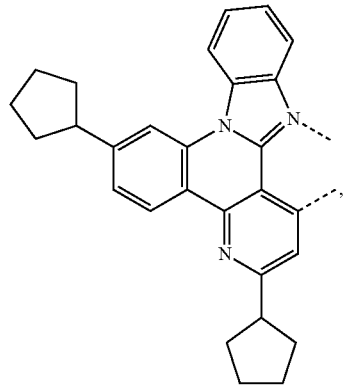
L_{A254}
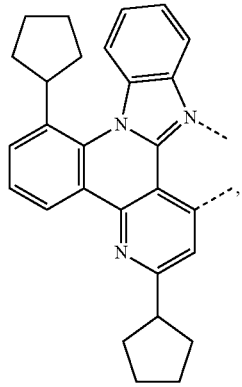
L_{A255}

L_{A256}
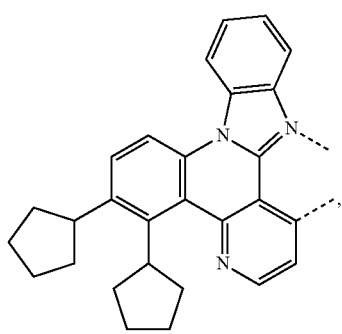
L_{A257}
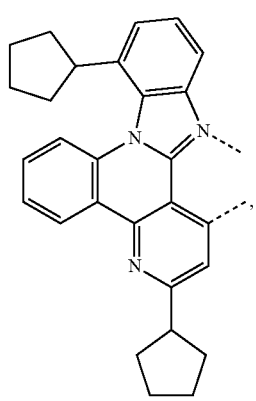
L_{A259}
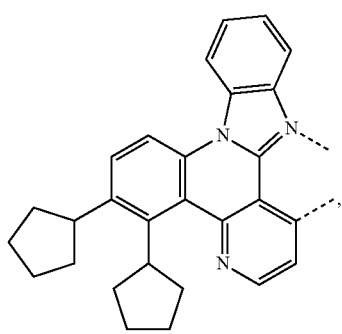
L_{A260}
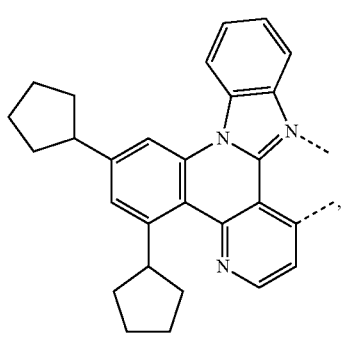
L_{A258}
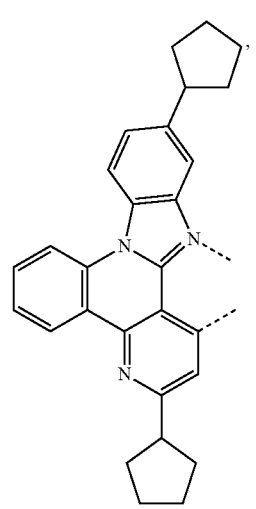
L_{A261}
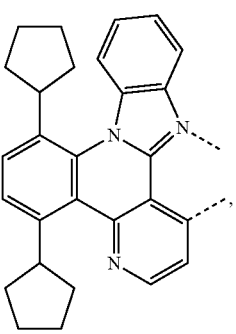
L_{A262}
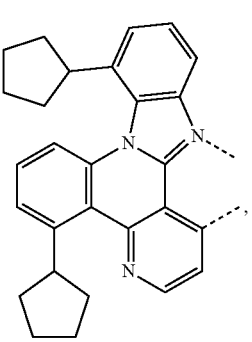

L_{A263}
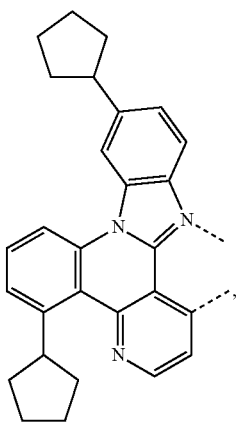
L_{A264}
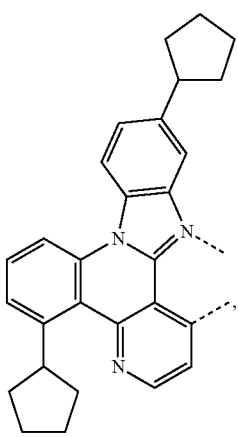
L_{A265}
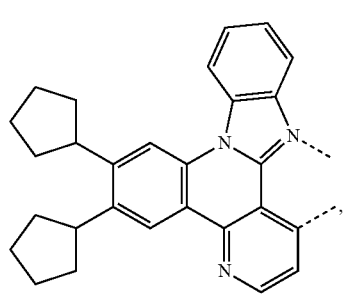
L_{A266}
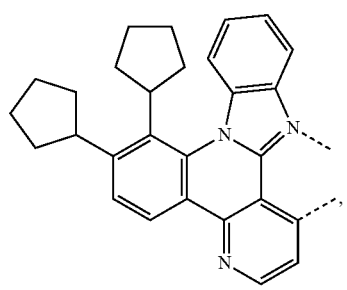
L_{A267}
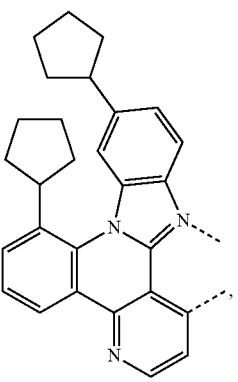
L_{A268}
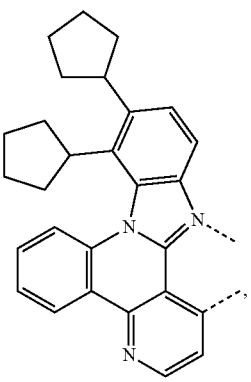
L_{A269}
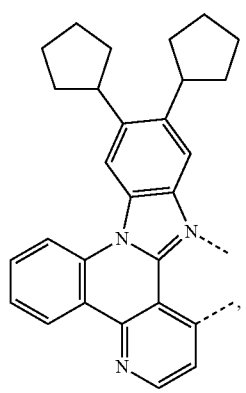
L_{A270}
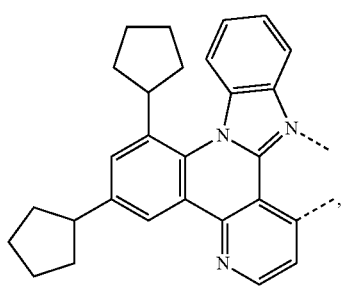

L<sub>A271</sub>
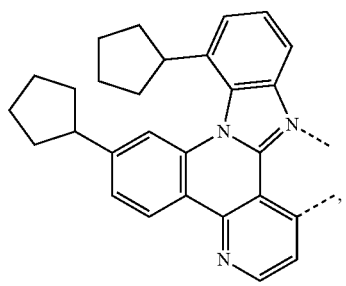
L<sub>A272</sub>
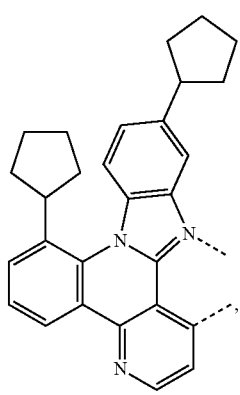
L<sub>A273</sub>
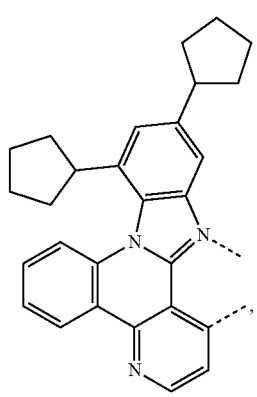
L<sub>A274</sub>
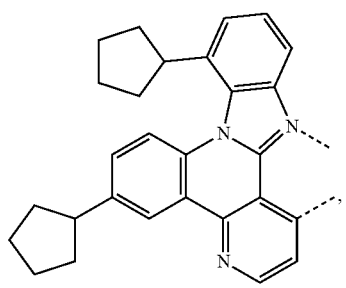
L<sub>A275</sub>
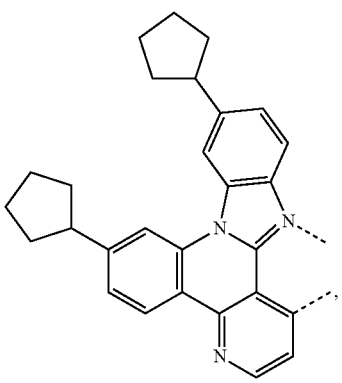
L<sub>A276</sub>
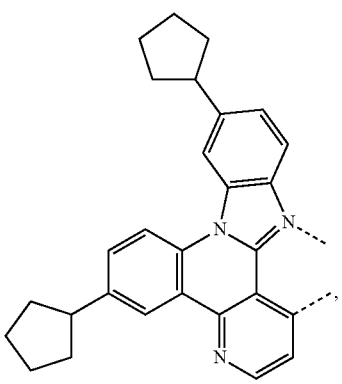
L<sub>A277</sub>
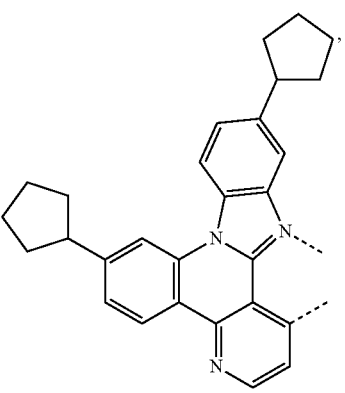
L<sub>A278</sub>
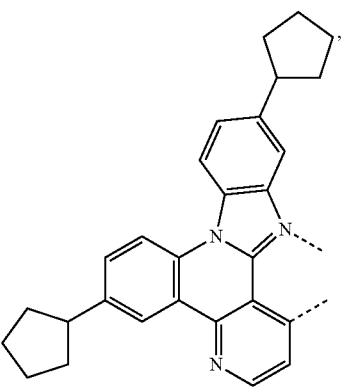

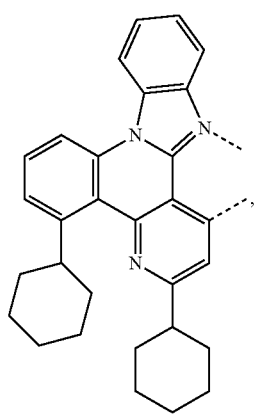 L_{A279}
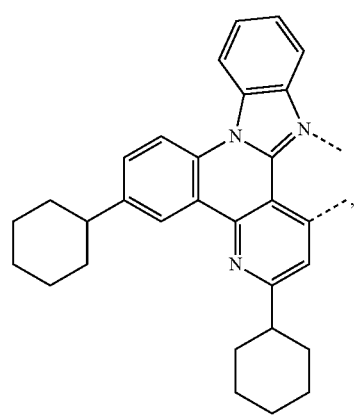 L_{A280}
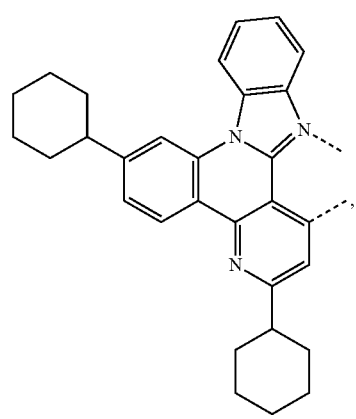 L_{A281}
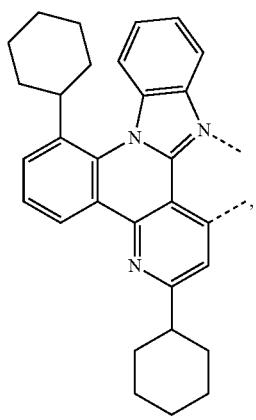 L_{A282}
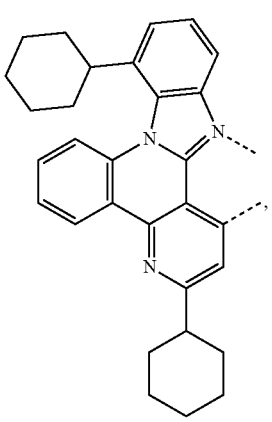 L_{A283}
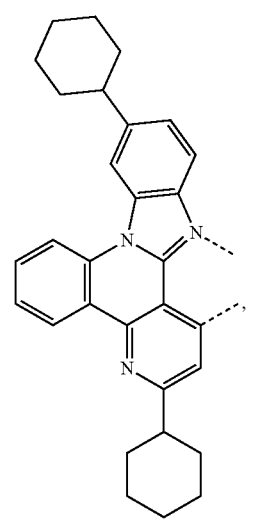 L_{A284}

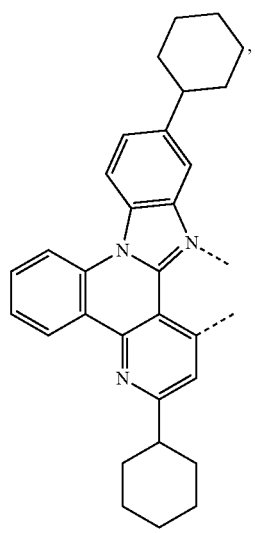 L_{A285}
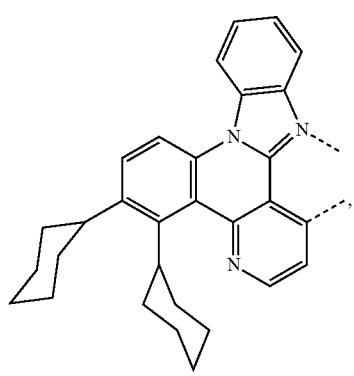 L_{A286}
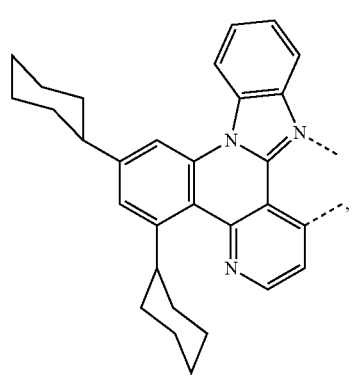 L_{A287}
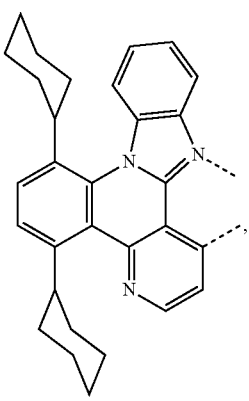 L_{A288}
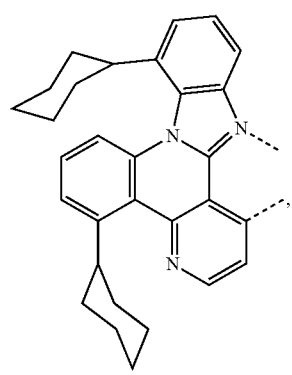 L_{A289}
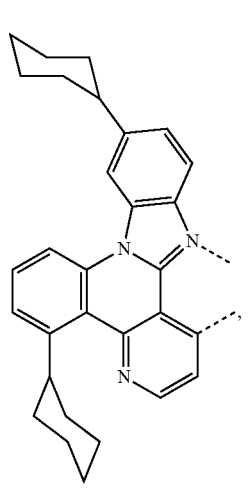 L_{A290}

L<sub>A291</sub>
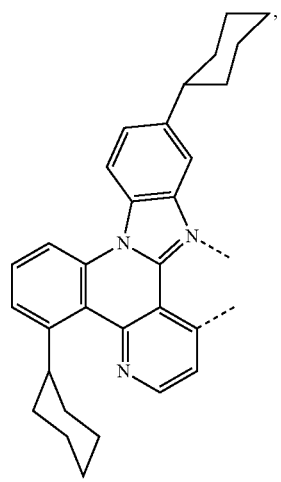
L<sub>A292</sub>
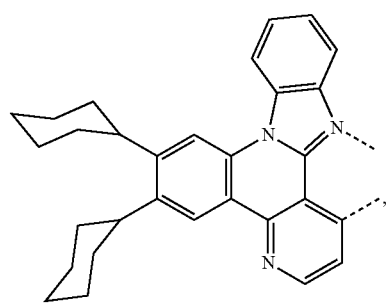
L<sub>A293</sub>
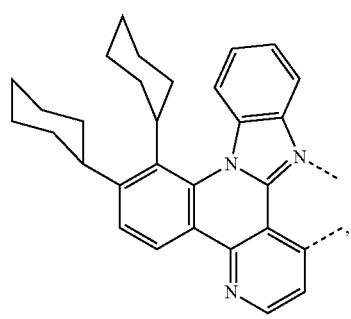
L<sub>A294</sub>
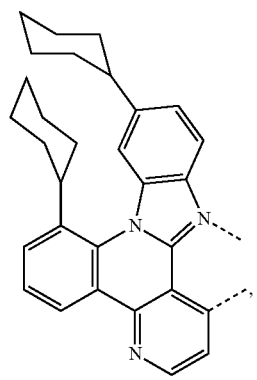
L<sub>A295</sub>
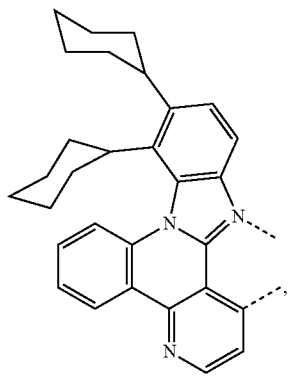
L<sub>A296</sub>
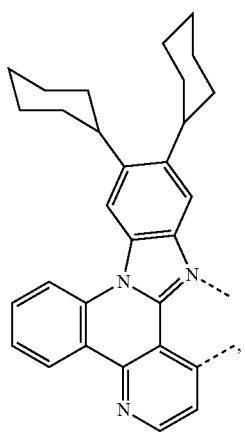
L<sub>A297</sub>
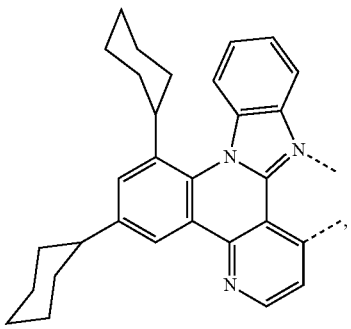
L<sub>A298</sub>
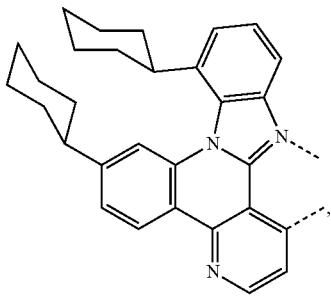

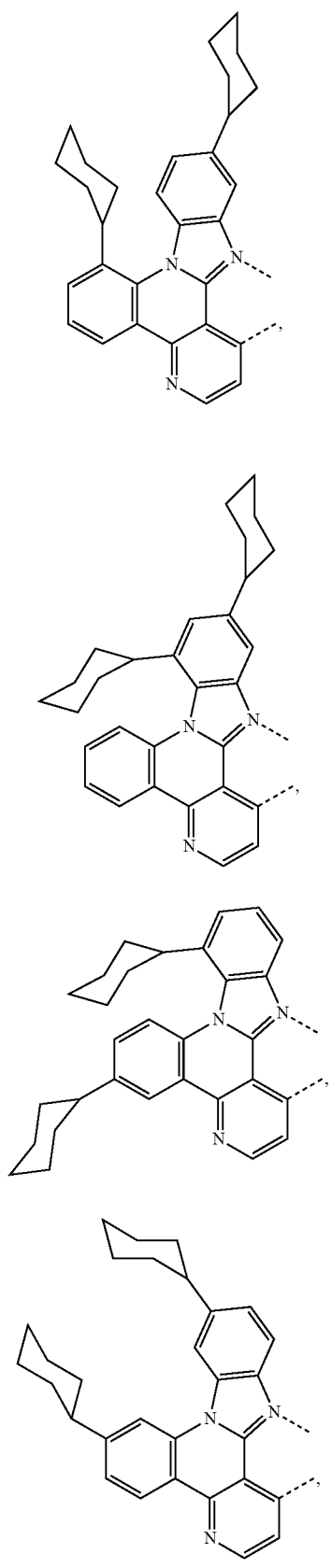
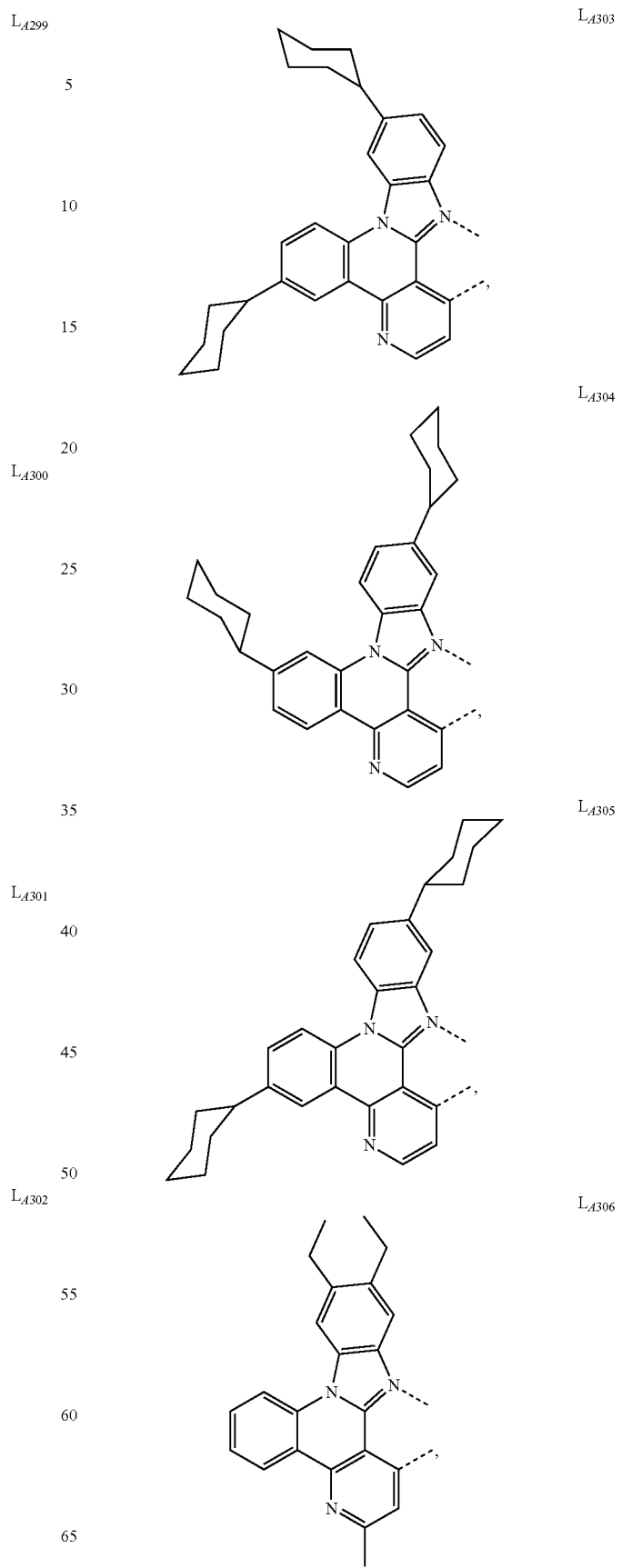

-continued
L<sub>A307</sub>
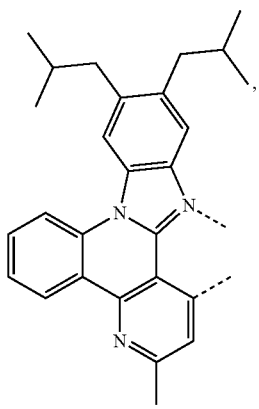
L<sub>A308</sub>
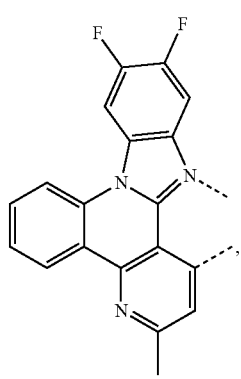
L<sub>A309</sub>
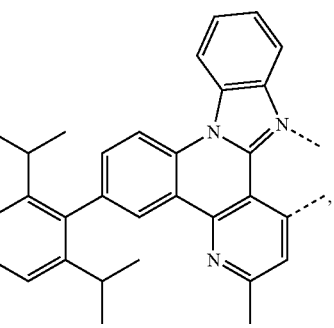
L<sub>A310</sub>
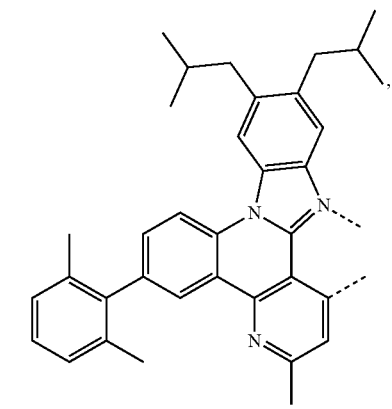
-continued
L<sub>A311</sub>
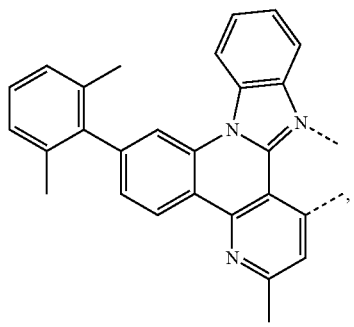
L<sub>A312</sub>
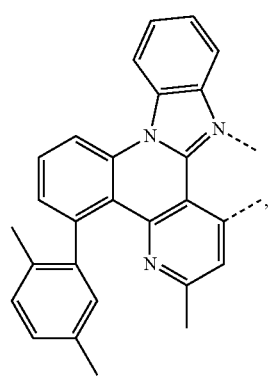
L<sub>A313</sub>
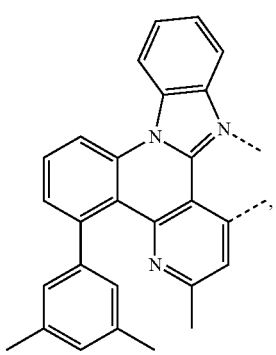
L<sub>A314</sub>
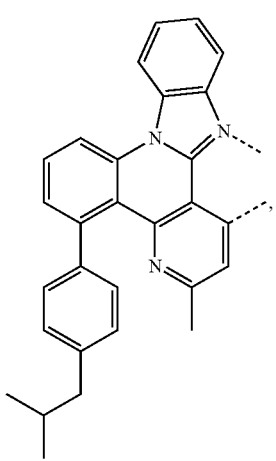

L<sub>A315</sub> 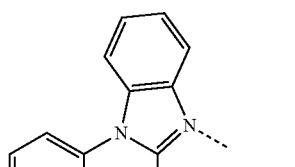

L<sub>A316</sub> 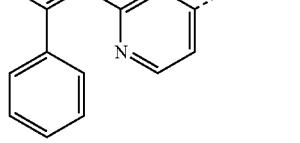, and

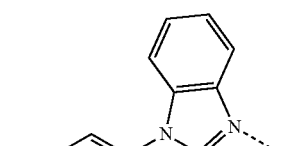.

In some embodiments, the compound comprises two or more ligands $L_A$, wherein the two or more ligands $L_A$ are the same ligands. In other embodiments, the compound comprises two or more ligands $L_A$, wherein at least one of the ligands $L_A$ is a different ligand from the other ligands $L_A$. In some embodiments, the compound comprises at least one ligand $L_A$ and at least one ligand $L_B$, wherein $L_B$ is a different ligand from $L_A$. $L_B$ is not particularly limited. In one embodiment, $L_B$ is a bidentate ligand. Additionally, ligands $L_B$ may be optionally substituted, and any adjacent substituents may be optionally fused or joined to form a ring or form a multidentate ligand. In one embodiment, the $L_B$ is chosen such that the HOMO energy in $Ir(L_B)_3$ is deeper than that in $Ir(L_A)_3$.

In one embodiment, $L_B$ is selected from the group consisting of:

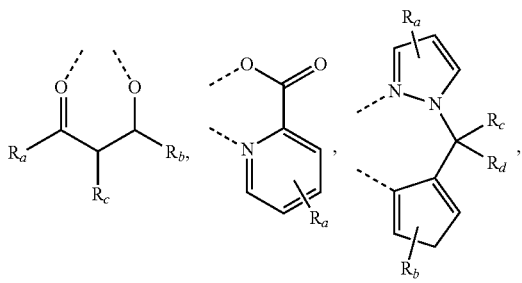

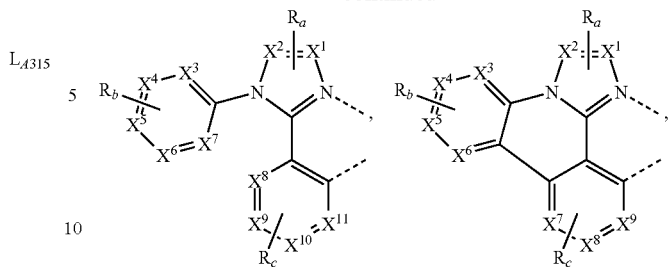

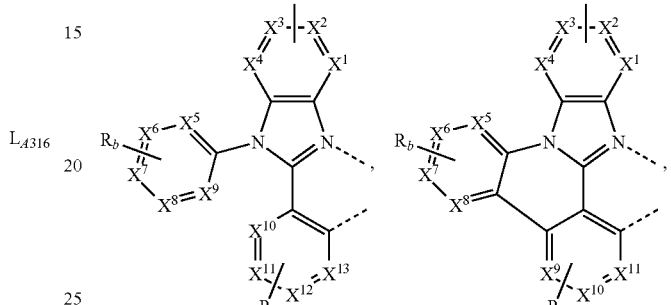

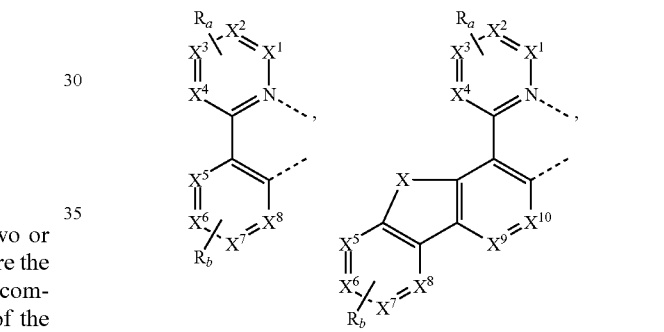

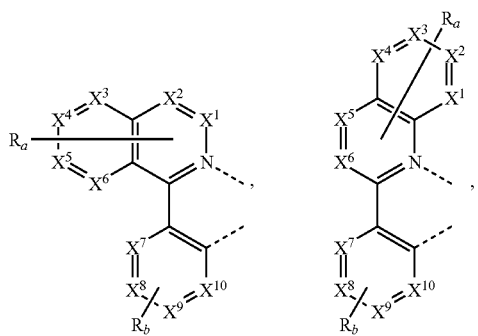

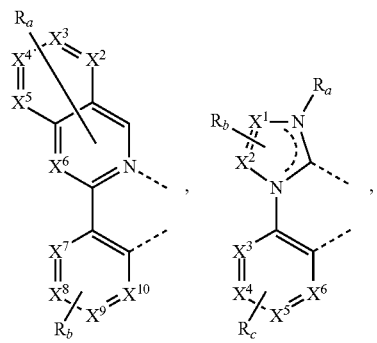

-continued

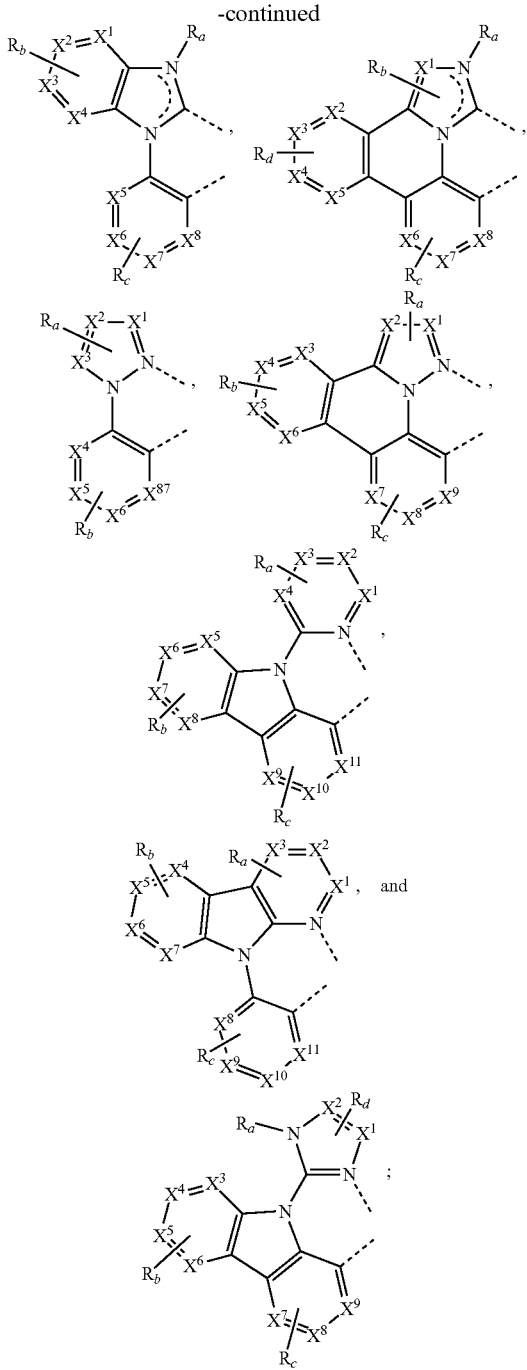

wherein each $X^1$ to $X^{13}$ are independently selected from the group consisting of carbon and nitrogen;

wherein X is selected from the group consisting of BR', NR', PR', O, S, Se, C=O, S=O, SO$_2$, CR'R", SiR'R", and GeR'R";

wherein R' and R" are optionally fused or joined to form a ring;

wherein each $R_a$, $R_b$, $R_c$, and $R_d$ may represent from mono substitution to the possible maximum number of substitution, or no substitution;

wherein $R_a$, $R_b$, $R_c$, and $R_d$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein when $R_a$, $R_b$, $R_c$, and $R_d$ represent at least di substitution, each of the two adjacent $R_a$, two adjacent $R_b$, two adjacent $R_c$, and two adjacent $R_d$ are optionally fused or joined to form a ring or form a multidentate ligand.

In one embodiment, $L_B$ is selected from the group consisting of:

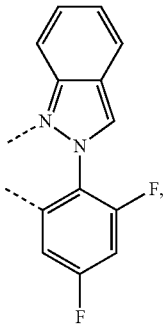

$L_{B1}$

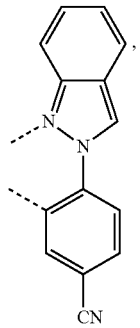

$L_{B2}$

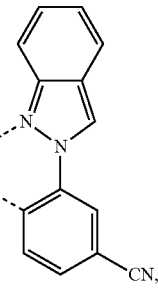

$L_{B3}$

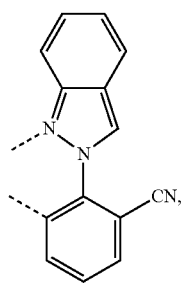

$L_{B4}$

-continued
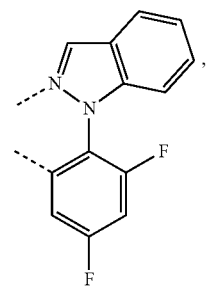, L<sub>B5</sub>
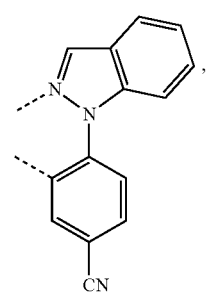, L<sub>B6</sub>
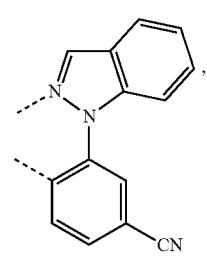, L<sub>B7</sub>
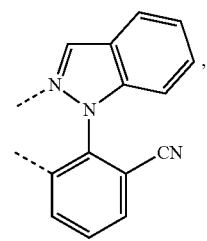, L<sub>B8</sub>
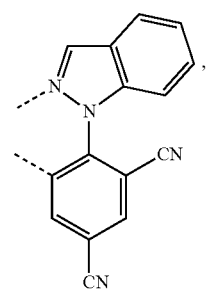, L<sub>B9</sub>
-continued
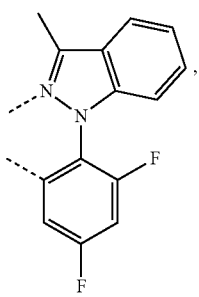, L<sub>B10</sub>
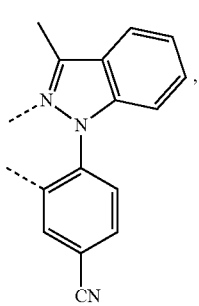, L<sub>B11</sub>
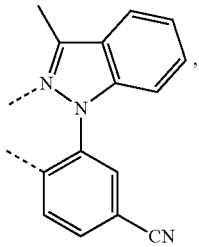, L<sub>B12</sub>
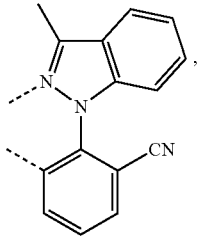, L<sub>B13</sub>
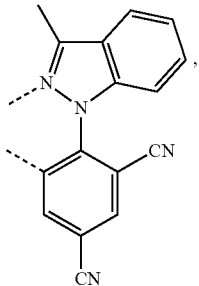, L<sub>B14</sub>

L_{B15} 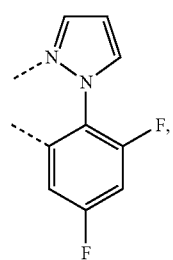
L_{B16} 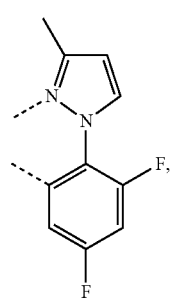
L_{B17} 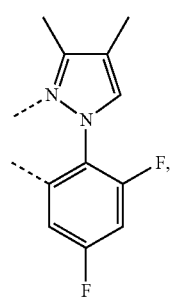
L_{B18} 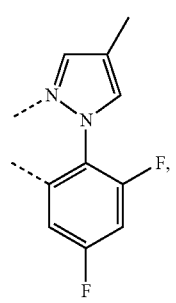
L_{B19} 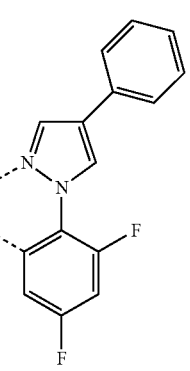
L_{B20} 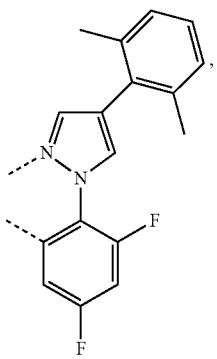
L_{B21} 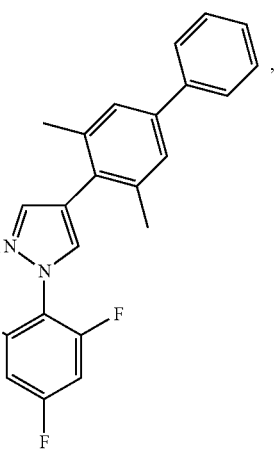
L_{B22} 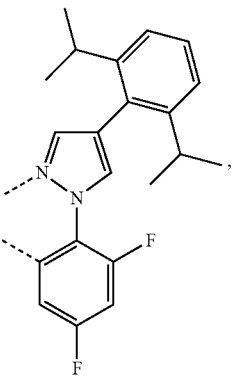
L_{B23} 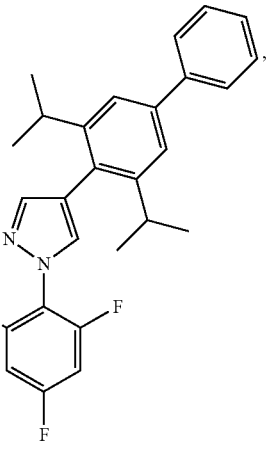

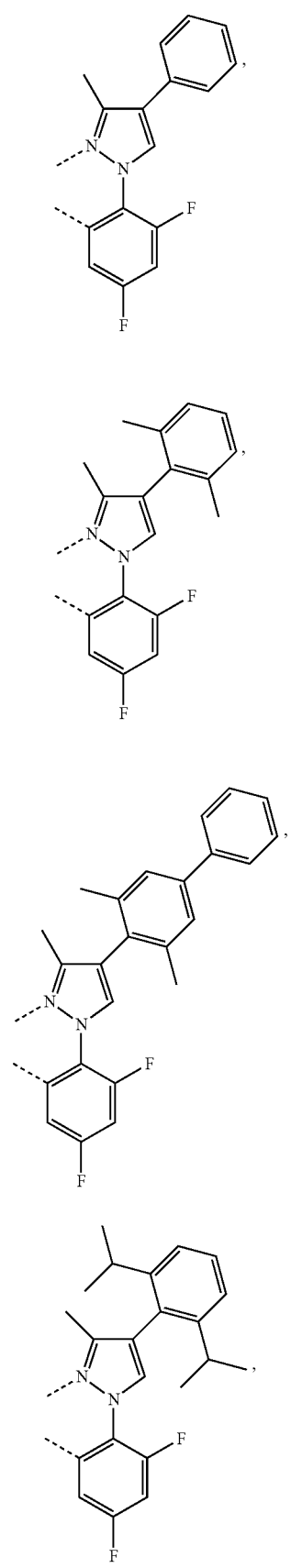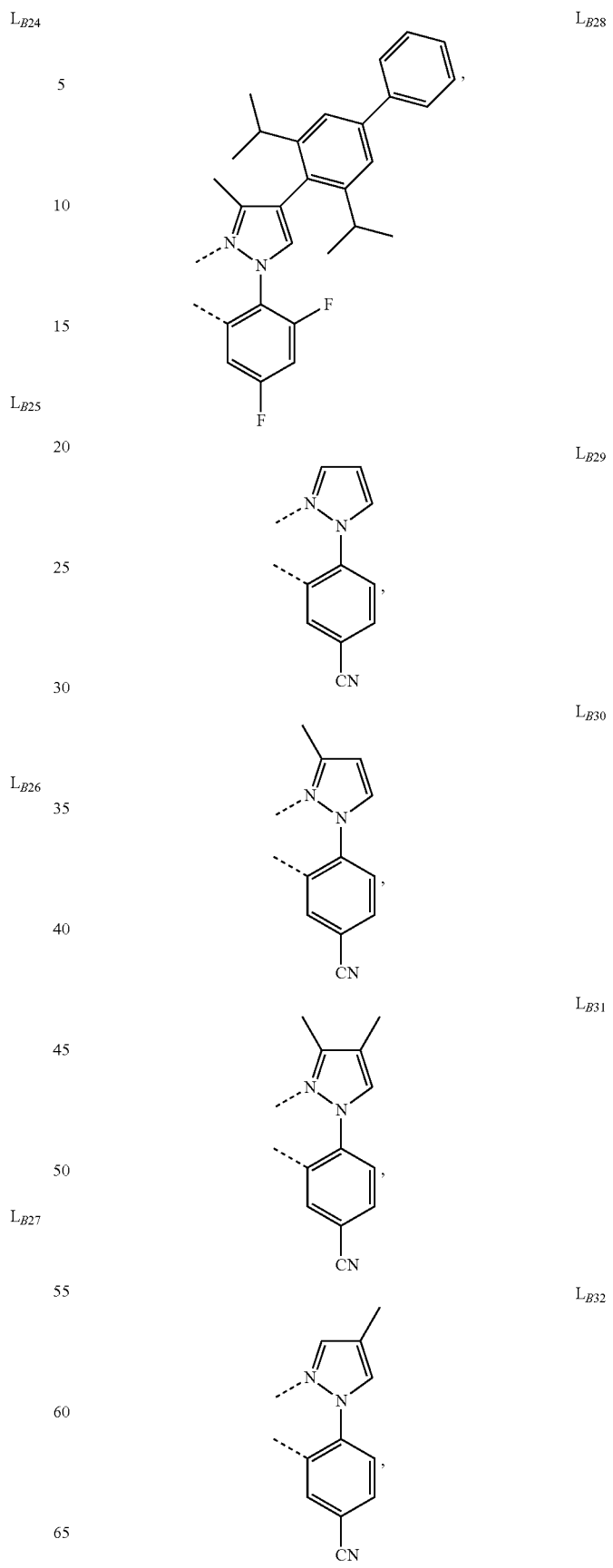

L_{B33}
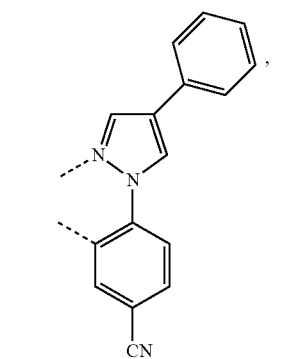
L_{B34}
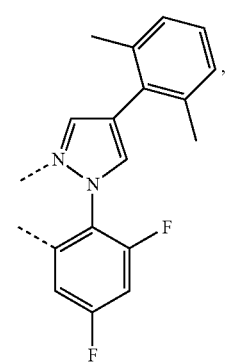
L_{B35}
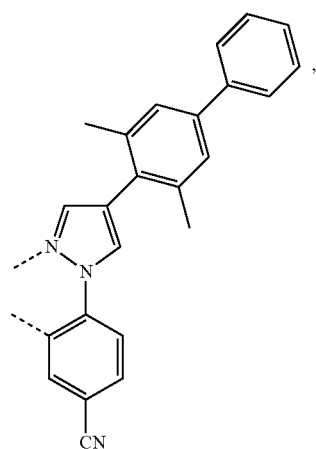
L_{B36}
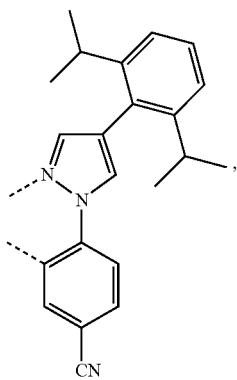
L_{B37}
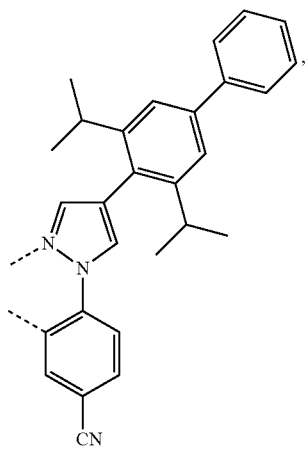
L_{B38}
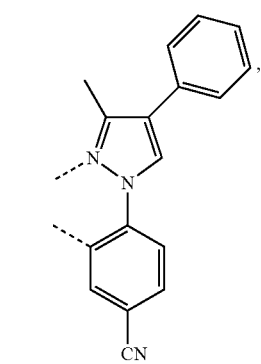
L_{B39}
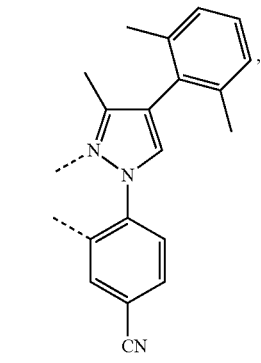
L_{B40}
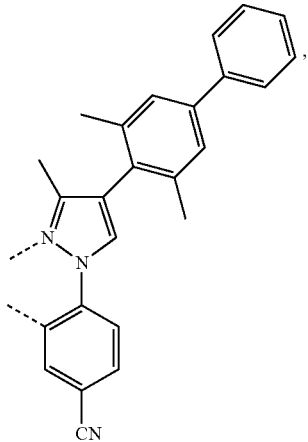

-continued
L_{B41}
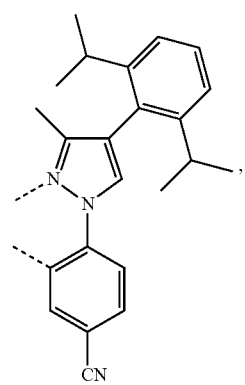
L_{B42}
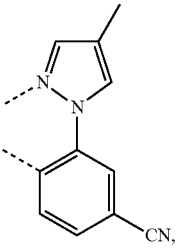
L_{B43}
L_{B44}
L_{B45}
-continued
L_{B46}
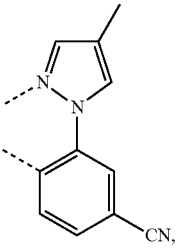
L_{B47}
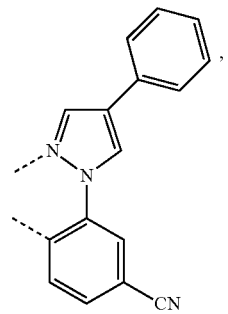
L_{B48}
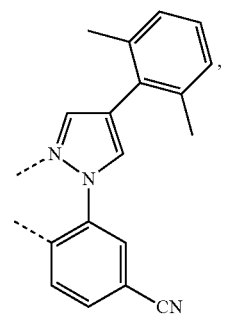
L_{B49}
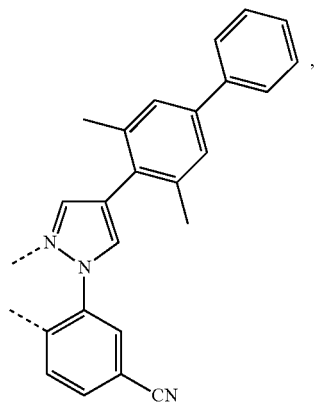
L_{B50}
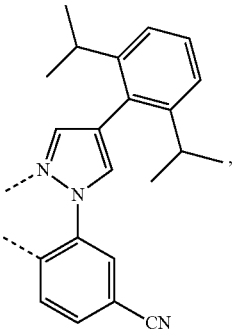

L<sub>B51</sub>
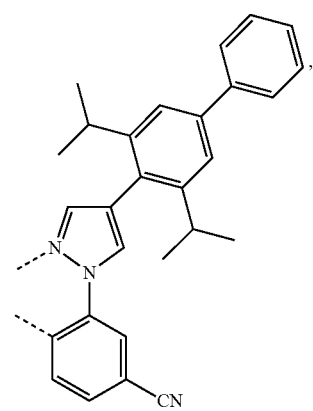
L<sub>B52</sub>
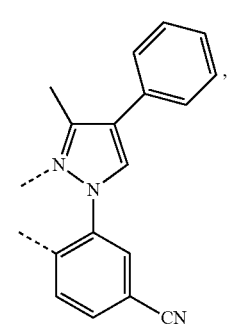
L<sub>B53</sub>
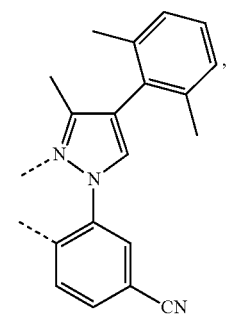
L<sub>B54</sub>
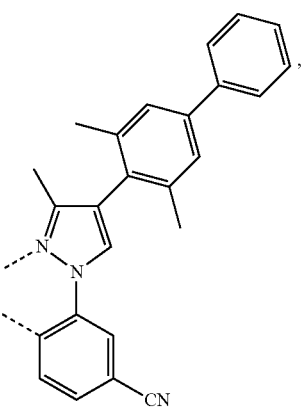
L<sub>B55</sub>
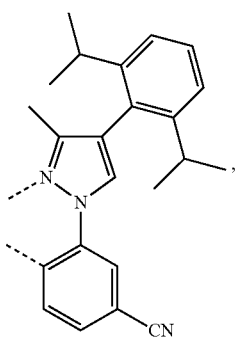
L<sub>B56</sub>
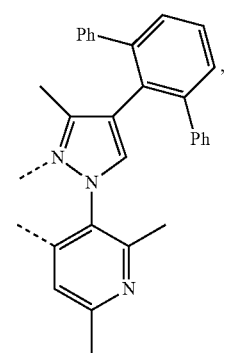
L<sub>B57</sub>
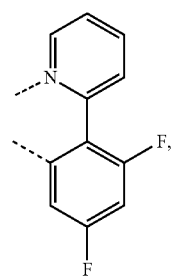
L<sub>B58</sub>
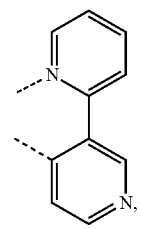
L<sub>B59</sub>
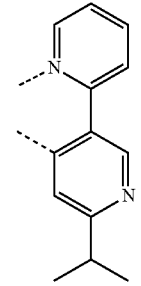

L_{B60}
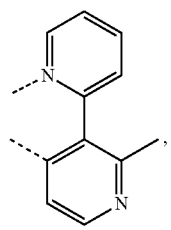
L_{B61}
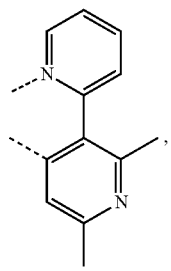
L_{B62}
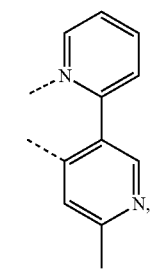
L_{B63}
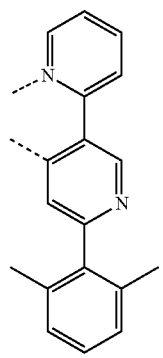
L_{B634}
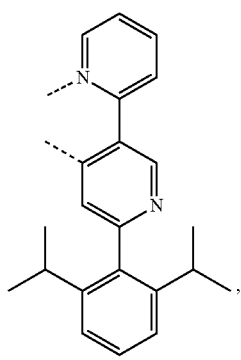
L_{B65}
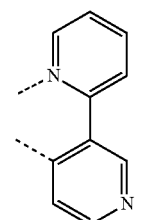
L_{B66}
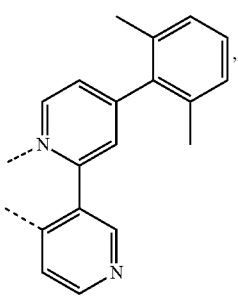
L_{B67}
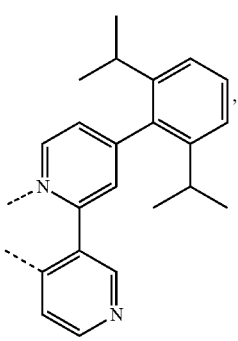
L_{B68}
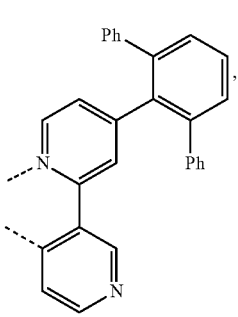

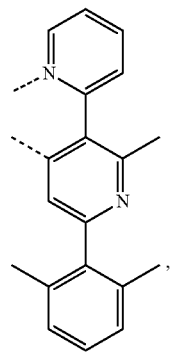
L<sub>B69</sub>
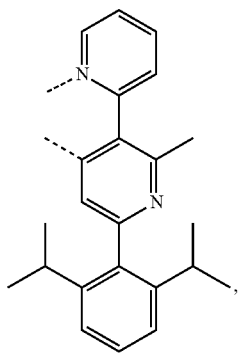
L<sub>B70</sub>
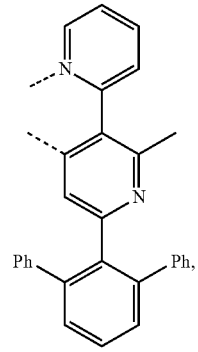
L<sub>B71</sub>
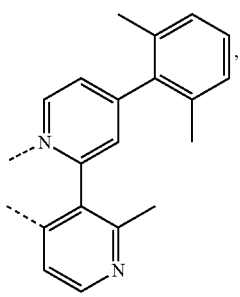
L<sub>B72</sub>
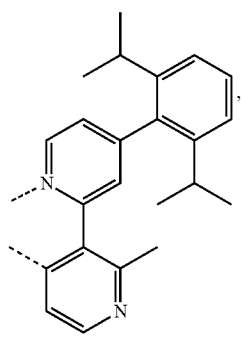
L<sub>B73</sub>
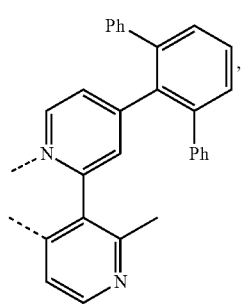
L<sub>B74</sub>
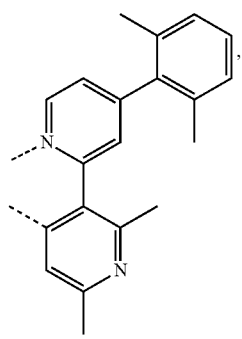
L<sub>B75</sub>
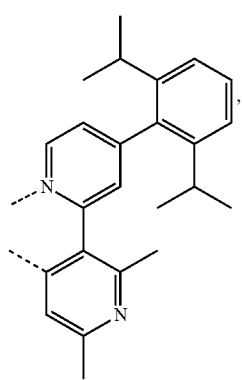
L<sub>B76</sub>

-continued
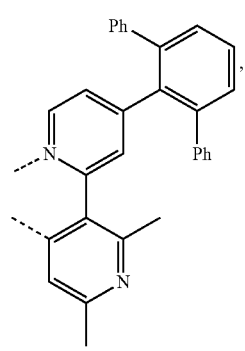 L_{B77}
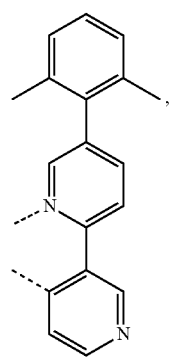 L_{B78}
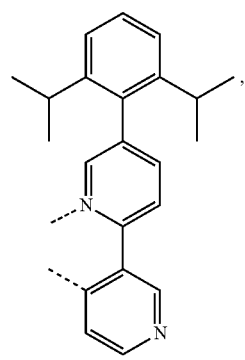 L_{B79}
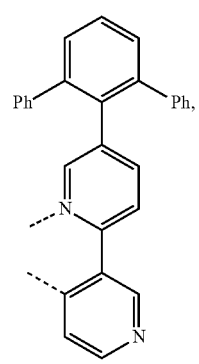 L_{B80}
-continued
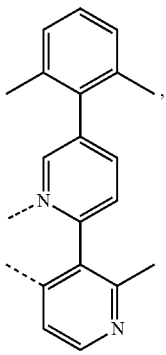 L_{B81}
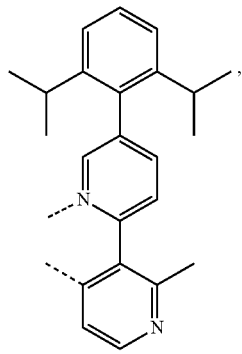 L_{B82}
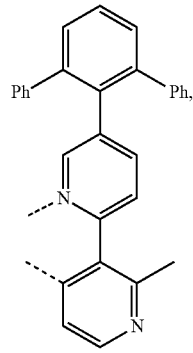 L_{B83}
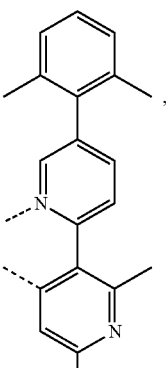 L_{B84}

125
-continued
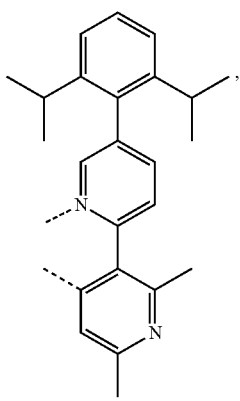
L<sub>B85</sub>
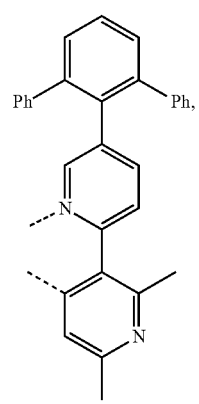
L<sub>B86</sub>
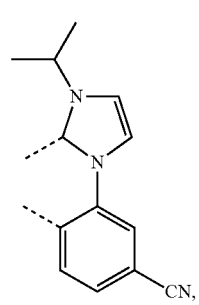
L<sub>B87</sub>
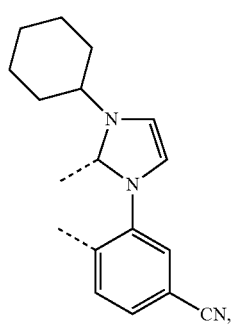
L<sub>B88</sub>
126
-continued
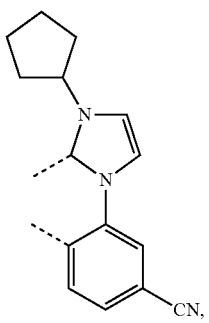
L<sub>B89</sub>
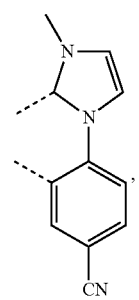
L<sub>B90</sub>
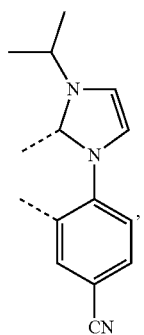
L<sub>B91</sub>
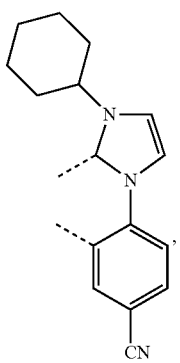
L<sub>B92</sub>

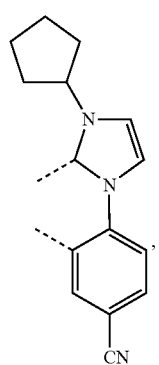 L_{B93}
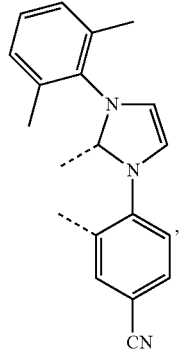 L_{B97}
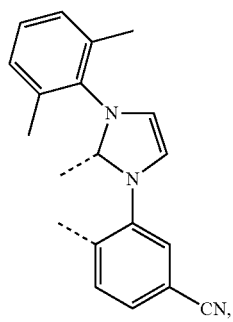 L_{B94}
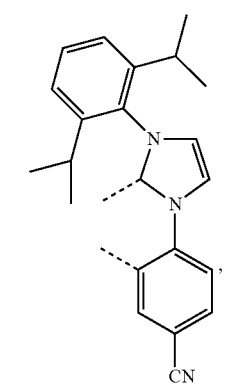 L_{B98}
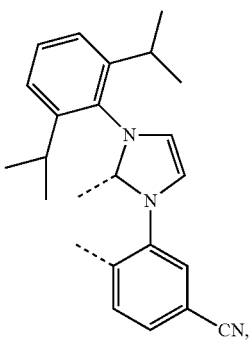 L_{B95}
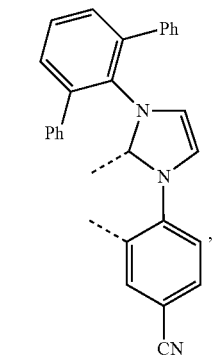 L_{B99}
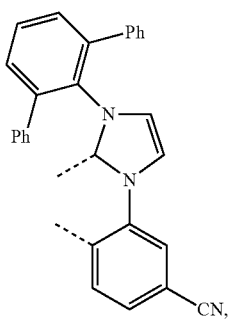 L_{B96}
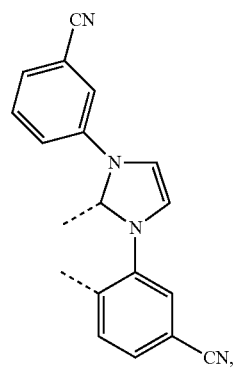 L_{B100}

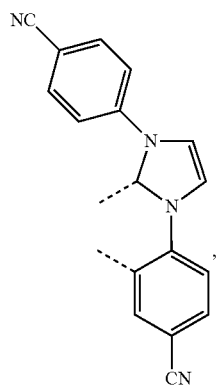 L_{B101}
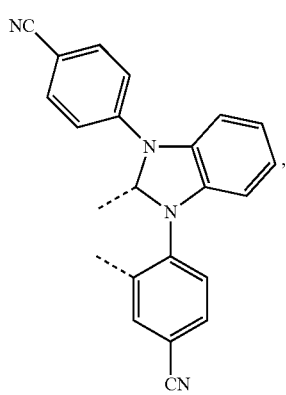 L_{B102}
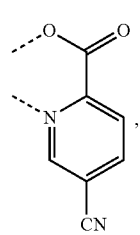 L_{B103}
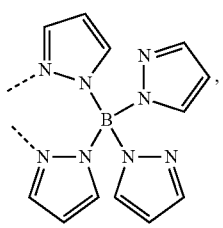 L_{B104}
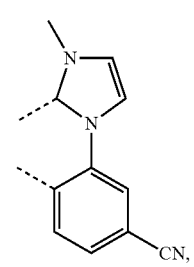 L_{B105}
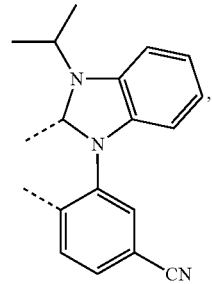 L_{B106}
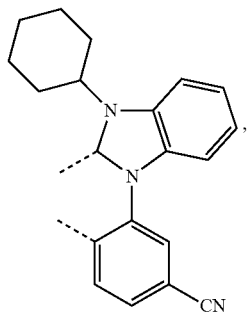 L_{B107}
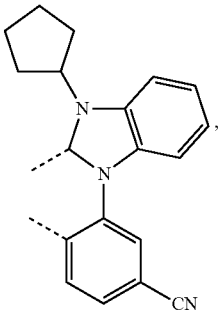 L_{B108}
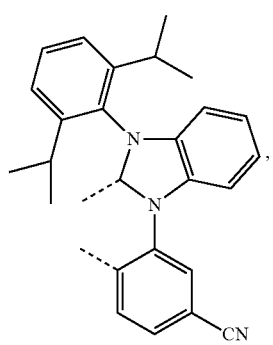 L_{B109}
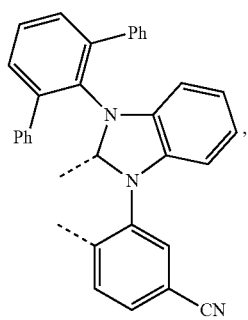 L_{B110}

-continued
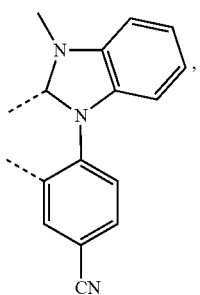 L_{B111}
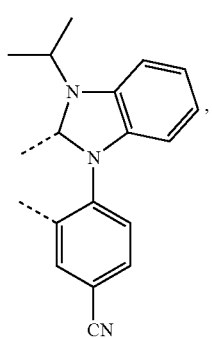 L_{B112}
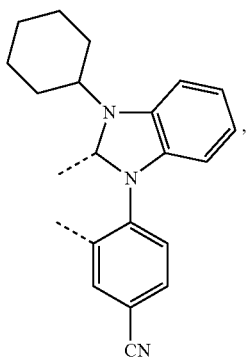 L_{B113}
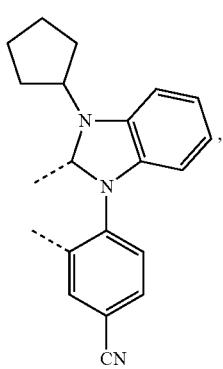 L_{B114}
-continued
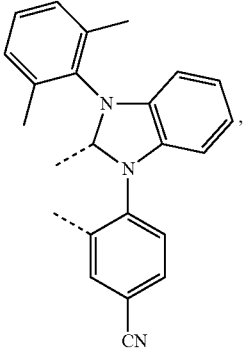 L_{B115}
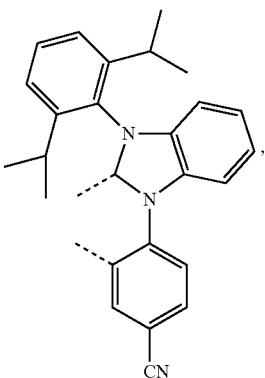 L_{B116}
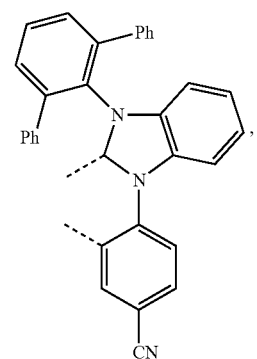 L_{B117}
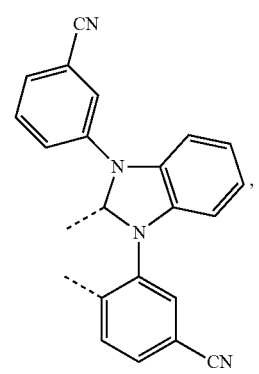 L_{B118}

-continued
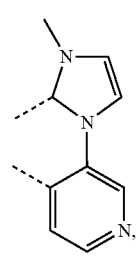  L_{B119}
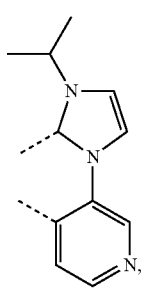  L_{B120}
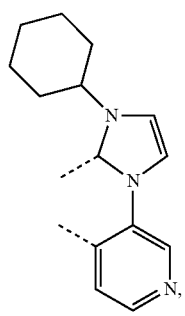  L_{B121}
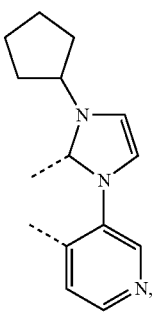  L_{B122}
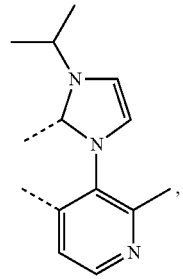  L_{B123}
-continued
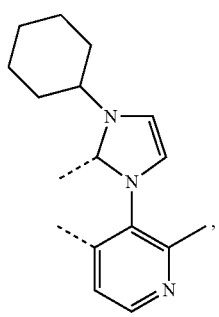  L_{B124}
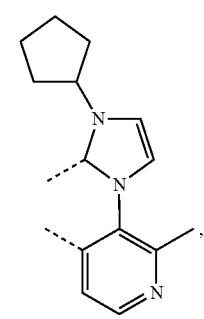  L_{B125}
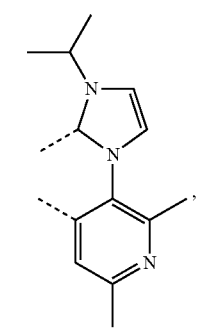  L_{B126}
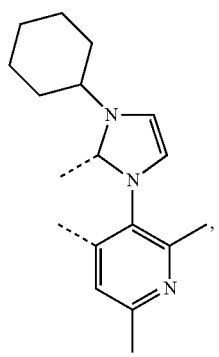  L_{B127}

$L_{B128}$
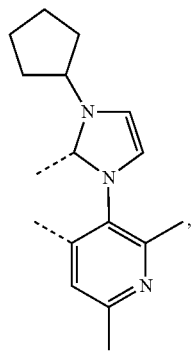
$L_{B129}$
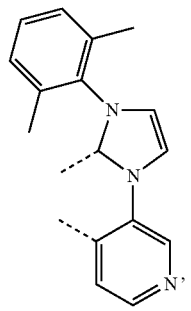
$L_{B130}$
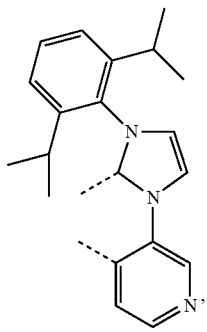
$L_{B131}$
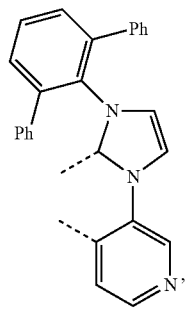
$L_{B132}$
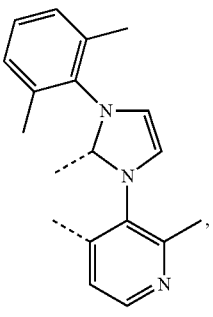
$L_{B133}$
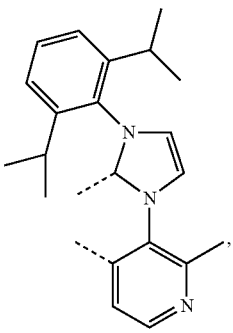
$L_{B134}$
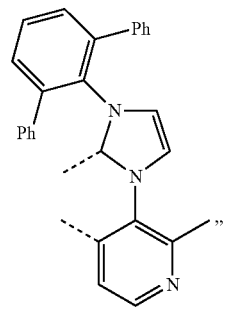
$L_{B135}$
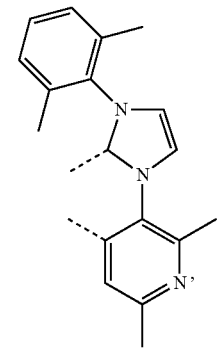
$L_{B136}$
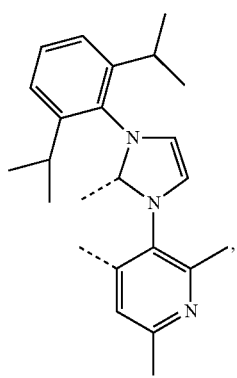

-continued
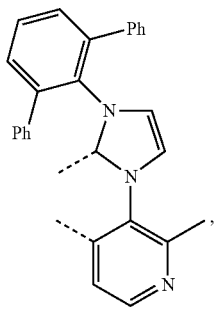
L<sub>B137</sub>
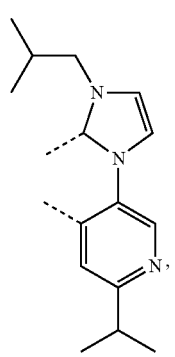
L<sub>B138</sub>
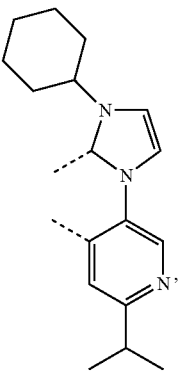
L<sub>B139</sub>
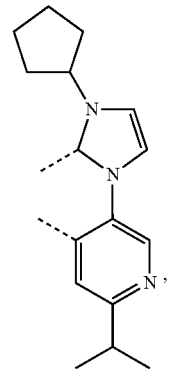
L<sub>B140</sub>
-continued
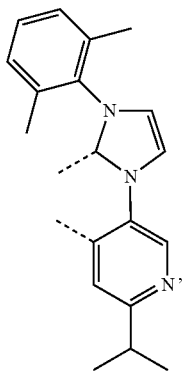
L<sub>B141</sub>
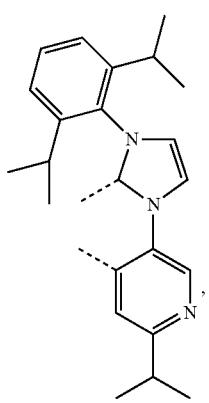
L<sub>B142</sub>
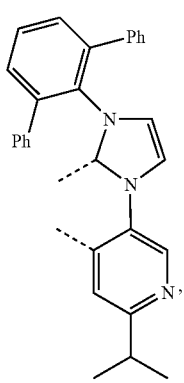
L<sub>B143</sub>
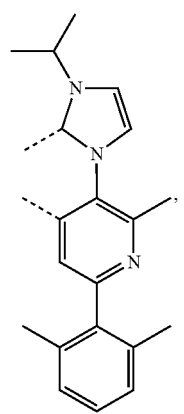
L<sub>B144</sub>

-continued
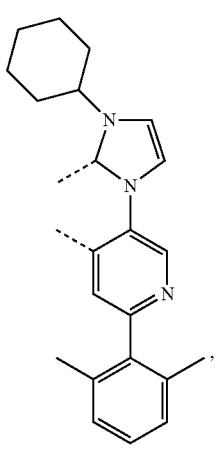
L_{B145}
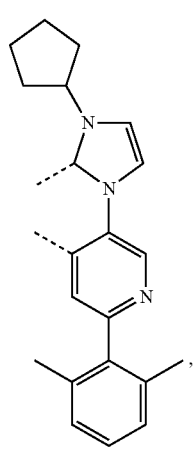
L_{B146}
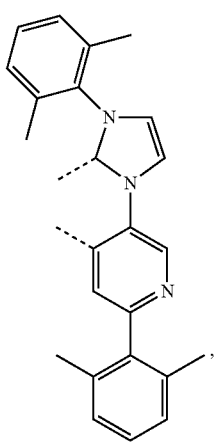
L_{B147}
-continued
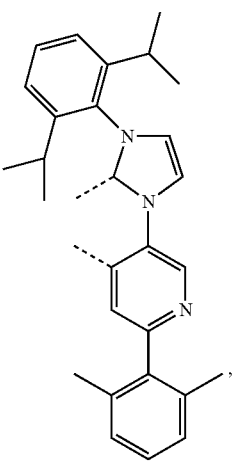
L_{B148}
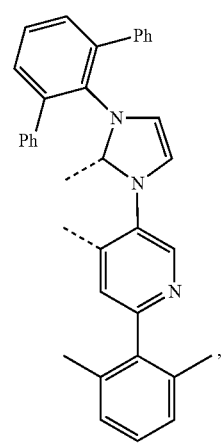
L_{B149}
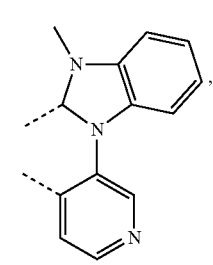
L_{B150}
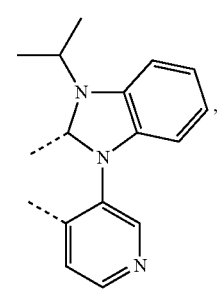
L_{B151}

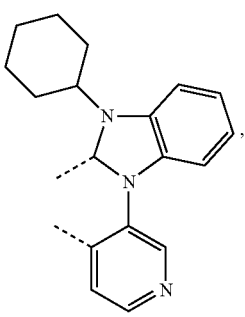 L_{B152}
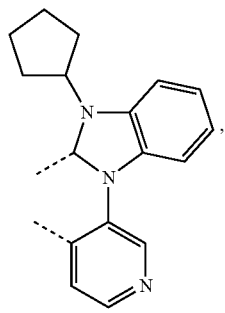 L_{B153}
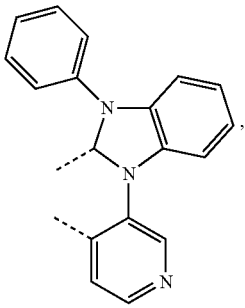 L_{B154}
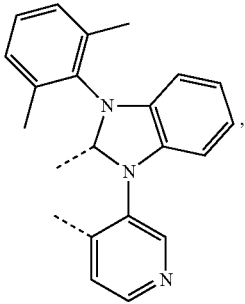 L_{B155}
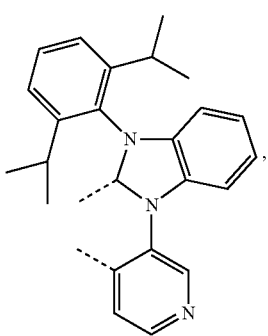 L_{B156}
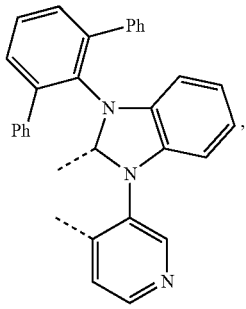 L_{B157}
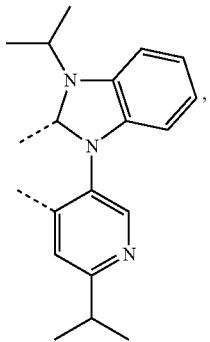 L_{B158}
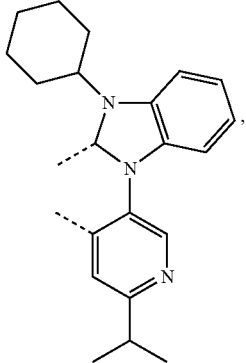 L_{B159}
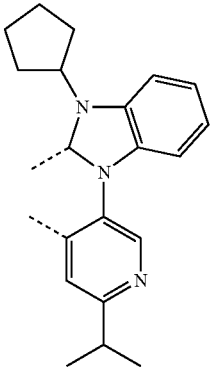 L_{B160}

-continued
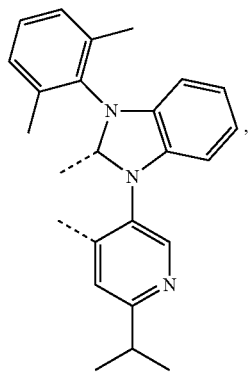 L<sub>B161</sub>
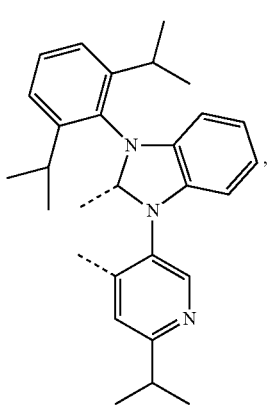 L<sub>B162</sub>
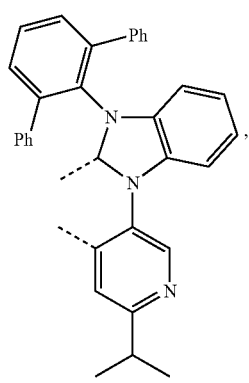 L<sub>B163</sub>
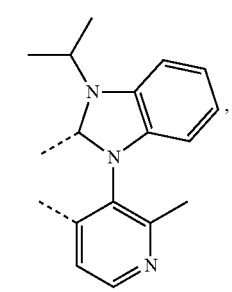 L<sub>B164</sub>
-continued
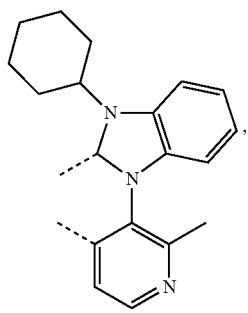 L<sub>B165</sub>
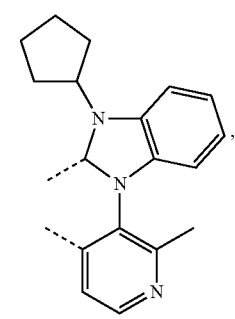 L<sub>B166</sub>
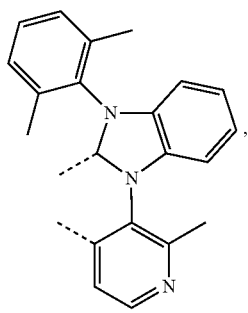 L<sub>B167</sub>
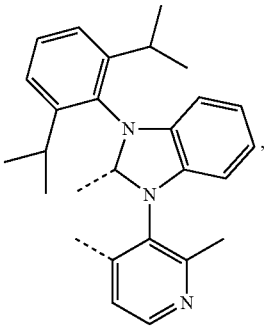 L<sub>B168</sub>
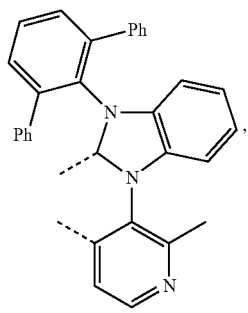 L<sub>B169</sub>

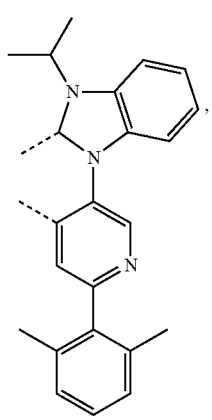 L_{B170}
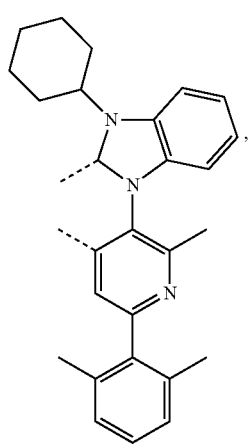 L_{B171}
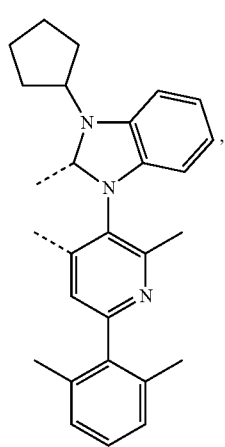 L_{B172}
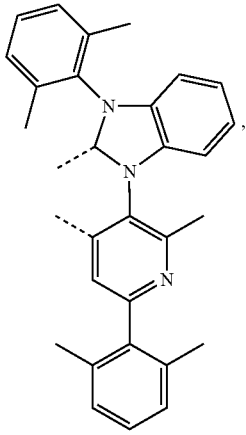 L_{B173}
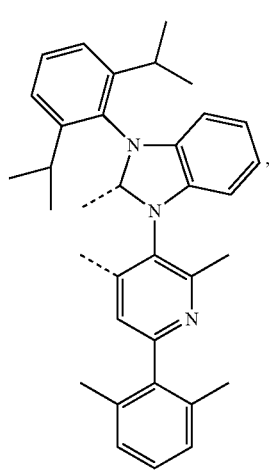 L_{B174}
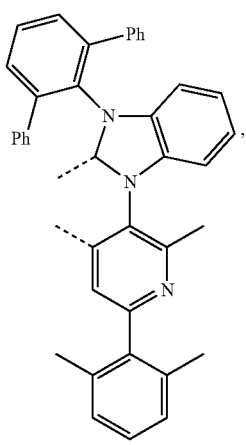 L_{B175}

L<sub>B176</sub>
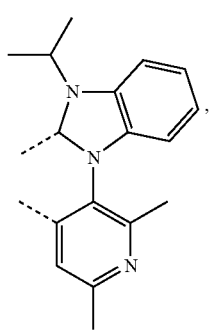
L<sub>B177</sub>
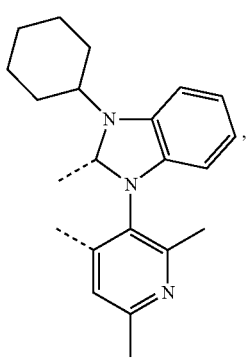
L<sub>B178</sub>
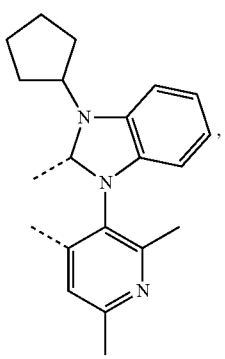
L<sub>B179</sub>
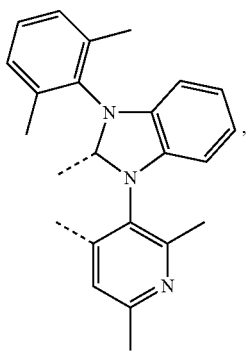
L<sub>B180</sub>
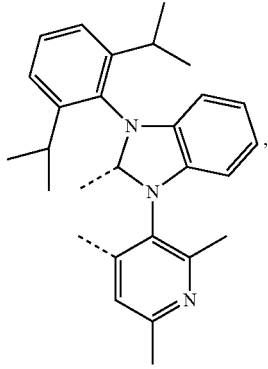
L<sub>B181</sub>
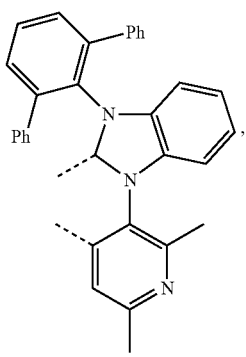
L<sub>B182</sub>
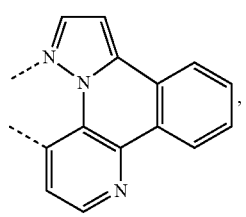
L<sub>B183</sub>
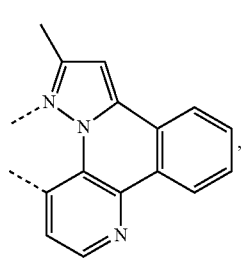
L<sub>B184</sub>
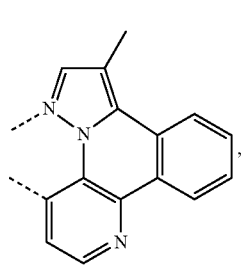

-continued
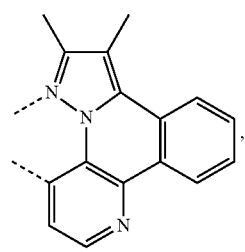
L_{B185}
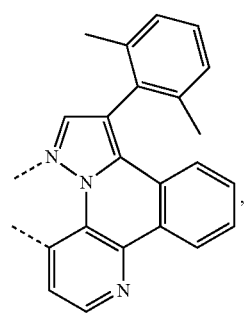
L_{B186}
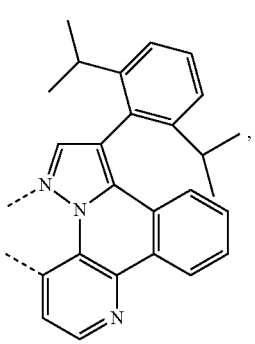
L_{B187}
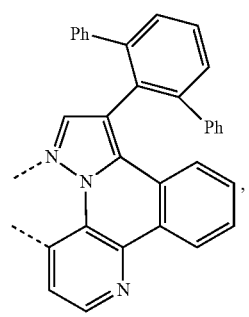
L_{B188}
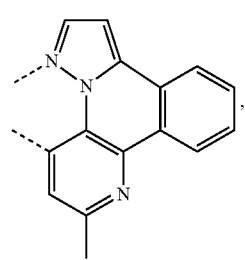
L_{B189}
-continued
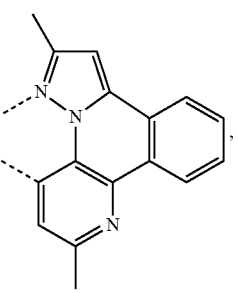
L_{B190}
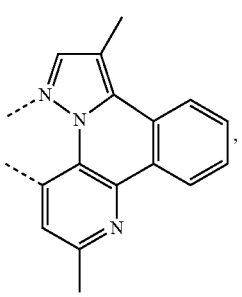
L_{B191}
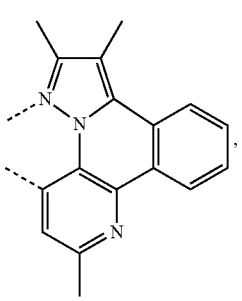
L_{B192}
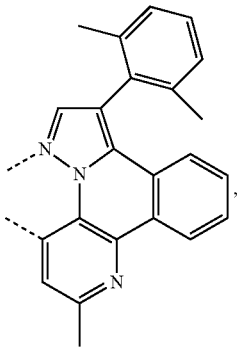
L_{B193}
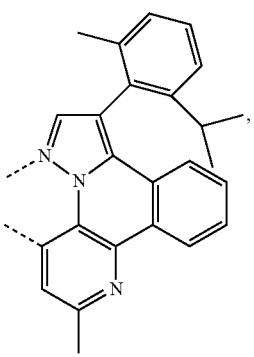
L_{B194}

L_{B195}
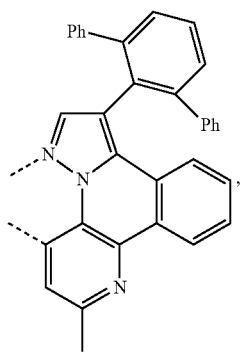
L_{B196}
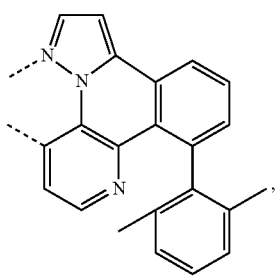
L_{B197}
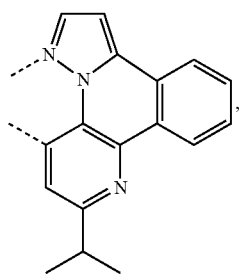
L_{B198}
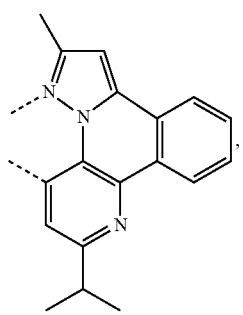
L_{B199}
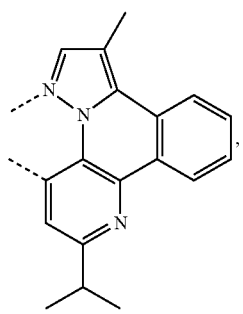
L_{B200}
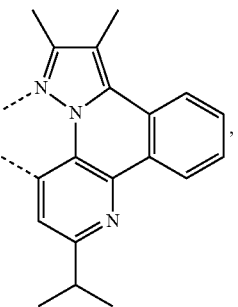
L_{B201}
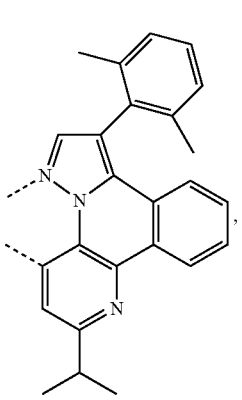
L_{B202}
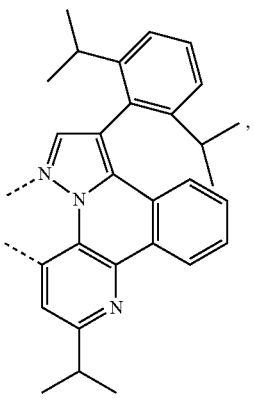
L_{B203}
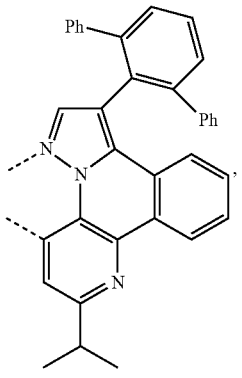

153
-continued
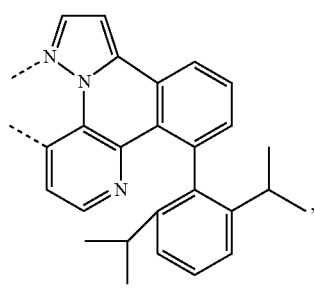
L_{B204}
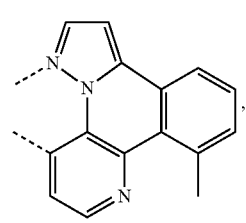
L_{B205}
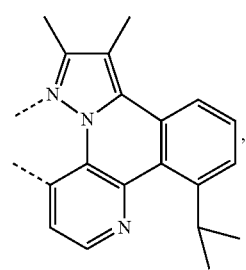
L_{B206}
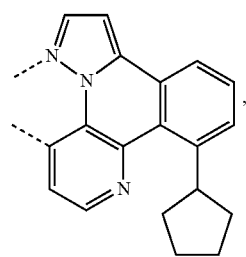
L_{B207}
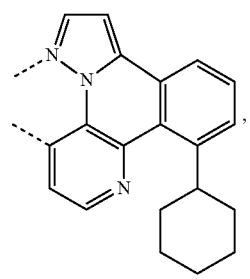
L_{B208}
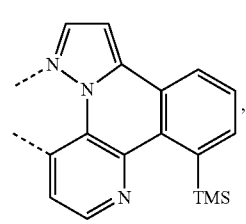
L_{B209}
154
-continued
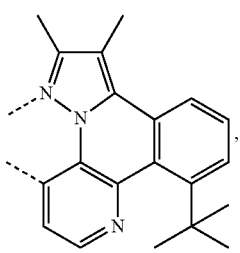
L_{B210}
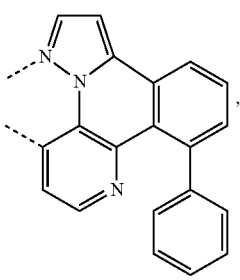
L_{B211}
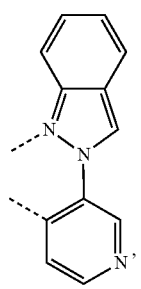
L_{B212}
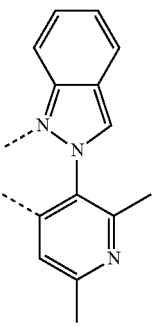
L_{B213}
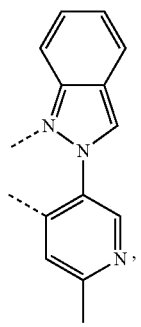
L_{B214}

L<sub>B215</sub> 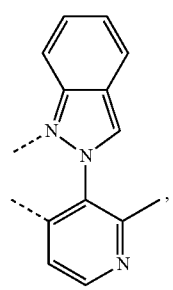
L<sub>B216</sub> 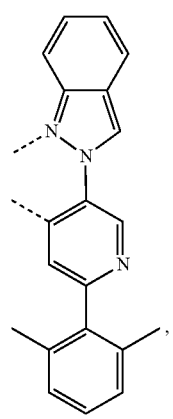
L<sub>B217</sub> 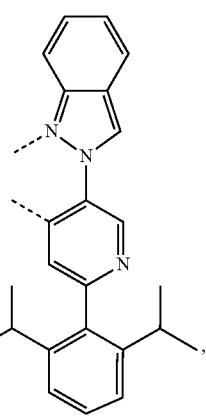
L<sub>B218</sub> 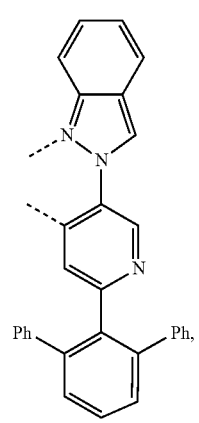
L<sub>B219</sub> 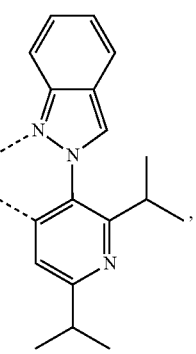
L<sub>B220</sub> 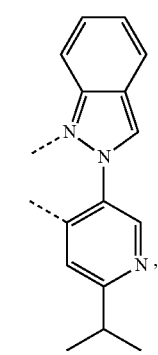
L<sub>B221</sub> 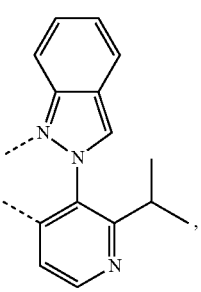
L<sub>B222</sub> 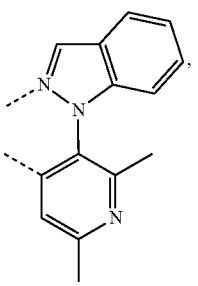
L<sub>B223</sub> 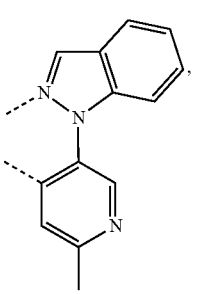

-continued
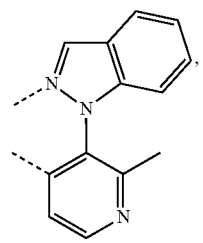
L_{B224}
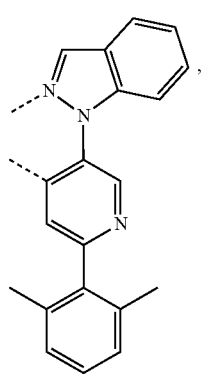
L_{B225}
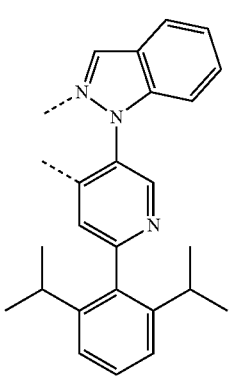
L_{B226}
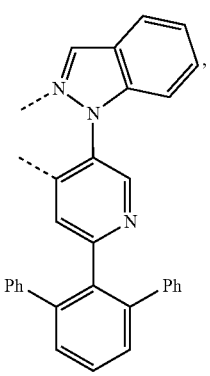
L_{B227}
-continued
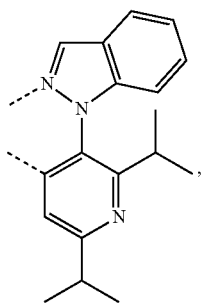
L_{B228}
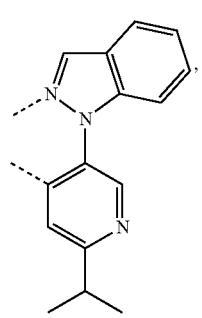
L_{B229}
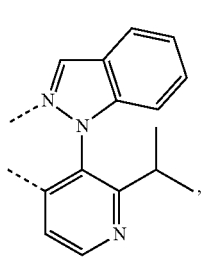
L_{B230}
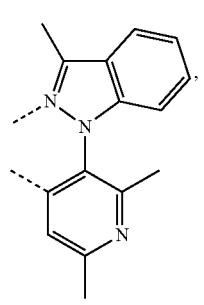
L_{B231}
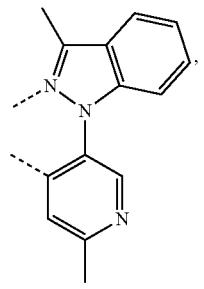
L_{B232}

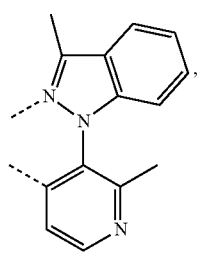 L<sub>B233</sub>
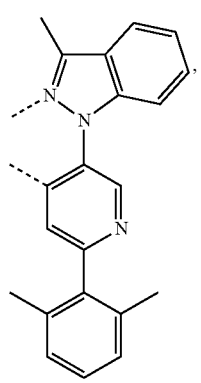 L<sub>B234</sub>
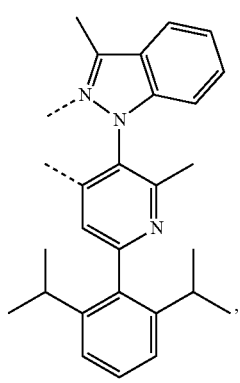 L<sub>B235</sub>
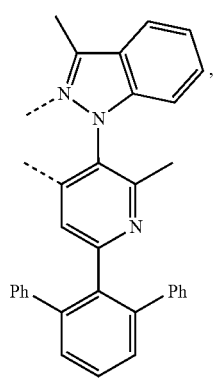 L<sub>B236</sub>
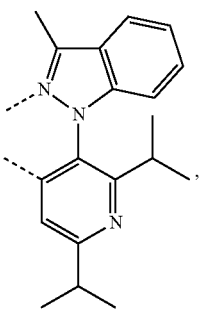 L<sub>B237</sub>
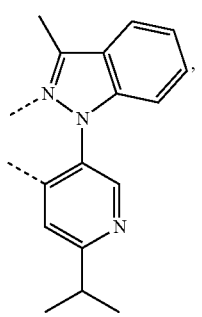 L<sub>B238</sub>
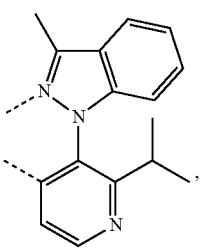 L<sub>B239</sub>
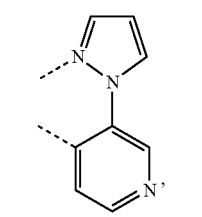 L<sub>B240</sub>
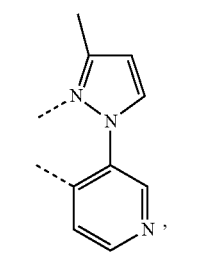 L<sub>B241</sub>
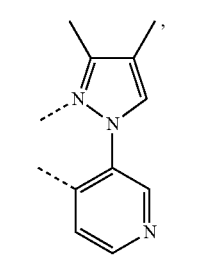 L<sub>B242</sub>

-continued
L_{B243} 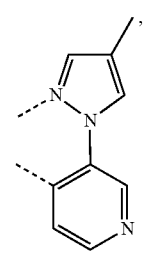
L_{B244} 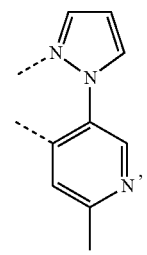
L_{B245} 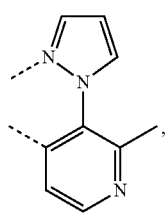
L_{B246} 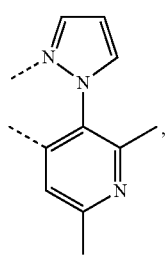
L_{B247} 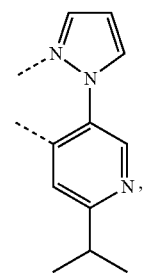
L_{B248} 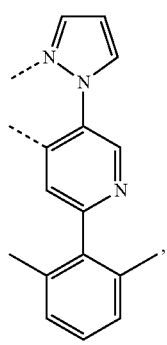
L_{B249} 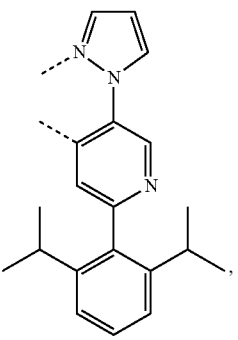
L_{B2450} 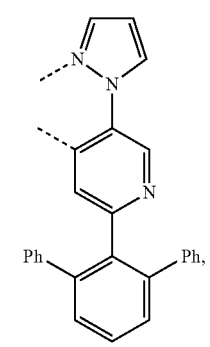
L_{B251} 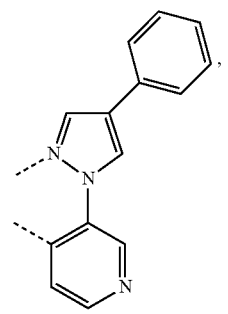
L_{B252} 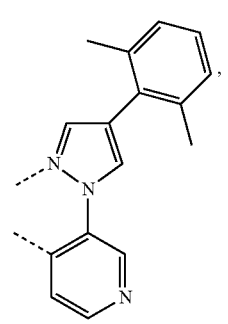

-continued
L_{B253} 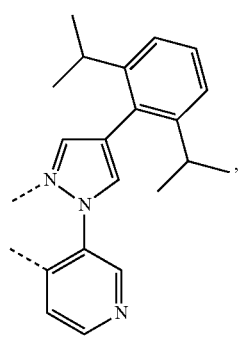
L_{B254} 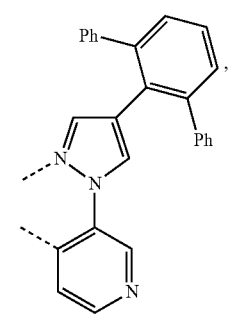
L_{B255} 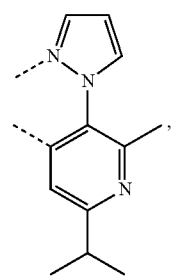
L_{B256} 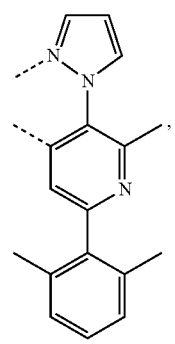
L_{B257} 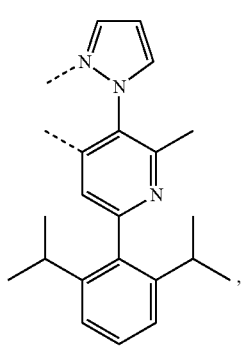
-continued
L_{B258} 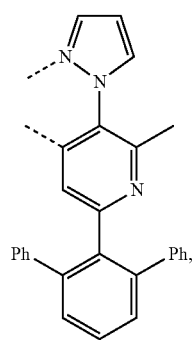
L_{B259} 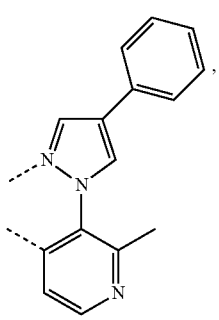
L_{B260} 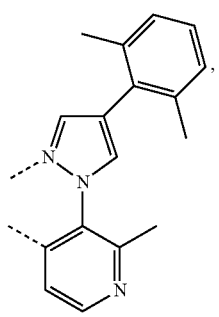
L_{B261} 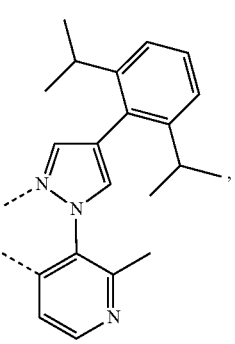
L_{B262} 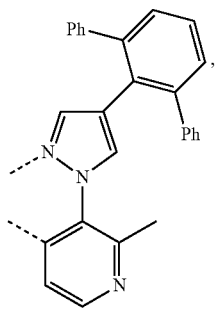

-continued

L_{B263}
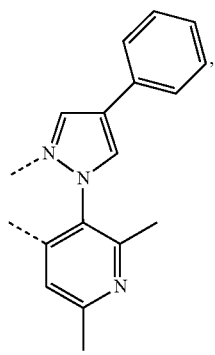

L_{B264}
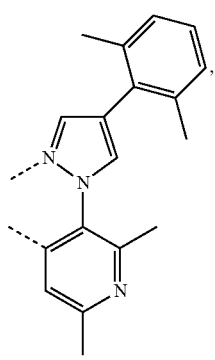

L_{B265}
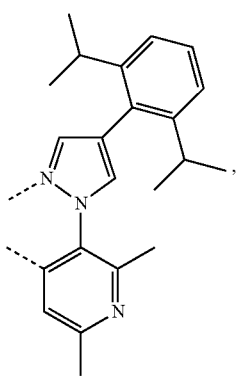

L_{B266}
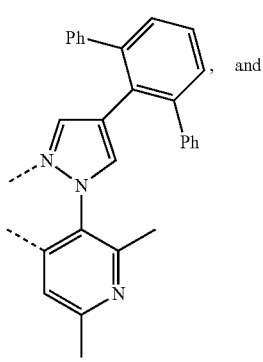
, and

-continued

L_{B267}
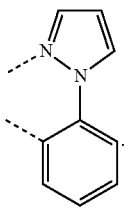

In one embodiment, the compound has the formula $M(L_A)_m(L_B)_n$, having the structure:

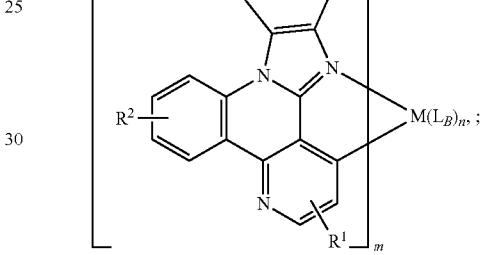

Formula II wherein $L_B$ is a different ligand from $L_A$; and
wherein m is an integer from 1 to the maximum number of ligands that may be coordinated to the metal M; m+n is the maximum number of ligands that may be coordinated to the metal M.

In one embodiment, the compound is selected from the group consisting of Compound 1 through Compound 316; wherein each Compound x has the formula $Ir(L_{Ai})_3$, and wherein x=i; i is an integer from 1 to 316. For example, if the compound has the formula $Ir(L_{A35})_3$, the compound is Compound 35. In another embodiment, the compound is selected from the group consisting of Compound 317 through Compound 84,688, wherein each Compound x has the formula $Ir(L_{Ai})(L_{Bj})_2$, and wherein x=316j+i; i is an integer from 1 to 316, and j is an integer from 1 to 267. For example, if the compound has formula $Ir(L_{A35})(L_{B15})_2$, the compound is Compound 4,775. In another embodiment, the compound is selected from the group consisting of Compound 84,689 through Compound 169,060, wherein each Compound x has the formula $Ir(L_{Ai})_2(L_{Bj})$, and wherein x=84,372+316j+i; i is an integer from 1 to 316, and j is an integer from 1 to 267. In one embodiment, ligand $L_{Ai}$ is at least one ligand $L_A$. In one embodiment, ligand $L_{Bj}$ is at least one ligand $L_B$.

In one embodiment, the compound has the structure:
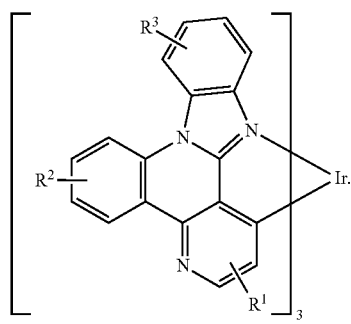
In one embodiment, the compound has the structure:
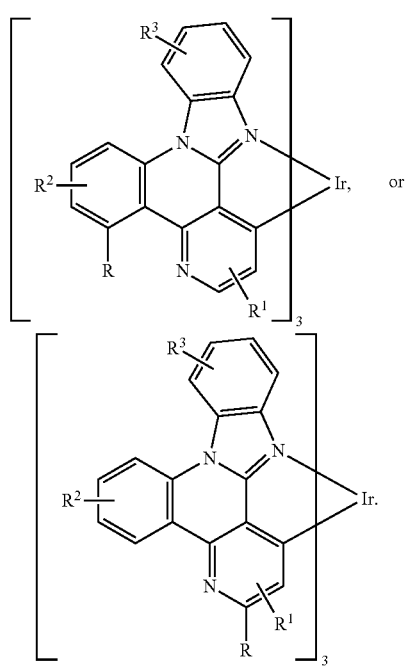
In one embodiment, the compound is selected from the group consisting of:
Compound 306
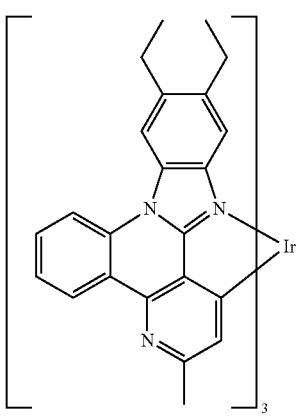
Compound 307
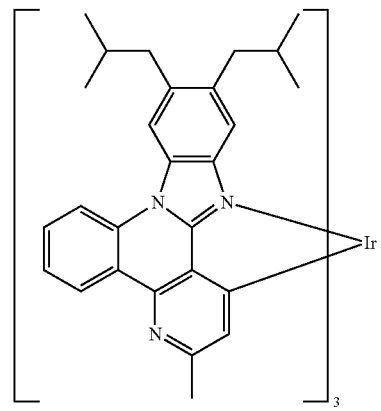
Compound 308
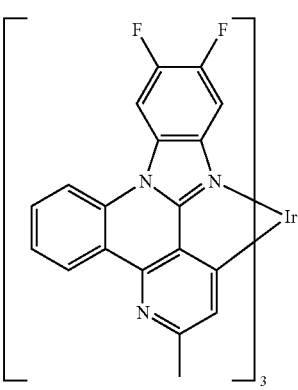
Compound 110
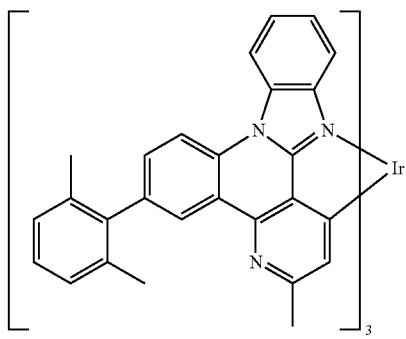
Compound 309
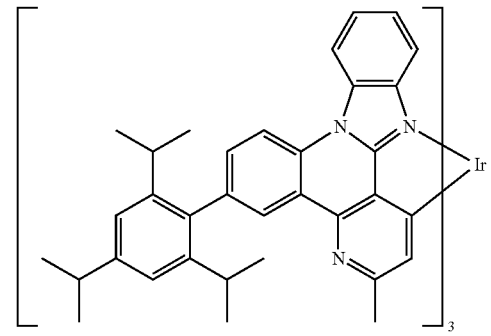

Compound 310
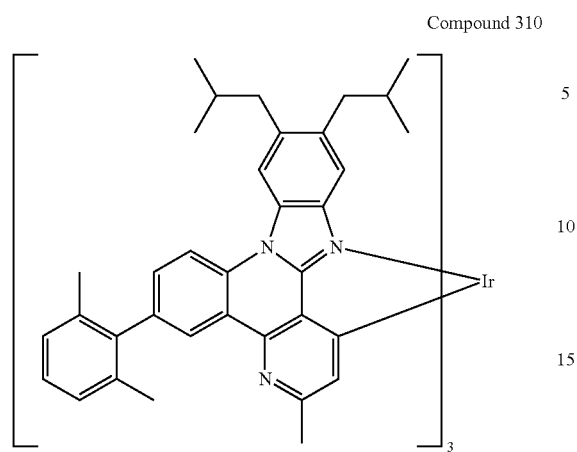
Compound 311
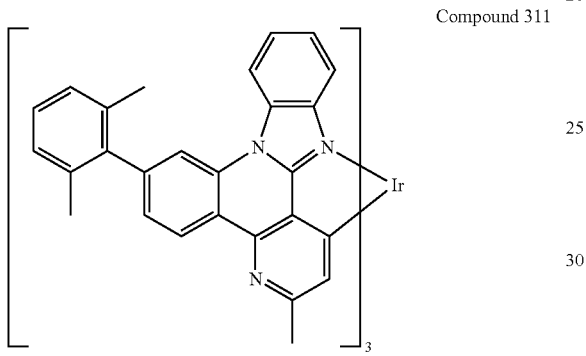
Compound 4
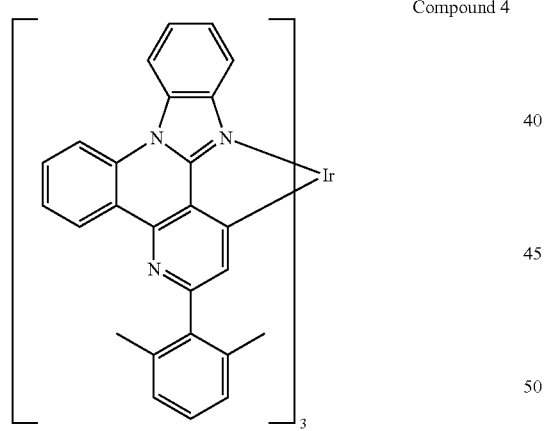
Compound 7
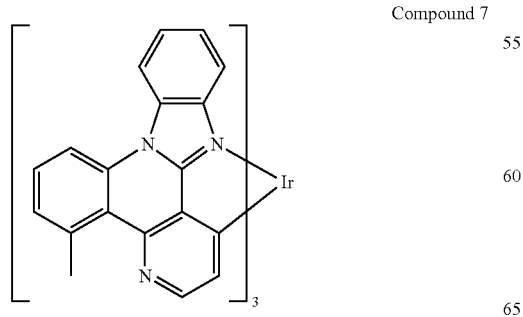
Compound 312
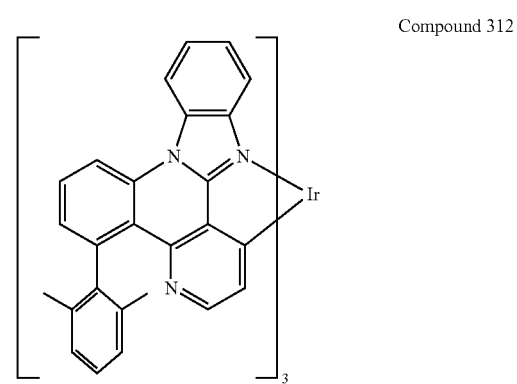
Compound 313
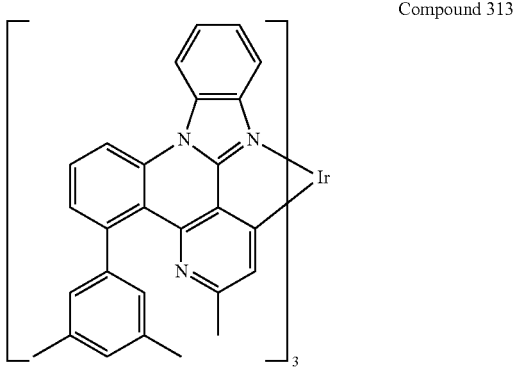
Compound 314
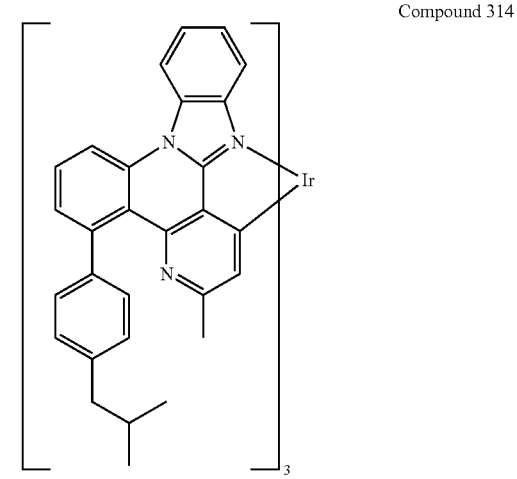
Compound 84678
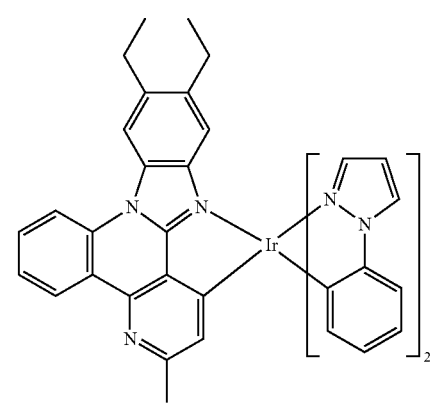

-continued

Compound 5046

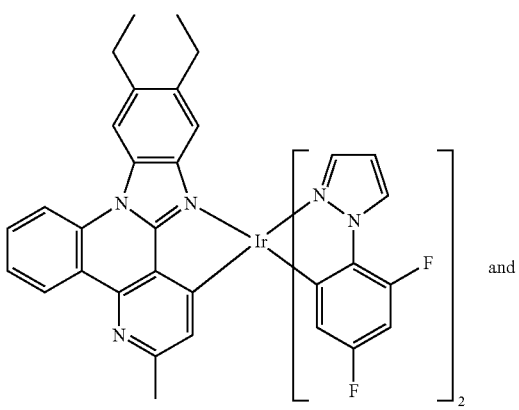

Compound 18318

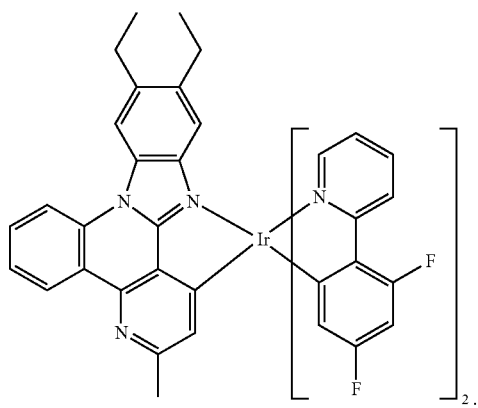

In some embodiments, the compound can be an emissive dopant. In some embodiments, the compound can produce emissions via phosphorescence, fluorescence, thermally activated delayed fluorescence, i.e., TADF (also referred to as E-type delayed fluorescence), triplet-triplet annihilation, or combinations of these processes.

Devices:

According to another aspect of the present disclosure, a first device is also provided. The first device includes a first organic light emitting device, that includes an anode, a cathode, and an organic layer disposed between the anode and the cathode. The organic layer may include a host and a phosphorescent dopant. The emissive layer can include a compound according to Formula I, and its variations as described herein.

The first device can be one or more of a consumer product, an electronic component module, an organic light-emitting device and a lighting panel. The organic layer can be an emissive layer and the compound can be an emissive dopant in some embodiments, while the compound can be a non-emissive dopant in other embodiments. The organic layer can be a charge transporting layer and the compound can be a charge transporting material in the organic layer in some embodiments. The organic layer can be a blocking layer and the compound can be a blocking material in the organic layer in some embodiments.

The organic layer can also include a host. In some embodiments, the host can include a metal complex. The host can be a triphenylene containing benzo-fused thiophene or benzo-fused furan. Any substituent in the host can be an unfused substituent independently selected from the group consisting of $C_nH_{2n+1}$, $OC_nH_{2n+1}$, $OA_{r1}$, $N(C_nH_{2n+1})_2$, $N(Ar_1)(Ar_2)$, $CH=CH-C_nH_{2n+1}$, $C\equiv C-C_nH_{2n+1}$, $Ar_1$, $Ar_1-Ar_2$, and $C_nH_{2n}Ar_1$, or no substitution. In the preceding substituents n can range from 1 to 10; and $Ar_1$ and $Ar_2$ can be independently selected from the group consisting of benzene, biphenyl, naphthalene, triphenylene, carbazole, and heteroaromatic analogs thereof.

The host can be a compound comprising at least one chemical group selected from the group consisting of triphenylene, carbazole, dibenzothiphene, dibenzofuran, dibenzoselenophene, azatriphenylene, azacarbazole, aza-dibenzothiophene, aza-dibenzofuran, and aza-dibenzoselenophene. The host can include a metal complex. The host can be a specific compound selected from the group consisting of:

173
-continued
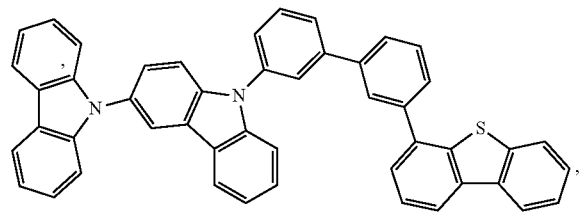
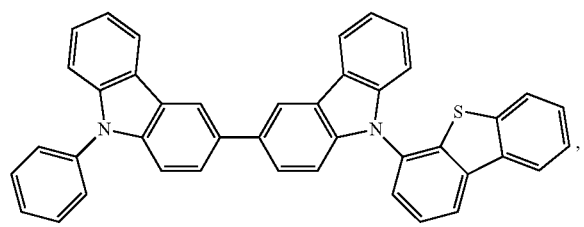
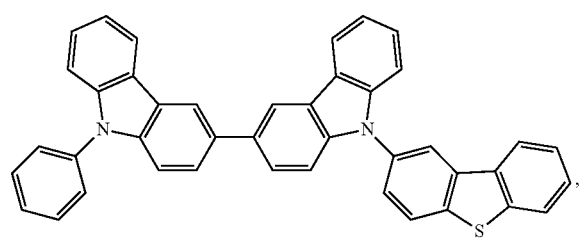
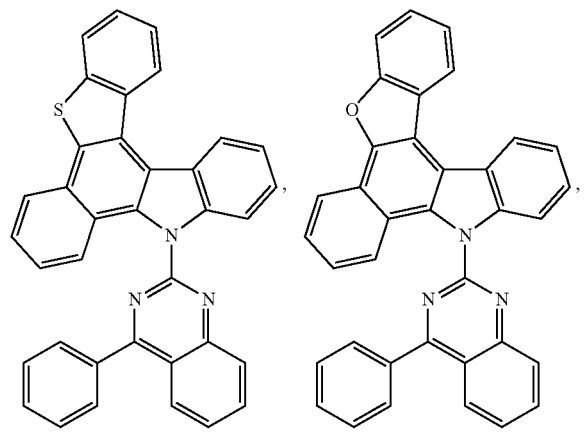
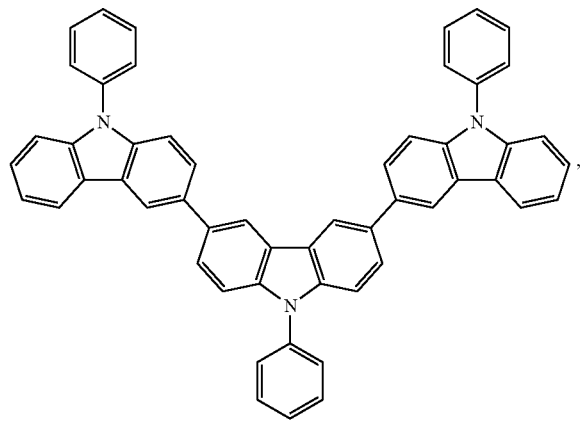
174
-continued
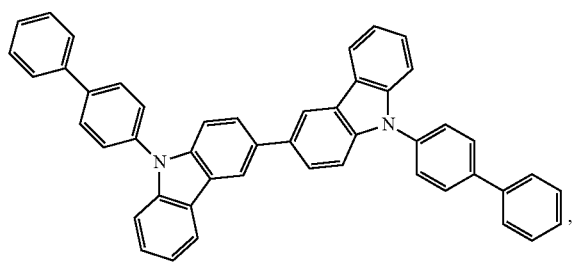
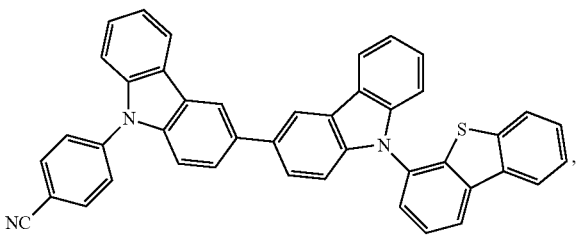
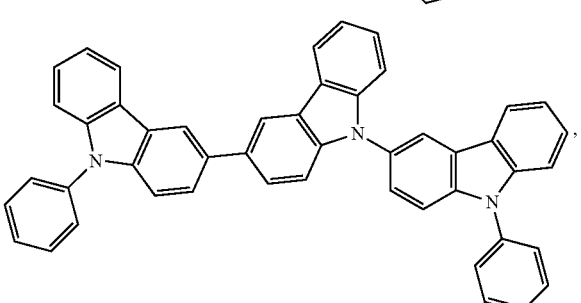
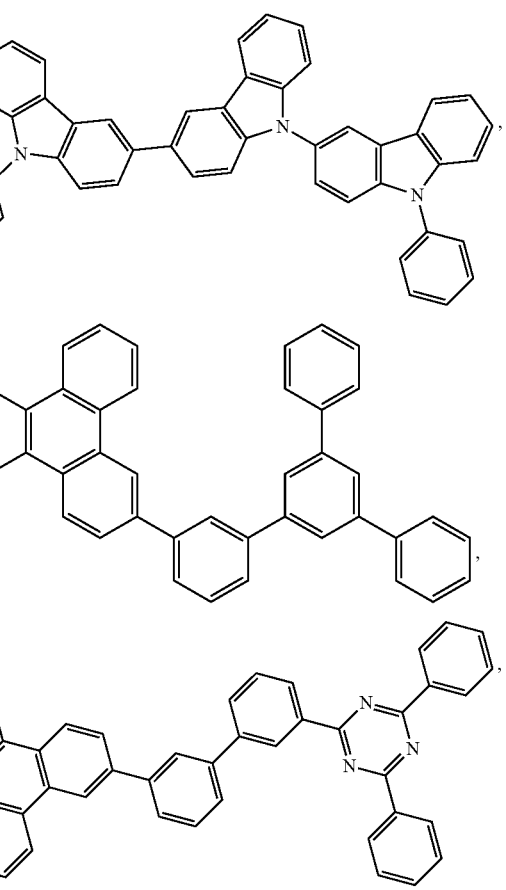
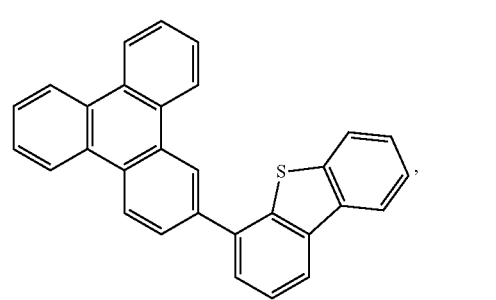

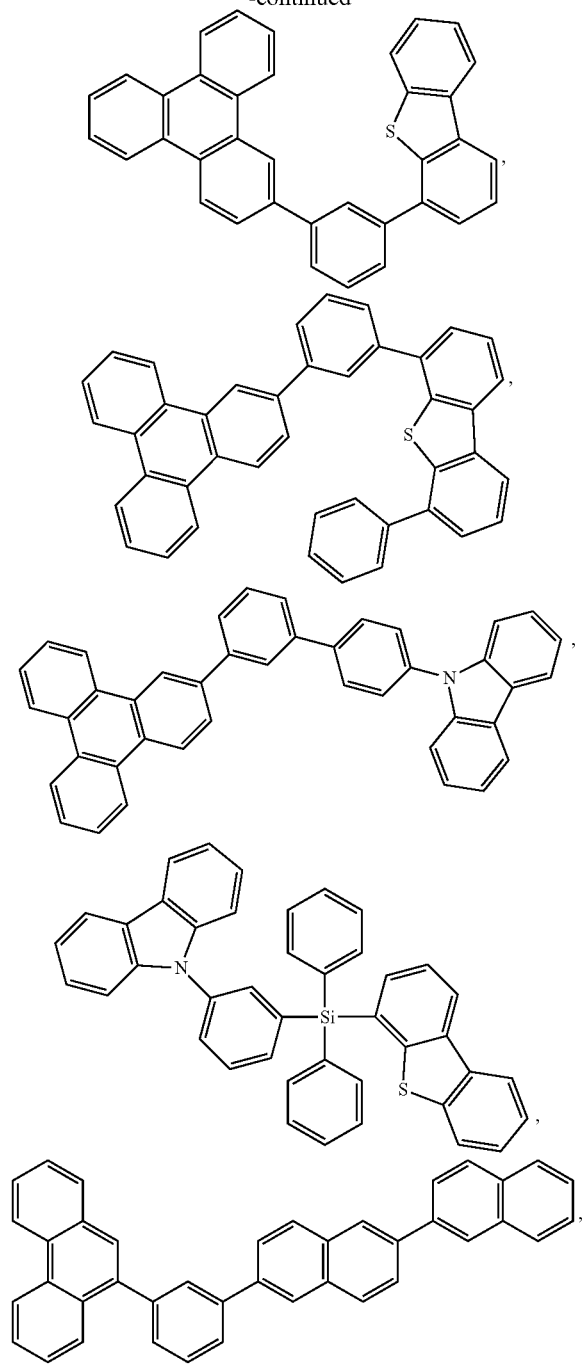

and combinations thereof.

Formulations:

In yet another aspect of the present disclosure, a formulation that comprises a compound according to Formula I is described. The formulation can include one or more components selected from the group consisting of a solvent, a host, a hole injection material, hole transport material, and an electron transport layer material, disclosed herein.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

HIL/HTL:

A hole injecting/transporting material to be used in the present invention is not particularly limited, and any compound may be used as long as the compound is typically used as a hole injecting/transporting material. Examples of the material include, but are not limited to: a phthalocyanine or porphyrin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as $MoO_x$; a p-type semiconducting organic compound, such as 1,4,5,8,9,12-Hexaazatriphenylenehexacarbonitrile; a metal complex, and cross-linkable compounds.

Examples of aromatic amine derivatives used in HIL or HTL include, but are not limited to the following general structures:

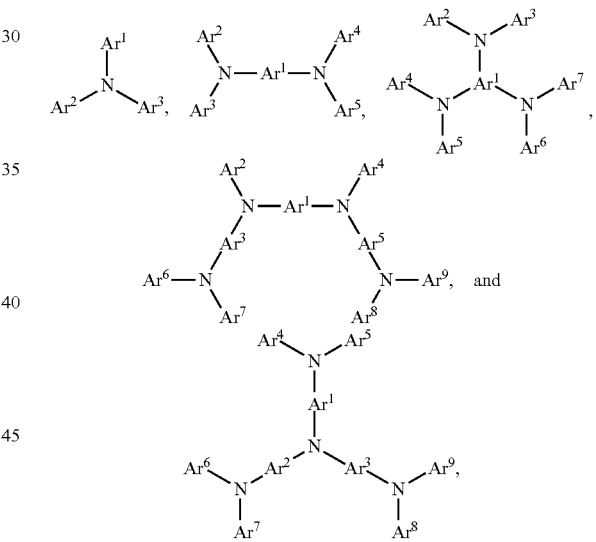

Each of $Ar^1$ to $Ar^9$ is selected from the group consisting of aromatic hydrocarbon cyclic compounds such as benzene, biphenyl, triphenyl, triphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each Ar is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, $Ar^1$ to $Ar^9$ is independently selected from the group consisting of:

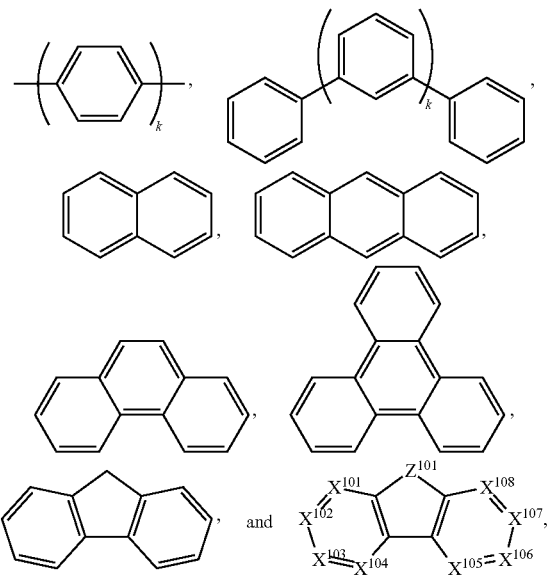

wherein k is an integer from 1 to 20; $X^{101}$ to $X^{108}$ is C (including CH) or N; $Z^{101}$ is $NAr^1$, O, or S; $Ar^1$ has the same group defined above.

Examples of metal complexes used in HIL or HTL include, but are not limited to the following general formula:

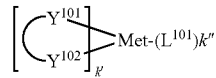

wherein Met is a metal, which can have an atomic weight greater than 40; $(Y^{101}-Y^{102})$ is a bidentate ligand, $Y^{101}$ and $Y^{102}$ are independently selected from C, N, O, P, and S; $L^{101}$ is an ancillary ligand; k' is an integer value from 1 to the maximum number of ligands that may be attached to the metal; and k'+k" is the maximum number of ligands that may be attached to the metal.

In one aspect, $(Y^{101}-Y^{102})$ is a 2-phenylpyridine derivative. In another aspect, $(Y^{101}-Y^{102})$ is a carbene ligand. In another aspect, Met is selected from Ir, Pt, Os, and Zn. In a further aspect, the metal complex has a smallest oxidation potential in solution vs. $Fc^+/Fc$ couple less than about 0.6 V.
Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. While the Table below categorizes host materials as preferred for devices that emit various colors, any host material may be used with any dopant so long as the triplet criteria is satisfied.

Examples of metal complexes used as host are preferred to have the following general formula:

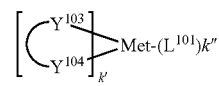

wherein Met is a metal; $(Y^{103}-Y^{104})$ is a bidentate ligand, $Y^{103}$ and $Y^{104}$ are independently selected from C, N, O, P, and S; $L^{101}$ is an another ligand; k' is an integer value from 1 to the maximum number of ligands that may be attached to the metal; and k'+k" is the maximum number of ligands that may be attached to the metal.

In one aspect, the metal complexes are:

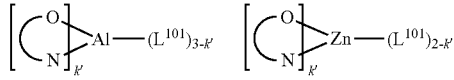

wherein (O—N) is a bidentate ligand, having metal coordinated to atoms O and N.

In another aspect, Met is selected from Ir and Pt. In a further aspect, $(Y^{103}-Y^{104})$ is a carbene ligand.

Examples of organic compounds used as host are selected from the group consisting of aromatic hydrocarbon cyclic compounds such as benzene, biphenyl, triphenyl, triphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each group is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, the host compound contains at least one of the following groups in the molecule:

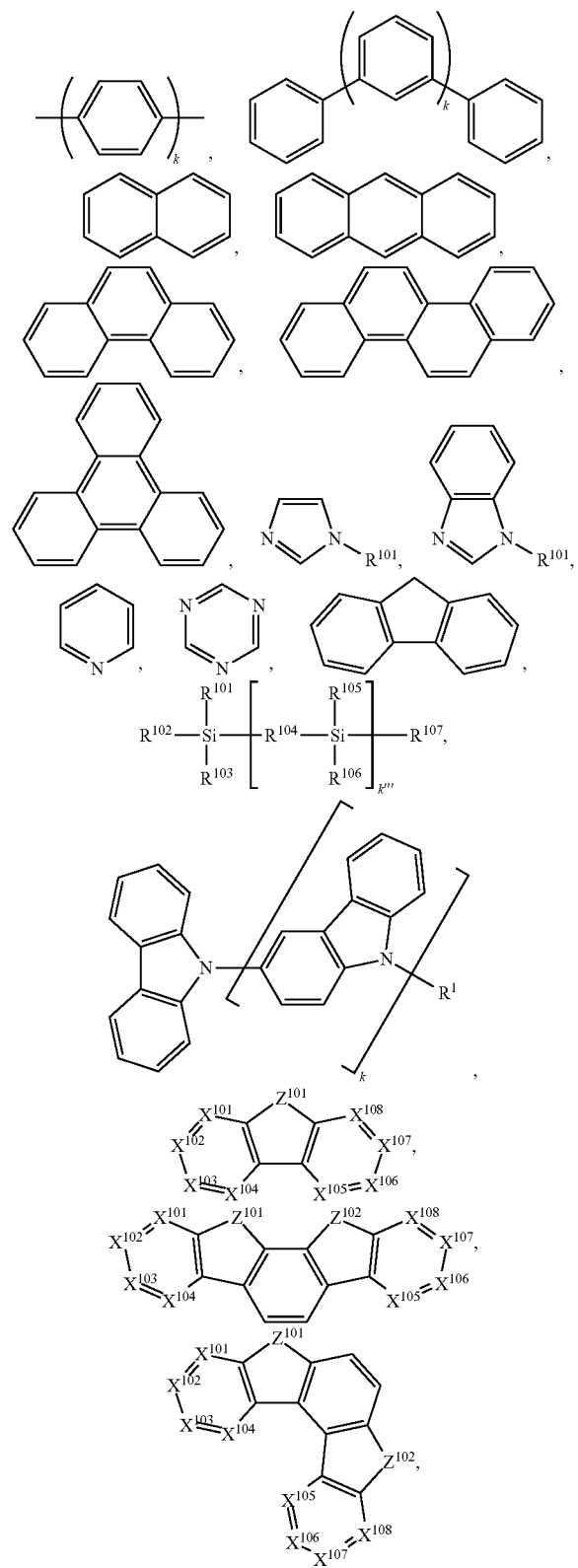

-continued

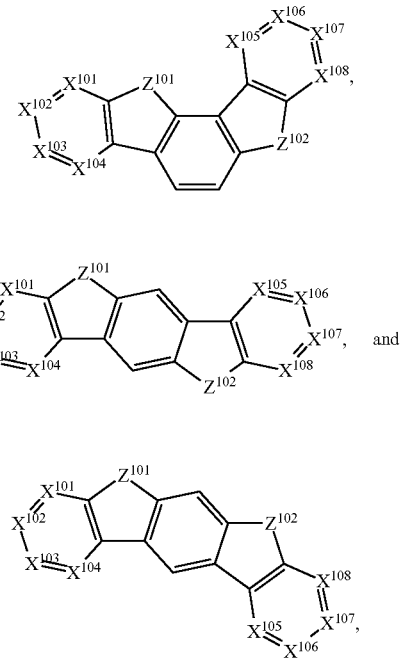

wherein $R^{101}$ to $R^{107}$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above. k is an integer from 0 to 20 or 1 to 20; k''' is an integer from 0 to 20. $X^{101}$ to $X^{108}$ is selected from C (including CH) or N. $Z^{101}$ and $Z^{102}$ is selected from $NR^{101}$, O, or S.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one aspect, the compound used in the HBL contains the same molecule or the same functional groups used as the host described above.

In another aspect, the compound used in the HBL contains at least one of the following groups in the molecule:

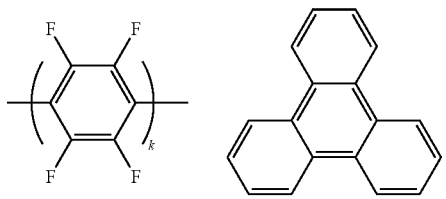

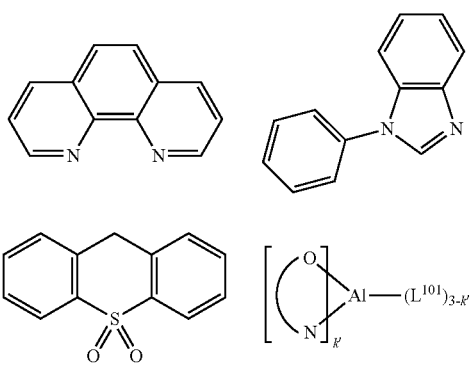

wherein k is an integer from 1 to 20; $L^{101}$ is an another ligand, k' is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, the compound used in ETL contains at least one of the following groups in the molecule:

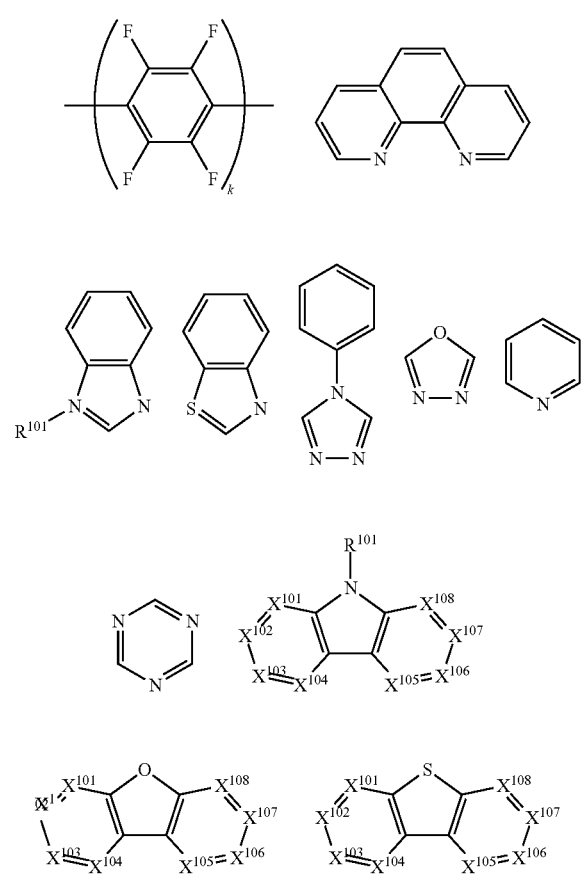

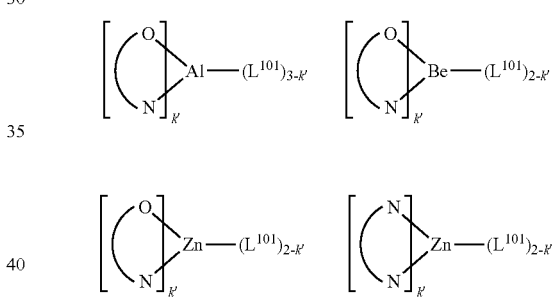

wherein $R^{101}$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above. $Ar^1$ to $Ar^a$ has the similar definition as Ar's mentioned above. k is an integer from 1 to 20. $X^{101}$ to $X^{108}$ is selected from C (including CH) or N.

In another aspect, the metal complexes used in ETL contains, but is not limited to, the following general formula:

wherein (O—N) or (N—N) is a bidentate ligand, having metal coordinated to atoms O, N or N, N; $L^{101}$ is another ligand; k' is an integer value from 1 to the maximum number of ligands that may be attached to the metal.

In any above-mentioned compounds used in each layer of the OLED device, the hydrogen atoms can be partially or fully deuterated. Thus, any specifically listed substituent, such as, without limitation, methyl, phenyl, pyridyl, etc. encompasses undeuterated, partially deuterated, and fully deuterated versions thereof. Similarly, classes of substituents such as, without limitation, alkyl, aryl, cycloalkyl, heteroaryl, etc. also encompass undeuterated, partially deuterated, and fully deuterated versions thereof.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table A below. Table A lists non-limiting classes of materials, non-limiting examples of compounds for each class, and references that disclose the materials.

TABLE A

| MATERIAL | EXAMPLES OF MATERIAL | PUBLICATIONS |
|---|---|---|
| Hole injection materials | | |
| Phthalocyanine and porphyrin compounds | 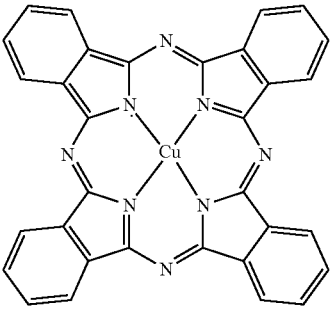 | Appl. Phys. Lett. 69, 2160 (1996) |
| Starburst triarylamines | 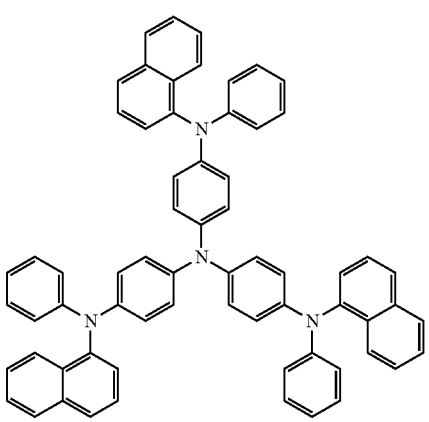 [SMILES: c1ccc(N(c2ccc(N(c3ccc(N(c4ccccc4)c4cccc5ccccc45)cc3)c3ccc(N(c4ccccc4)c4cccc5ccccc45)cc3)cc2)c2cccc3ccccc23)cc1] | J. Lumin. 72-74, 985 (1997) |
| $CF_x$ Fluorohydrocarbon polymer | $-[CH_xF_y]_n-$ | Appl. Phys. Lett. 78, 673 (2001) |
| Conducting polymers (e.g., PEDOT:PSS, polyaniline, polythiophene) | 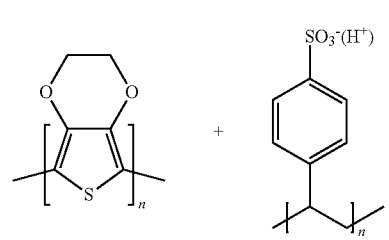 | Synth. Met. 87, 171 (1997) WO2007002683 |
| Phosphonic acid and silane SAMs | 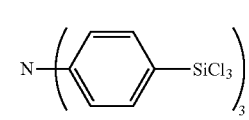 | US20030162053 |
| Triarylamine or polythiophene polymers with conductivity dopants | 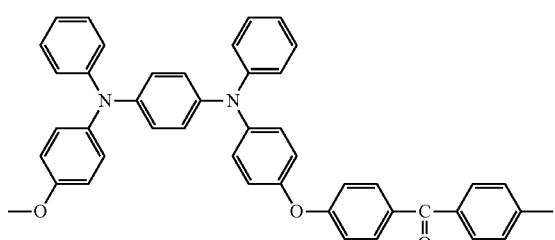 and | EP1725079A1 |

TABLE A-continued
| MATERIAL | EXAMPLES OF MATERIAL | PUBLICATIONS |
|---|---|---|
| | 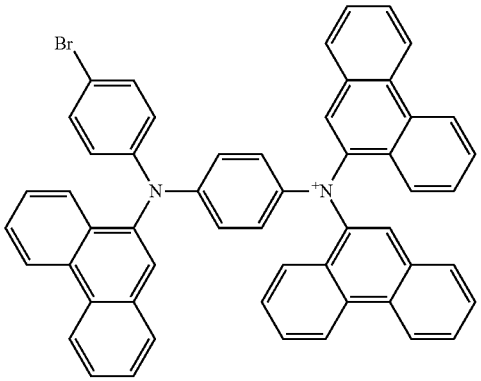 [SMILES: Brc1ccc(N(c2ccc([NH+](c3cc4ccccc4c4ccccc34)c3cc4ccccc4c4ccccc34)cc2)c2cc3ccccc3c3ccccc23)cc1] | |
| | 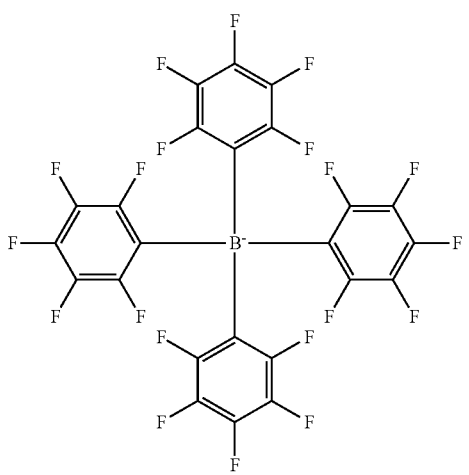 [SMILES: Fc1c(F)c(F)c([B-](c2c(F)c(F)c(F)c(F)c2F)(c2c(F)c(F)c(F)c(F)c2F)c2c(F)c(F)c(F)c(F)c2F)c(F)c1F] | |
| Organic compounds with conductive inorganic compounds, such as molybdenum and tungsten oxides | 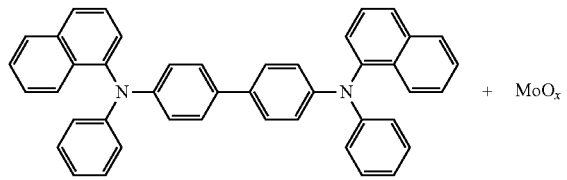 [SMILES: c1ccc(N(c2ccc(-c3ccc(N(c4ccccc4)c4cccc5ccccc45)cc3)cc2)c2cccc3ccccc23)cc1] | US20050123751<br>SID Symposium Digest, 37, 923 (2006)<br>WO2009018009 |
| n-type semiconducting organic complexes | 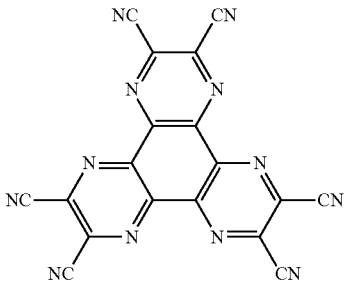 [SMILES: N#Cc1nc2c3nc(C#N)c(C#N)nc3c3nc(C#N)c(C#N)nc3c2nc1C#N] | US20020158242 |
| Metal organometallic complexes | 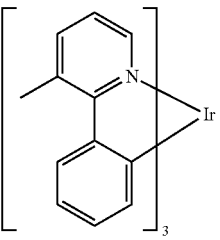 | US20060240279 |

TABLE A-continued

| MATERIAL | EXAMPLES OF MATERIAL | PUBLICATIONS |
| --- | --- | --- |
| Cross-linkable compounds | | US20080220265 |
| Polythiophene based polymers and copolymers | | WO 2011075644<br>EP2350216 |
| Hole transporting materials | | |
| Triarylamines (e.g., TPD, α-NPD) | | Appl. Phys. Lett. 51, 913 (1987) |
| | | US5061569 |

TABLE A-continued

| MATERIAL | EXAMPLES OF MATERIAL | PUBLICATIONS |
|---|---|---|
| | | EP650955 |
| | | J. Mater. Chem. 3, 319 (1993) |
| | | Appl. Phys. Lett. 90, 183503 (2007) |

TABLE A-continued

| MATERIAL | EXAMPLES OF MATERIAL | PUBLICATIONS |
|---|---|---|
| | | Appl. Phys. Lett. 90, 183503 (2007) |
| Triarylamine on spirofluorene core | | Synth. Met. 91, 209 (1997) |
| Arylamine carbazole compounds | | Adv. Mater. 6, 677 (1994), US20080124572 |
| Triarylamine with (di)benzothiophene/ (di)benzofuran | | US20070278938, US20080106190 US20110163302 |

TABLE A-continued
| MATERIAL | EXAMPLES OF MATERIAL | PUBLICATIONS |
|---|---|---|
| Indolocarbazoles | 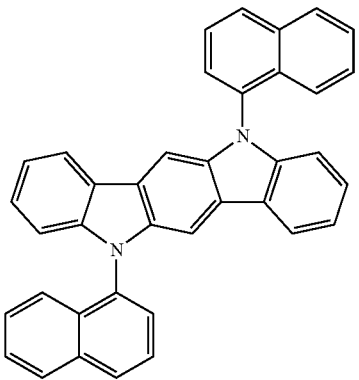 [SMILES: c1ccc2c(-n3c4ccccc4c4cc5c(cc43)c3ccccc3n5-c3cccc4ccccc34)cccc2c1] | Synth. Met. 111, 421 (2000) |
| Isoindole compounds | 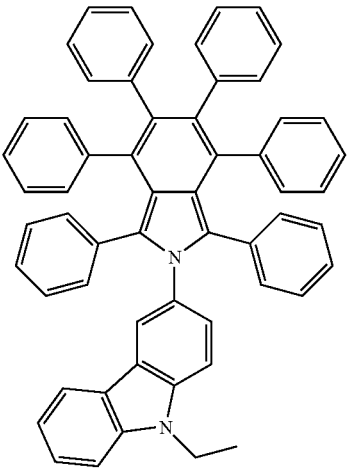 [SMILES: CCn1c2ccccc2c2cc(-n3c(-c4ccccc4)c4c(-c5ccccc5)c(-c5ccccc5)c(-c5ccccc5)c(-c5ccccc5)c4c3-c3ccccc3)ccc21] | Chem. Mater. 15, 3148 (2003) |
| Metal carbene complexes | 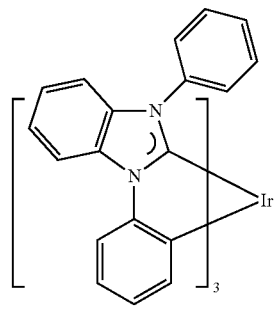 | US20080018221 |
Phosphorescent OLED host materials
Red hosts
| Arylcarbazoles | 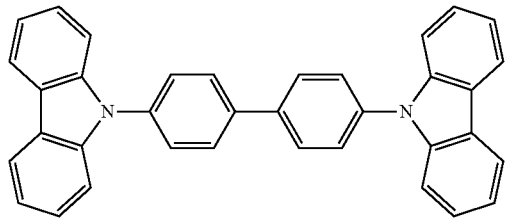 [SMILES: c1ccc2c(c1)c1ccccc1n2-c1ccc(-c2ccc(-n3c4ccccc4c4ccccc43)cc2)cc1] | Appl. Phys. Lett. 78, 1622 (2001) |

TABLE A-continued

| MATERIAL | EXAMPLES OF MATERIAL | PUBLICATIONS |
| --- | --- | --- |
| Metal 8-hydroxyquinolates (e.g., Alq3, BAlq) | | Nature 395, 151 (1998) |
| | | US20060202194 |
| | | WO2005014551 |
| | | WO2006072002 |
| Metal phenoxybenzothiazole compounds | | Appl. Phys. Lett. 90, 123509 (2007) |
| Conjugated oligomers and polymers (e.g., polyfluorene) | | Org. Electron. 1, 15 (2000) |
| Aromatic fused rings | | WO2009066779, WO2009066778, WO2009063833, US20090045731, US20090045730, WO2009008311, US20090008605, US20090009065 |

TABLE A-continued

| MATERIAL | EXAMPLES OF MATERIAL | PUBLICATIONS |
|---|---|---|
| Zinc complexes | | WO2010056066 |
| Chrysene based compounds | | WO2011086863 |

Green hosts

| MATERIAL | EXAMPLES OF MATERIAL | PUBLICATIONS |
|---|---|---|
| Arylcarbazoles | | Appl. Phys. Lett. 78, 1622 (2001) |
| | | US20030175553 |
| | | WO2001039234 |
| Aryltriphenylene compounds | | US20060280965 |

TABLE A-continued
| MATERIAL | EXAMPLES OF MATERIAL | PUBLICATIONS |
|---|---|---|
| | 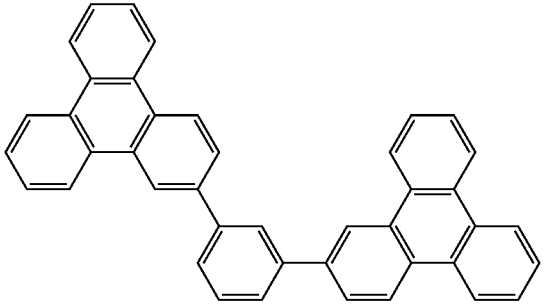 [SMILES: c1cc(-c2ccc3c4ccccc4c4ccccc4c3c2)cc(-c2ccc3c4ccccc4c4ccccc4c3c2)c1] | US20060280965 |
| | 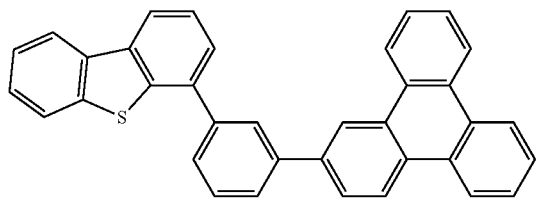 [SMILES: c1cc(-c2ccc3c4ccccc4c4ccccc4c3c2)cc(-c2cccc3c2sc2ccccc23)c1] | WO2009021126 |
| Poly-fused heteroaryl compounds | 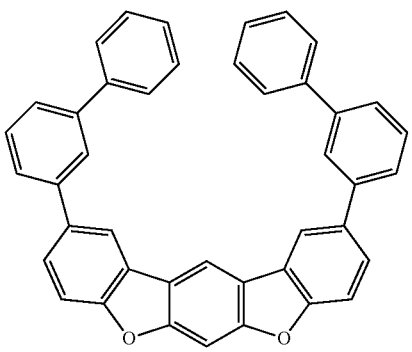 [SMILES: c1ccc(-c2cccc(-c3ccc4oc5cc6oc7ccc(-c8cccc(-c9ccccc9)c8)cc7c6cc5c4c3)c2)cc1] | US20090309488<br>US20090302743<br>US20100012931 |
| Donor acceptor type molecules | 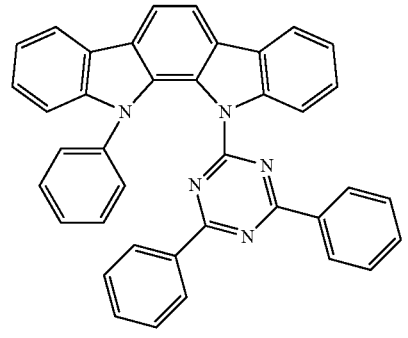 [SMILES: c1ccc(-c2nc(-c3ccccc3)nc(-n3c4ccccc4c4ccc5c6ccccc6n(-c6ccccc6)c5c43)n2)cc1] | WO2008056746 |
| | 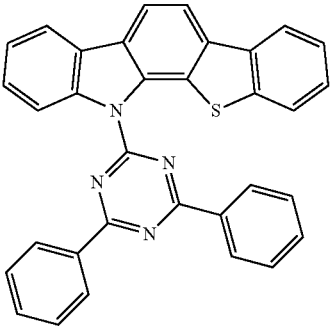 [SMILES: c1ccc(-c2nc(-c3ccccc3)nc(-n3c4ccccc4c4ccc5c6ccccc6sc5c43)n2)cc1] | WO2010107244 |

TABLE A-continued
| MATERIAL | EXAMPLES OF MATERIAL | PUBLICATIONS |
|---|---|---|
| Aza-carbazole/DBT/ DBF | 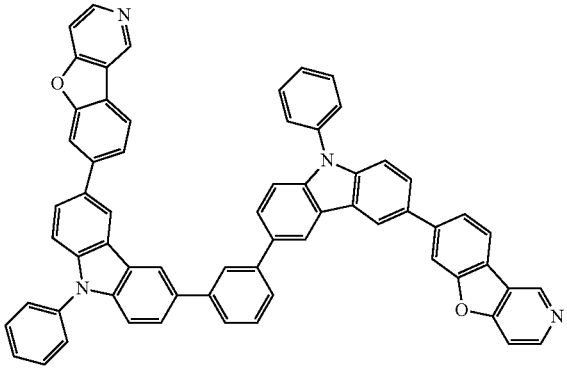 [SMILES: c1ccc(-n2c3ccc(-c4cccc(-c5ccc6c(c5)c5cc(-c7ccc8c(c7)oc7ccncc78)ccc5n6-c5ccccc5)c4)cc3c3cc(-c4ccc5c(c4)oc4ccncc45)ccc32)cc1] | JP2008074939 |
| | 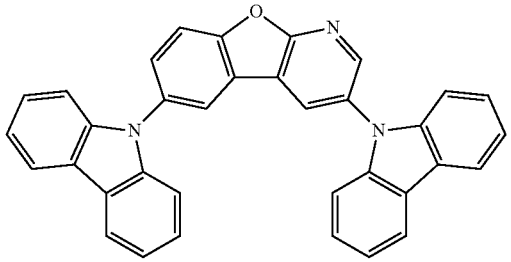 [SMILES: c1ccc2c(c1)c1ccccc1n2-c1ccc2oc3ncc(-n4c5ccccc5c5ccccc54)cc3c2c1] | US20100187984 |
| Polymers (e.g., PVK) | 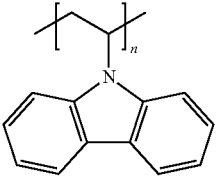 | Appl. Phys. Lett. 77, 2280 (2000) |
| Spirofluorene compounds | 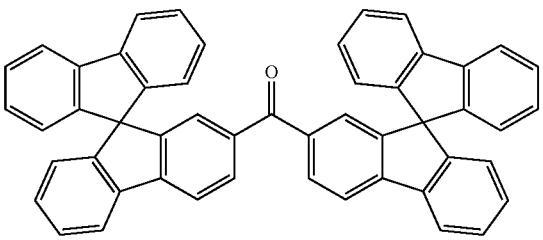 [SMILES: O=C(c1ccc2c(c1)C1(c3ccccc3-c3ccccc31)c1ccccc1-2)c1ccc2c(c1)C1(c3ccccc3-c3ccccc31)c1ccccc1-2] | WO2004093207 |
| Metal phenoxybenzooxazole compounds | 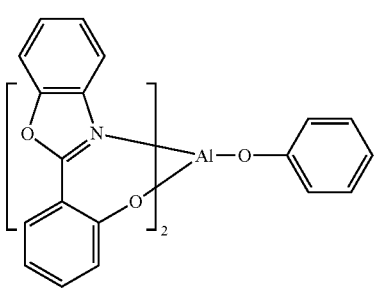 | WO2005089025 |

TABLE A-continued

| MATERIAL | EXAMPLES OF MATERIAL | PUBLICATIONS |
|---|---|---|
| | | WO2006132173 |
| | | JP200511610 |
| Spirofluorene-carbazole compounds | | JP2007254297 |
| | | JP2007254297 |
| Indolocarbazoles | | WO2007063796 |

TABLE A-continued

| MATERIAL | EXAMPLES OF MATERIAL | PUBLICATIONS |
|---|---|---|
| | | WO2007063754 |
| 5-member ring electron deficient heterocycles (e.g., triazole, oxadiazole) | | J. Appl. Phys. 90, 5048 (2001) |
| | | WO2004107822 |
| Tetraphenylene complexes | | US20050112407 |
| Metal phenoxypyridine compounds | | WO2005030900 |

TABLE A-continued

| MATERIAL | EXAMPLES OF MATERIAL | PUBLICATIONS |
|---|---|---|
| Metal coordination complexes (e.g., Zn, Al with N^N ligands) | | US20040137268, US20040137267 |

Blue hosts

| MATERIAL | EXAMPLES OF MATERIAL | PUBLICATIONS |
|---|---|---|
| Arylcarbazoles | | Appl. Phys. Lett. 82, 2422 (2003) |
| | | US20070190359 |
| Dibenzothiophene/ Dibenzofuran-carbazole compounds | | WO2006114966, US20090167162 |
| | | US20090167162 |
| | | WO2009086028 |

TABLE A-continued

| MATERIAL | EXAMPLES OF MATERIAL | PUBLICATIONS |
|---|---|---|
| | | US20090030202, US20090017330 |
| | | US20100084966 |
| Silicon aryl compounds | | US20050238919 |
| | | WO2009003898 |
| Silicon/Germanium aryl compounds | | EP2034538A |
| Aryl benzoyl ester | | WO2006100298 |

TABLE A-continued

| MATERIAL | EXAMPLES OF MATERIAL | PUBLICATIONS |
| --- | --- | --- |
| Carbazole linked by non-conjugated groups | | US20040115476 |
| Aza-carbazoles | | US20060121308 |
| High triplet metal organometallic complex | | US7154114 |

Phosphorescent dopants
Red dopants

| | | |
| --- | --- | --- |
| Heavy metal porphyrins (e.g., PtOEP) | | Nature 395, 151 (1998) |
| Iridium(III) organometallic complexes | | Appl. Phys. Lett. 78, 1622 (2001) |

TABLE A-continued

| MATERIAL | EXAMPLES OF MATERIAL | PUBLICATIONS |
|---|---|---|
| | | US20030072964 |
| | | US20030072964 |
| | | US20060202194 |
| | | US20060202194 |
| | | US20070087321 |

| MATERIAL | EXAMPLES OF MATERIAL | PUBLICATIONS |
| --- | --- | --- |
| | 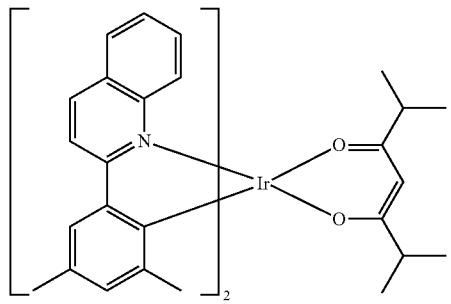 | US20080261076<br>US20100090591 |
| | 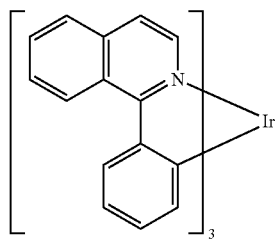 | US20070087321 |
| | 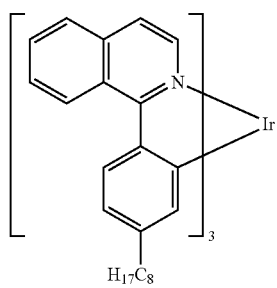 | Adv. Mater.<br>19, 739 (2007) |
| | 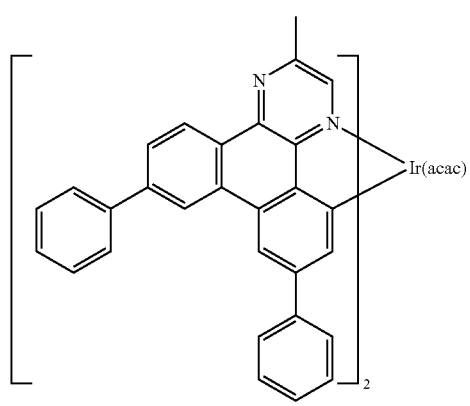 | WO2009100991 |
| | 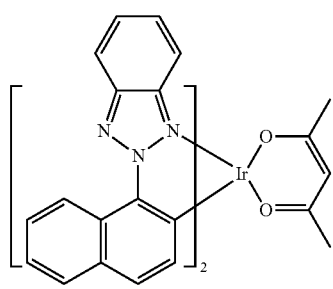 | WO2008101842 |

TABLE A-continued
| MATERIAL | EXAMPLES OF MATERIAL | PUBLICATIONS |
|---|---|---|
| | 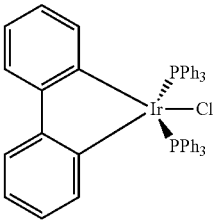 | US7232618 |
| Platinum(II) organometallic complexes | 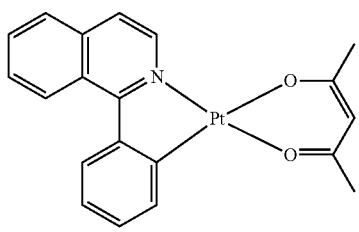 | WO2003040257 |
| | 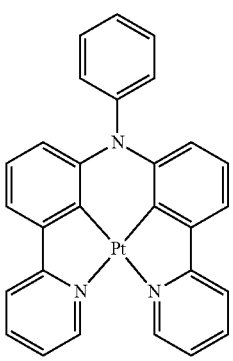 | US20070103060 |
| Osmium(III) complexes | 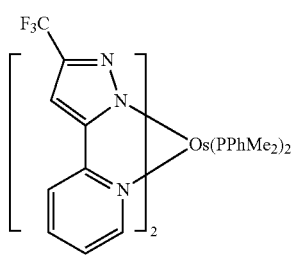 | Chem. Mater. 17, 3532 (2005) |
| Ruthenium(II) complexes | 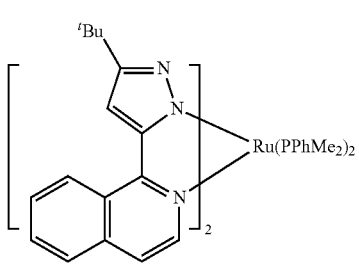 | Adv. Mater. 17, 1059 (2005) |
| Rhenium (I), (II), and (III) complexes | 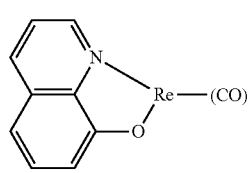 | US20050244673 |

TABLE A-continued
| MATERIAL | EXAMPLES OF MATERIAL | PUBLICATIONS |
|---|---|---|
| | Green dopants | |
| Iridium(III) organometallic complexes | 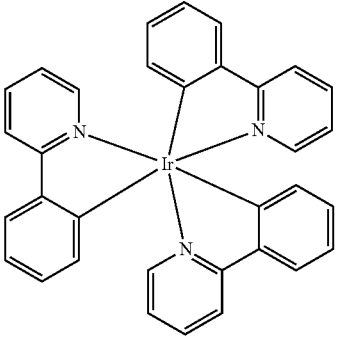<br>and its derivatives | Inorg. Chem. 40, 1704 (2001) |
| | 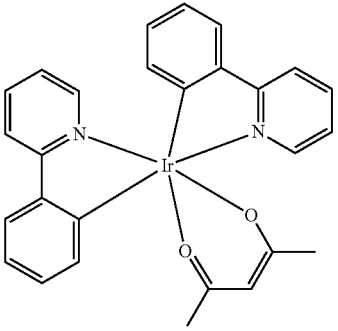 | US20020034656 |
| | 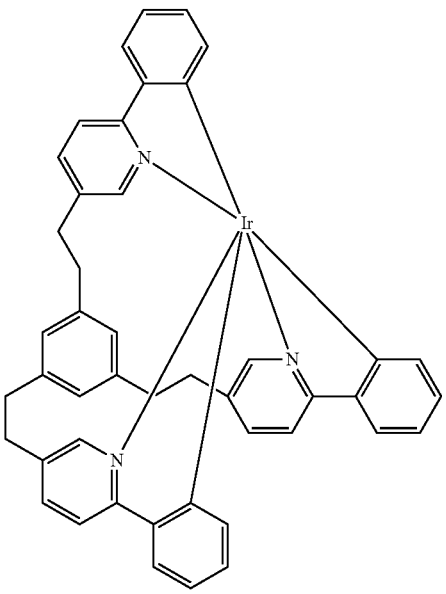 | US7332232 |

TABLE A-continued
| MATERIAL | EXAMPLES OF MATERIAL | PUBLICATIONS |
|---|---|---|
| | 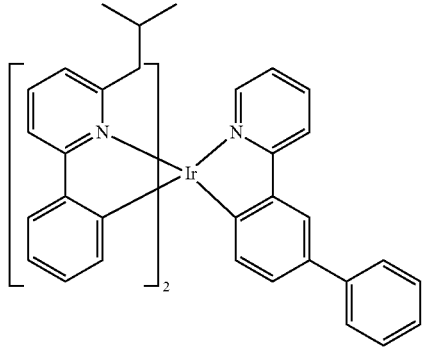 | US20090108737 |
| | 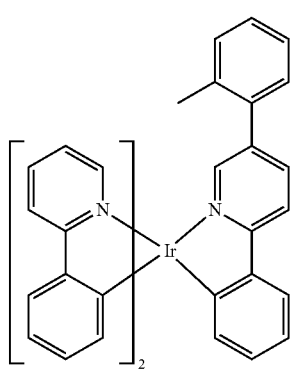 | WO2010028151 |
| | 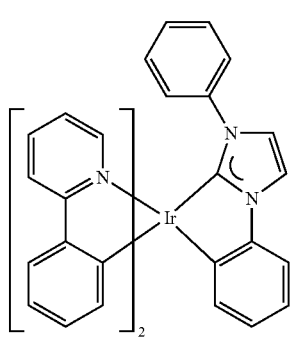 | EP1841834B |
| | 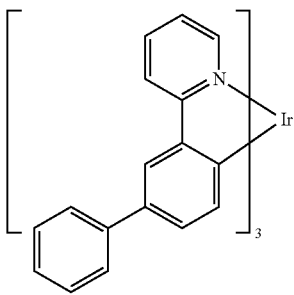 | US20060127696 |
| | 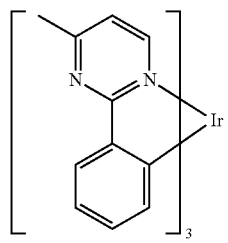 | US20090039776 |

TABLE A-continued

| MATERIAL | EXAMPLES OF MATERIAL | PUBLICATIONS |
|---|---|---|
| | | US6921915 |
| | | US20100244004 |
| | | US6687266 |
| | | Chem. Mater. 16, 2480 (2004) |
| | | US20070190359 |

TABLE A-continued

| MATERIAL | EXAMPLES OF MATERIAL | PUBLICATIONS |
|---|---|---|
| | | US 20060008670<br>JP2007123392 |
| | | WO2010086089,<br>WO2011044988 |
| | | Adv. Mater.<br>16, 2003 (2004) |
| | | Angew. Chem. Int.<br>Ed. 2006, 45, 7800 |
| | | WO2009050290 |
| | | US20090165846 |

TABLE A-continued
| MATERIAL | EXAMPLES OF MATERIAL | PUBLICATIONS |
|---|---|---|
| | 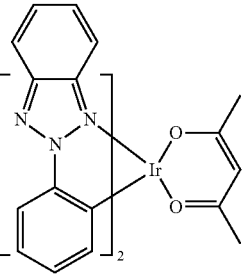 | US20080015355 |
| | 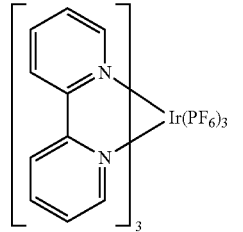 | US20010015432 |
| | 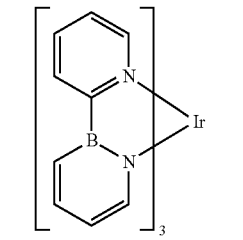 | US20100295032 |
| Monomer for polymeric metal organometallic compounds | 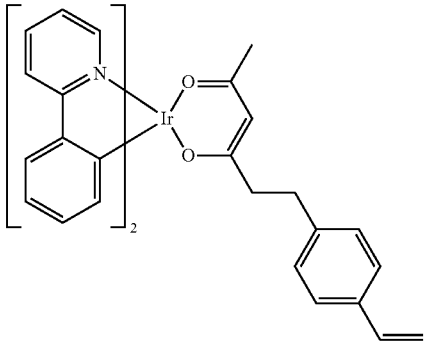 | US7250226, US7396598 |
| Pt(II) organometallic complexes, including polydentated ligands | 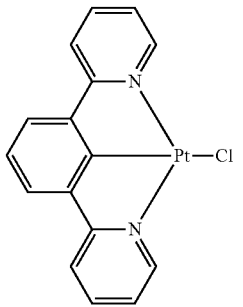 | Appl. Phys. Lett. 86, 153505 (2005) |

TABLE A-continued

| MATERIAL | EXAMPLES OF MATERIAL | PUBLICATIONS |
| --- | --- | --- |
| | | Appl. Phys. Lett. 86, 153505 (2005) |
| | | Chem. Lett. 34, 592 (2005) |
| | | WO2002015645 |
| | | US20060263635 |
| | | US20060182992<br>US20070103060 |

TABLE A-continued
| MATERIAL | EXAMPLES OF MATERIAL | PUBLICATIONS |
|---|---|---|
| Cu complexes | 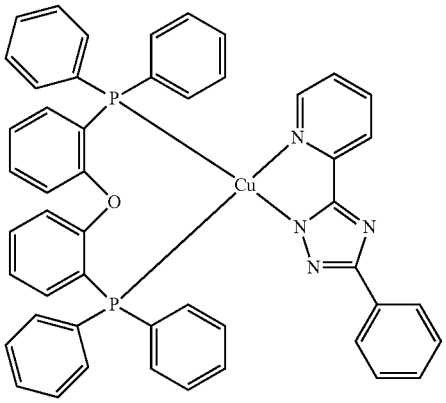 | WO2009000673 |
| | 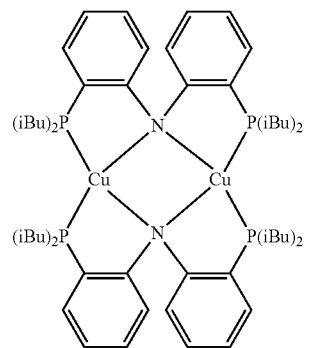 | US20070111026 |
| Gold complexes | 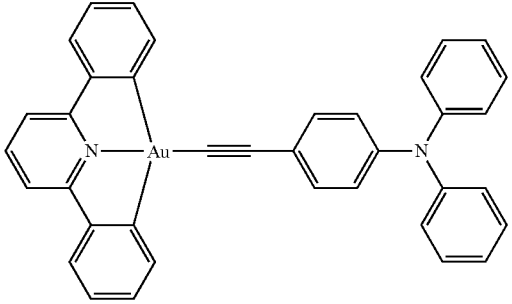 | Chem. Commun. 2906 (2005) |
| Rhenium(III) complexes | 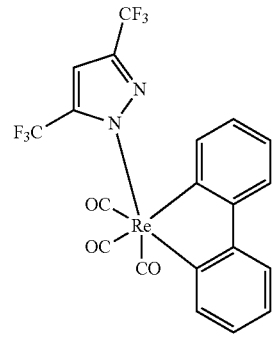 | Inorg. Chem. 42, 1248 (2003) |

| MATERIAL | EXAMPLES OF MATERIAL | PUBLICATIONS |
|---|---|---|
| Osmium(II) complexes | | US7279704 |
| Deuterated organometallic complexes | | US20030138657 |
| Organometallic complexes with two or more metal centers | | US20030152802 |
| | | US7090928 |

TABLE A-continued

| MATERIAL | EXAMPLES OF MATERIAL | PUBLICATIONS |
| --- | --- | --- |
| Blue dopants | | |
| Iridium(III) organometallic complexes | | WO2002002714 |
| | | WO2006009024 |
| | | US20060251923<br>US20110057559<br>US20110204333 |
| | | US7393599,<br>WO2006056418,<br>US20050260441,<br>WO2005019373 |
| | | US7534505 |
| | | WO2011051404 |

TABLE A-continued

| MATERIAL | EXAMPLES OF MATERIAL | PUBLICATIONS |
|---|---|---|
| | | US7445855 |
| | | US20070190359, US20080297033 US20100148663 |
| | | US7338722 |
| | | US20020134984 |
| | | Angew. Chem. Int. Ed. 47, 4542 (2008) |

TABLE A-continued
| MATERIAL | EXAMPLES OF MATERIAL | PUBLICATIONS |
|---|---|---|
| | 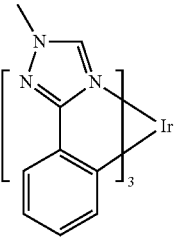 | Chem. Mater. 18, 5119 (2006) |
| | 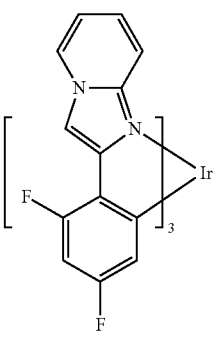 | Inorg. Chem. 46, 4308 (2007) |
| | 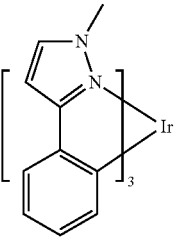 | WO2005123873 |
| | 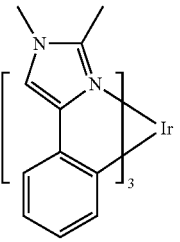 | WO2005123873 |
| | 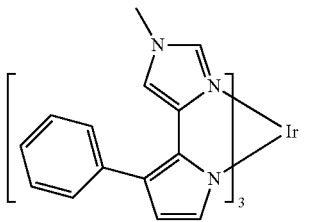 | WO2007004380 |

TABLE A-continued

| MATERIAL | EXAMPLES OF MATERIAL | PUBLICATIONS |
|---|---|---|
| | | WO2006082742 |
| Osmium(II) complexes | | US7279704 |
| | | Organometallics 23, 3745 (2004) |
| Gold complexes | | Appl. Phys. Lett. 74, 1361 (1999) |
| Platinum(II) complexes | | WO2006098120, WO2006103874 |

TABLE A-continued

| MATERIAL | EXAMPLES OF MATERIAL | PUBLICATIONS |
|---|---|---|
| Pt tetradentate complexes with at least one metal-carbene bond | 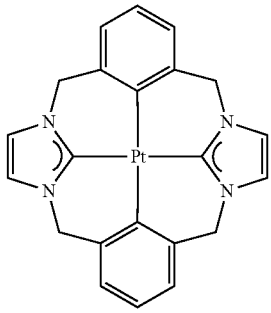 | US7655323 |
| Exciton/hole blocking layer materials | | |
| Bathocuprine compounds (e.g., BCP, BPhen) | 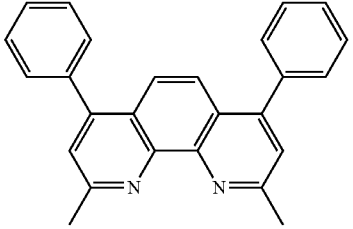 [SMILES: Cc1cc(-c2ccccc2)c2ccc3c(-c4ccccc4)cc(C)nc3c2n1] | Appl. Phys. Lett. 75, 4 (1999) |
| | 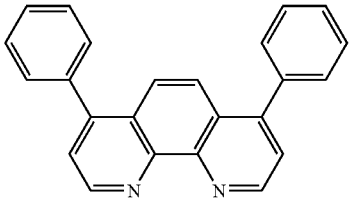 [SMILES: c1ccc(-c2ccnc3c2ccc2c(-c4ccccc4)ccnc23)cc1] | Appl. Phys. Lett. 79, 449 (2001) |
| Metal 8-hydroxyquinolates (e.g. BAlq) | 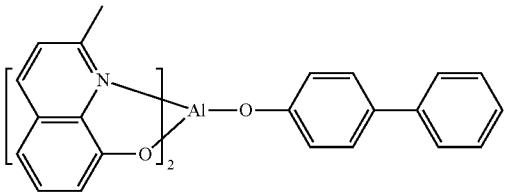 | Appl. Phys. Lett. 81, 162 (2002) |
| 5-member ring electron deficient heterocycles such as triazole, oxadiazole, imidazole, benzoimidazole | 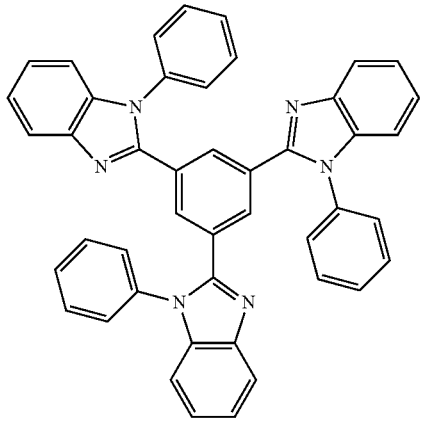 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 81, 162 (2002) |

TABLE A-continued

| MATERIAL | EXAMPLES OF MATERIAL | PUBLICATIONS |
| --- | --- | --- |
| Triphenylene compounds | | US20050025993 |
| Fluorinated aromatic compounds | | Appl. Phys. Lett. 79, 156 (2001) |
| Phenothiazine-S-oxide | | WO2008132085 |
| Silylated five-membered nitrogen, oxygen, sulfur or phosphorus dibenzoheterocycles | | WO2010079051 |

TABLE A-continued
| MATERIAL | EXAMPLES OF MATERIAL | PUBLICATIONS |
|---|---|---|
| Aza-carbazoles | 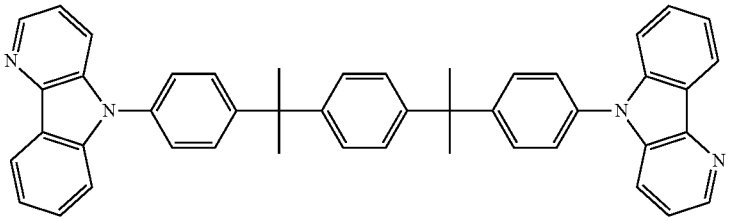 [SMILES: CC(C)(c1ccc(-n2c3ccccc3c3ncccc32)cc1)c1ccc(C(C)(C)c2ccc(-n3c4ccccc4c4ncccc43)cc2)cc1] | US20060121308 |
| Electron transporting materials | | |
| Anthracene-benzoimidazole compounds | 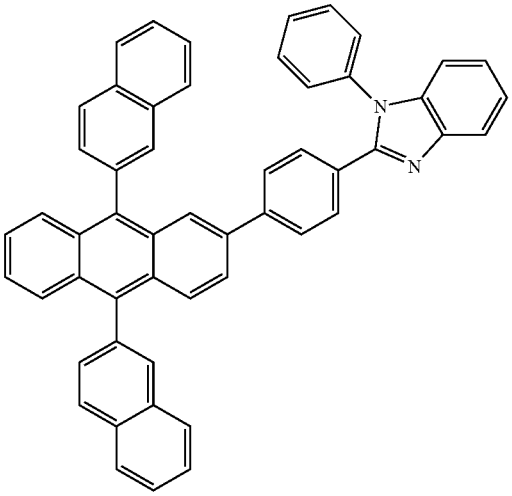 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1] | WO2003060956 |
| | 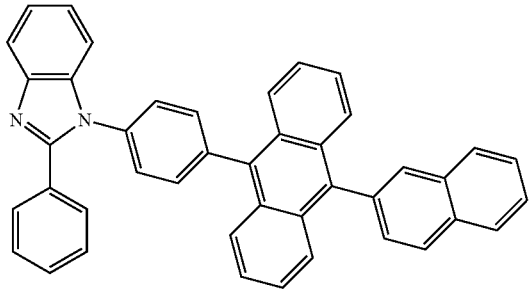 [SMILES: c1ccc(-c2nc3ccccc3n2-c2ccc(-c3c4ccccc4c(-c4ccc5ccccc5c4)c4ccccc34)cc2)cc1] | US20090179554 |
| Aza triphenylene derivatives | 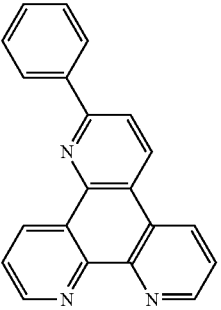 [SMILES: c1ccc(-c2ccc3c4cccnc4c4ncccc4c3n2)cc1] | US20090115316 |
| Anthracene-benzothiazole compounds | 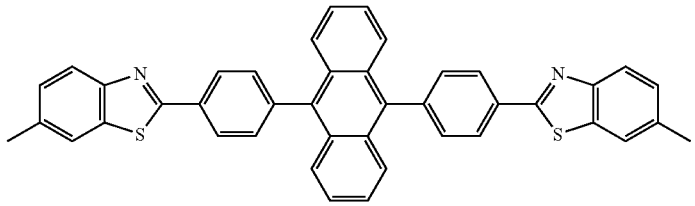 | Appl. Phys. Lett. 89, 063504 (2006) |

TABLE A-continued

| MATERIAL | EXAMPLES OF MATERIAL | PUBLICATIONS |
|---|---|---|
| Metal 8-hydroxyquinolates (e.g., Alq$_3$, Zrq$_4$) | | Appl. Phys. Lett. 51, 913 (1987) US7230107 |
| Metal hydroxybenzoquinolates | | Chem. Lett. 5, 905 (1993) |
| Bathocuprine compounds such as BCP, BPhen, etc | | Appl. Phys. Lett. 91, 263503 (2007) |
| | | Appl. Phys. Lett. 79, 449 (2001) |
| 5-member ring electron deficient heterocycles (e.g., triazole, oxadiazole, imidazole, benzoimidazole) | | Appl. Phys. Lett. 74, 865 (1999) |
| | | Appl. Phys. Lett. 55, 1489 (1989) |

TABLE A-continued
| MATERIAL | EXAMPLES OF MATERIAL | PUBLICATIONS |
|---|---|---|
| | 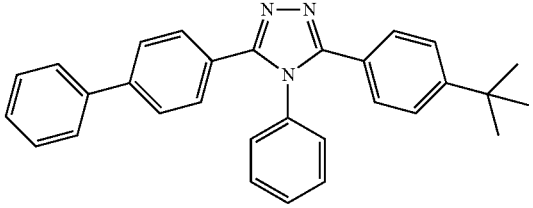 [SMILES: CC(C)(C)c1ccc(-c2nnc(-c3ccc(-c4ccccc4)cc3)n2-c2ccccc2)cc1] | Jpn. J. Apply. Phys. 32, L917 (1993) |
| Silole compounds | 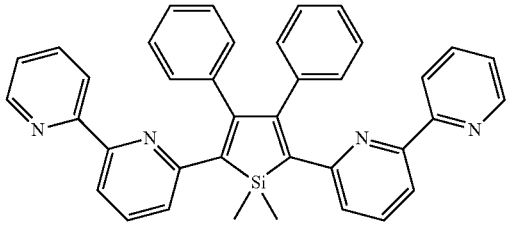 [SMILES: C[Si]1(C)C(c2cccc(-c3ccccn3)n2)=C(c2ccccc2)C(c2ccccc2)=C1c1cccc(-c2ccccn2)n1] | Org. Electron. 4, 113 (2003) |
| Arylborane compounds | 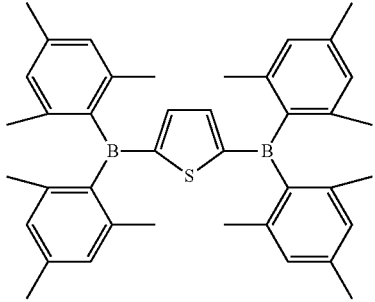 | J. Am. Chem. Soc. 120, 9714 (1998) |
| Fluorinated aromatic compounds | 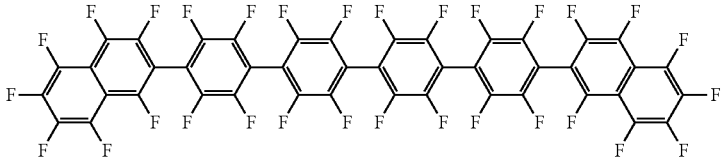 [SMILES: Fc1c(F)c(-c2c(F)c(F)c(-c3c(F)c(F)c4c(F)c(F)c(F)c(F)c4c3F)c(F)c2F)c(F)c(F)c1-c1c(F)c(F)c(-c2c(F)c(F)c(-c3c(F)c(F)c4c(F)c(F)c(F)c(F)c4c3F)c(F)c2F)c(F)c1F] | J. Am. Chem. Soc. 122, 1832 (2000) |
| Fullerene (e.g., C60) | 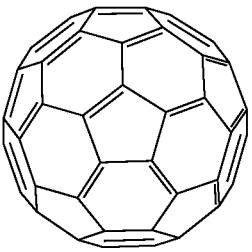 [SMILES: C1=CC2C3C4=c5c6c7c8c(ccc9c%10ccc%11c%12ccc%13c1c3c1c5c3c6c(c89)c%10c%11c3c%12c%131)C1C=CC2C4C71] | US20090101870 |
| Triazine complexes | 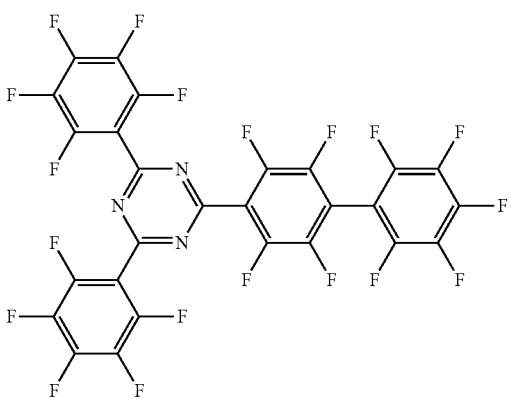 [SMILES: Fc1c(F)c(F)c(-c2nc(-c3c(F)c(F)c(F)c(F)c3F)nc(-c3c(F)c(F)c(-c4c(F)c(F)c(F)c(F)c4F)c(F)c3F)n2)c(F)c1F] | US20040036077 |

TABLE A-continued

| MATERIAL | EXAMPLES OF MATERIAL | PUBLICATIONS |
| --- | --- | --- |
| Zn (N^N) complexes | | US6528187 |

EXPERIMENTAL

A nitrogen substitution in the benzimidazole phenanthridine ligand system is shown to have a desirably strong blue-shifting effect, by calculation and comparison to analogous structures, such as Iridium tris pyridyl-pyridine.

DFT calculations are shown in Table B below. DFT calculations were performed using the B3LYP/cep-31g/THF functional, basis set and solvent polarization, respectively.

Figure 3:
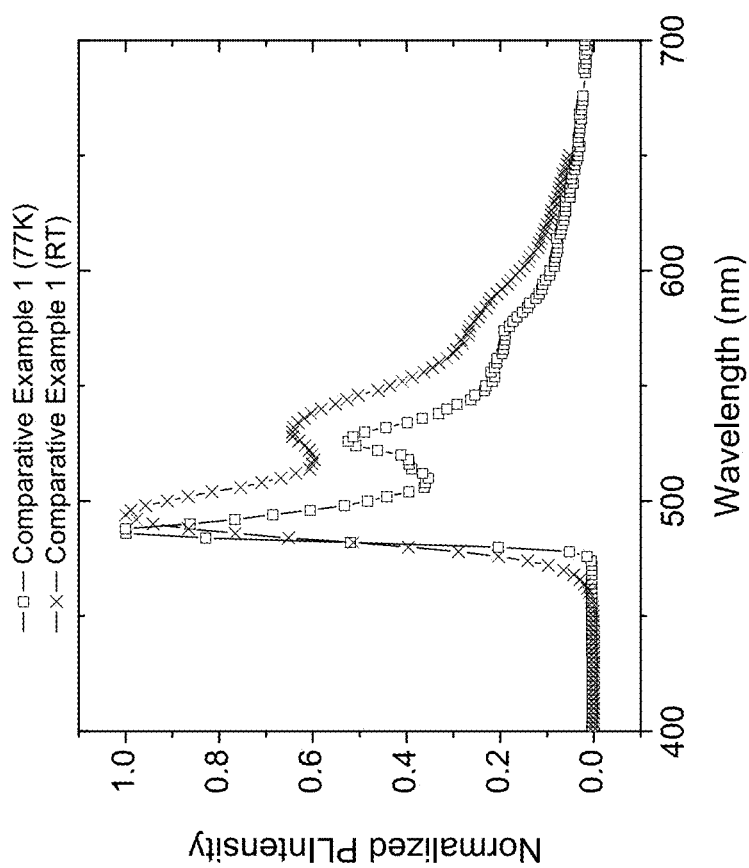
FIG. 3 shows spectral data for Comparative Example 1 at room temperature and at 77K in 2-methyltetrahydrofuran solvent.

The blue-shifting effect of the uncoordinated nitrogen is clearly shown in density functional theory (DFT) calculations, comparing Compounds 1, 7, 315, and 316 to Comparative Example 1, shown in Table B. Compounds 1, 7, 315, and 316 have calculated triplet energies in the range of 460-470 nm, while the triplet of Comparative Example 1 is calculated to be 493 nm. Experimental data for Comparative Example 1 is shown in FIG. 3. The highest energy peak emission for Comparative Example 1 in room temperature and 77K 2-methyltetrahydrofuran solvent is 494 and 487 nm, matching up well with the calculated value.

The uncoordinated nitrogen of the benzimidazole-azaphenanthridine ligand may be susceptible to being protonated in the excited state. Although not wishing to be bound by any particular theory, protonation of the uncoordinated nitrogen is believed to be an irreversible degradation event in an OLED device, leading to anionic and cationic degradation species.

A demonstrated herein, the benzimidazole-azaphenanthridine ligand provides a useful scaffold where a substituent on the ligand, such as aryl, can be used to sterically block the potentially reactive site of the ligand without lowering the triplet energy.

It can be seen in a space filling model of Compound 315, calculated by density functional theory (DFT), and shown in FIG. 4, that an aryl substituent sterically shields the uncoordinated nitrogen from close contact of a neighboring intra or intermolecular proton atom. The un-substituted Compound 1 has an unprotected nitrogen that may be susceptible to being protonated by any neighboring molecule in the solid state. Therefore a site blocking substituent may be a desirable feature for improving the stability. Aryl substitution is one example of a desired site blocking substitution. Furthermore, as the aryl substitution at this site necessarily twists out of the plane of the ligand, there is a minimal effect on the triplet energy of the complex.

Figure 5:
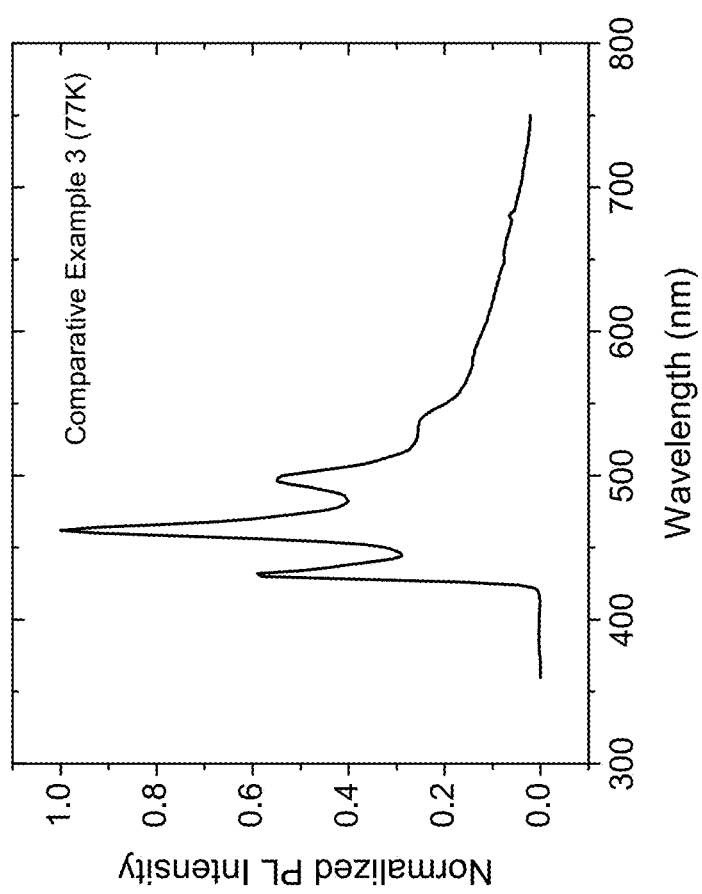
FIG. 5 shows spectral data for Comparative Example 3 at 77K in 2-methyltetrahydrofuran as solvent.

Compounds 1, 7, 315, and 316 are compared to Comparative Examples 2 and 3 in order to demonstrate how the exemplary benzimidazole modification provides desirable features compared to unsubstituted imidazole. DFT calculations for Comparative Examples 2 and 3, the facial (fac) and meridional (mer) isomers of tris iridium imidazole aza-phenanthridine complexes, show triplet energies of 447 and 448 nm. Furthermore, Comparative Example 3 has been synthesized and the 77K solution emission spectrum is shown in FIG. 5. The highest energy peak emission for Comparative Example 3 is 431 nm. The complex was found to be nonemissive in room temperature solution. Therefore, while Comparative Examples 2 and 3 have deep blue emission, they are actually too high in energy to be supported by conventional host materials that typically contain carbazole, dibenzofuran and dibenzothiophene moieties, due to triplet quenching. Therefore the exemplary benzimidazole modification can red shift the emission energy into a desirable range where conventional OLED materials can be used for the fabrication of high efficiency and stable devices.

TABLE B (where not explicitly stated, all complexes are facial (fac) isomers):

| | Structure | HOMO (eV) | LUMO (ev) | Gap (ev) | Dipole (Debye) | $S1_{THF}$ (nm) | $T1_{THF}$ (nm) |
| --- | --- | --- | --- | --- | --- | --- | --- |
| Compound 1 | 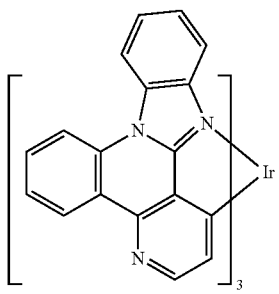 | −5.70 | −1.86 | −3.84 | 11.02 | 413 | 469 |

TABLE B-continued (where not explicitly stated, all complexes are facial (fac) isomers):

| Structure | HOMO (eV) | LUMO (ev) | Gap (ev) | Dipole (Debye) | S1$_{THF}$ (nm) | T1$_{THF}$ (nm) |
|---|---|---|---|---|---|---|
| Compound 7 | −5.63 | −1.82 | −3.81 | 9.25 | 414 | 471 |
| Compound 315 | −5.65 | −1.88 | −3.78 | 10.94 | 421 | 474 |
| Compound 316 | −5.66 | −1.86 | −3.79 | 12.21 | 417 | 472 |
| Comparative Example 1 | −5.14 | −1.62 | −3.52 | 7.01 | 451 | 493 |

TABLE B-continued (where not explicitly stated, all complexes are facial (fac) isomers):

| | Structure | HOMO (eV) | LUMO (ev) | Gap (ev) | Dipole (Debye) | $S1_{THF}$ (nm) | $T1_{THF}$ (nm) |
|---|---|---|---|---|---|---|---|
| Comparative Example 2 | *(fac structure shown)* | −5.56 | −1.52 | −4.04 | 10.35 | 411 | 447 |
| Comparative Example 3 | *(mer structure shown)* | −5.57 | −1.50 | −4.08 | 6.03 | 390 | 448 |

Representative Photophysical Properties (Compound 7)

Figure 6:
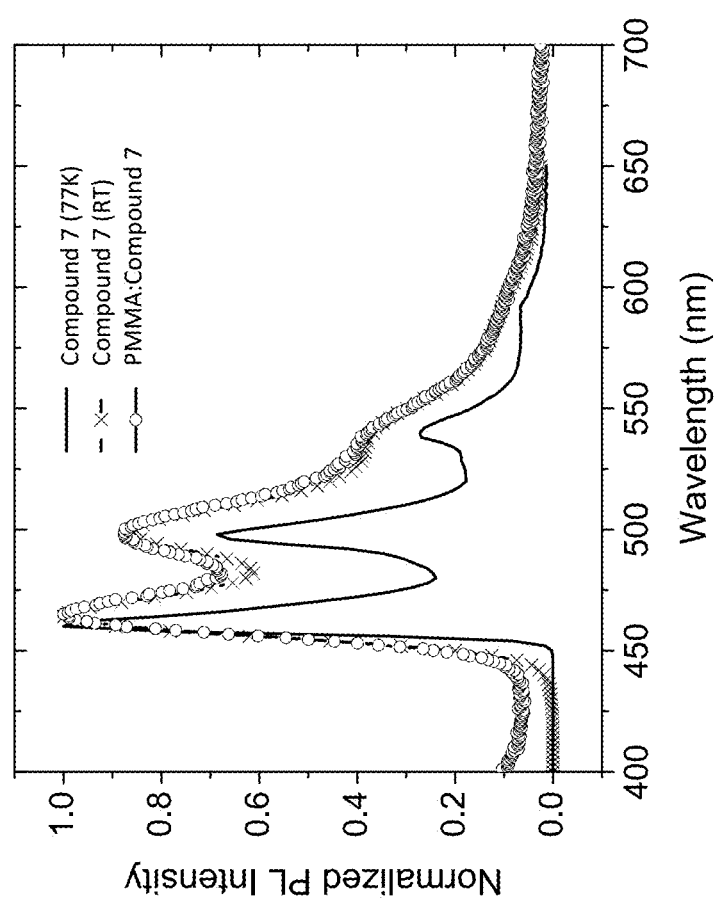
FIG. 6 shows an emission spectrum of Compound 7 in room temperature and a 77K emission spectrum in 2-methyl THF solvent and PMMA matrix.

The photophysical properties of Compound 7 are described as a representative example of this family of blue emitters. The spectrum of Compound 7 in room temperature and 77K 2-methyltetrahydrofuran solvent and solid state polymethylmethacrylate (PMMA) matrix are shown in FIG. 6. In 2-methyltetrahydrofuran solvent, Compound 7 has a peak emission at 459 nm and 463 nm, respectively, with well-defined vibronic structure. The excited state lifetime at 77K was measured to be 2.9 microseconds, which is shorter than the lifetime of Iridium tris-phenylpyridine [Ir(ppy)$_3$=4 microseconds]. The photoluminescent quantum yield (PLQY) was measured for Compound 7 doped in a solid state PMMA matrix drop cast at 1 wt % on a quartz substrate. The PLQY was measured to be 100% efficient with a corresponding excited state lifetime of 2.3 microseconds. These results demonstrate that this family of compounds has excellent intrinsic photophysical properties as blue phosphorescent emitters with high efficiency and short excited state lifetime.

Device Data

OLED devices were prepared using Compound 307 and Compound 308 as emitters.

LG101 was used at HIL

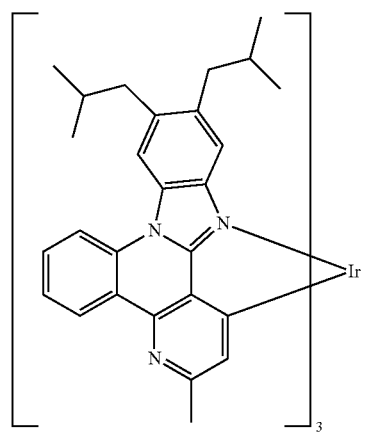

Compound 307

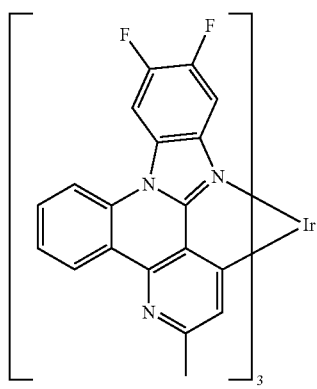

Compound 308

HTL 1
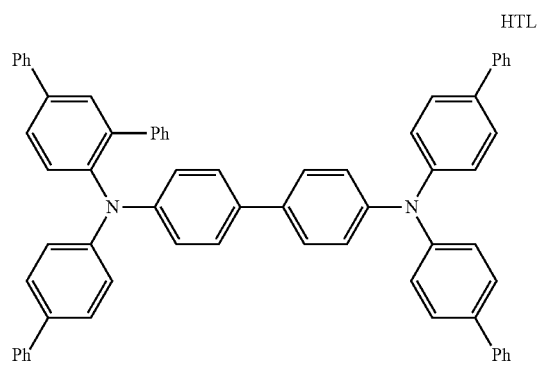
Host 1
Host 2
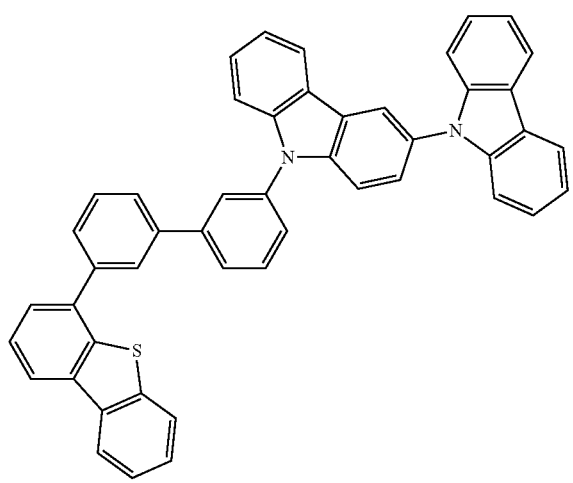
EBL1
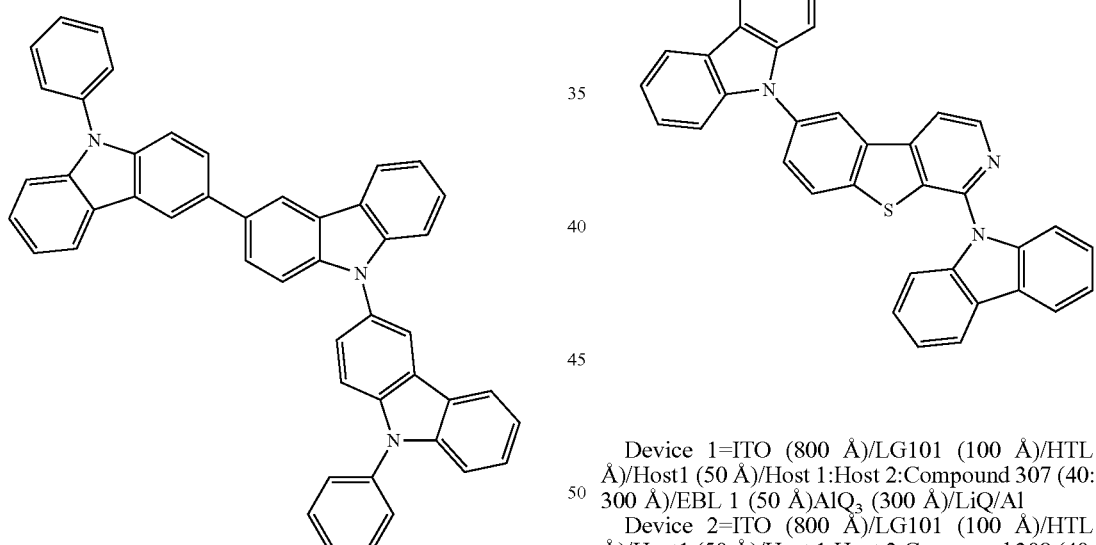
Device 1=ITO (800 Å)/LG101 (100 Å)/HTL 1 (250 Å)/Host1 (50 Å)/Host 1:Host 2:Compound 307 (40:50:10%, 300 Å)/EBL 1 (50 Å)AlQ$_3$ (300 Å)/LiQ/Al
Device 2=ITO (800 Å)/LG101 (100 Å)/HTL 1 (250 Å)/Host1 (50 Å)/Host 1:Host 2:Compound 308 (40:50:10%, 300 Å)/EBL 1 (50 Å)AlQ$_3$ (300 Å)/LiQ/Al
|  | 1931 CIE | | | | At 1000 nits | | | At 20 mA/cm$^2$ |
| --- | --- | --- | --- | --- | --- | --- | --- | --- |
|  | | | | | Voltage | LE | EQE | PE | LT80 |
|  | x | y | λ max | FWHM | (V) | [cd/A] | [%] | [lm/W] | [h] |
| Device 1 | 0.165 | 0.341 | 472 | 58 | 4.3 | 12.0 | 5.9 | 8.8 | 3.1 |
| Device 2 | 0.163 | 0.319 | 490 | 71 | 5.2 | 7.3 | 3.7 | 4.4 | 0.6 |

Synthesis of Exemplary Ligands and Complexes
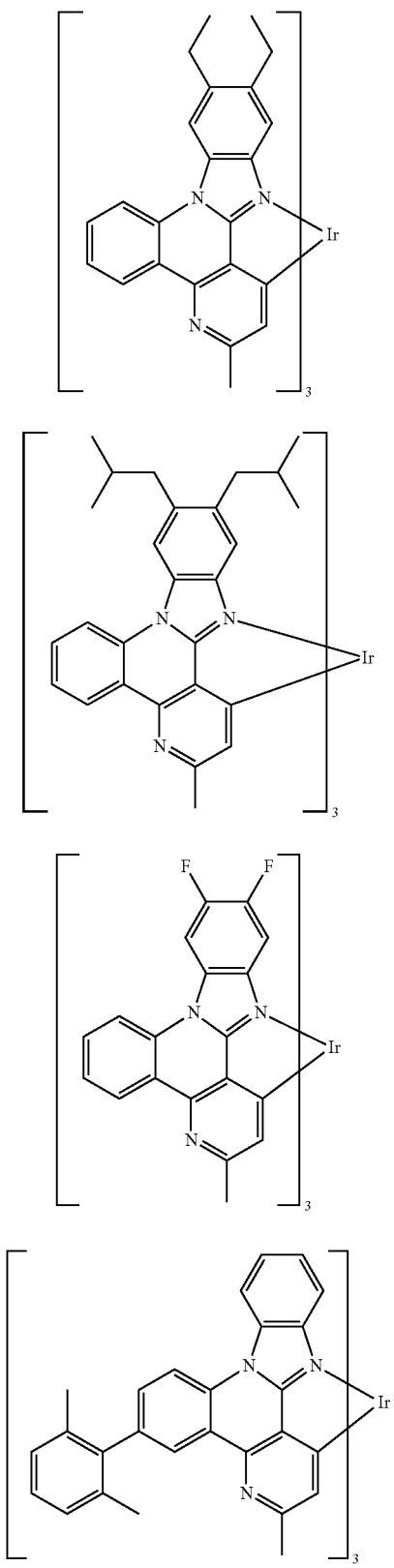
Compound 306
Compound 307
Compound 308
Compound 110
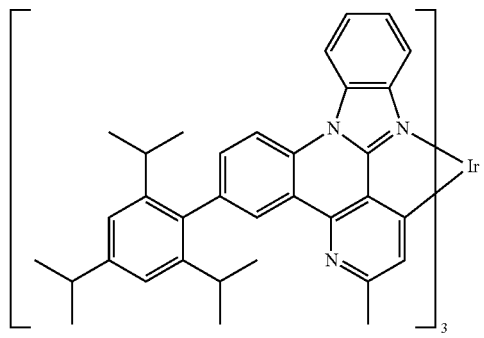
Compound 309
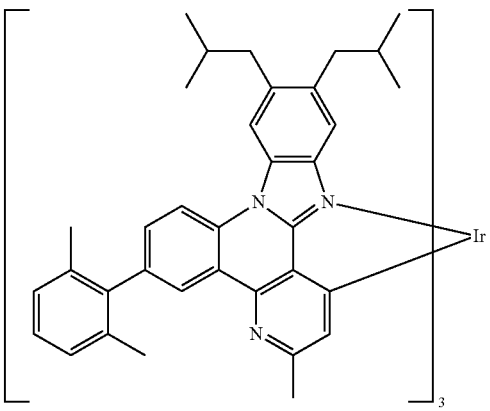
Compound 310
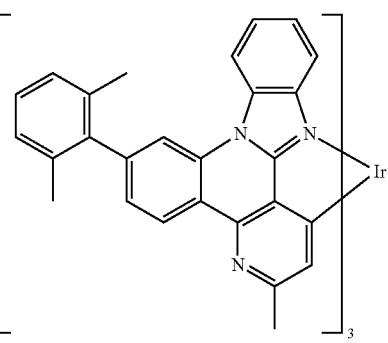
Compound 311
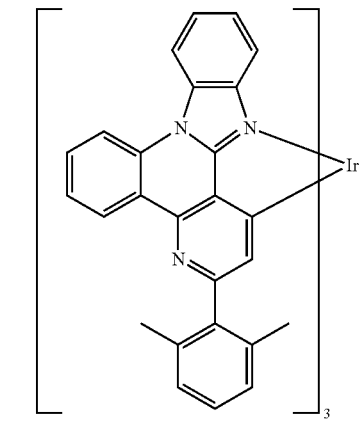
Compound 4

-continued

Compound 7

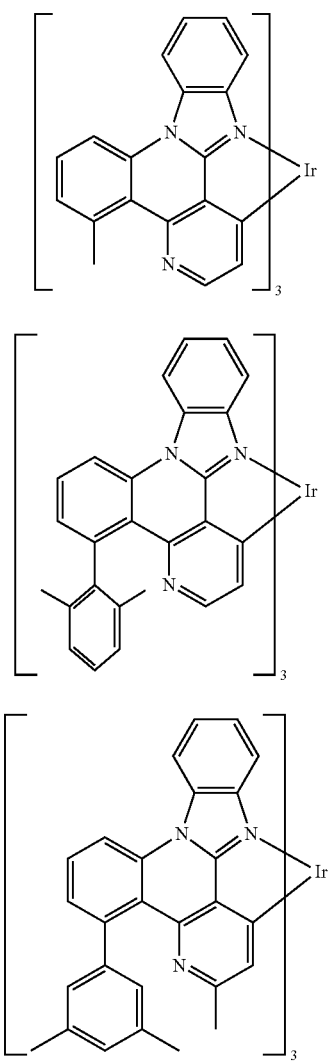

Compound 312

Compound 313

-continued

Compound 314

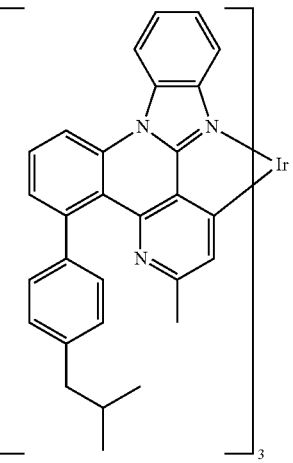

Synthesis of Compounds 306-308

Figure 7:
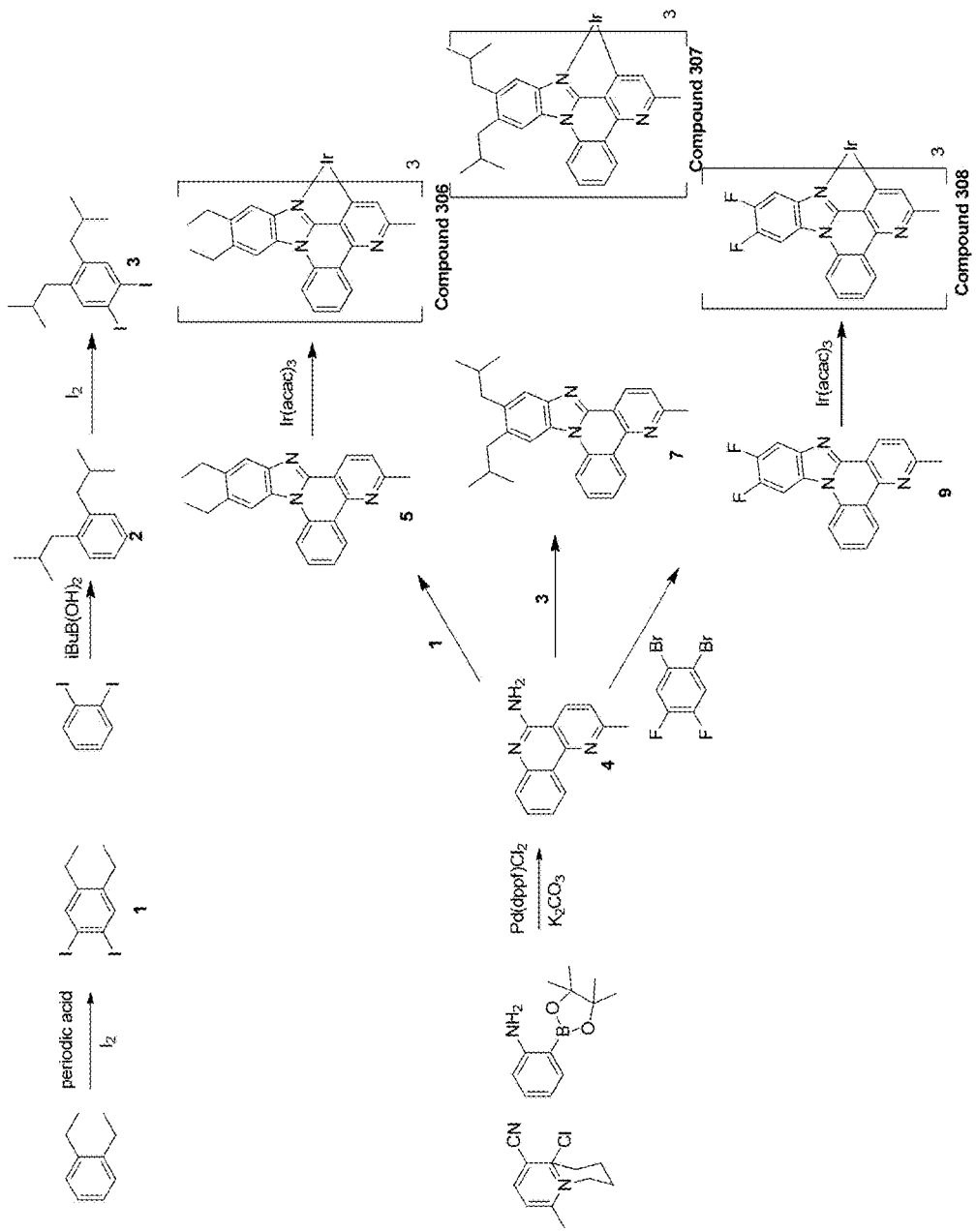
FIG. 7 shows an exemplary synthetic scheme of Compounds 306-308.

(See FIG. 7 for exemplary synthetic scheme)

Synthesis of 1,2-diethyl-4,5-diiodobenzene (1)

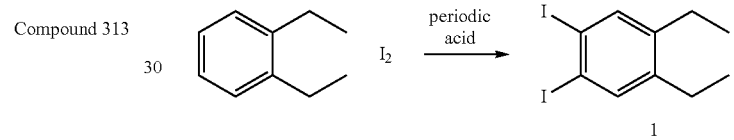

1,2-diethyl benzene (4.0 grams, 29.8 mmol) was placed in a flask. Acetic acid (20 mL), water (4 mL) and sulfuric acid (0.6 mL) were added. Iodine (6.81 grams (26.8 mmol) and periodic acid (2.69 grams, 11.92 mmol) were then added and the reaction was stirred in an oil bath at 75° C. for 18 hours. The mixture was then poured into aqueous sodium bisulfite and the product was extracted with DCM. The organic layer was washed with aqueous sodium bicarbonate solution and evaporated to a yellow oil (10.1 grams, 88%).

Synthesis of 1,2-diisobutylbenzene (2)

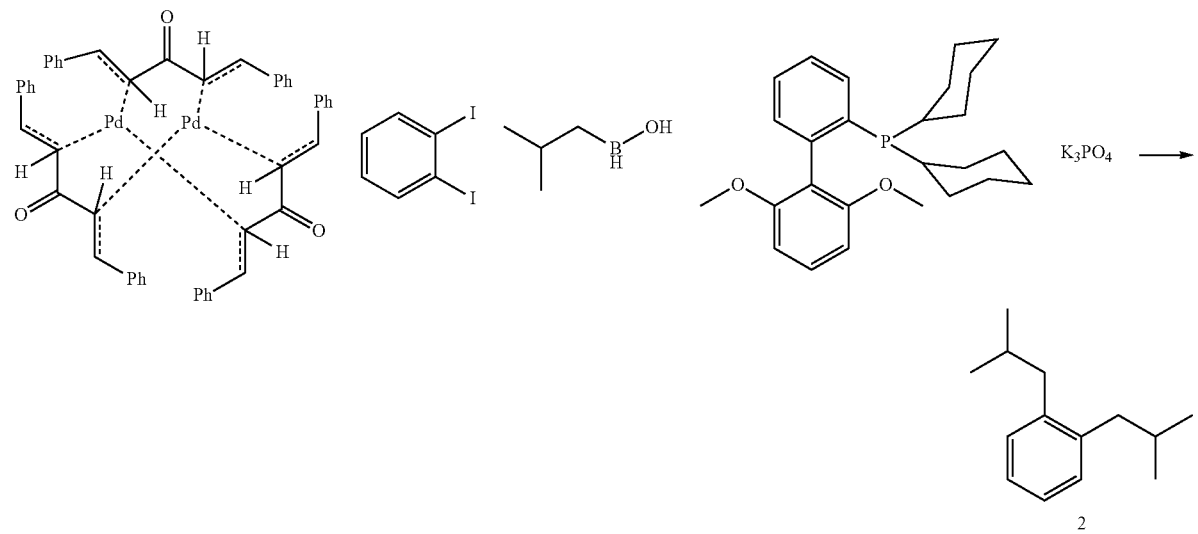

Pd$_2$(dba)$_3$ (1.33 g, 1.45 mmol), 1,2-diiodobenzene (12 g, 36.4 mmol), isobutylboronic acid (14.83 g, 145 mmol), S-Phos (2.39 g, 5.82 mmol) and K$_3$PO$_4$ (38.6 g, 182 mmol) were refluxed in degassed toluene (350 mL) and water (175 mL) overnight. The mixture was filtered through celite and washed with heptanes. The layers were separated and the organic fractions were evaporated to a dark red oil. Heptane was added to this oil and the mixture was again filtered and evaporated. The crude material was passed through a silica gel plug, eluting with 1:1 DCM/heptanes, ultimately yielding 6.54 g of product as an oil, 94%.

Synthesis of 1,2-diiodo-4,5-diisobutylbenzene (3)

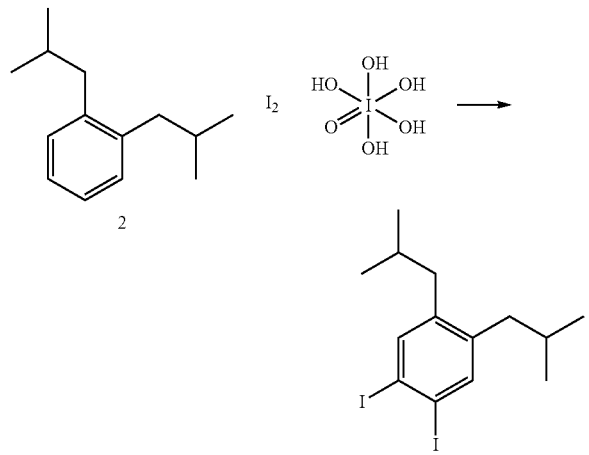

A mixture of 1,2-diisobutylbenzene 2 (6.5 g, 34.2 mmol), diiodine (8.23 g, 32.4 mmol) and orthoperiodic acid (3.09 g, 13.7 mmol) in acetic acid (30 mL), water (20 mL) and conc. sulfuric acid (0.90 mL) was stirred at 70° C. for 1 day. The mixture was poured into aqueous sodium thiosulfate and extracted with DCM. The organic layer was washed with sodium bicarbonate, then water, and solvent was removed under vacuum. The crude oil was passed through a silica gel plug and eluted with heptanes, yielding 10.5 g of yellow oil, 70%.

Synthesis of 2-methylbenzo[h][1,6]naphthyridin-5-amine (4)

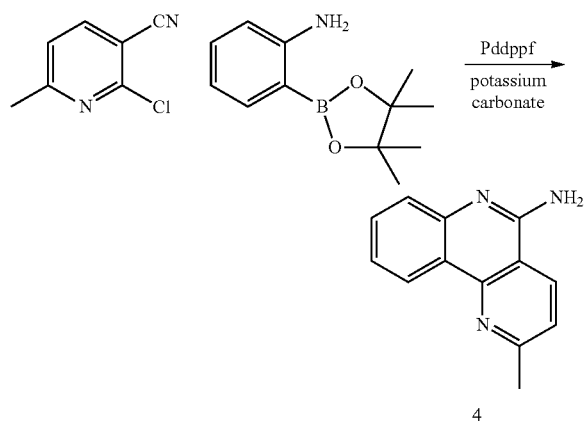

A 500 ml, flask was charged with 2-chloro-6-methylnicotinonitrile (6.0 grams, 39.3 mmol), 2-aminophenylboronic acid pinacol ester (10.34 grams, 47.2 mmol), Palladium dppf-dichloride dichloromethane adduct (1.44 grams, 1.97 mmol) and potassium carbonate (5.43 grams, 39.3 mmol). Dioxane (120 mL) and water (24 mL) were then added. This mixture was stirred at reflux for 18 hours. The crude mix was then diluted with ethyl acetate and filtered through celite. The filtrate was evaporated and chromatographed to give 7.6 grams (92%) of product.

Synthesis of 11,12-diethyl-3-methylbenzo[h]benzo[4,5]imidazo[2,1-f][1,6]naphthyridine (5)

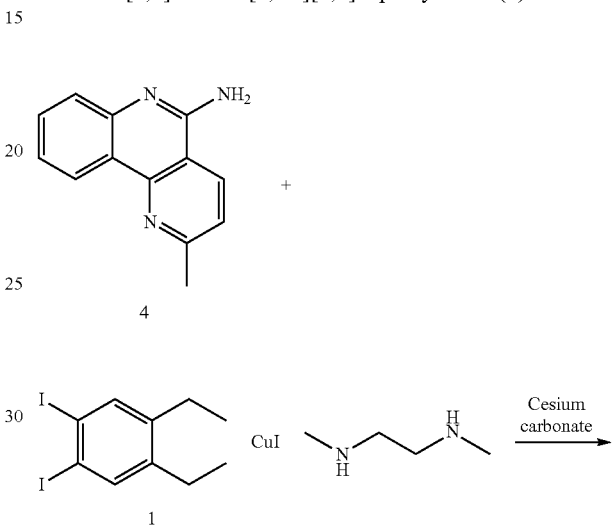

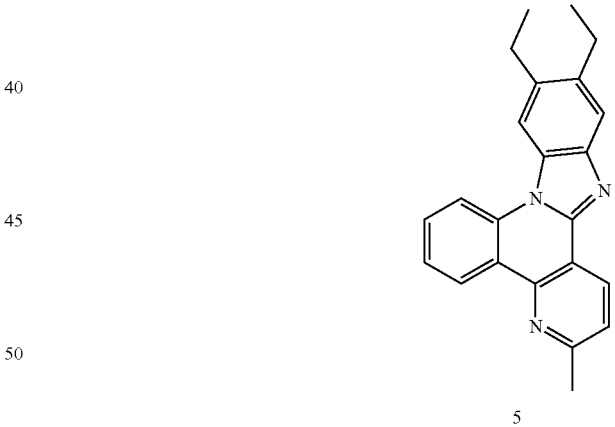

A 250 mL flask was charged with 4 (3.0 grams, 14.3 mmol), 1 (6.64 grams, 17.2 mmol), copper iodide (0.41 grams, 2.15 mmmol), N,N'-dimethylethylenediamine (0.46 mL, 4.3 mmol) and cesium carbonate (9.34 grams, 28.7 mmol). This was evacuated and backfilled with nitrogen. N-methyl-2-pyrrolidinone (100 mL) was then added and this was stirred in an oil bath at 150° C. for 20 hours. The mix was then filtered through celite and the cake was washed with ethyl acetate. The filtrate was washed with brine and water. Column chromatography of the organic extracts yielded 2.4 grams (49.3%) of product as a beige solid.

Synthesis of Compound 306

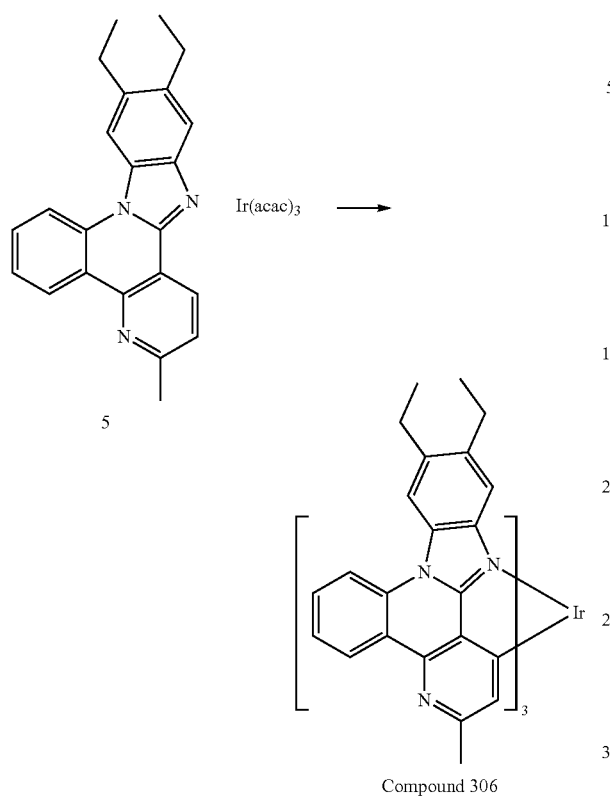

Compound 306

Ligand 5 (1.8 grams, 5.30 mmol) was placed into a Schlenk tube. Ir(acac)₃ (0.52 grams, 1.06 mmol) and pentadecane (3 mL) were added. This was evacuated and backfilled with nitrogen. The reaction was stirred in a sand bath at 300° C. for 4 days. The mix was diluted with DCM and chromatographed using MeOH/DCM. The solid was purified by repeated precipitation from DCM using MeOH to yield 0.4 grams (31%) of Compound 306 as a yellow solid.

Synthesis of 11,12-diisobutyl-3-methylbenzo[h]benzo[4,5]imidazo[2,1-f][1,6]naphthyridine (7)

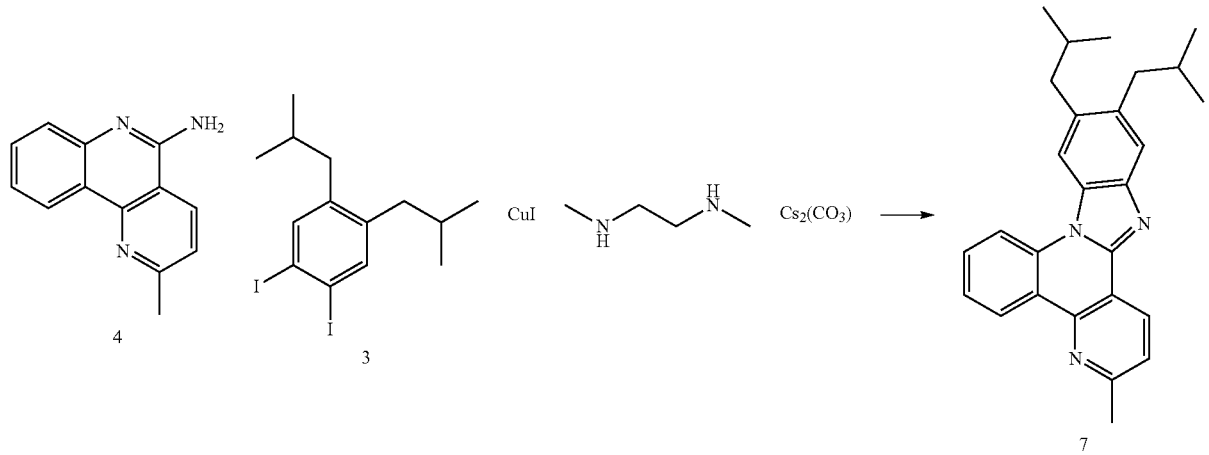

4 (2.00 g, 9.56 mmol) and cesium carbonate (6.23 g, 19.12 mmol) were combined in a 3-neck flask, which was flushed with nitrogen. 3 (4.23 g, 9.56 mmol) was added, followed by a solution of copper(I) iodide (0.273 g, 1.434 mmol) and N1,N2-dimethylethane-1,2-diamine (0.309 ml, 2.87 mmol) in dry N-methyl-2-pyrrolidinone (100 ml). The mixture was heated at 150° C. overnight. The reaction mixture was diluted with ethyl acetate and filtered through celite. Solvent was removed under vacuum and the residue was coated on celite and purified by column chromatography to yield 1.33 g of beige/orange solid that was recrystallized from MeCN to give a pale yellow fluff, 1.26 g (33%).

Synthesis of Compound 307

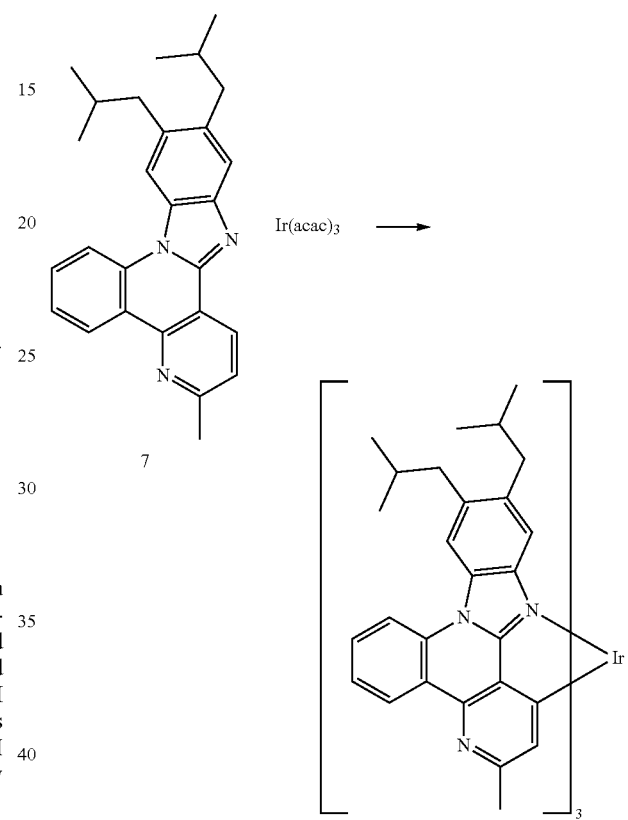

Compound 307

7 (1.25 g, 3.16 mmol) and Ir(acac)₃ (0.30 g, 0.613 mmol) were combined in pentadecane (3 ml). The mixture was degassed then heated at reflux under nitrogen for 2 days. The mixture was coated on celite and the product was purified by silica gel column chromatography, yielding 450 mg of yellow solids that were sonicated in ~20 mL heptanes, yielding 344 mg of light yellow solid Compound 307.

Synthesis of 11,12-difluoro-3-methylbenzo[h]benzo[4,5]imidazo[2,1-f][1,6]naphthyridine (9)

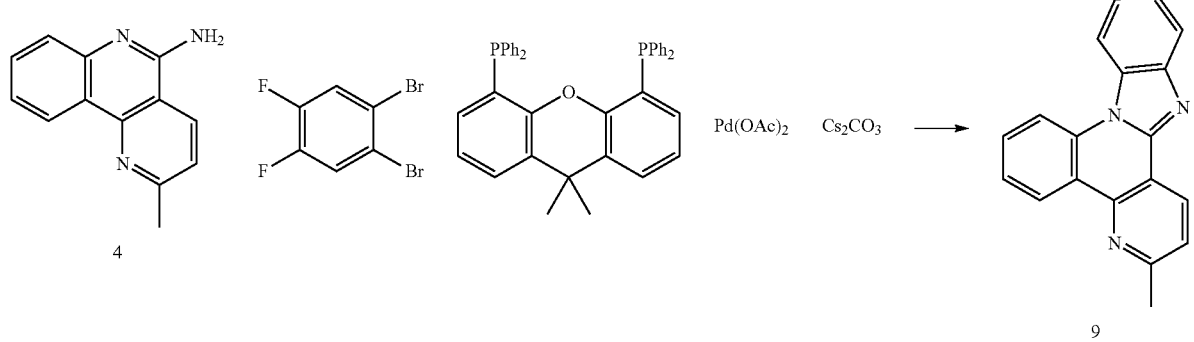

4 (2.53 g, 12.09 mmol), 1,2-dibromo-4,5-difluorobenzene (3.62 g, 13.30 mmol), XantPhos (0.350 g, 0.605 mmol), diacetoxypalladium (0.136 g, 0.605 mmol) and Cs$_2$CO$_3$ (15.76 g, 48.4 mmol) were combined in a flask, flushed with nitrogen, then degassed toluene (48.4 ml) was added and the mixture was heated at reflux for three days. Solvent was removed under vacuum and the residue was suspended in 100 mL water. Solids were filtered off and washed with Et$_2$O and dried under vacuum. Trituration of the solids in 20 mL DCM yielded 9 as a light solid, 2.85 g (74%).

Synthesis of Compound 308

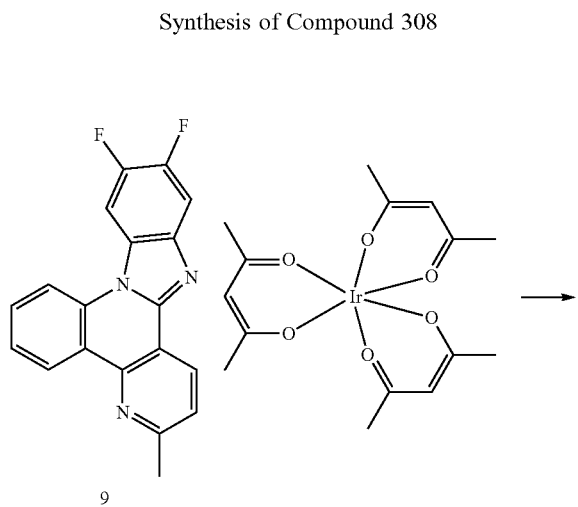

-continued

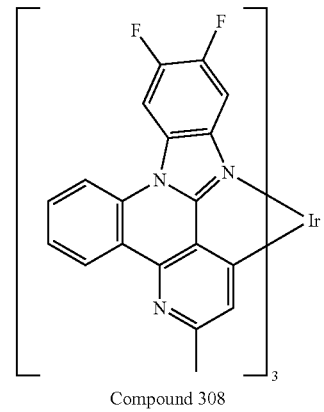

Compound 308

9 (2.409 g, 7.54 mmol) and Ir(acac)$_3$ (0.739 g, 1.510 mmol) were combined in pentadecane (3 ml), the mixture was degassed and refluxed for 5 days. The mixture was cooled to room temperature, dissolved in ~400 mL DCM (some dark precipitates still there), and passed through a deactivated neutral alumina column, flushing with DCM. Excess ligand was removed from the isolated yellow solid was removed in a sublimator and the residue was triturated in DCM to yield 0.41 g of Compound 308.

Synthesis of Compounds 110, 309, and 310

Figure 8:
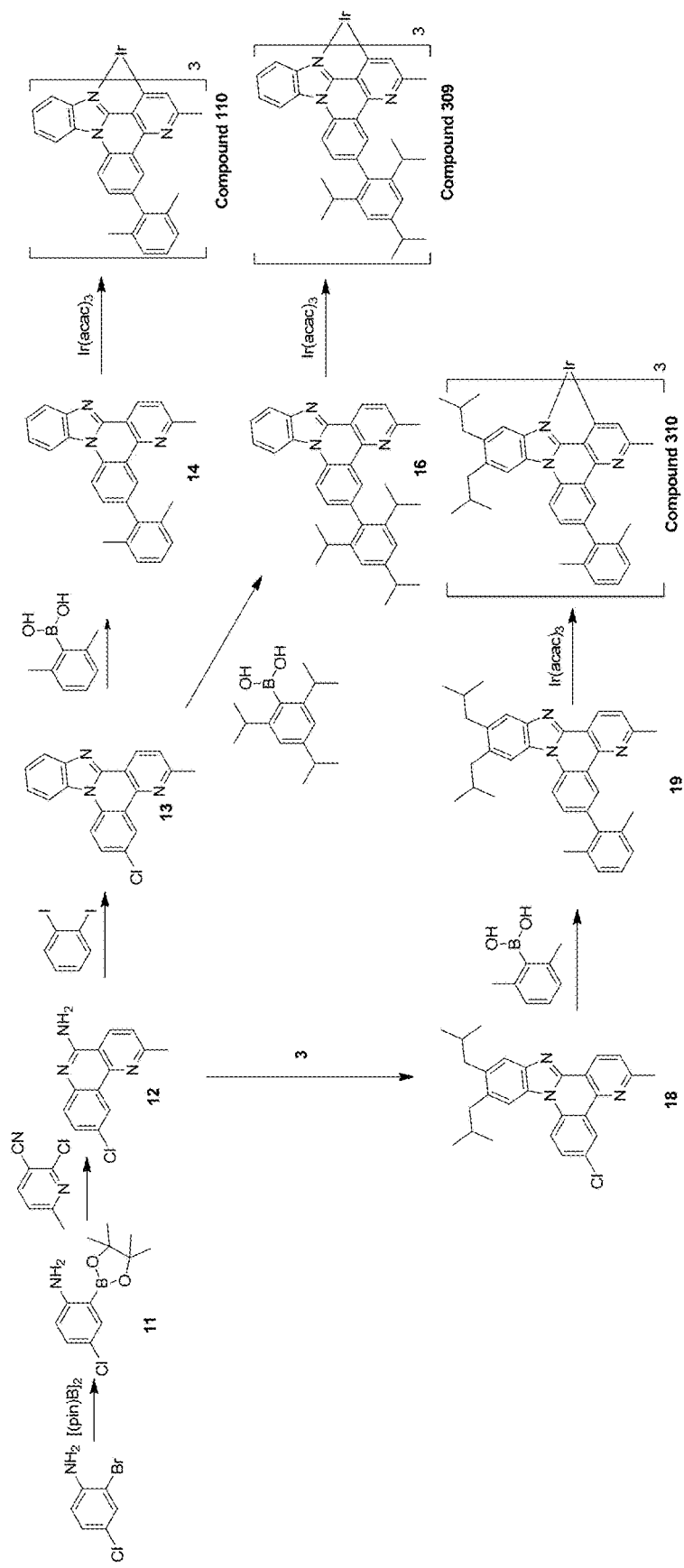
FIG. 8 shows an exemplary synthetic scheme of Compounds 110, 309, and 310.

(See FIG. 8 for exemplary synthetic scheme)

Synthesis of 4-chloro-2-(4,4,5,5-tetramethyl-1,3,2-dioxaborolan-2-yl)aniline (11)

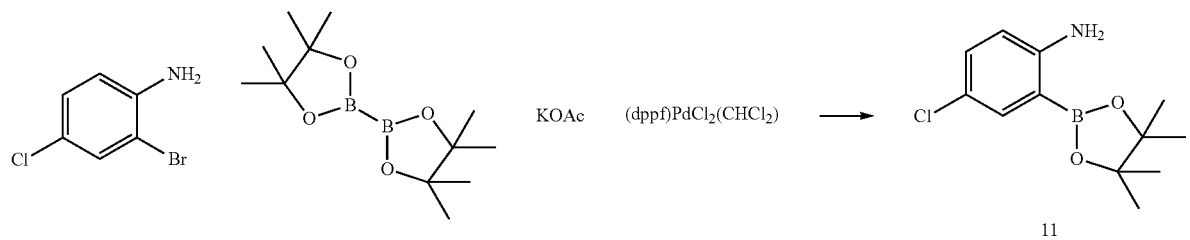

A mixture of 2-bromo-4-chloroaniline (10 g, 48.4 mmol), 4,4,4',4',5,5,5',5'-octamethyl-2,2'-bi(1,3,2-dioxaborolane) (14.76 g, 58.1 mmol), potassium acetate (14.26 g, 145 mmol), and (dppf)PdCl$_2$(CH$_2$Cl$_2$) (5%) was refluxed overnight in dioxane (240 mL). The mixture was diluted with EtOAc and filtered through celite. After evaporation, the crude material was chromatographed on silica gel to yield 8 g of 11 as a pale yellow solid (65%).

Synthesis of 9-chloro-2-methylbenzo[h][1,6]naphthyridin-5-amine (12)

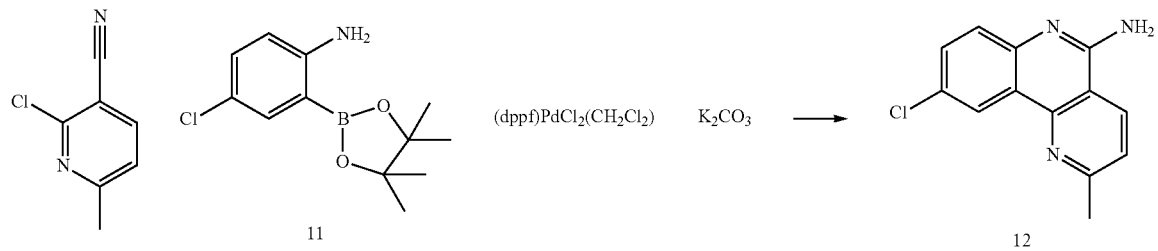

A mixture of 2-chloro-6-methylnicotinonitrile (4 g, 26.2 mmol), 11 (7.31 g, 28.8 mmol), (dppf)PdCl$_2$(CH$_2$Cl$_2$) (1.07 g, 1.31 mmol), and potassium carbonate (3.62 g, 26.2 mmol) was refluxed in dioxane (150 mL) and water (30 mL) overnight. The mixture was cooled to RT, diluted with EtOAc and filtered through celite. After separation and drying of the organic layer the material was chromatographed on silica gel to yield 6.55 g of material that was triturated in ether and heptanes to yield 5.24 g of 12 (82%).

Synthesis of 6-chloro-3-methylbenzo[h]benzo[4,5]imidazo[2,1-f][1,6]naphthyridine (13)

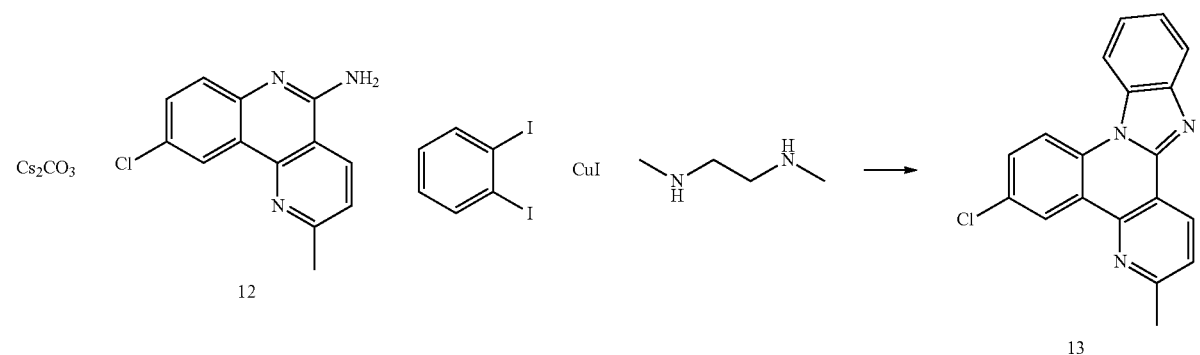

A mixture of Cs₂CO₃ (13.90 g, 42.7 mmol), 12 (5.2 g, 21.3 mmol), 1,2-diiodobenzene (3.07 mL, 7.74 g, 23.5 mmol), CuI (0.610 g, 3.20 mmol), and N,N'-dimethylethane-1,2-diamine (0.69 mL, 6.40 mmol) was stirred at 150° C. in NMP (200 mL) for 20 hours. The cooled reaction mixture was diluted with ethyl acetate and filtered through celite. The filtrate was washed with water, concentrated and chromatographed using silica gel to give 2.9 g of 13 as a beige solid, 43%.

Synthesis of 6-(2,6-dimethylphenyl)-3-methylbenzo[h]benzo[4,5]imidazo[2,1-f][1,6]naphthyridine (14)

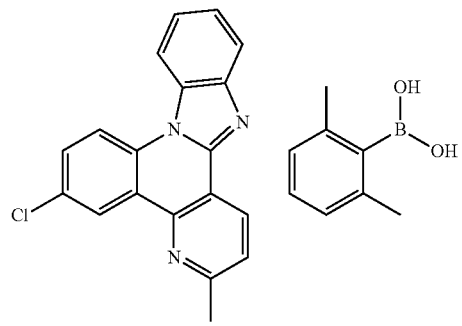

13

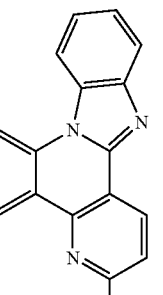

14

A 250 mL flask was charged with 13 (1.8 grams, 5.66 mmol), 2,6-dimethyphenylboronic acid (1.27 grams, 8.5 mmol), Pd₂(dba)₃, (0.119 grams, 0.142 mmol), S-Phos (0.27 grams, 0.566 mmol) and potassium phosphate (3.61 grams, 16.99 mmol). This was diluted with dioxane (50 mL) and water (10 mL) and refluxed for 24 hours. The crude was diluted with DCM and filtered through celite. The filtrate was washed with brine and concentrated. Column gave 1.83 grams (83%) of 14.

Synthesis of Compound 110

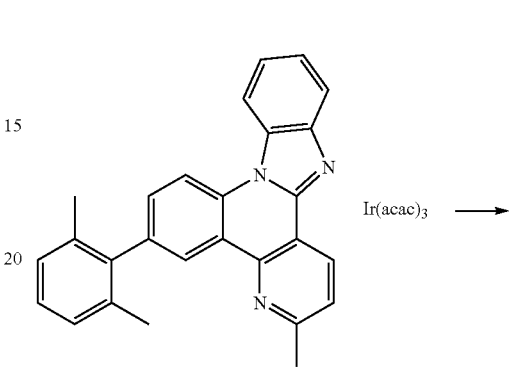

14

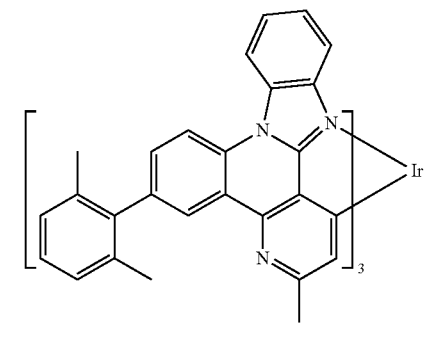

Compound 110

14 (1.6 grams, 4.13 mmol), Ir(acac)₃ (0.404 grams, 0.826 mmol) and pentadecane (3 mL) were placed in a Schlenk tube. This was stirred at 300° C. for 3 days. The product was chromatographed on silica gel and triturated in 1:1 DCM-heptane to give 0.4 grams (36%) of Compound 110.

Synthesis of 3-methyl-6-(2,4,6-triisopropylphenyl)benzo[h]benzo[4,5]imidazo[2,1-f][1,6]naphthyridine (16)

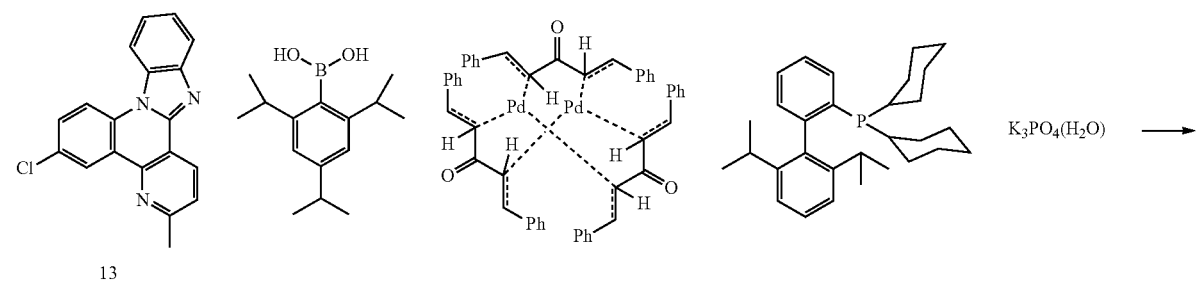

13

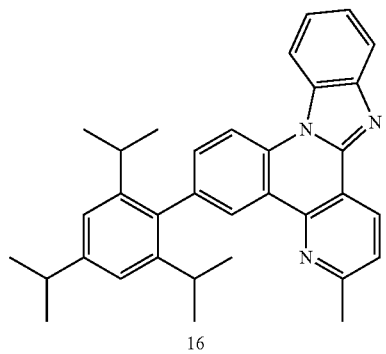

16

13 (1.89 g, 5.95 mmol), (2,4,6-triisopropylphenyl)boronic acid (2.95 g, 11.90 mmol) and potassium phosphate monohydrate (4.11 g, 17.84 mmol) were combined in a Schlenk tube under nitrogen. Separately, a flask containing Pd$_2$(dba)$_3$ (0.109 g, 0.119 mmol) and X-Phos (0.227 g, 0.476 mmol) was purged with nitrogen, then nitrogen-sparged 5:1 dioxane/water (60 ml) was added and heated until the solution turns orange. The catalyst solution was added to the solid reagents and the mixture was refluxed overnight. The mixture was partitioned between water/brine and DCM. The organics were washed with brine and dried and purification of 16 was performed by silica gel chromatography, yielding a yellow-tinged solid, 2.11 g (73%).

Synthesis of Compound 309

-continued

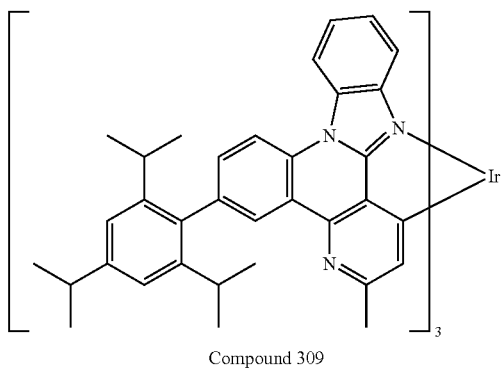

Compound 309

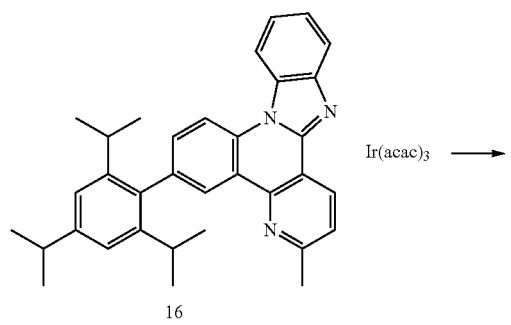

16    Ir(acac)$_3$ →

Ligand 16 (1.974 g, 4.07 mmol) and Ir(acac)$_3$ (0.398 g, 0.813 mmol) were combined in pentadecane (3 ml), then heated at reflux under nitrogen for 5 days. Purification of the crude mixture by silica gel chromatography yielded 0.81 g of Compound 9.

Synthesis of 6-chloro-11,12-diisobutyl-3-methyl-benzo[h]benzo[4,5]imidazo[2,1-f][1,6]naphthyridine (18)

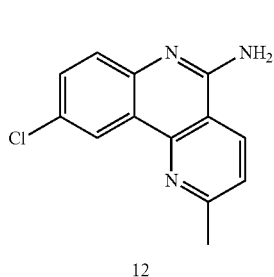

12

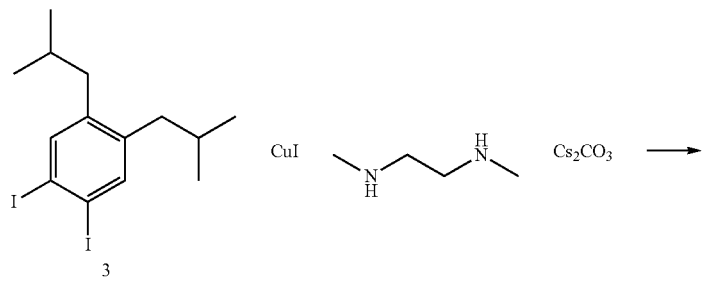

3    CuI    Cs$_2$CO$_3$ →

-continued

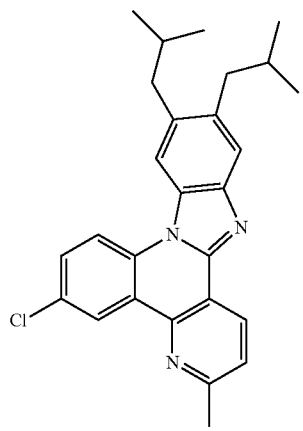

18

A mixture of 12 (4 g, 16.4 mmol), 3 (7.26 g, 16.4 mmol), CuI (0.47 g, 2.46 mmol), N1,N2-dimethylethane-1,2-diamine (0.53 mL, 4.92 mmol), Cs$_2$CO$_3$ (10.7 g, 32.8 mmol) was stirred in NMP at 150° C. overnight. The mixture was diluted with EtOAc and filtered through celite. The filtrate was washed with brine then water, and the organic layer was chromatographed on silica gel columns to yield 2.87 g of 18 as a pale yellow solid, 41%.

Synthesis of 6-(2,6-dimethylphenyl)-11,12-diisobutyl-3-methylbenzo[h]benzo[4,5]imidazo[2,1-f][1,6]naphthyridine (19)

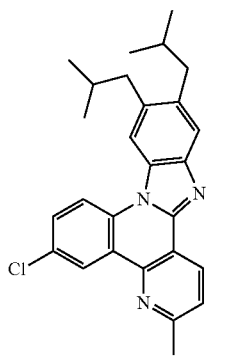

18

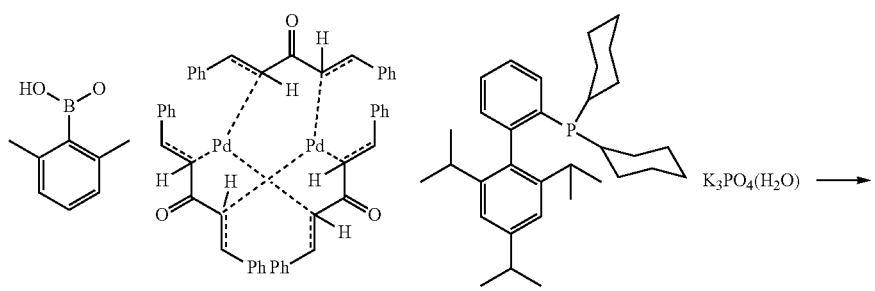

K$_3$PO$_4$(H$_2$O) ⟶

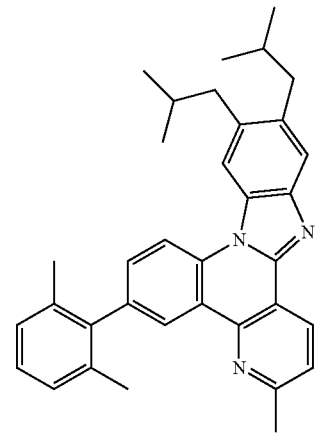

19

18 (1.383 g, 3.22 mmol), (2,6-dimethylphenyl)boronic acid (0.627 g, 4.18 mmol) and potassium phosphate monohydrate (2.222 g, 9.65 mmol) were combined in a Schlenk tube under nitrogen. Separately Pd$_2$(dba)$_3$ (0.059 g, 0.064 mmol) and X-Phos (0.123 g, 0.257 mmol) were heated in 5:1 dioxane/water (30 ml) until orange. The catalyst solution was added to the solid reactants and refluxed for 4 hours. After partitioning between brine/water/DCM the aqueous layer was extracted three times with DCM, the combined organic layers were dried and coated on celite. The product was purified by silica gel chromatography, yielding a solid that was recrystallized from MeCN to yield 1.3 g of light yellow 19.

Synthesis of Compound 310

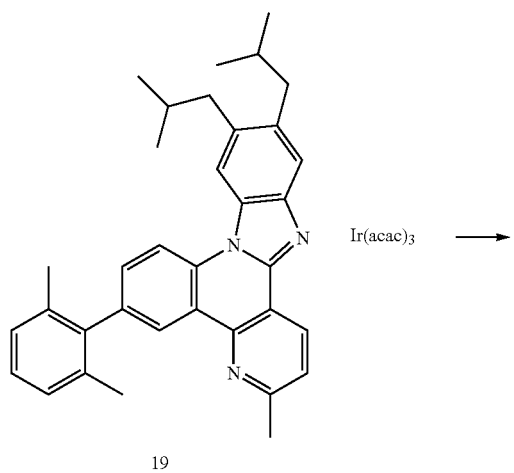

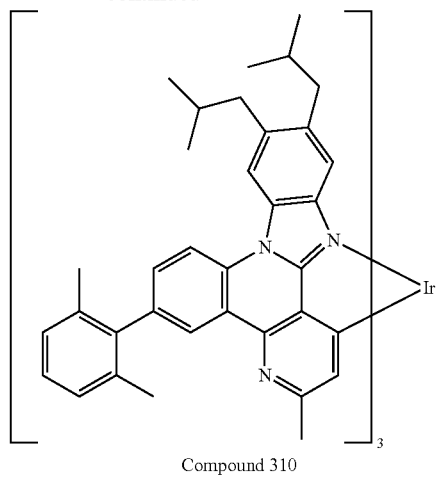

Compound 310

19 (1.32 g, 2.64 mmol) and Ir(acac)$_3$ (0.25 g, 0.511 mmol) were combined in pentadecane (3 ml). The mixture was degassed then heated at reflux for 3 days. The mixture was coated on celite and purified by column chromatography to yield a solid that was triturated in MeOH, yielding 312 mg of Compound 310 as a pale yellow powder (36%).

Synthesis of Compound 311

Figure 9:
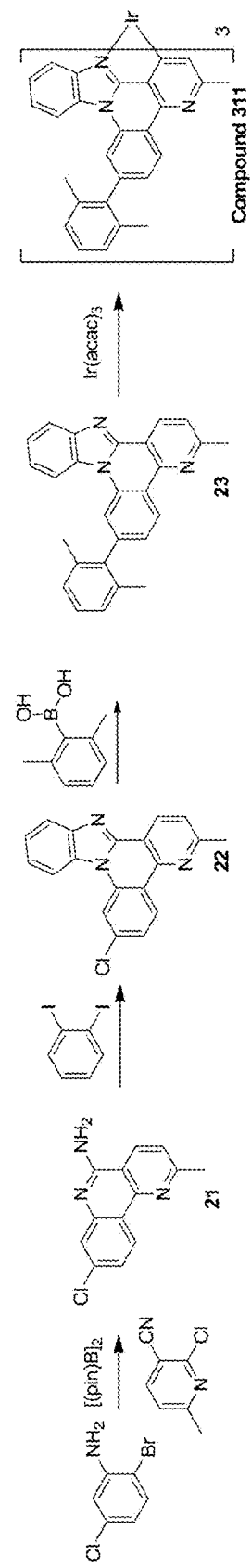
FIG. 9 shows an exemplary synthetic scheme of Compound 311.

(See FIG. 9 for exemplary synthetic scheme)

Synthesis of 8-chloro-2-methylbenzo[h][1,6]naphthyridin-5-amine (21)

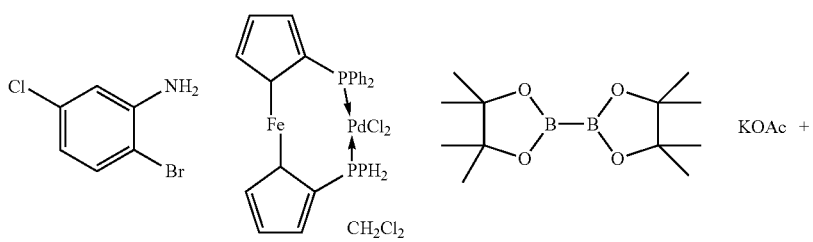

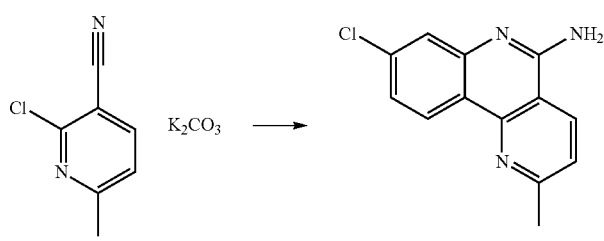

A mixture of 2-bromo-5-chloroaniline (9.66 g, 46.8 mmol), PdCl$_2$(dppf)DCM (1.124 g, 1.376 mmol), 4,4,4',4',5,5,5',5'-octamethyl-2,2'-bi(1,3,2-dioxaborolane) (13.40 g, 52.8 mmol), and potassium acetate (9.01 g, 92 mmol) was dissolved in dioxane (70 ml) and stirred at reflux for 5 hours. After cooling to room temperature, 2-chloro-6-methylnicotinonitrile (7 g, 45.9 mmol) and potassium carbonate (6.34 g, 45.9 mmol) were added followed by degassed dioxane (30 ml) and water (20 ml) and the mixture was brought to reflux overnight. Solvents were removed under vacuum and the residual solids were triturated in 20 mL of diethyl ether and the solids were washed with water and more ether. The solids were dissolved in 10% MeOH/DCM and washed with brine/1M NaOH. Evaporation of the organic layer yielded 21 as a grey product, 64%.

Synthesis of 7-chloro-3-methylbenzo[h]benzo[4,5]imidazo[2,1-f][1,6]naphthyridine (22)

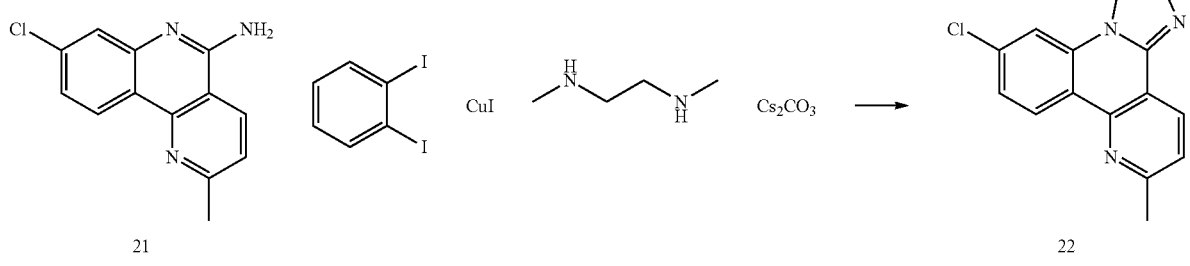

A mixture of 21 (6 g, 24.62 mmol), copper(I) iodide (0.703 g, 3.69 mmol), N1,N2-dimethylethane-1,2-diamine (0.795 ml, 7.39 mmol), and cesium carbonate (16.04 g, 49.2 mmol) was vacuumed and back-filled with nitrogen several times and 1,2-diiodobenzene (3.54 ml, 27.1 mmol) and NMP (75 ml) were added to the flask. The reaction was heated at 150° C. overnight, quenched with water and the precipitated solids were filtered and washed with water. The solid was washed with DCM/1 M NaOH (aq) and brine. The organic fraction was evaporated and washed with diethyl ether to afford greyish 22, 61%

Synthesis of 7-(2,6-dimethylphenyl)-3-methylbenzo[h]benzo[4,5]imidazo[2,1-f][1,6]naphthyridine (23)

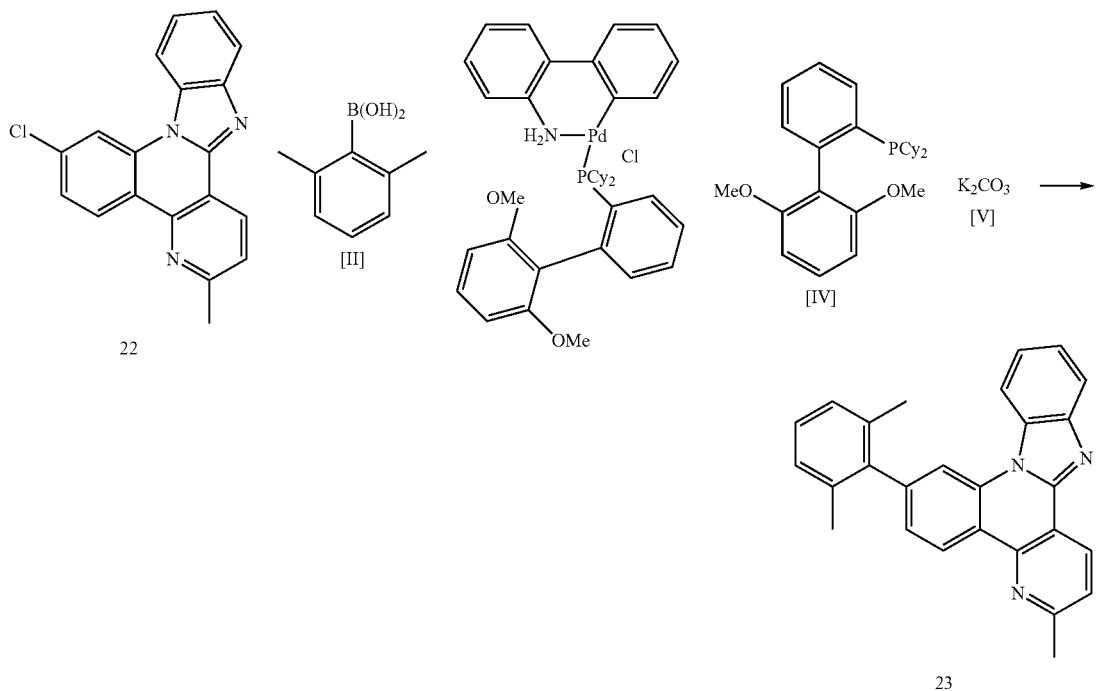

A mixture of 22 (4.8 g, 15.11 mmol), (2,6-dimethylphenyl)boronic acid (2.72 g, 18.13 mmol), S-Phos Pd G2 catalyst (0.327 g, 0.453 mmol), S-Phos (0.186 g, 0.453 mmol), and potassium carbonate (2.088 g, 15.11 mmol) was vacuumed and back-filled with nitrogen several times. Dioxane (60 ml) and water (15 ml) were added and the mixture was refluxed for 3 hours. Solvents were removed under vacuum and the residue was dissolved in DCM and washed with brine/1 M KOH (aq). The organic layer was purified by silica gel chromatography and washed with diethyl ether to yield 23, 85%.

Synthesis of Compound 311

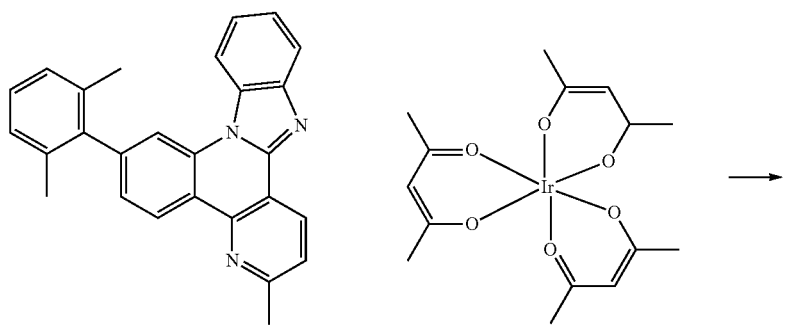

23

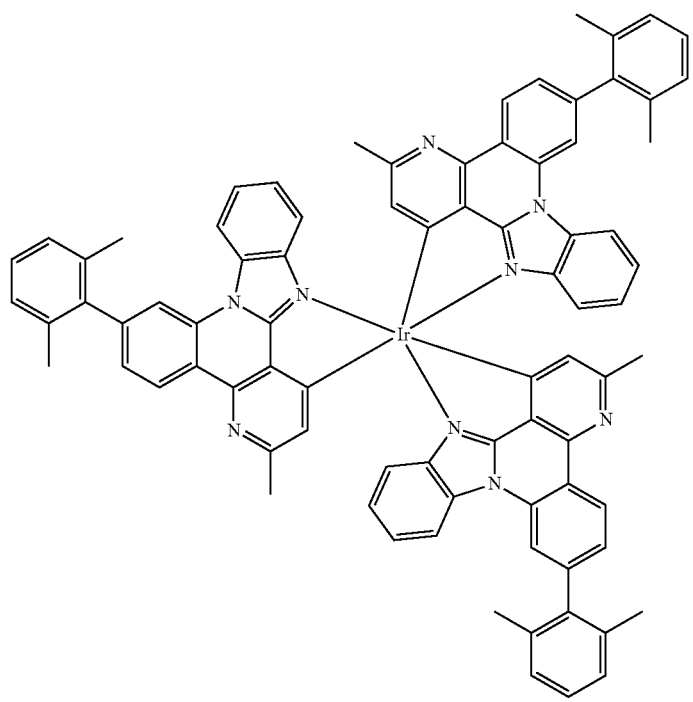

Compound 311

Ligand 23 (1.4 g) and Ir(acac)$_3$ (0.354 g) were combined in a Schlenk tube and degassed, then heated to 295° C. in a sand bath for 3 days. The cooled reaction mixture was coated on celite using DCM and purified by column chromatography on silica gel and neutral alumina to afford Compound 311, 16%.

285
Synthesis of Compound 4

Figure 10:
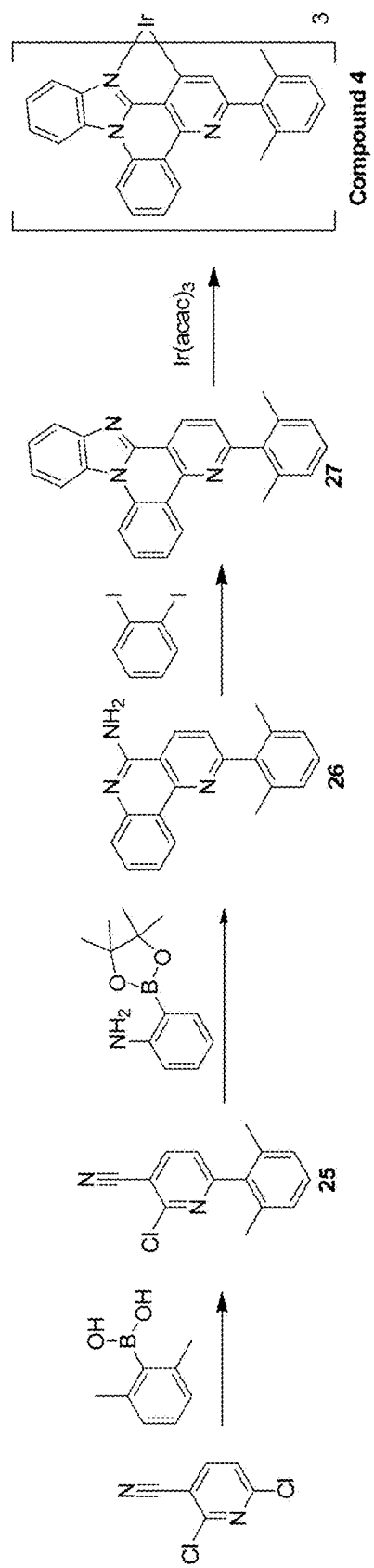
FIG. 10 shows an exemplary synthetic scheme of Compound 4.

(See FIG. 10 for exemplary synthetic scheme)

Synthesis of
2-chloro-6-(2,6-dimethylphenyl)nicotinonitrile (25)

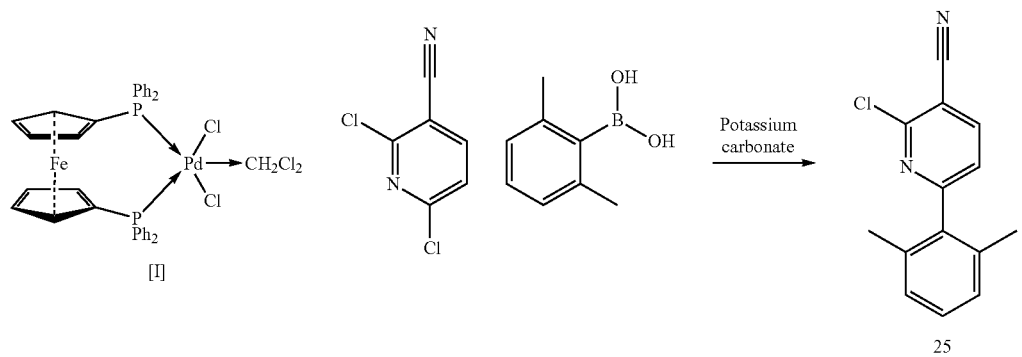

A 1 L flask was charged with 2,6-dichloronicotinonitrile (10 grams, 57.8 mmol), 2,6-dimethylphenylboronic acid (8.67 grams, 57.8 mmol), potassium carbonate (8.0 grams, 57.8 mmol) and Pd(dppf)Cl$_2$ DCM adduct (1.42 grams, 1.73 mmol). This was diluted with dioxane (300 mL) and water (60 mL). The mix was stirred at reflux for 18 hours. This was diluted with ethyl acetate and brine. The organic layer was concentrated and chromatographed on silica gel to give 10.6 grams of 25.

Synthesis of 2-(2,6-dimethylphenyl)benzo[h][1,6]
naphthyridin-5-amine (26)

286

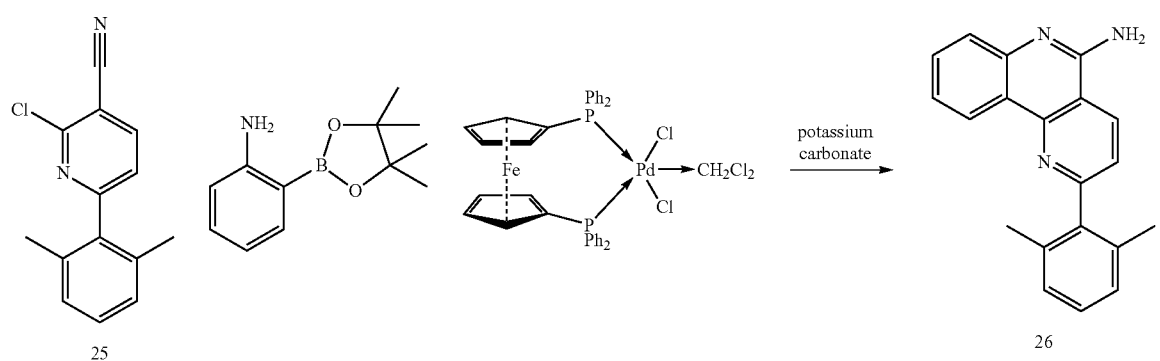

A 1 L flask was charged with 25 (10.5 grams, 43.3 mmol), 2-aminophenylboronic acid pinacol ester (9.48 grams, 43.3 mmol), Pd(dppf)Cl$_2$ DCM adduct (1.77 grams, 2.16 mmol) and potassium carbonate (5.98 grams, 43.3 mmol). The mix was diluted with dioxane (300 mL) and water (60 mL) and this was stirred at reflux for 18 hours. The mix was cooled and diluted with DCM. This was filtered through celite. The fitrate was washed with brine and concentrated. Chromatography on silica gel gave 5.36 grams (41%) of 26.

287

Synthesis of 3-(2,6-dimethylphenyl)benzo[h]benzo[4,5]imidazo[2,1-f][1,6]naphthyridine (27)

288

Synthesis of Compound 4

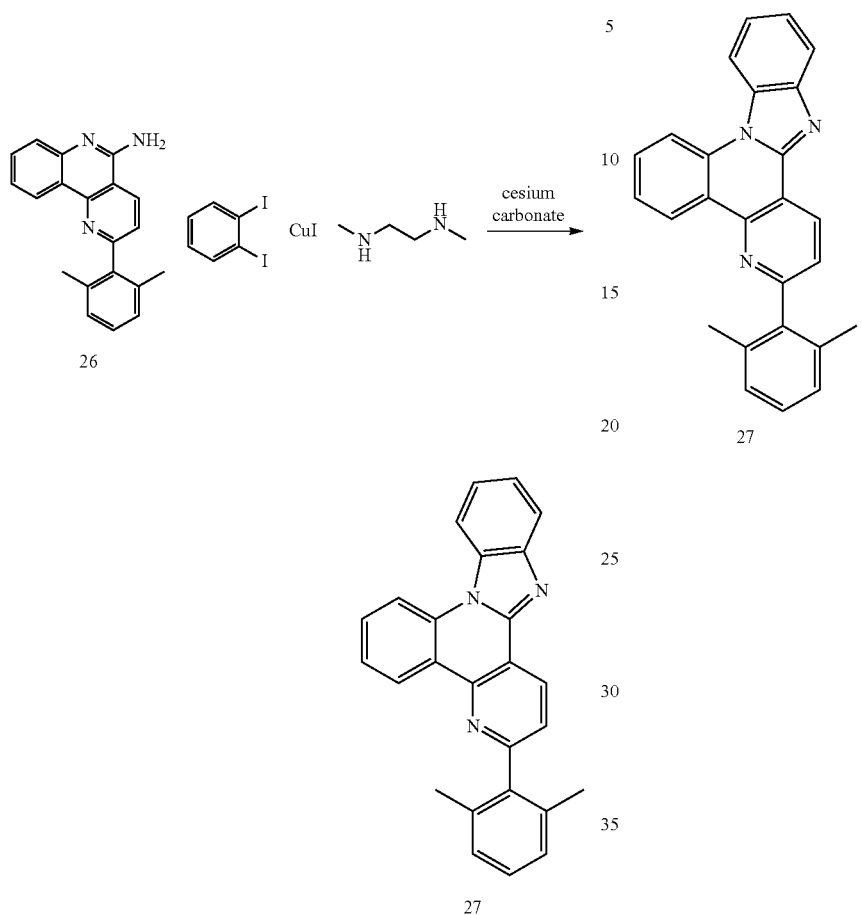

A 250 mL flask was charged with 26 (5.3 grams, 17.7 mmol), 1,2-diiodobenzene (5.84 grams, 17.7 mmol), copper iodide (0.51 grams, 2.66 mmol), N,N'-dimethylethylenediamine (0.57 mL, 5.31 mmol) and cesium carbonate (11.54 grams, 35.4 mmol). This was diluted with N-methyl pyrrolidinone (100 mL). The reaction was stirred at 150° C. for 20 hours. The crude product was diluted with DCM and filtered through celite. The filtrate was washed with water and concentrated and residual NMP was removed by kugelrohr. Silica gel chromatography yielded 4.4 grams (67%) of 27.

Ligand 27 (3.0 grams, 8.03 mmol), Ir(acac)$_3$ (0.787 grams, 1.6 mmol) and pentadecane (4.5 mL) were all placed in a 50 mL Schlenk tube. The flask was evacuated and backfilled with nitrogen. The mix was stirred in a sand bath at 295° C. for 4 days. The crude material was diluted with DCM and chromatographed on a silica gel column to give 610 mg of pure Compound 4.

Synthesis of Compound 7

Figure 11:
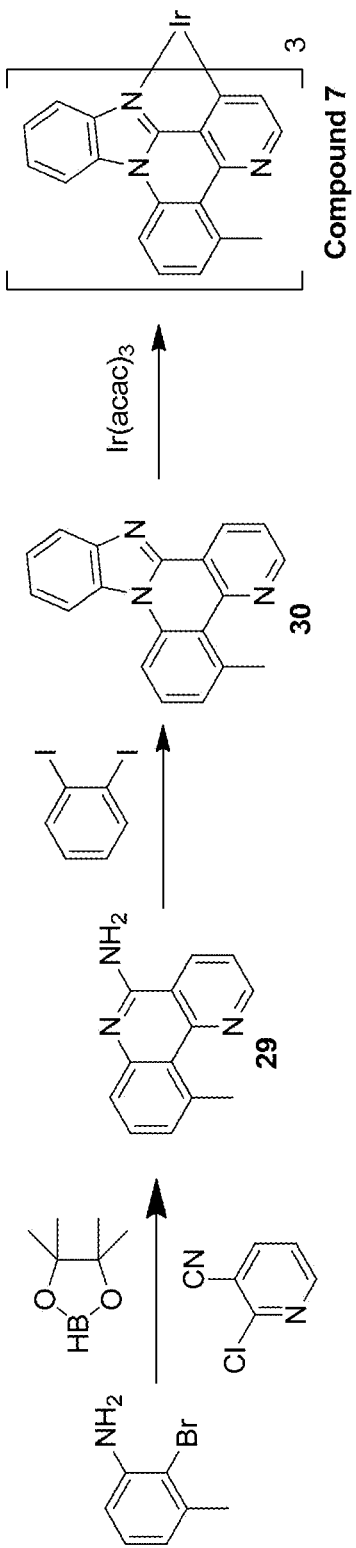
FIG. 11 shows an exemplary synthetic scheme of Compound 7.

(See FIG. 11 for exemplary synthetic scheme)

Synthesis of 10-methylbenzo[h][1,6]naphthyridin-5-amine (29)

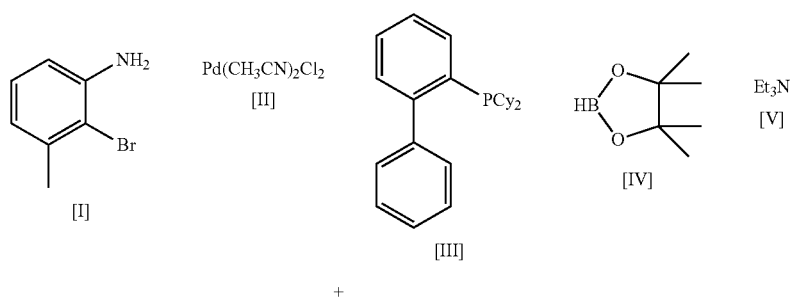

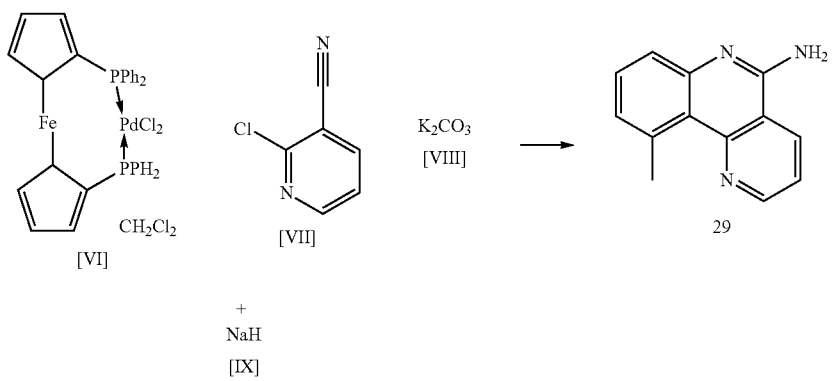

A mixture of 2-bromo-3-methylaniline (5.41 ml, 43.3 mmol), PdCl$_2$(dppf)DCM (0.884 g, 1.083 mmol), 4,4,5,5-tetramethyl-1,3,2-dioxaborolane (15.27 ml, 87 mmol), and CyJohnPhos (0.759 g, 2.165 mmol) in dioxane (65 ml) was refluxed for 5 hours. The reaction mixture was cooled to room temperature and 2-chloronicotinonitrile (5 g, 36.1 mmol) and potassium carbonate (4.99 g, 36.1 mmol) were added to the flask. Degassed dioxane (20 ml) and water (17 ml) were added to the solution and refluxed was continued overnight. Solvents were removed and the residue was dissolved in 10% MeOH/DCM and washed with brine/KOH (aq). The organic layer evaporated and re-dissolved in THF (50 mL) and cooled in an ice bath. Sodium hydride (1.155 g, 28.9 mmol) was added and stirred at room temperature for 15 minutes. The reaction was quenched with water and extracted with DCM/brine. The resulting product was evaporated and triturated in diethyl ether/hexane (~1:5) to afford brown 29 (45%).

Synthesis of 5-methylbenzo[h]benzo[4,5]imidazo[2,1-f][1,6]naphthyridine (30)

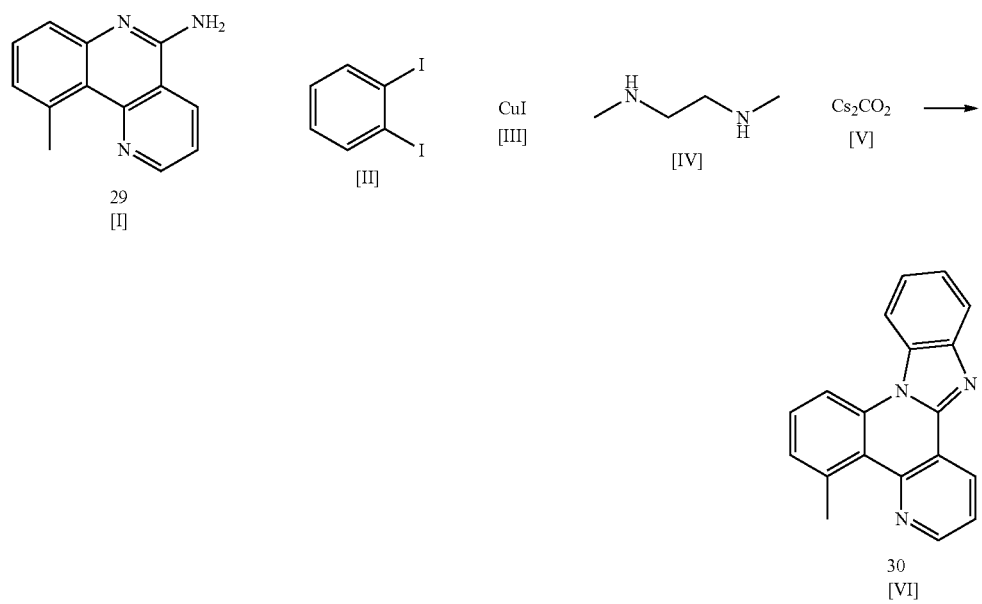

A mixture of 29 (3.4 g, 16.25 mmol), copper(I) iodide (0.464 g, 2.437 mmol), N1,N2-dimethylethane-1,2-diamine (0.525 ml, 4.87 mmol), and cesium carbonate (10.59 g, 32.5 mmol) was vacuumed and back-filled with nitrogen several times and 1,2-diiodobenzene (2.336 ml, 17.87 mmol) and NMP (45 ml) were added to the solution. The reaction was heated at 150° C. for 3 hours. The reaction was diluted with water and precipitated solids were collected by filtration and washed with water. The solid was purified by silica gel chromatography and triturated in diethyl ether to afford light brick-colored solid (48%).

Figure 12:
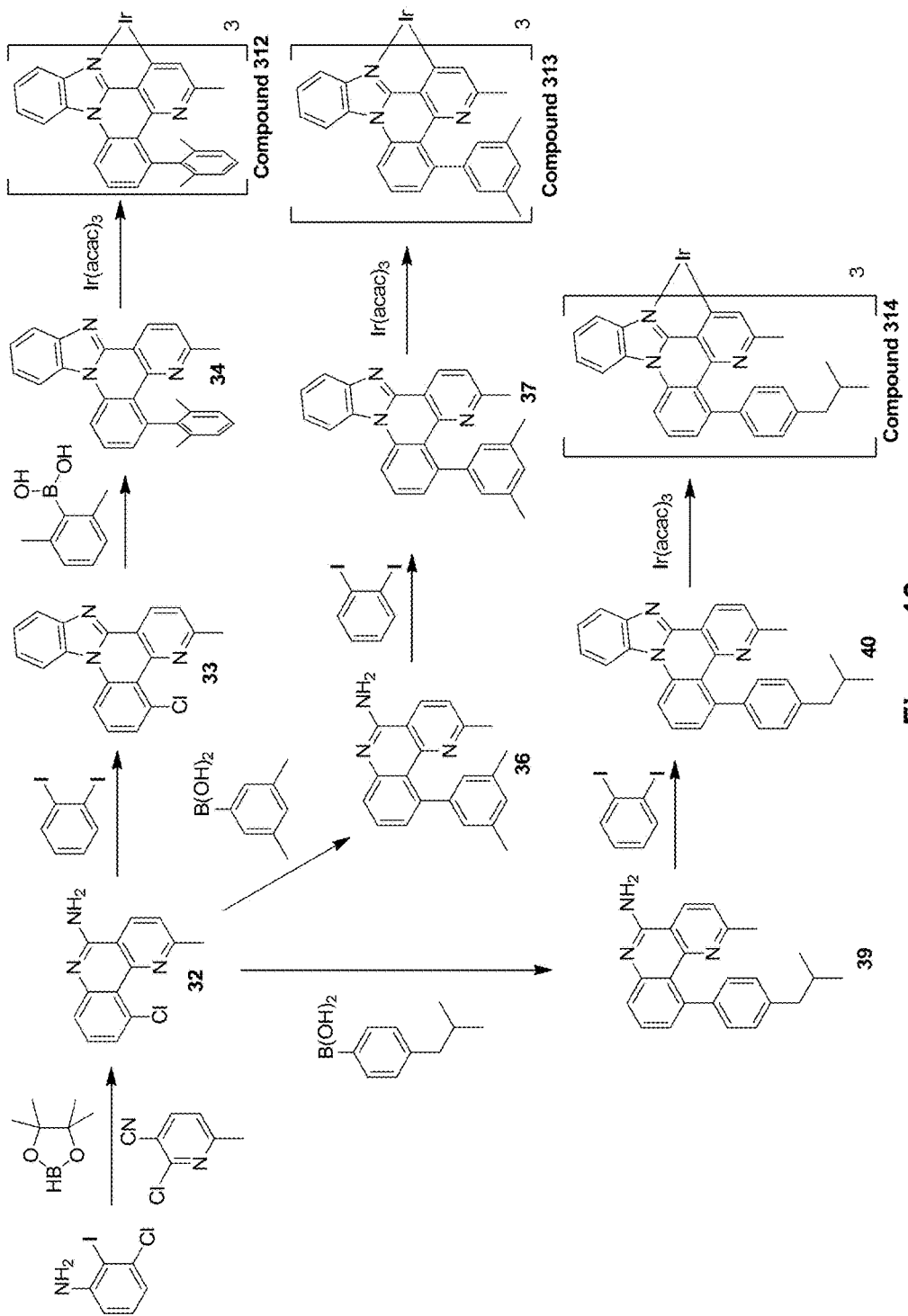
FIG. 12 shows an exemplary synthetic scheme of Compounds 312-314.

Synthesis of Compound 7
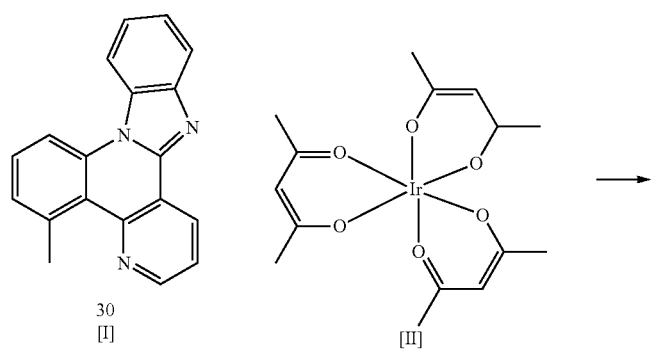
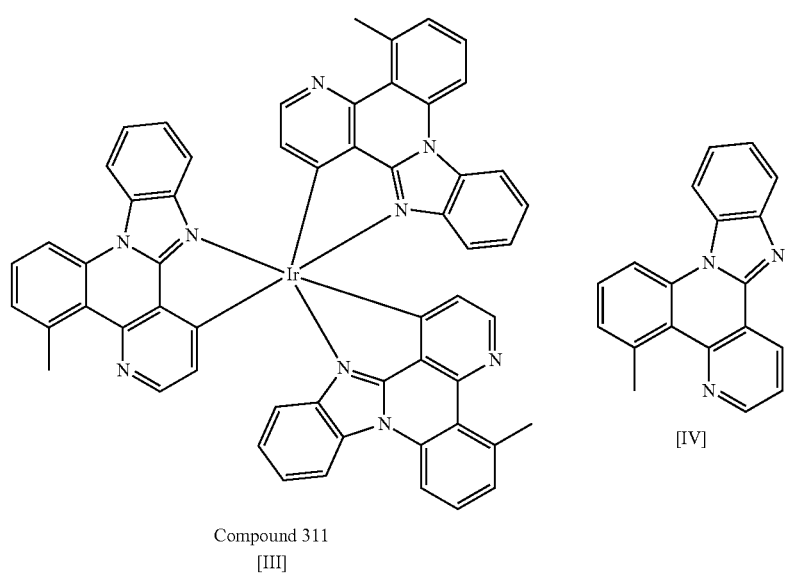
Compound 311
[III]
Ligand 30 (1.5 g) and Ir(acac)₃ (0.518 g) were combined in pentadecane in a Schlenk tube and degassed, then heated to 285° C. in a sand bath for 3 days. The product was purified by silica gel chromatography to afford Compound 7 (11%).
Synthesis of Compounds 312-314
(See FIG. 12 for an exemplary synthetic scheme)
Synthesis of 10-chloro-2-methylbenzo[h][1,6]naph-thyridin-5-amine (32)
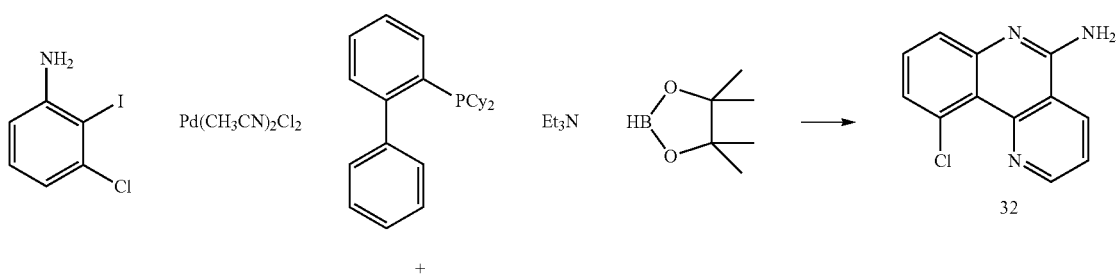

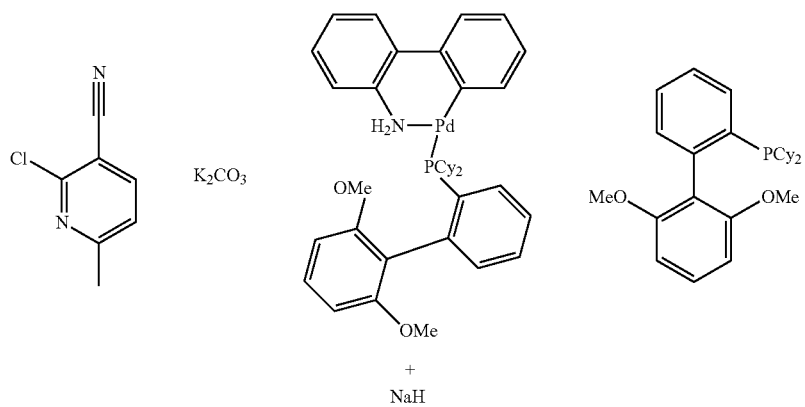

A mixture of Pd(CH₃CN)₂Cl₂ (0.136 g, 0.524 mmol) and CyJohnPhos (0.368 g, 1.049 mmol) was dissolved in dioxane (60 ml). 3-chloro-2-iodoaniline (6.98 g, 27.5 mmol), triethylamine (10.96 ml, 79 mmol), and 4,4,5,5-tetramethyl-1,3,2-dioxaborolane (7.99 ml, 55.1 mmol) were added to the solution in sequence via syringe. The reaction was reflux for 3 hours. The mixture was cooled to room temperature and solid 2-chloro-6-methylnicotinonitrile (4 g, 26.2 mmol), S-Phos Pd G2 (0.378 g, 0.524 mmol), S-Phos (0.215 g, 0.524 mmol), and potassium carbonate (7.25 g, 52.4 mmol) were added to the reaction mixture dioxane (15 ml) and water (15 ml) and the reaction was heated to 80° C. overnight. Solvents were removed under vacuum and the crude residue was dissolved in DCM and washed with KOH(aq)/brine. After evaporation of the organic layer the solids were re-dissolved in THF (35 mL) and sodium hydride (1.573 g, 39.3 mmol) was added to the solution at 0° C. and stirred for 10 min. The reaction was quenched with water and extracted with DCM. Evaporation of the organic layer and trituration in 1:1 diethyl ether and hexane (~1:1) yielded 32 as a yellow crystalline solid (46%).

Synthesis of 5-chloro-3-methylbenzo[h]benzo[4,5]imidazo[2,1-f][1,6]naphthyridine (33)

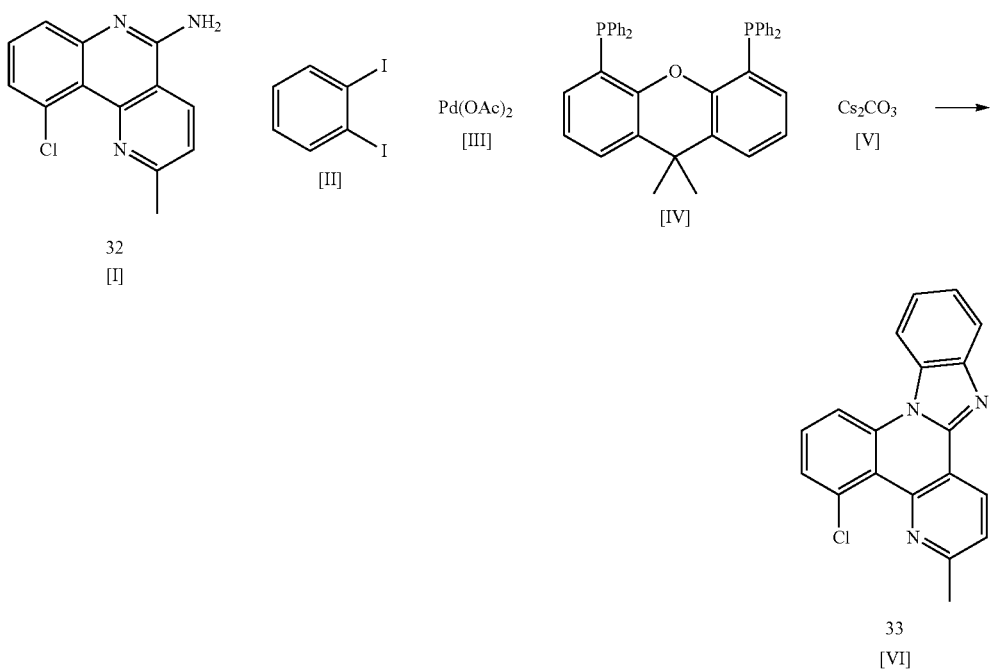

A mixture of 32 (200 mg, 0.821 mmol), diacetoxypalladium (9.21 mg, 0.041 mmol), Xantphos (23.74 mg, 0.041 mmol), and cesium carbonate (1070 mg, 3.28 mmol) was vacuumed and back-filled with nitrogen several times and 1,2-diiodobenzene (0.118 ml, 0.903 mmol) and toluene (8 ml) were added. The reaction was reflux for 2 hours, cooled to room temperature and extracted with DCM. The organic layer was dried, evaporated and the solids were triturated with diethyl ether and used in the next step without further purification.

Synthesis of 5-(2,6-dimethylphenyl)-3-methylbenzo[h]benzo[4,5]imidazo[2,1-f][1,6]naphthyridine (34)

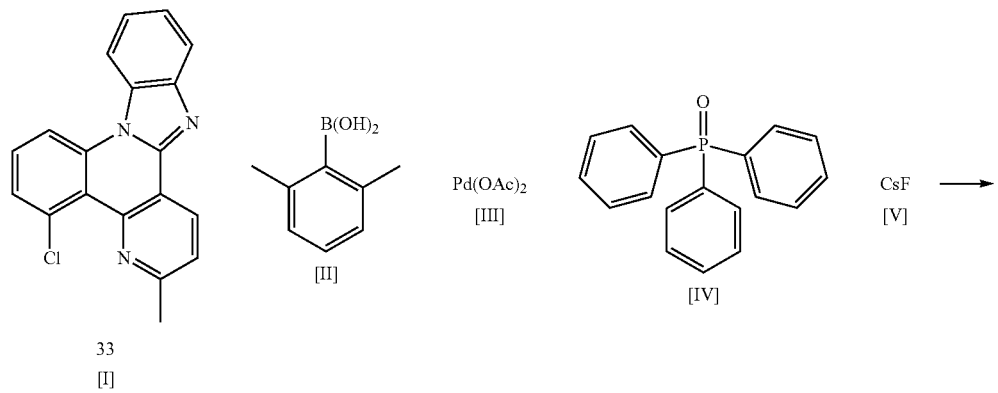

A mixture of 33 (3.0 g, 9.44 mmol), (2,6-dimethylphenyl) boronic acid (2.83 g, 18.88 mmol), diacetoxypalladium (0.212 g, 0.944 mmol), triphenylphosphine oxide (0.525 g, 1.888 mmol), and cesium fluoride (3.59 g, 23.60 mmol) was vacuumed and back-filled with nitrogen several times. THF (60 ml) was added and the mixture was refluxed overnight. After cooling to room temperature the mixture was coated on celite and purified by silica gel chromatography and the product was triturated in hexane to yield 34 (50%).

Synthesis of Compound 312

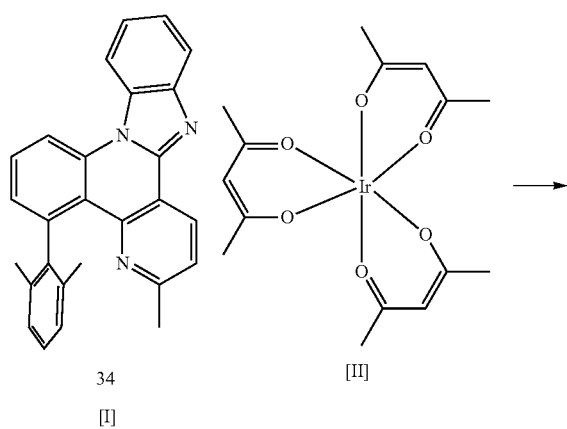

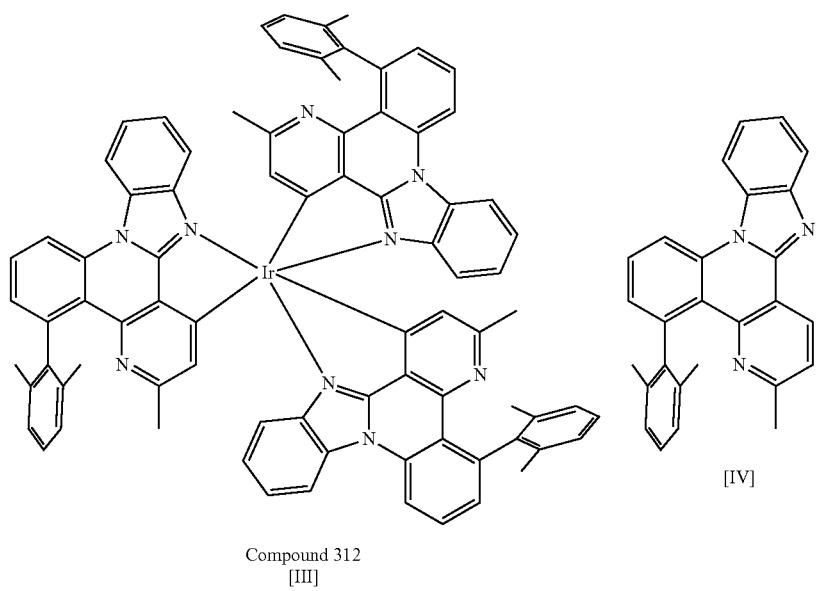

Compound 312
[III]

[IV]

Ligand 34 (1.5 g) and Ir(acac)₃ (0.379 g) were combined in a Schlenk tube in pentadecane (2 mL), degassed and heated to 295° C. in a sand bath for 3 days. The mixture was dissolved in DCM, filtered, then purified by silica gel and neutral alumina chromatography to afford Compound 312 (5%).

Synthesis of 10-(3,5-dimethylphenyl)-2-methyl-benzo[h][1,6]naphthyridin-5-amine (36)

A mixture of 32 (2 g, 8.21 mmol), (3,5-dimethylphenyl)boronic acid (2.216 g, 14.77 mmol), S-Phos Pd G2 (0.237 g, 0.328 mmol), S-Phos (0.135 g, 0.328 mmol), and potassium carbonate (1.134 g, 8.21 mmol) was vacuumed and back-filled with nitrogen several times. Dioxane (35 ml) and water (7 ml) were added and the mixture was refluxed overnight. After evaporation of the solvent the residue was dissolved in a small amount of MeOH and precipitated using water/brine. The solids formed were filtered, dried and used without further purification, quantitative yield.

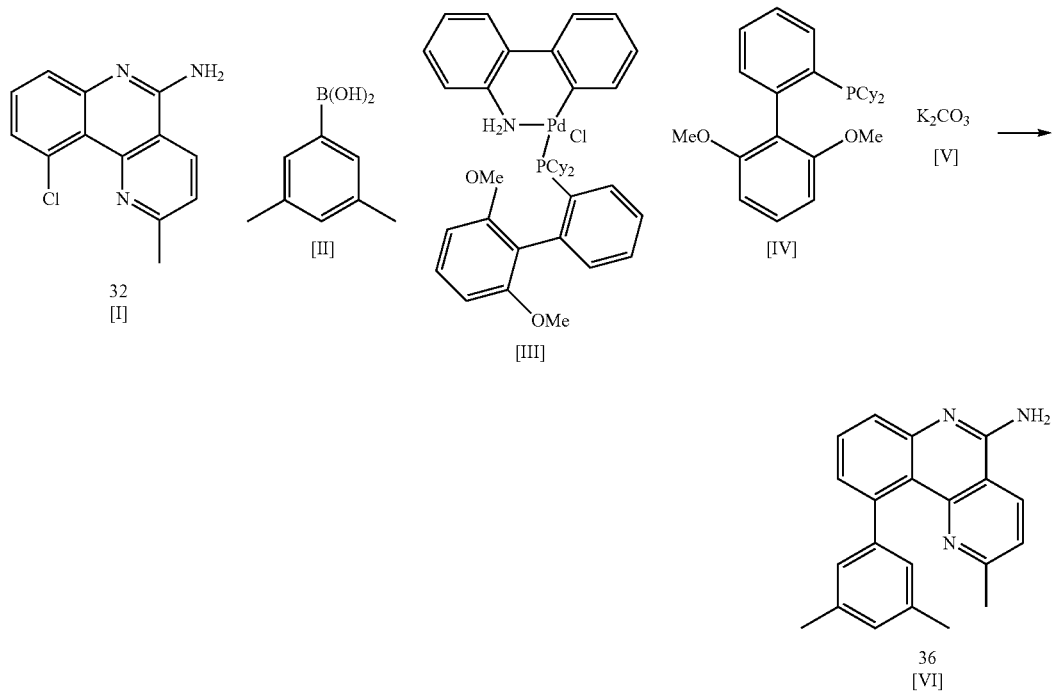

Synthesis of 5-(3,5-dimethylphenyl)-3-methylbenzo[h]benzo[4,5]imidazo[2,1-f][1,6]naphthyridine (37)

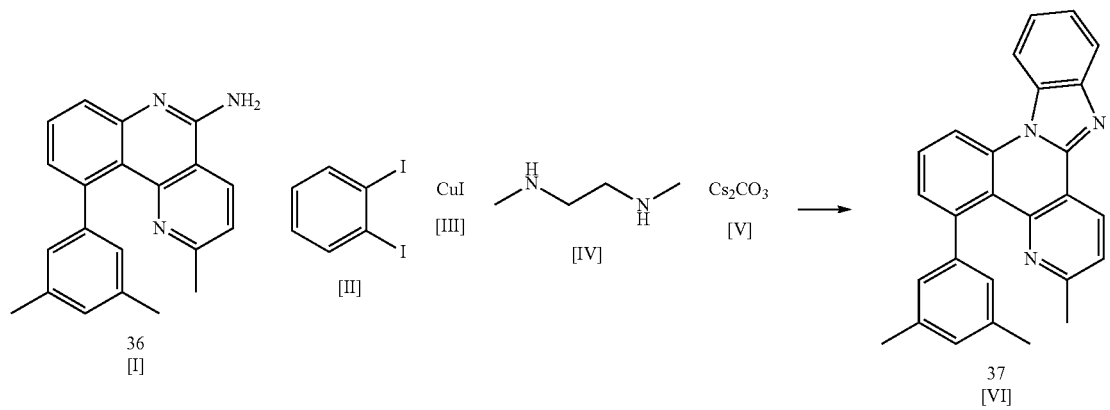

A mixture of 36 (2.57 g, 8.20 mmol), copper(I) iodide (0.234 g, 1.230 mmol), N1,N2-dimethylethane-1,2-diamine (0.265 ml, 2.460 mmol), and cesium carbonate (5.34 g, 16.40 mmol) was vacuumed and back-filled with nitrogen several times and 1,2-diiodobenzene (1.393 ml, 10.66 mmol) and NMP (35 ml) were added. The reaction was heated at 150° C. overnight and addition of water/brine formed precipitates that were filtered. The solid was dissolved in DCM, washed and washed with brine. 37 was isolated by silica gel chromatography and washed with diethyl ether to afford an off-white solid (1.36 g, 43% over two steps).

Synthesis of Compound 313

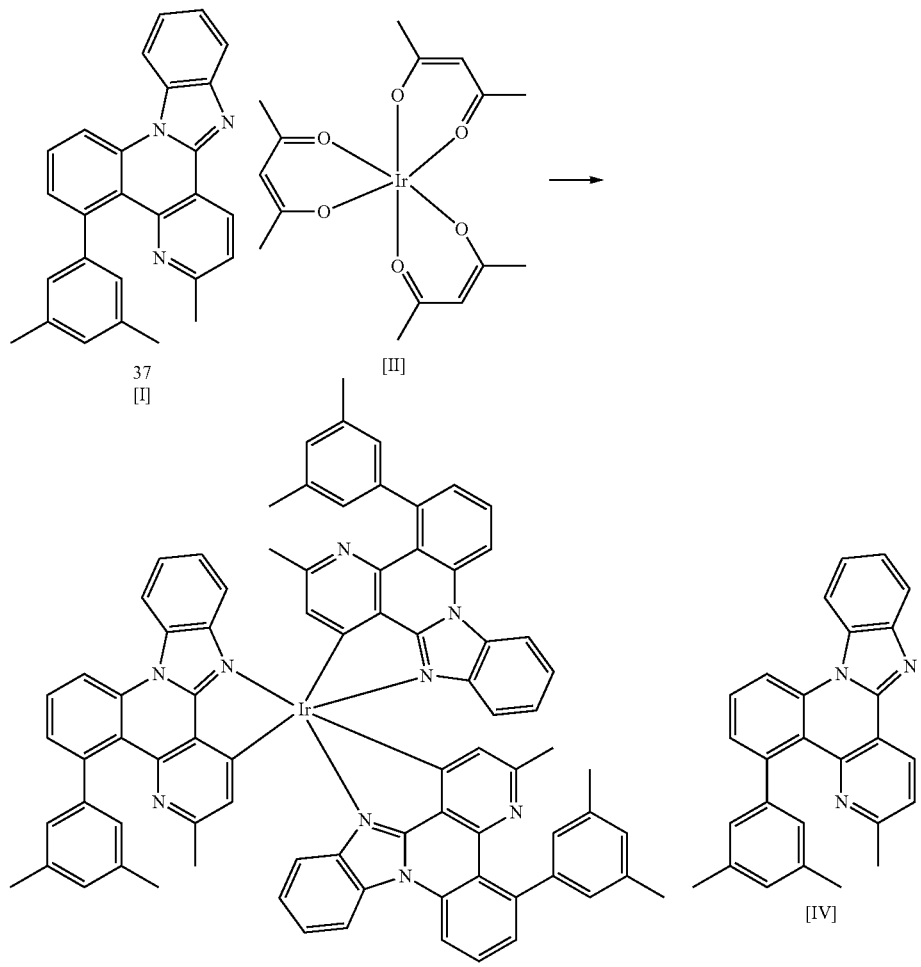

Ligand 37 (1 g) and Ir(acac)$_3$ (0.253 g) were combined in pentadecane (2 mL) in a 23 mL parr bomb which was heated to 290° C. in a sand bath for 3 days. The product was triturated in DCM to afford Compound 313 (85%).

Synthesis of 10-(4-isobutylphenyl)-2-methylbenzo[h][1,6]naphthyridin-5-amine (39)

0.059 mmol), S-Phos (24.26 mg, 0.059 mmol), and potassium carbonate (204 mg, 1.477 mmol) was vacuumed and back-filled with nitrogen several times. Dioxane (10 ml) and water (2 ml) were added and the mixture was refluxed overnight. Removal of solvent yielded a residue that was washed with water and dried and used in the next step without further purification.

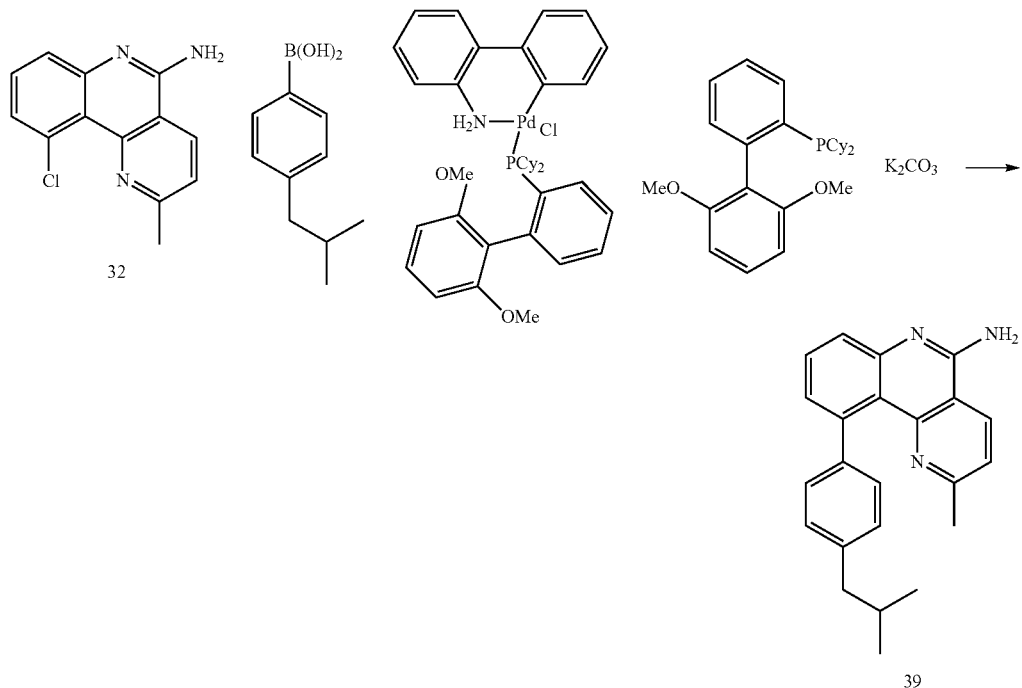

A mixture of 32 (360 mg, 1.477 mmol), (4-isobutylphenyl) boronic acid (473 mg, 2.66 mmol), S-Phos Pd G2 (42.6 mg, Synthesis of 5-(4-isobutylphenyl)-3-methylbenzo[h]benzo[4,5]imidazo[2,1-f][1,6]naphthyridine (40)

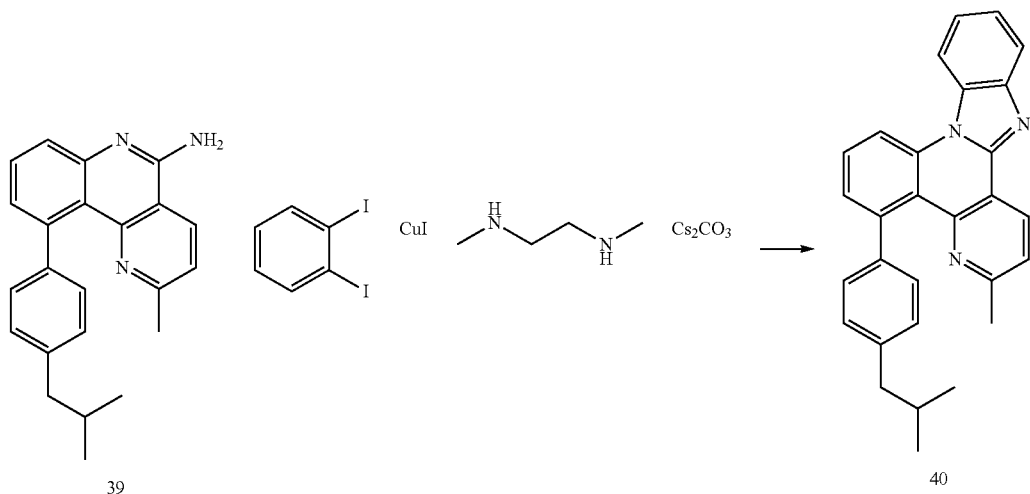

A mixture of 39 (504 mg, 1.476 mmol), copper(I) iodide (42.2 mg, 0.221 mmol), N1,N2-dimethylethane-1,2-diamine (0.048 ml, 0.443 mmol), and cesium carbonate (962 mg, 2.95 mmol) was vacuumed and back-filled with nitrogen several times and 1,2-diiodobenzene (0.289 ml, 2.214 mmol) and NMP (10 ml) were added. The reaction was heated at 150° C. overnight, then water was added to form precipitates which were filtered. This solid was dissolved in DCM and washed with brine. The organic layer was purified by column chromatography to yield 40 (32% over two steps).

Synthesis of Compound 314

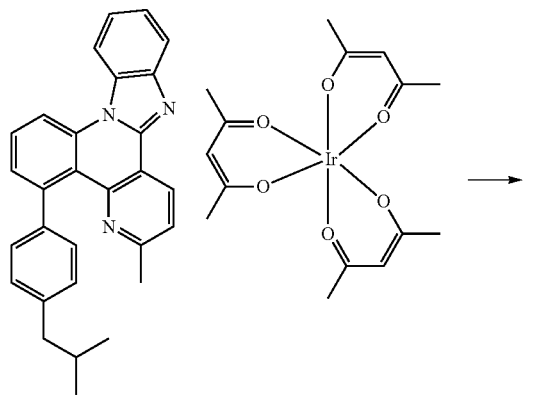

40

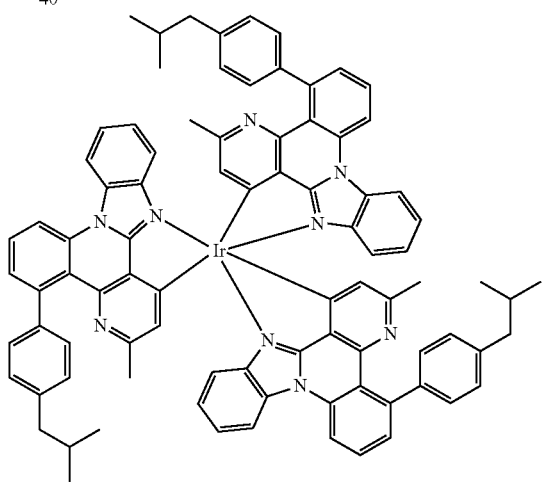

Compound 314

Ligand 40 (180 mg) and Ir(acac)$_3$ (42.4 mg) were combined in pentadecane (0.5 mL) in a 25 mL Schlenk tube, degassed, then heated to 290° C. for 2 days. The mixture was separated using neutral alumina chromatography and isolated Compound 314 (20%) was triturated in diethyl ether.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

We claim:

1. A compound comprising a ligand $L_A$ of Formula I:

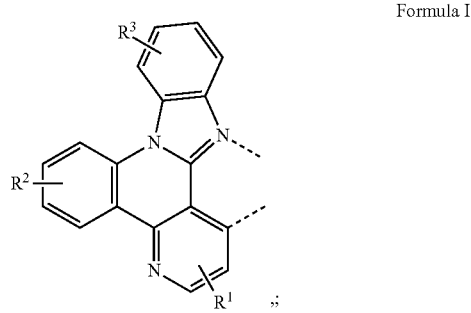

Formula I wherein $R^1$ represents mono, or di-substitution, or no substitution;
wherein $R^2$ and $R^3$ each independently represent mono, di, tri, or tetra-substitution, or no substitution;
wherein any adjacent substitutions in $R^1$, $R^2$ and $R^3$ are optionally linked together to form a ring;
wherein $R^1$, $R^2$ and $R^3$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, carboxylic acid, ester, nitrile, and isonitrile;
wherein the ligand $L_A$ is coordinated to a metal M; and
wherein the ligand $L_A$ is optionally linked with other ligands to form a tridentate, tetradentate, pentadentate or hexadentate ligand.

2. The compound of claim 1, wherein the compound has the formula $M(L_A)_m(L_B)_n$, having the structure:

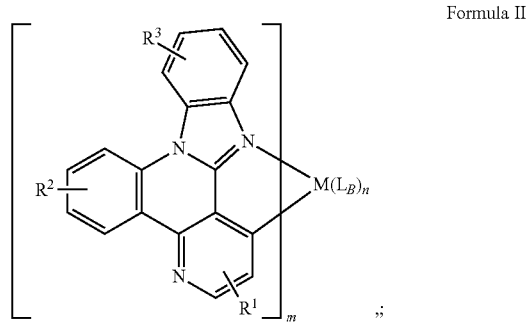

Formula II wherein $L_B$ is a different ligand from $L_A$; and
wherein m is an integer from 1 to the maximum number of ligands that may be coordinated to the metal M; m+n is the maximum number of ligands that may be coordinated to the metal M.

3. The compound of claim 1, wherein M is selected from the group consisting of Ir, Rh, Re, Ru, Os, Pt, Au, and Cu.

4. The compound of claim 1, wherein M is Ir.

5. The compound of claim 1, wherein the ligand $L_A$ has the structure of:

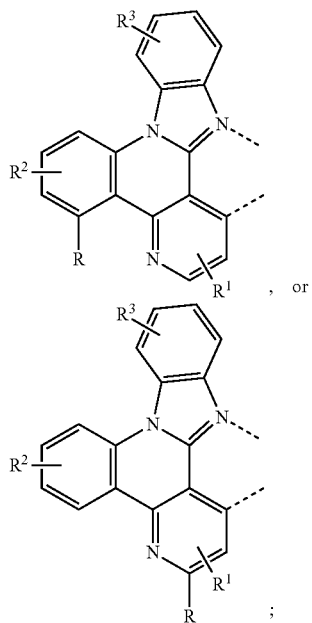

wherein R is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, and isonitrile.

6. The compound of claim 5, wherein R is selected from the group consisting of alkyl, cycloalkyl, silyl, aryl, heteroaryl, and combinations thereof.

7. A formulation comprising a compound comprising a ligand $L_A$ of Formula I:

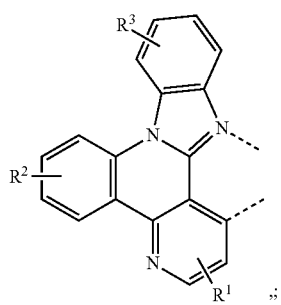

Formula I wherein $R^1$ represents mono, or di-substitution, or no substitution;
wherein $R^2$ and $R^3$ each independently represent mono, di, tri, or tetra-substitution, or no substitution;
wherein any adjacent substitutions in $R^1$, $R^2$ and $R^3$ are optionally linked together to form a ring;
wherein $R^1$, $R^2$ and $R^3$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, carboxylic acids, ester, nitrile, and isonitrile;
wherein the ligand $L_A$ is coordinated to a metal M; and
wherein the ligand $L_A$ is optionally linked with other ligands to form a tridentate, tetradentate, pentadentate or hexadentate ligand.

8. The compound of claim 1, wherein the compound has the structure:

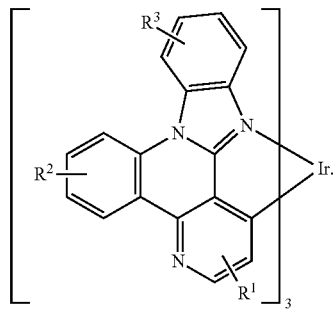

9. The compound of claim 5, wherein the compound has the structure:

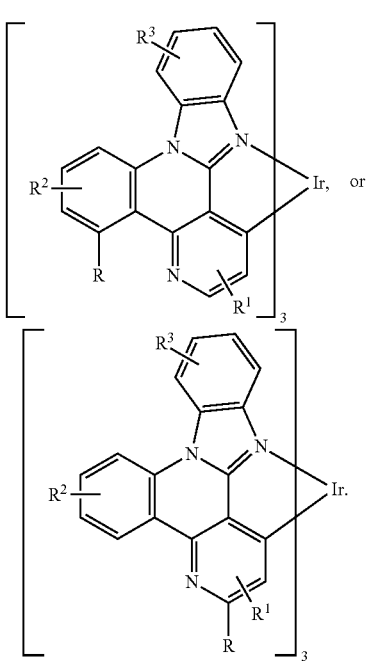

10. The compound of claim 1, wherein the ligand $L_A$ is selected from the group consisting of:

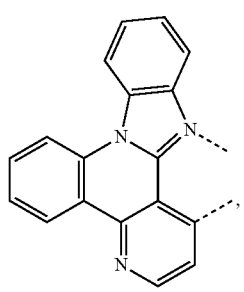

$L_{A1}$ $L_{A2}$
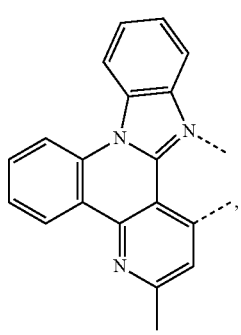
$L_{A3}$
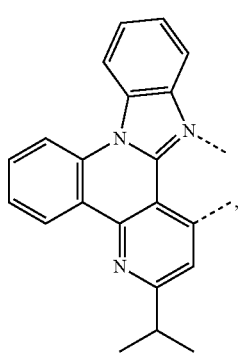
$L_{A4}$
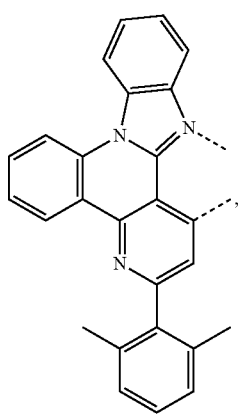
$L_{A5}$
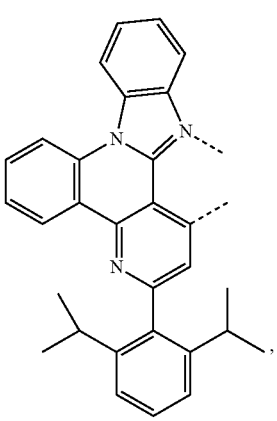
$L_{A6}$
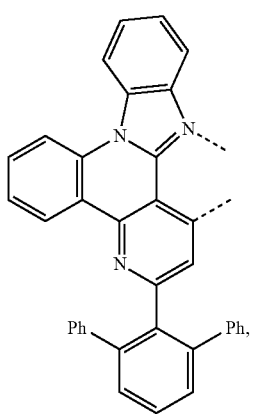
$L_{A7}$
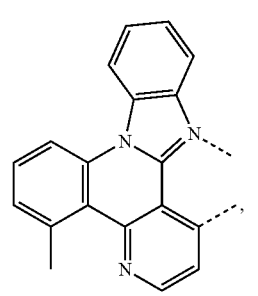
$L_{A8}$
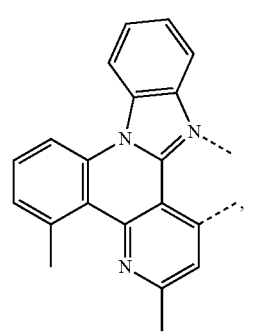
$L_{A9}$
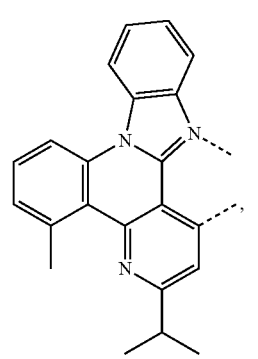

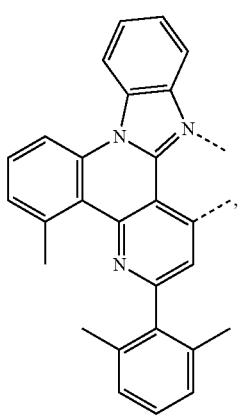 L_{A10}
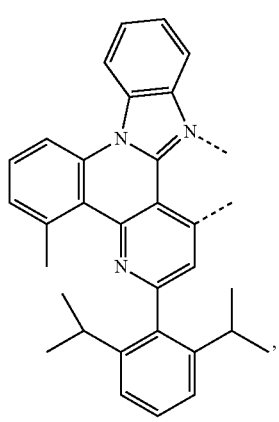 L_{A11}
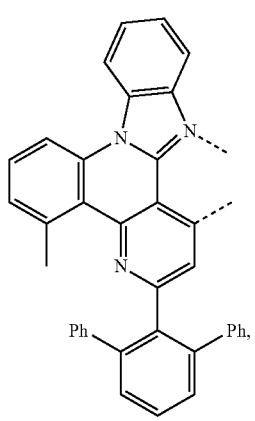 L_{A12}
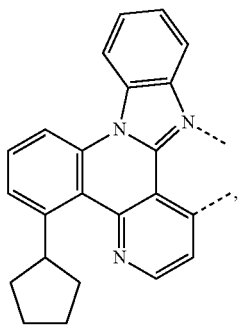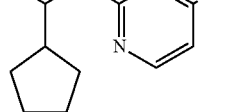 L_{A13}
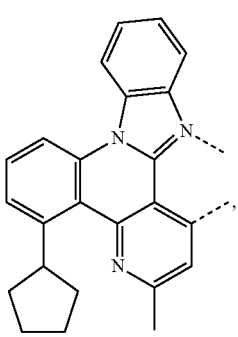 L_{A14}
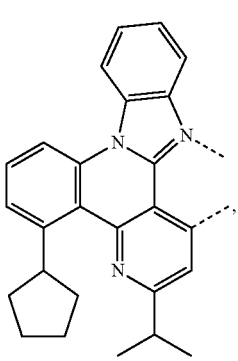 L_{A15}
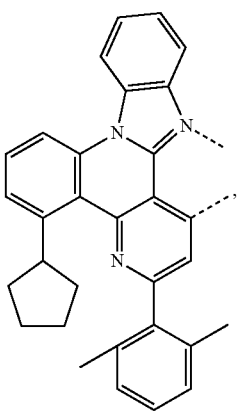 L_{A16}
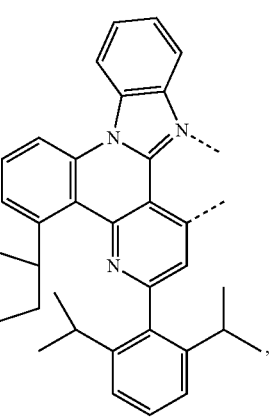 L_{A17}

311
-continued
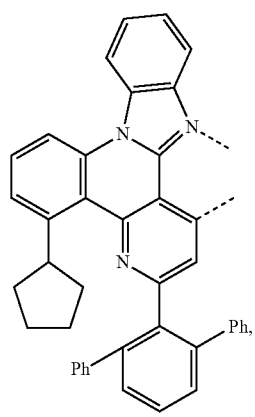
$L_{A18}$
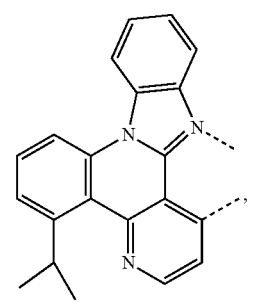
$L_{A19}$
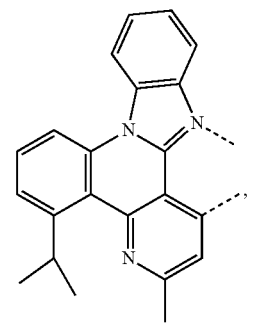
$L_{A20}$
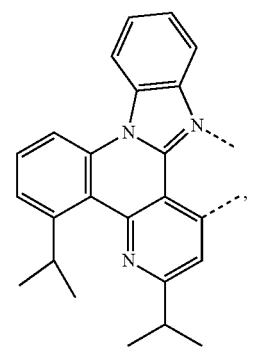
$L_{A21}$
312
-continued
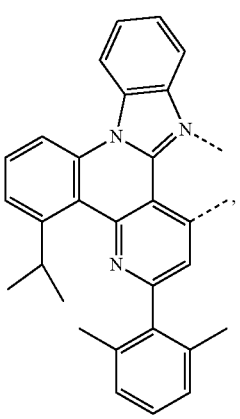
$L_{A22}$
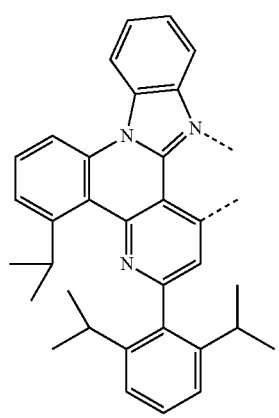
$L_{A23}$
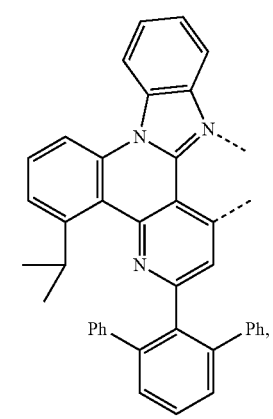
$L_{A24}$
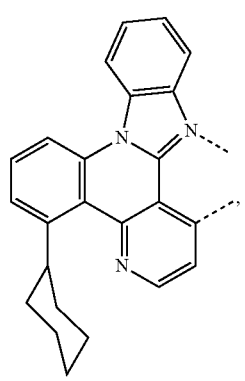
$L_{A25}$ L_{A26}
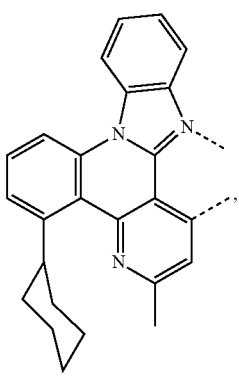
L_{A27}
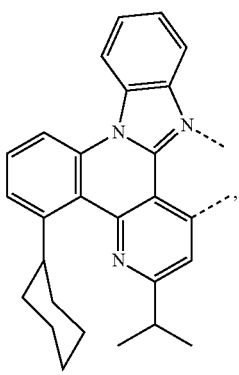
L_{A28}
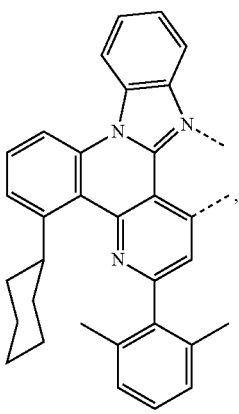
L_{A29}
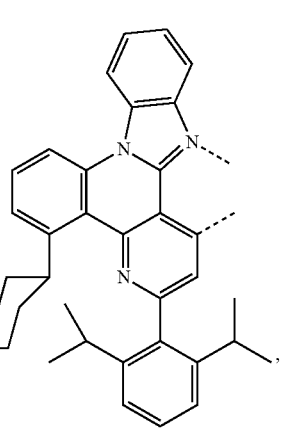
L_{A30}
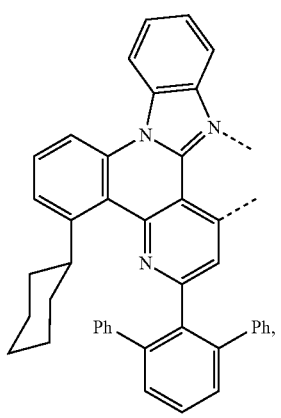
L_{A31}
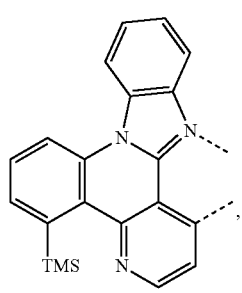
L_{A32}
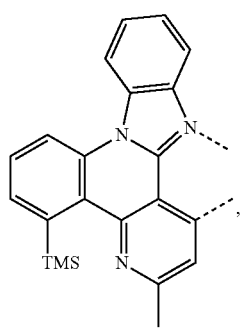
L_{A33}
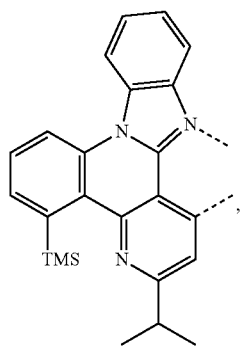

-continued
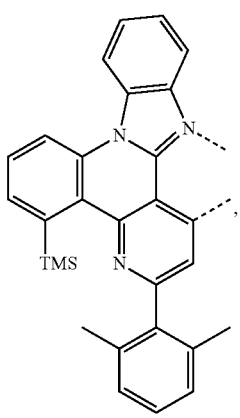
L<sub>A34</sub>
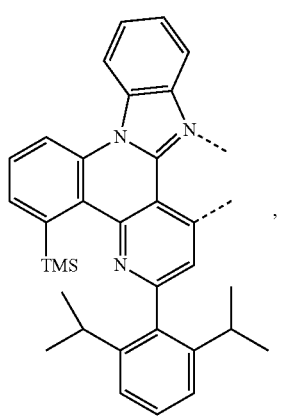
L<sub>A35</sub>
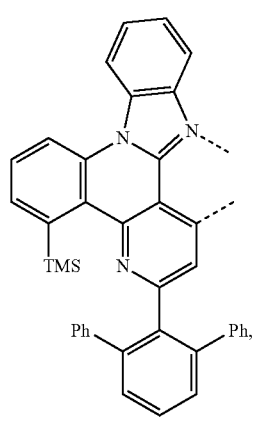
L<sub>A36</sub>
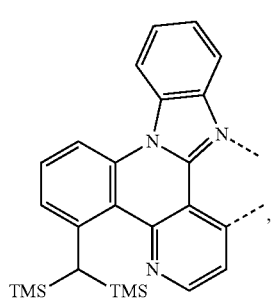
L<sub>A37</sub>
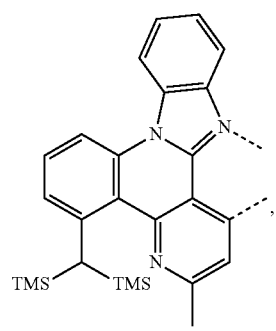
L<sub>A38</sub>
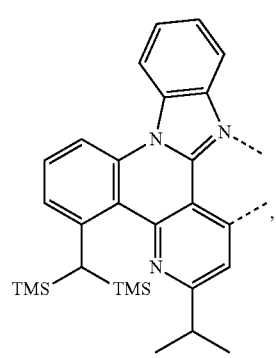
L<sub>A39</sub>
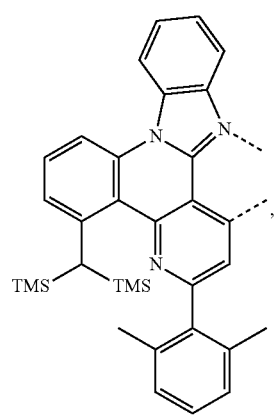
L<sub>A40</sub>
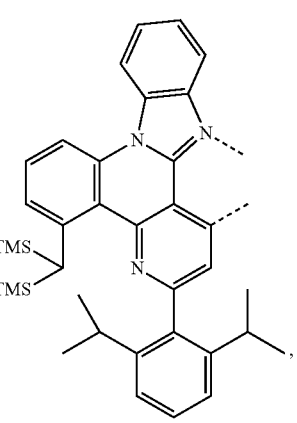
L<sub>A41</sub>

-continued
$L_{A42}$
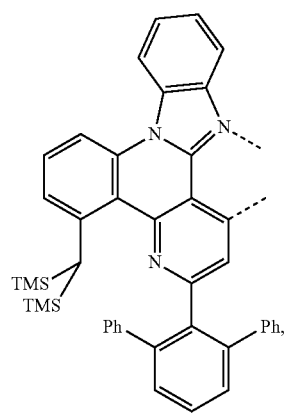
$L_{A43}$
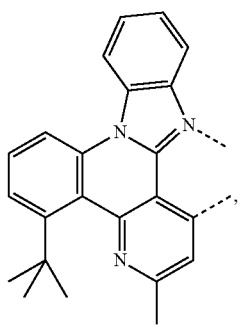
$L_{A44}$
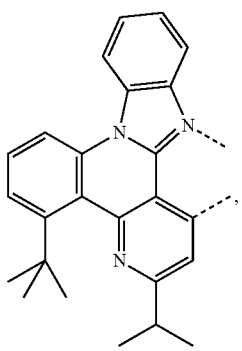
$L_{A45}$
-continued
$L_{A46}$
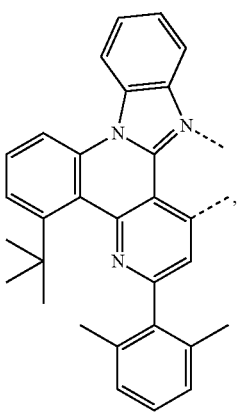
$L_{A47}$
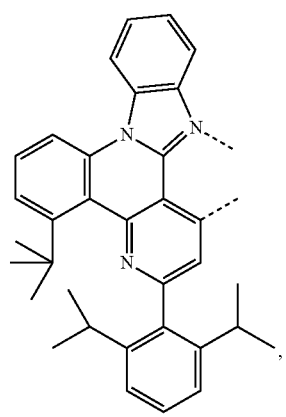
$L_{A48}$
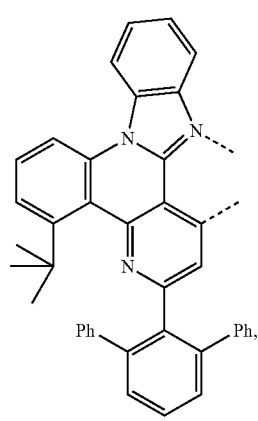
$L_{A49}$
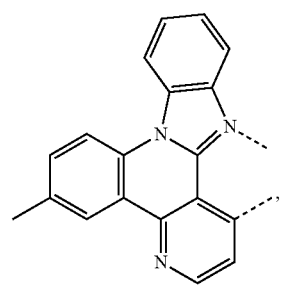

319
-continued
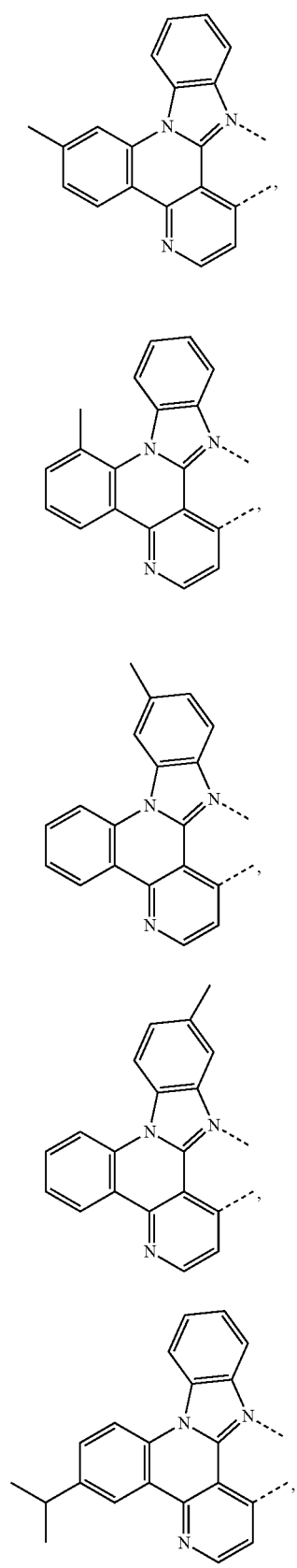
320
-continued
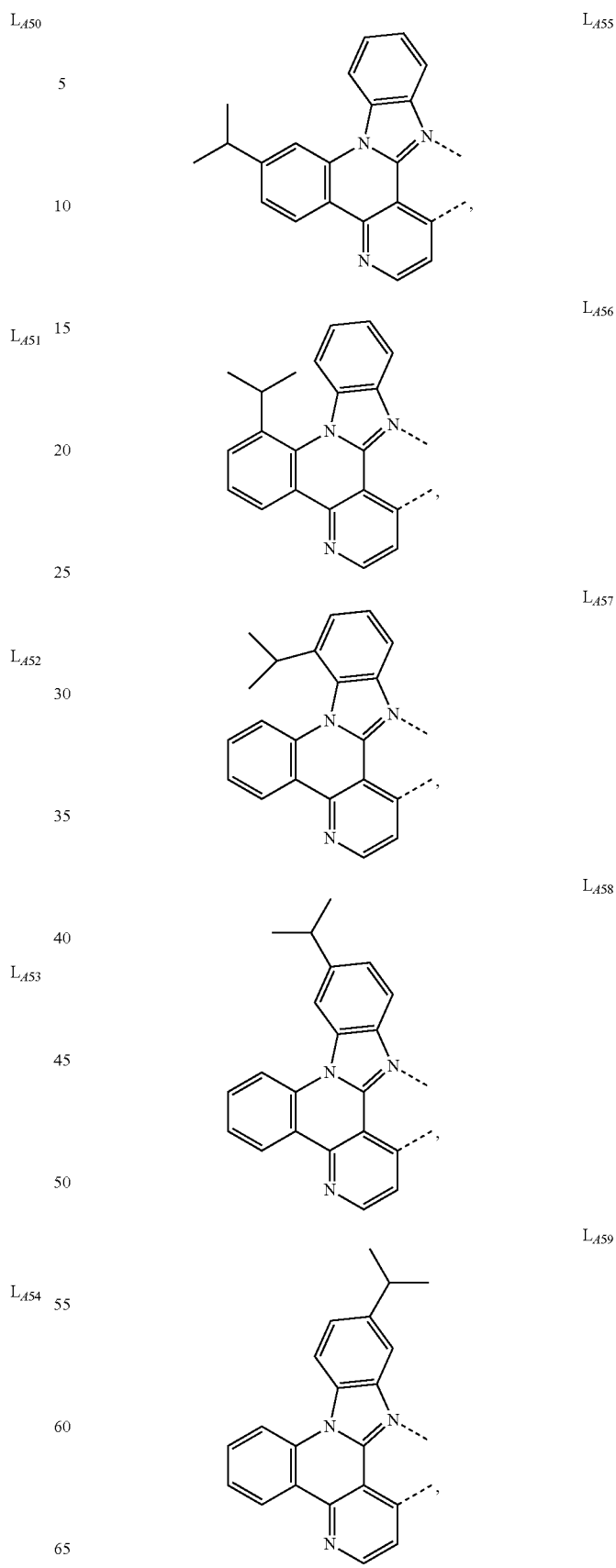

-continued
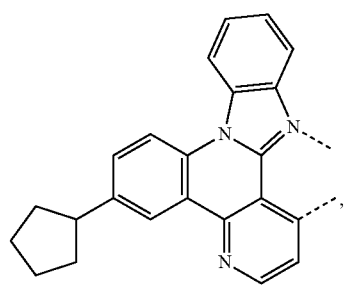 L<sub>A60</sub>
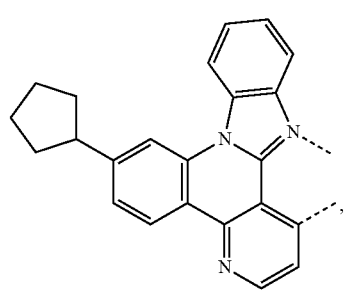 L<sub>A61</sub>
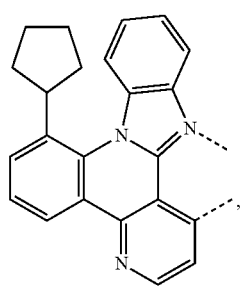 L<sub>A62</sub>
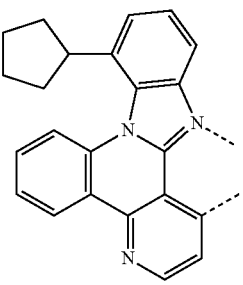 L<sub>A63</sub>
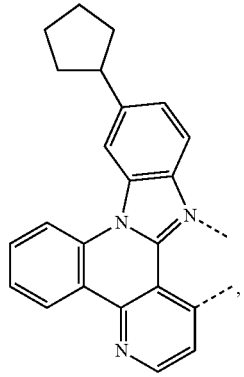 L<sub>A64</sub>
-continued
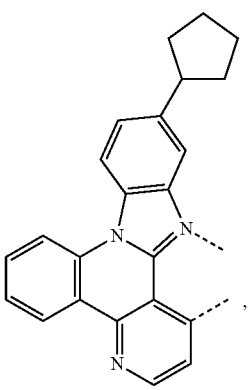 L<sub>A65</sub>
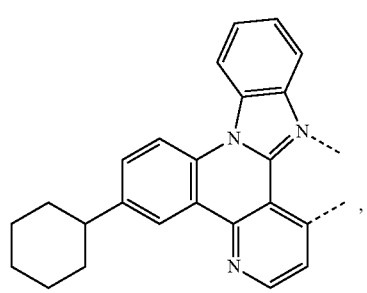 L<sub>A66</sub>
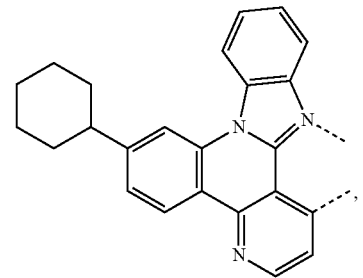 L<sub>A67</sub>
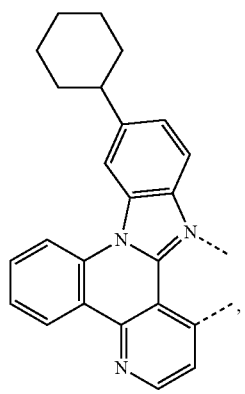 L<sub>A68</sub>

L_{A69}
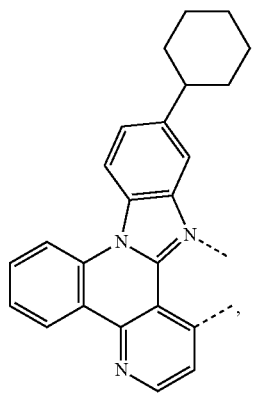
L_{A70}
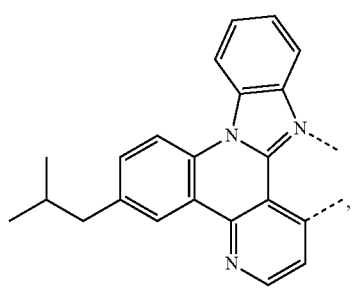
L_{A71}
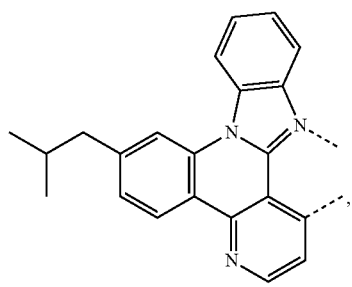
L_{A72}
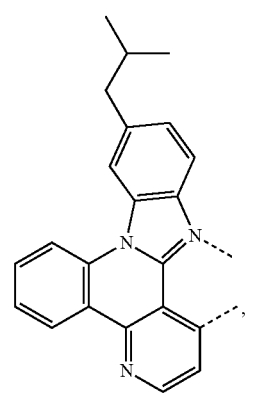
L_{A73}
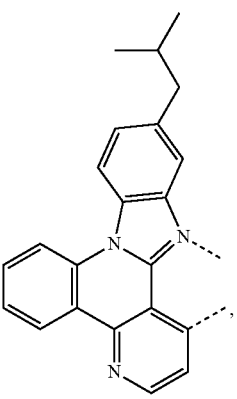
L_{A74}
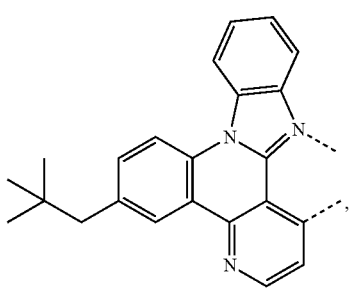
L_{A75}
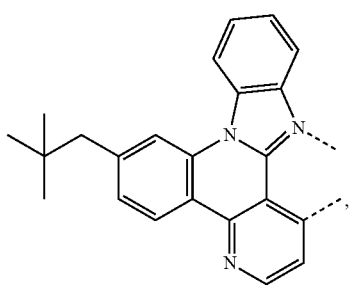
L_{A76}
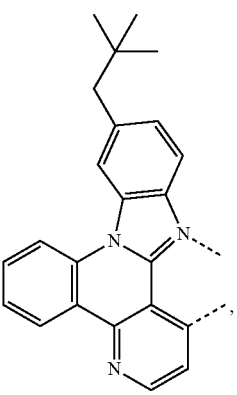

L<sub>A77</sub> 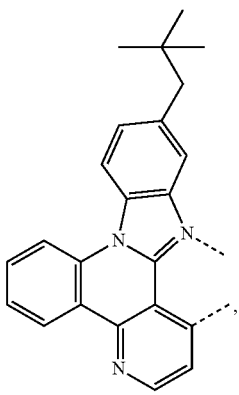
L<sub>A78</sub> 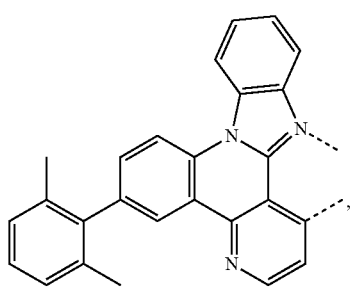
L<sub>A79</sub> 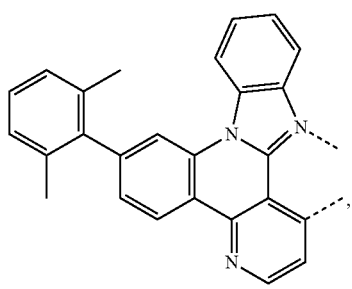
L<sub>A80</sub> 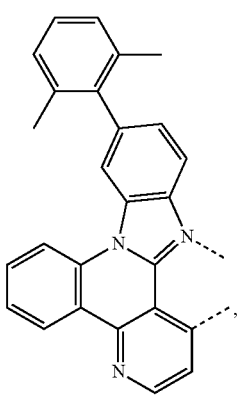
L<sub>A81</sub> 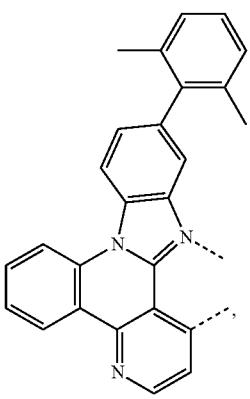
L<sub>A82</sub> 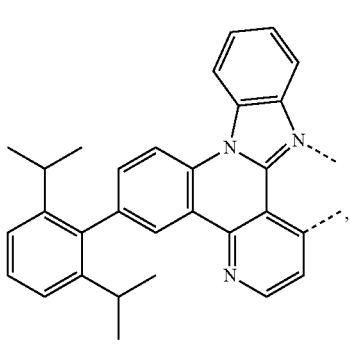
L<sub>A83</sub> 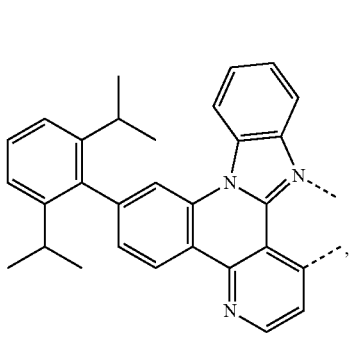
L<sub>A84</sub> 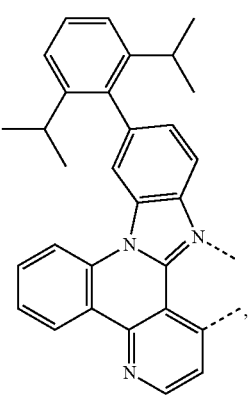

327
-continued
L<sub>A85</sub>
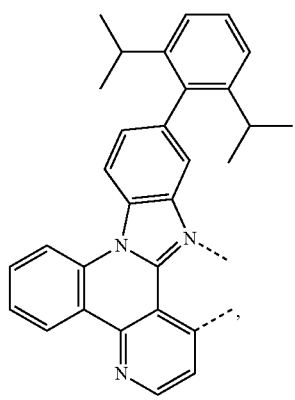
L<sub>A86</sub>
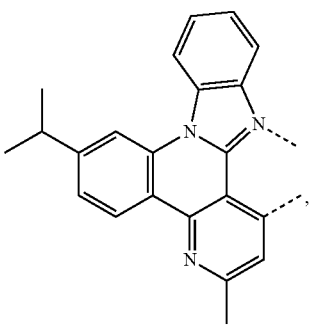
L<sub>A87</sub>
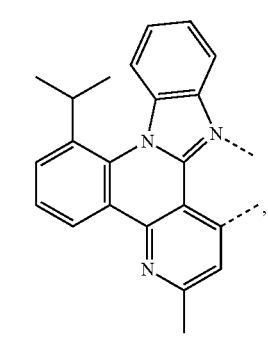
L<sub>A88</sub>
328
-continued
L<sub>A89</sub>
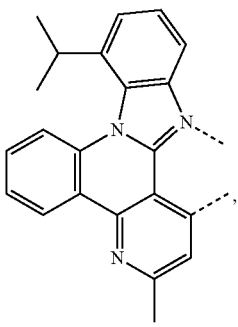
L<sub>A90</sub>
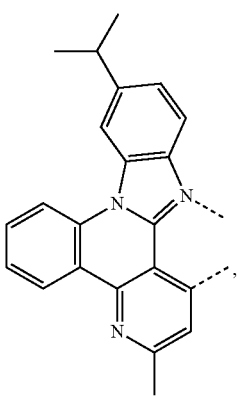
L<sub>A91</sub>
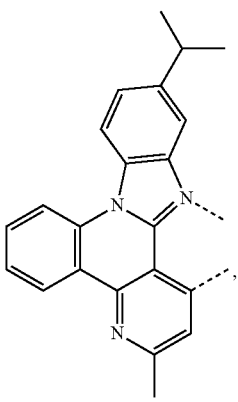
L<sub>A92</sub>
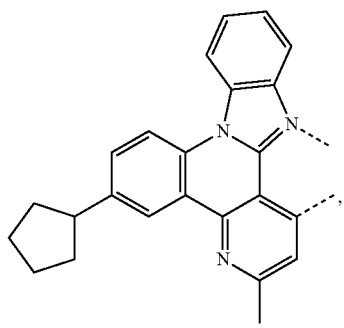

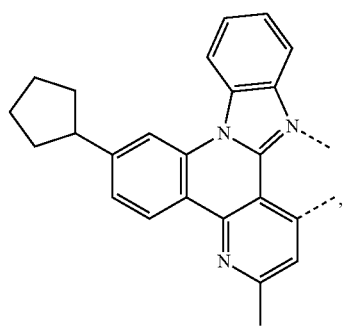
L_{A93}
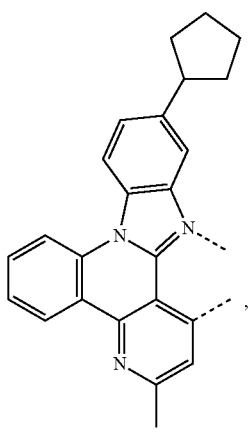
L_{A97}
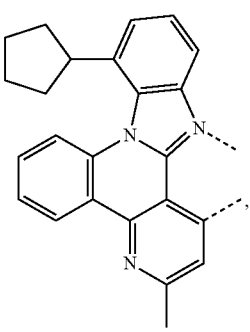
L_{A94}
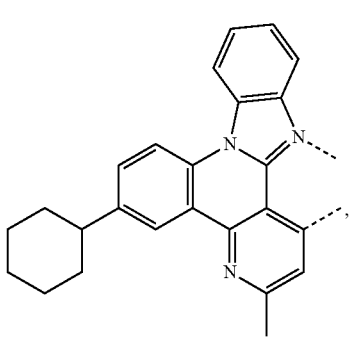
L_{A98}
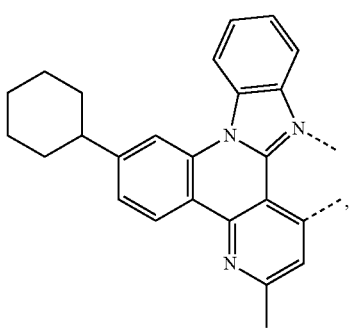
L_{A99}
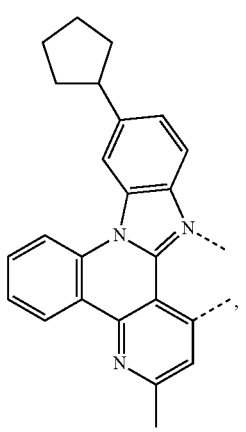
L_{A95}
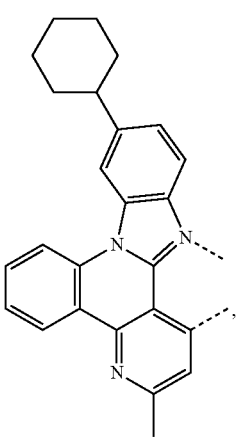
L_{A100}
L_{A96}

331
-continued
L<sub>A101</sub>
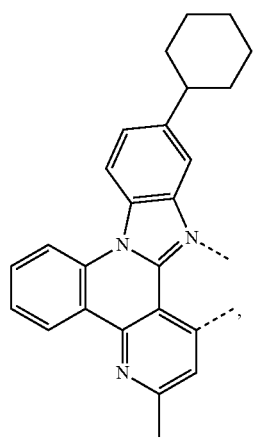
L<sub>A102</sub>
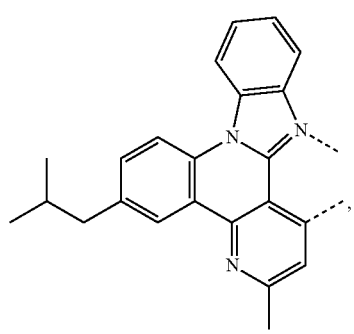
L<sub>A103</sub>
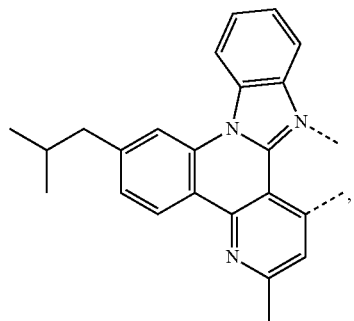
L<sub>A104</sub>
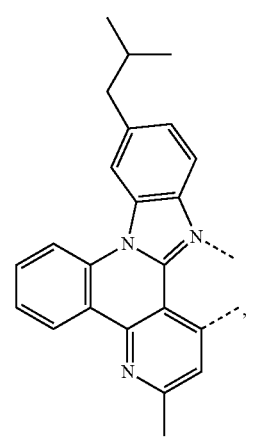
332
-continued
L<sub>A105</sub>
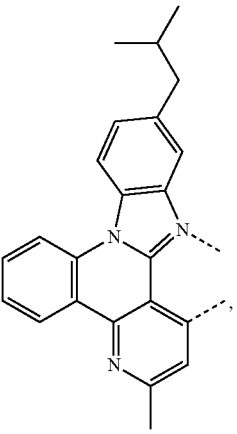
L<sub>A016</sub>
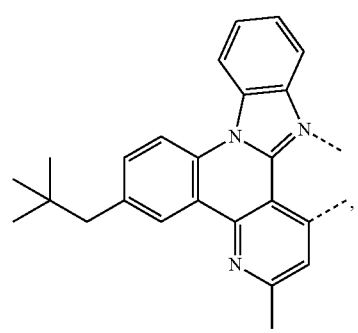
L<sub>A107</sub>
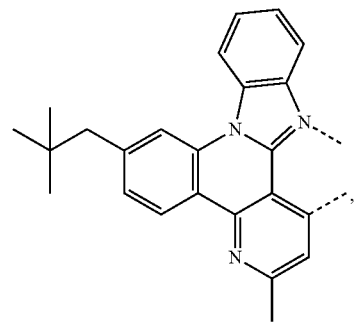
L<sub>A108</sub>
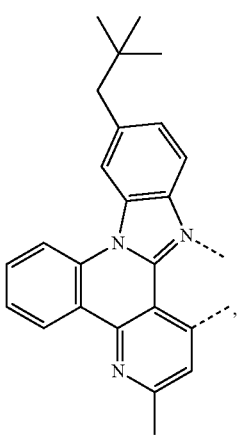

$L_{A109}$ $L_{A110}$ $L_{A111}$ $L_{A112}$ $L_{A113}$ $L_{A114}$ $L_{A115}$ $L_{A116}$

-continued
L<sub>A117</sub>
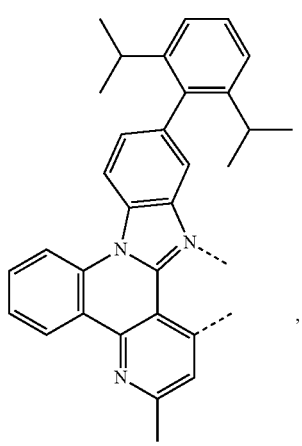
L<sub>A118</sub>
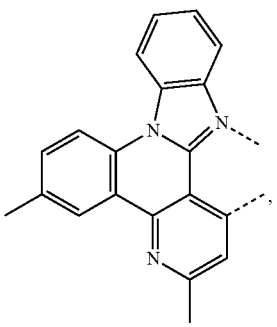
L<sub>A119</sub>
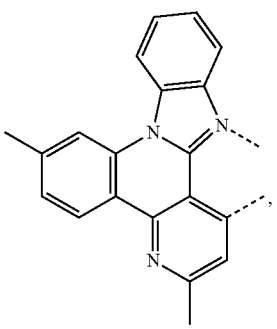
L<sub>A120</sub>
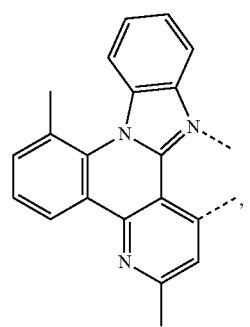
-continued
L<sub>A121</sub>
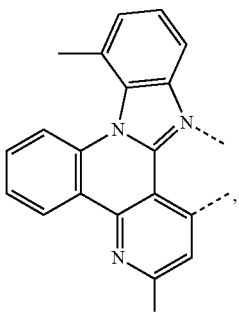
L<sub>A122</sub>
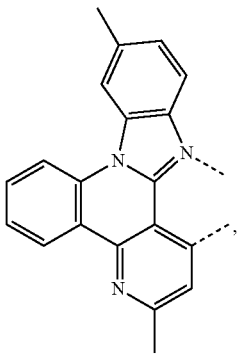
L<sub>A123</sub>
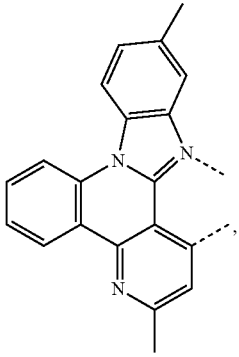
L<sub>A124</sub>
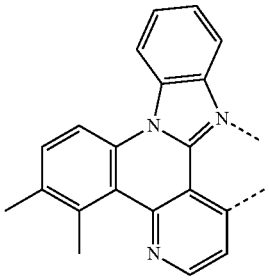
L<sub>A125</sub>
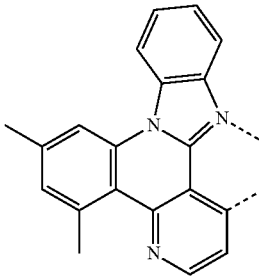

L<sub>A126</sub> 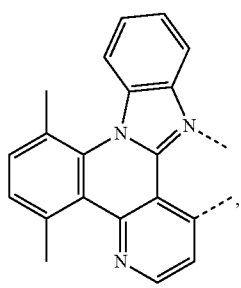
L<sub>A127</sub> 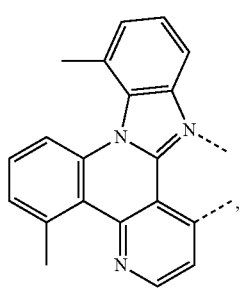
L<sub>A128</sub> 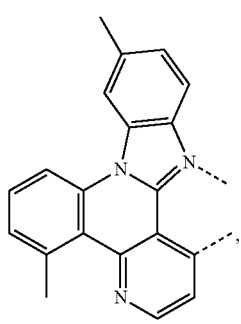
L<sub>A129</sub> 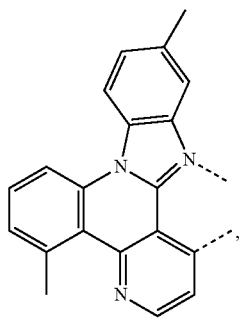
L<sub>A130</sub> 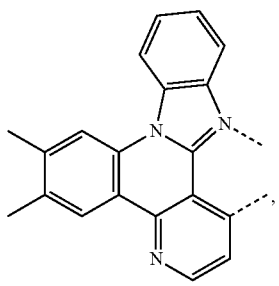
L<sub>A131</sub> 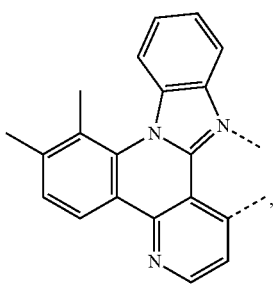
L<sub>A132</sub> 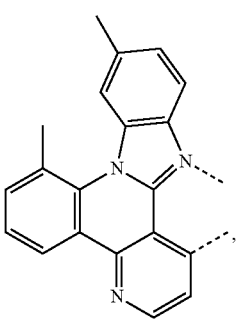
L<sub>A133</sub> 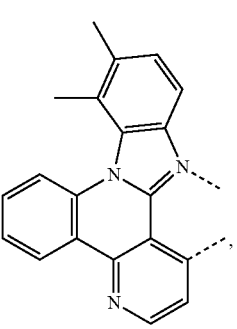
L<sub>A134</sub> 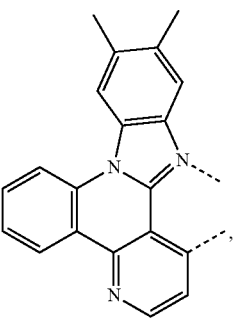
L<sub>A135</sub> 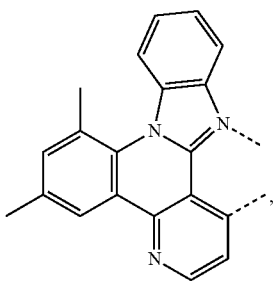

| | |
|---|---|
| L_{A136} 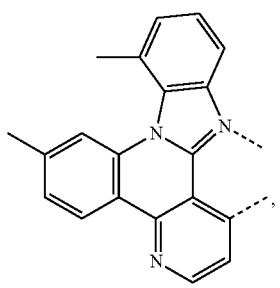 | L_{A141} 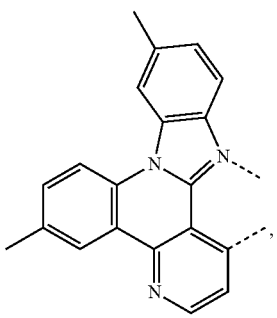 |
| L_{A137} 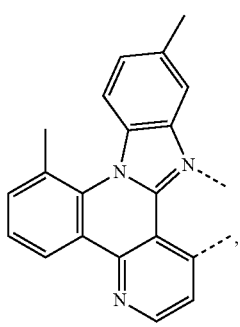 | L_{A142} 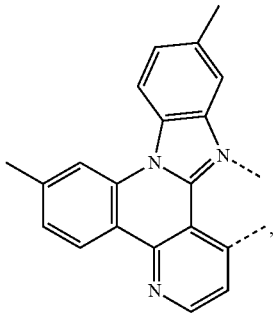 |
| L_{A138} 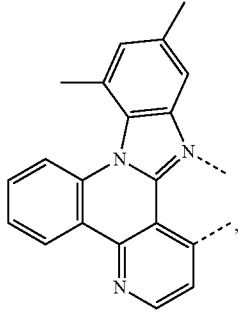 | L_{A143} 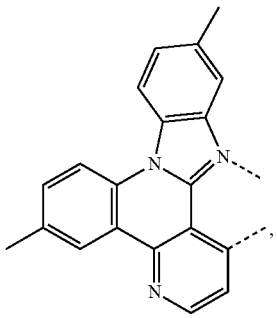 |
| L_{A139} 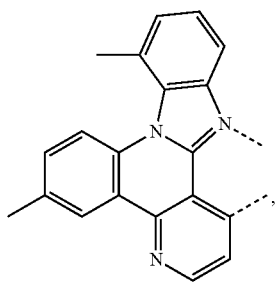 | L_{A144} 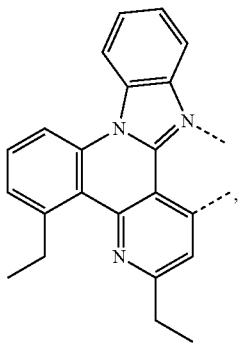 |
| L_{A140} 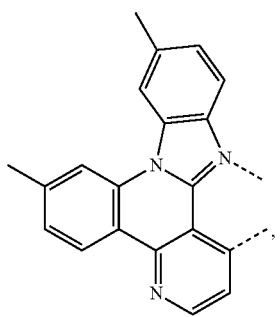 | |

341
-continued
L_{A145}
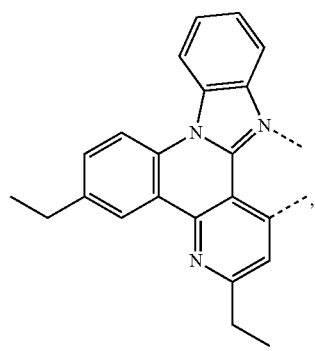
L_{A146}
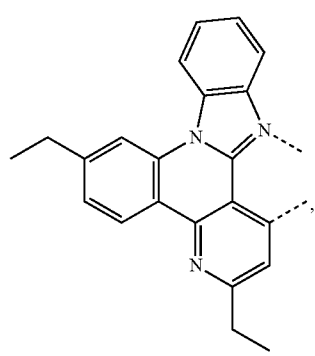
L_{A147}
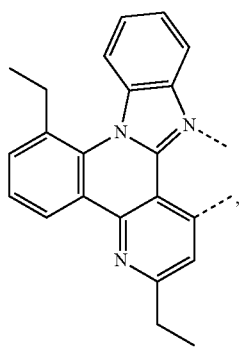
L_{A148}
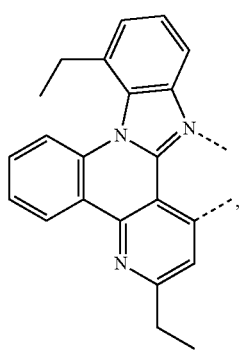
342
-continued
L_{A149}
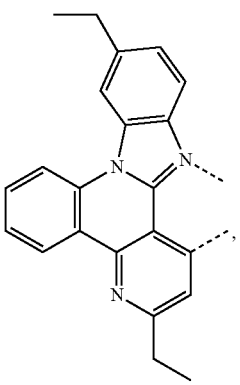
L_{A150}
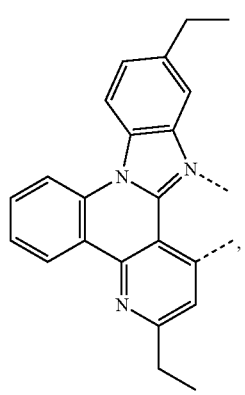
L_{A151}
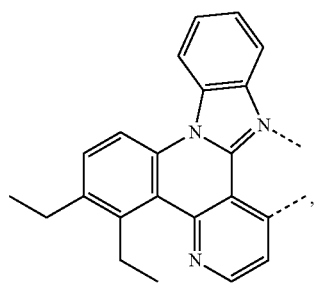
L_{A152}
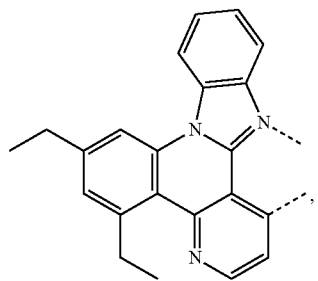
L_{A153}
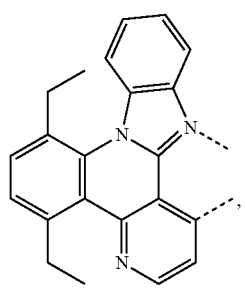

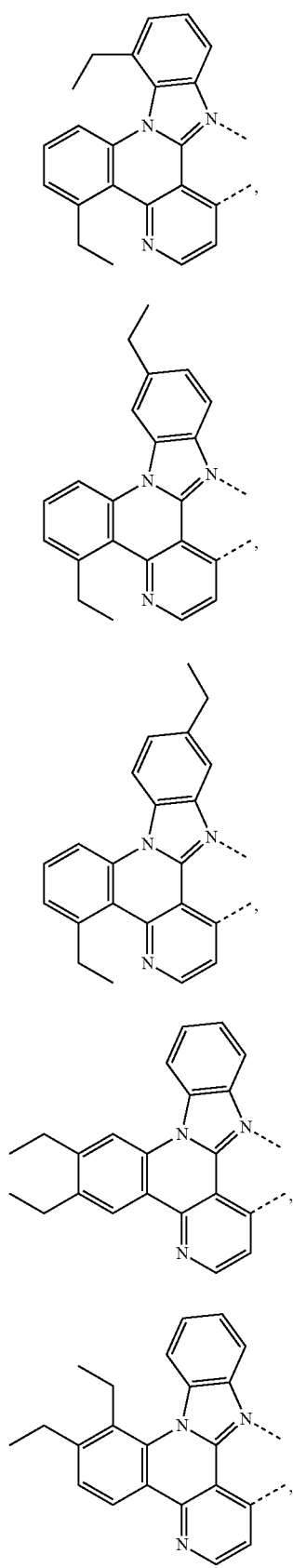
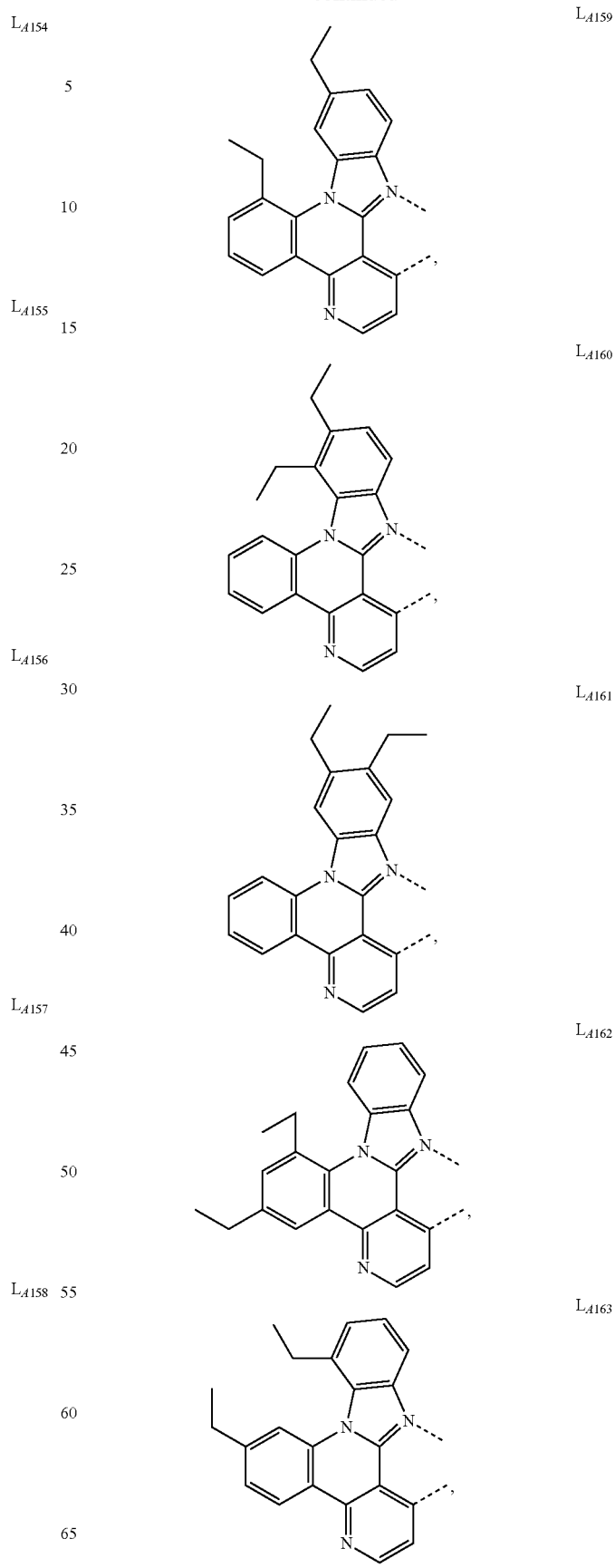

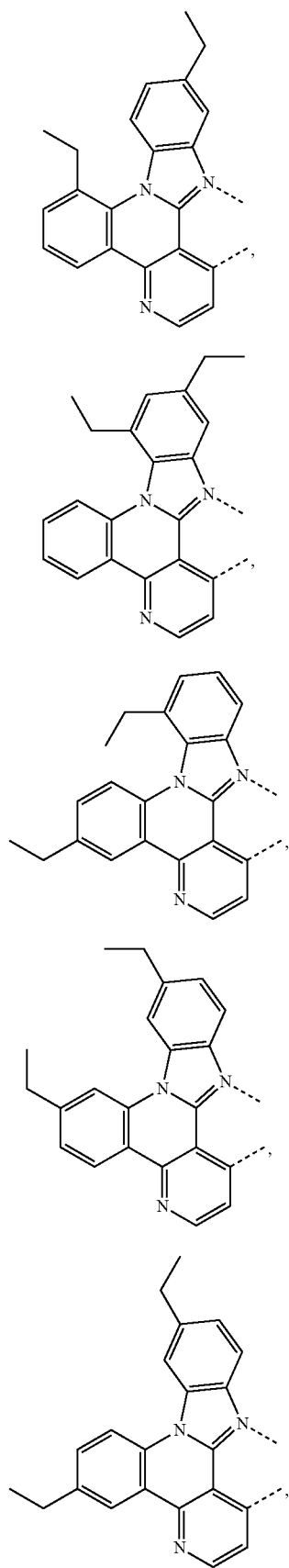
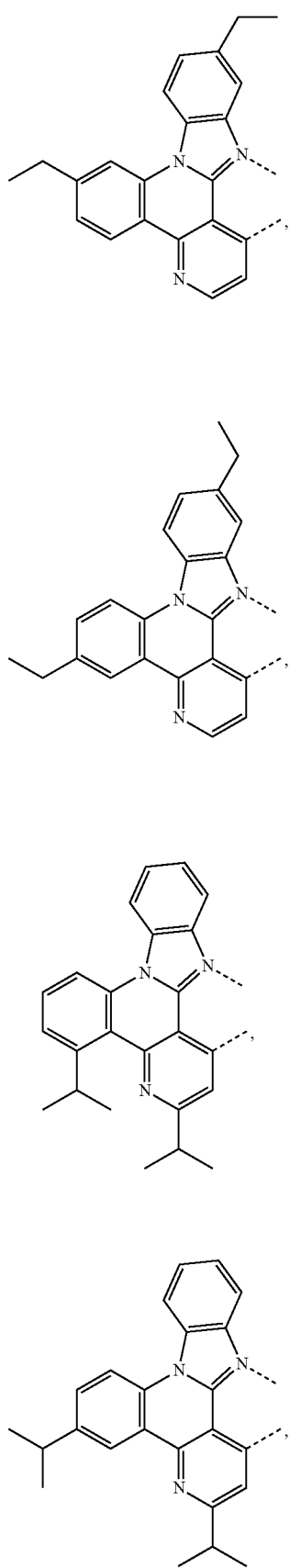

-continued
L<sub>A173</sub>
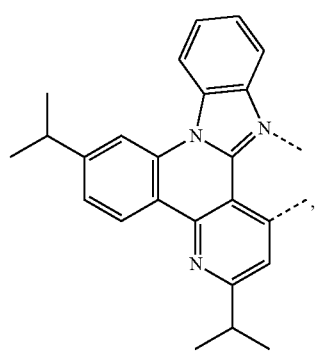
L<sub>A174</sub>
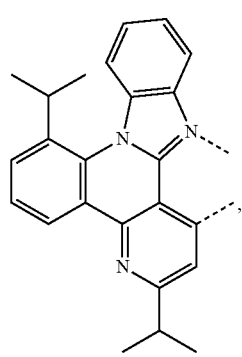
L<sub>A175</sub>
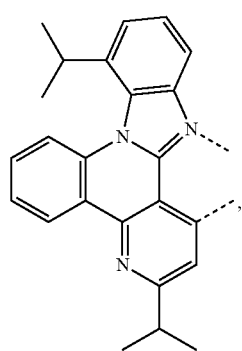
L<sub>A176</sub>
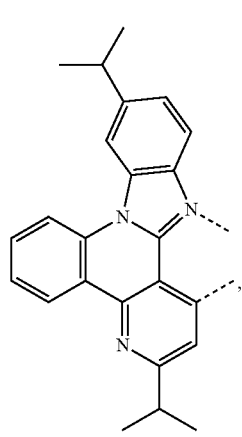
-continued
L<sub>A177</sub>
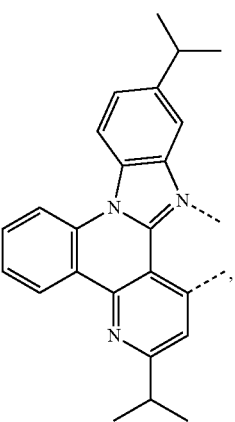
L<sub>A178</sub>
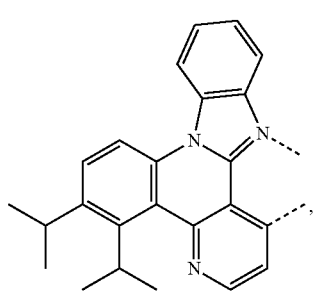
L<sub>A179</sub>
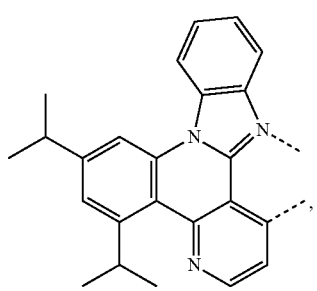
L<sub>A180</sub>
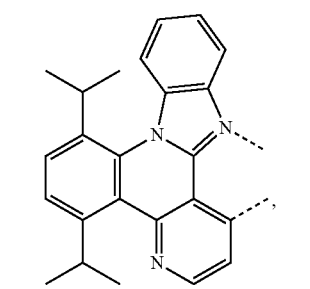
L<sub>A181</sub>
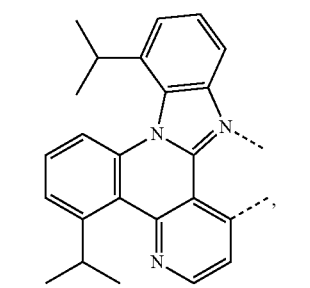

-continued
L_{A182}
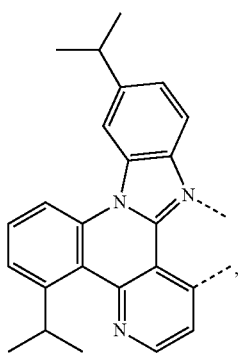
L_{A183}
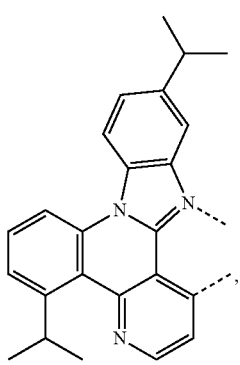
L_{A184}
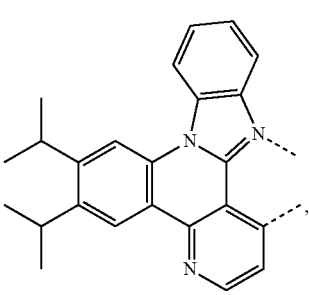
L_{A185}
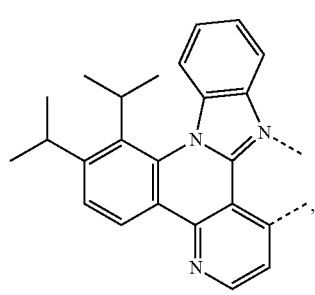
L_{A182}
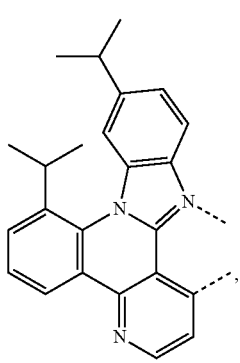
-continued
L_{A187}
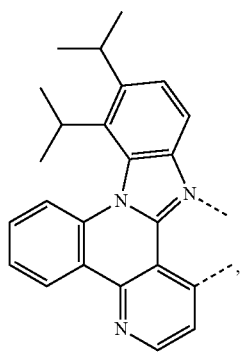
L_{A188}
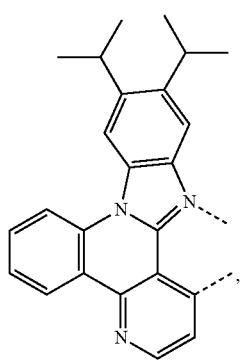
L_{A189}
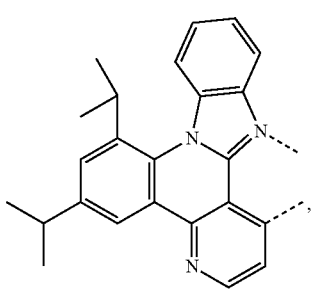
L_{A190}
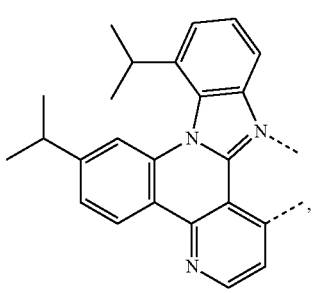
L_{A191}
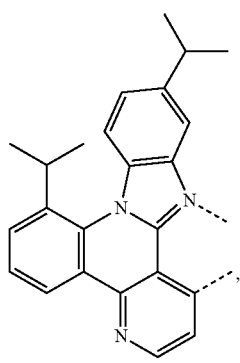

-continued
L_{A192}
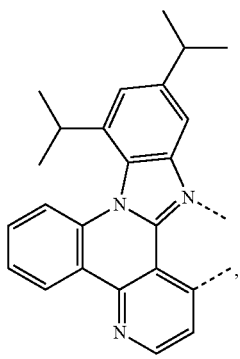
L_{A193}
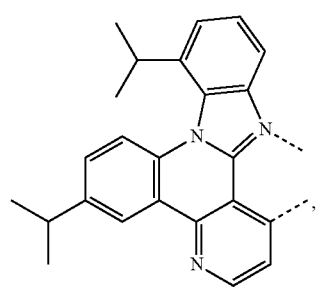
L_{A194}
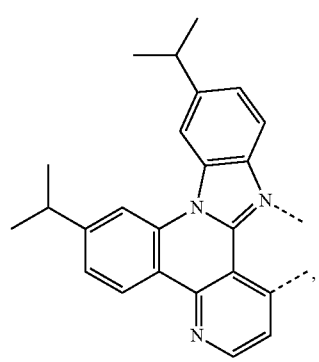
L_{A195}
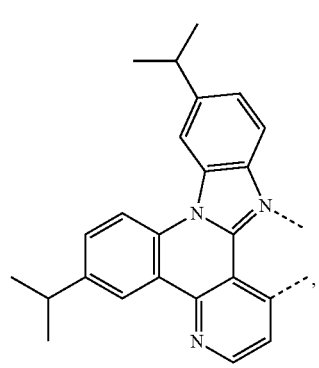
-continued
L_{A196}
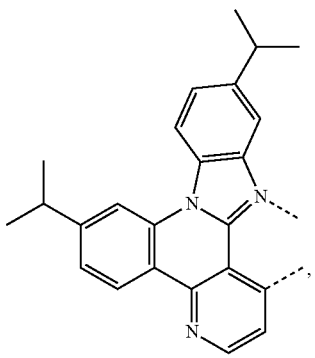
L_{A197}
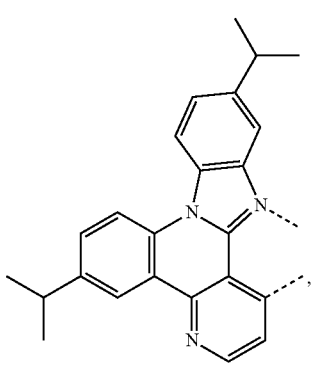
L_{A198}
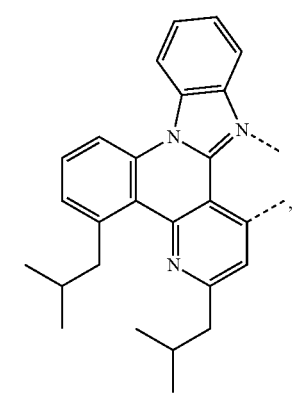
L_{A199}
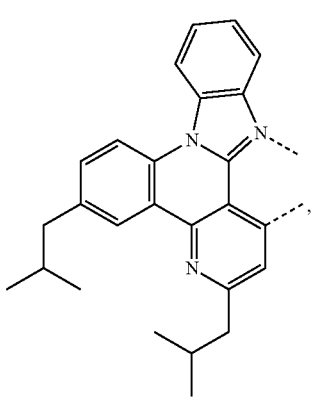

-continued
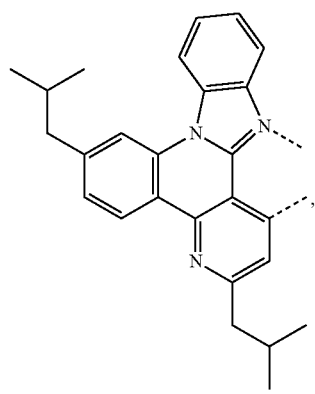
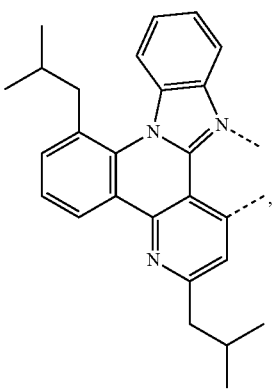
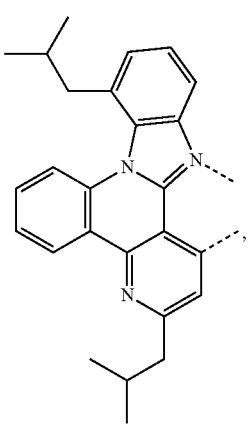
-continued
L_{A200}
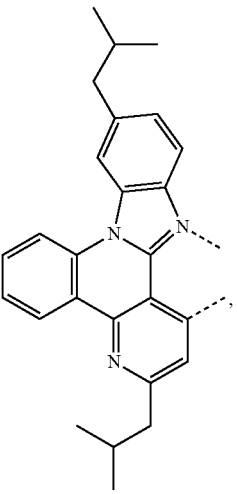
L_{A201}
L_{A202}
L_{A203}
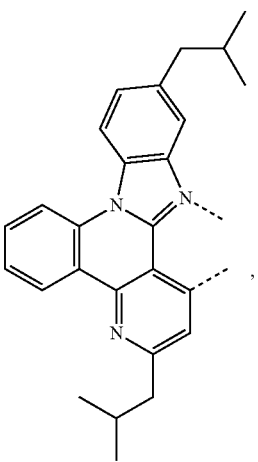
L_{A204}
L_{A205}
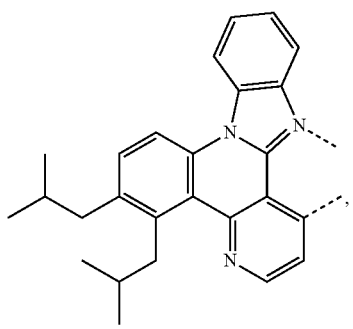
L_{A206}
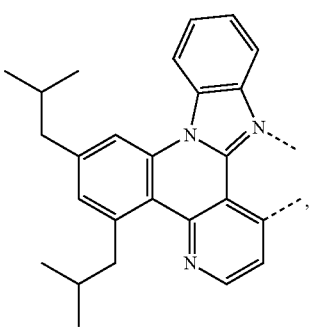

L<sub>A207</sub>
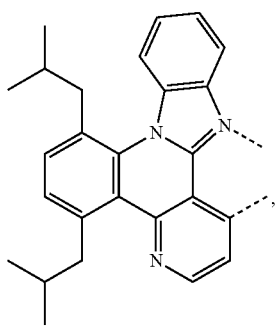
L<sub>A208</sub>
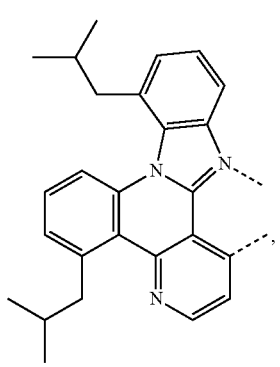
L<sub>A209</sub>
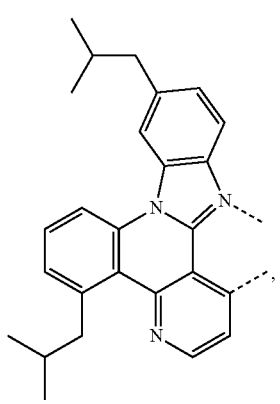
L<sub>A210</sub>
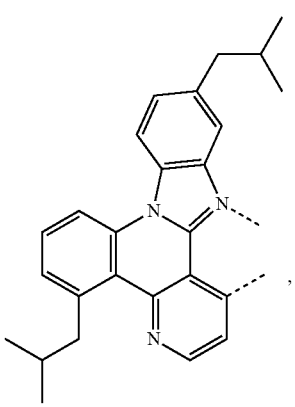
L<sub>A211</sub>
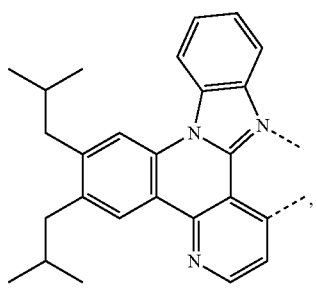
L<sub>A212</sub>
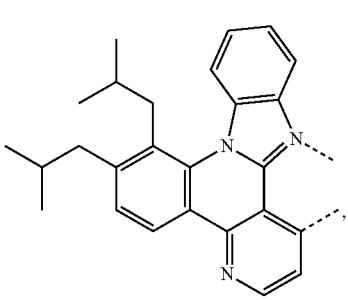
L<sub>A213</sub>
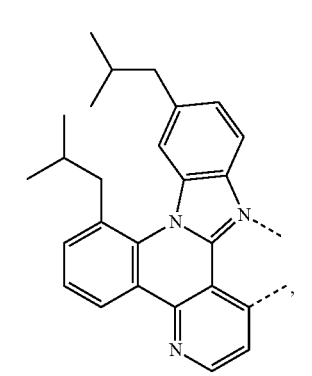
L<sub>A214</sub>
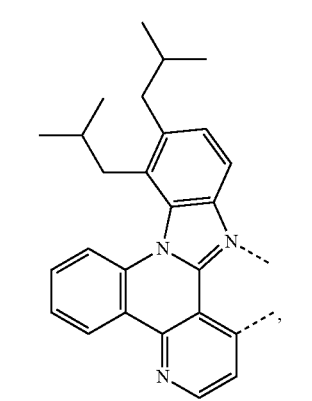

L<sub>A215</sub>
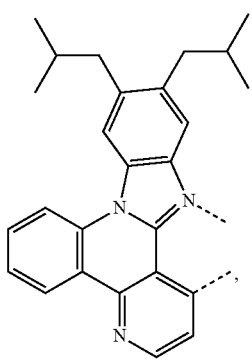
L<sub>A216</sub>
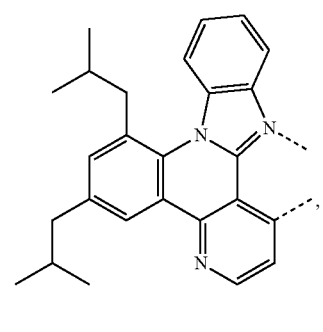
L<sub>A217</sub>
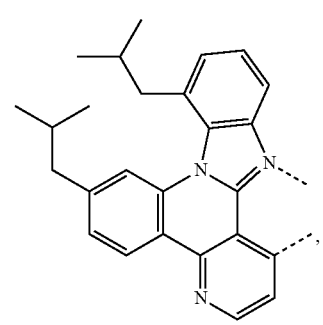
L<sub>A218</sub>
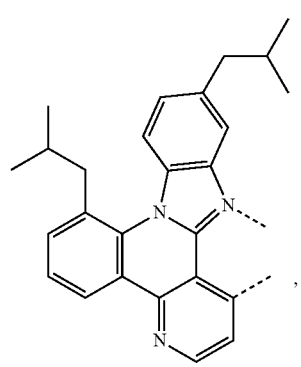
L<sub>A219</sub>
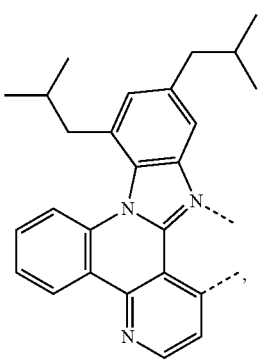
L<sub>A220</sub>
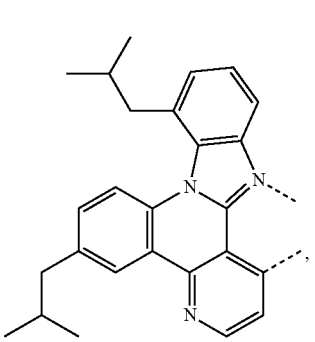
L<sub>A221</sub>
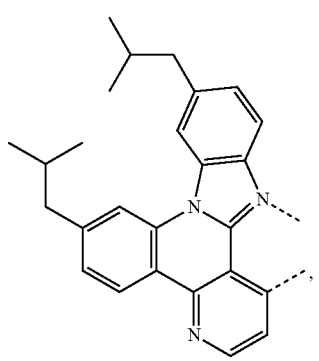
L<sub>A222</sub>
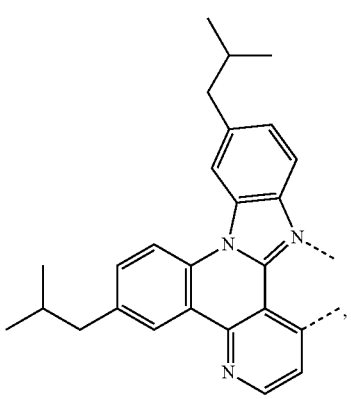

L<sub>A223</sub>
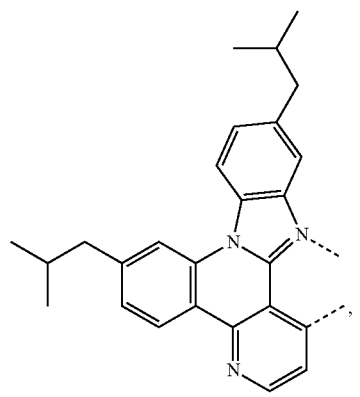
L<sub>A224</sub>
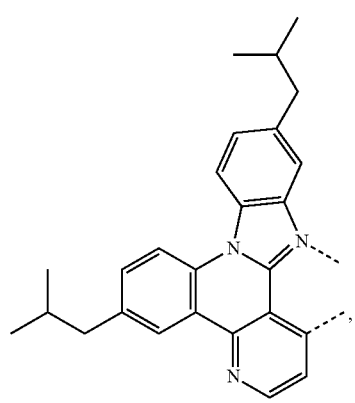
L<sub>A225</sub>
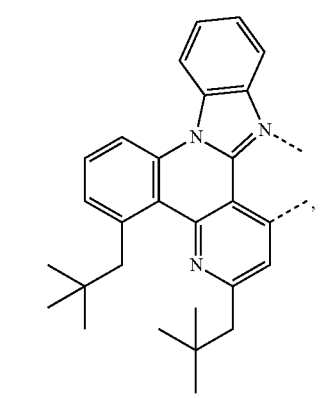
L<sub>A226</sub>
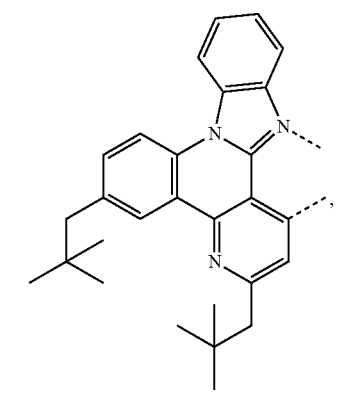
L<sub>A227</sub>
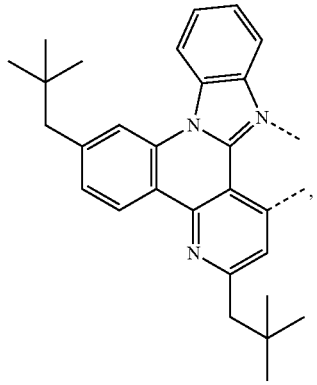
L<sub>A228</sub>
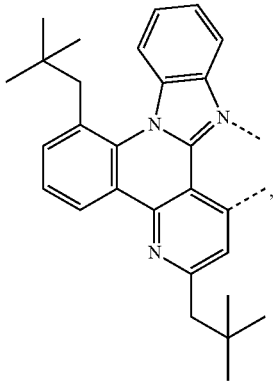
L<sub>A229</sub>
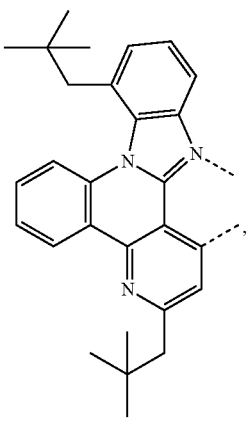

361
-continued
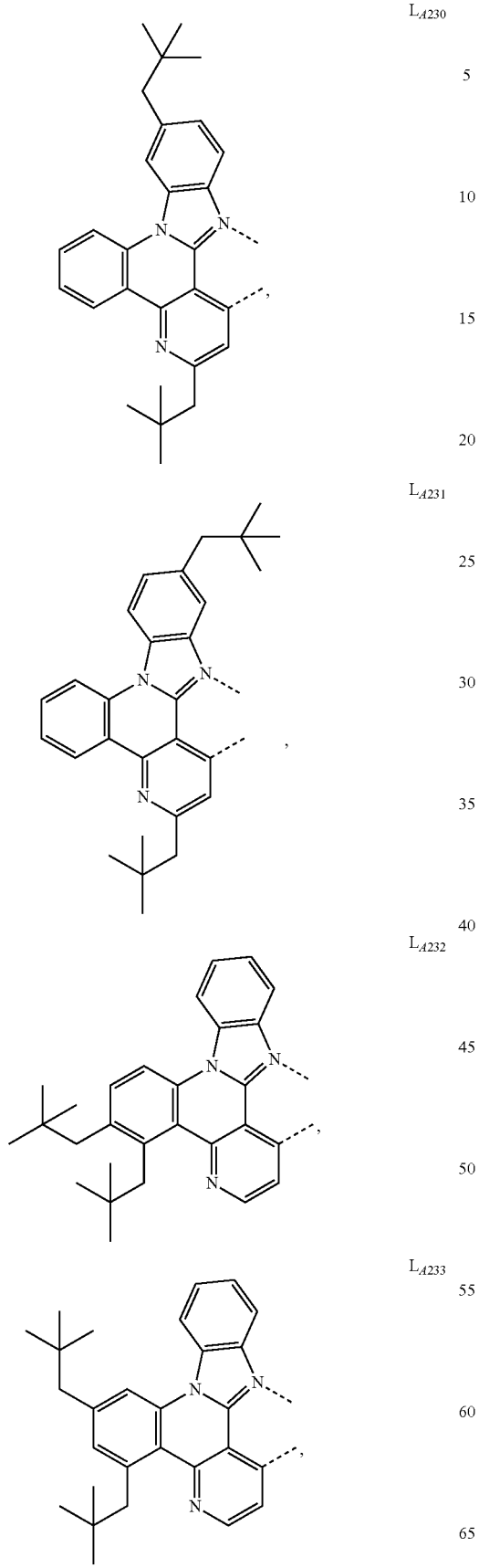
362
-continued
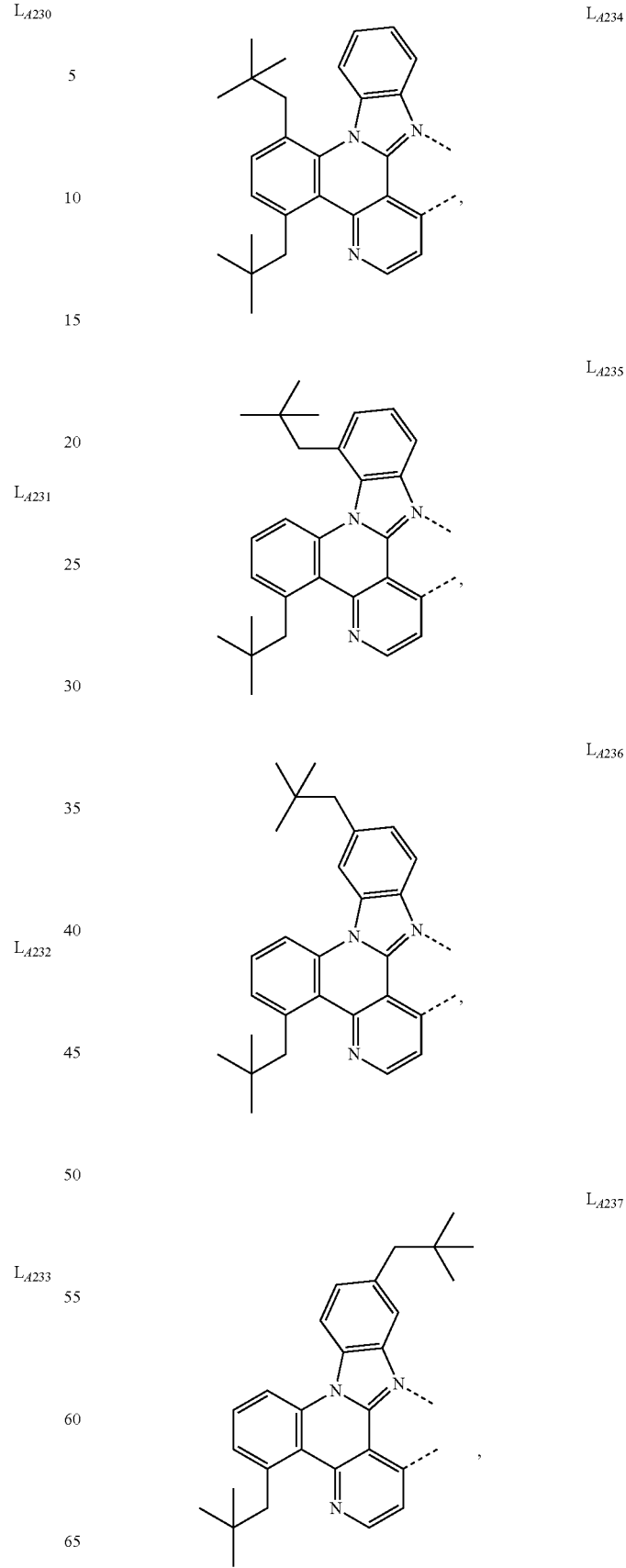

363
-continued
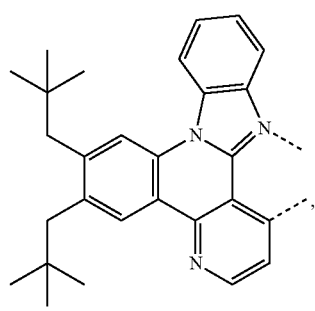
L_{A238}
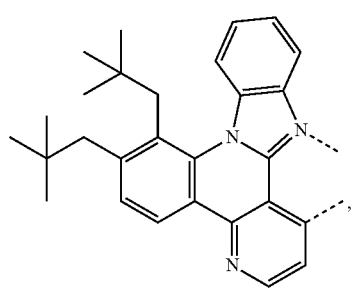
L_{A239}
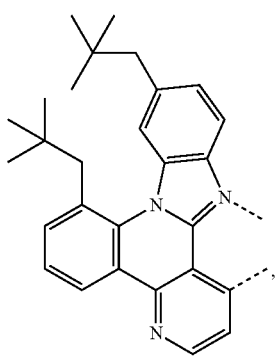
L_{A240}
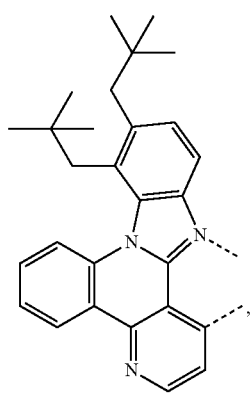
L_{A241}
364
-continued
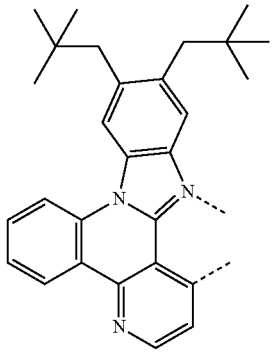
L_{A242}
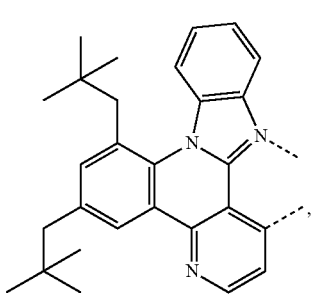
L_{A243}
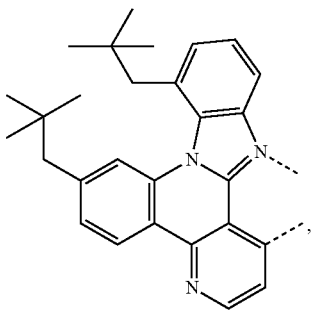
L_{A244}
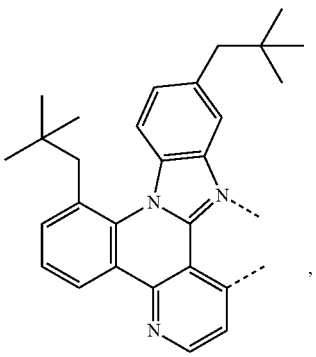
L_{A245}

-continued
L<sub>A246</sub>
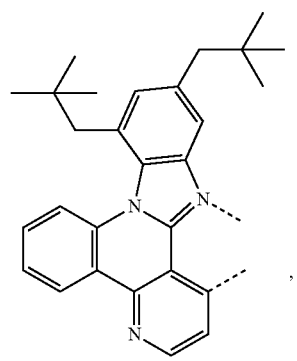
L<sub>A247</sub>
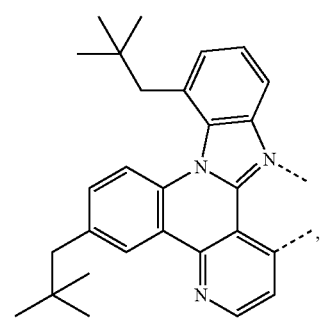
L<sub>A248</sub>
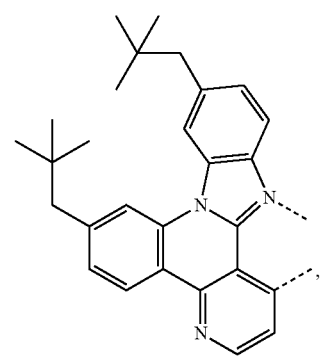
L<sub>A249</sub>
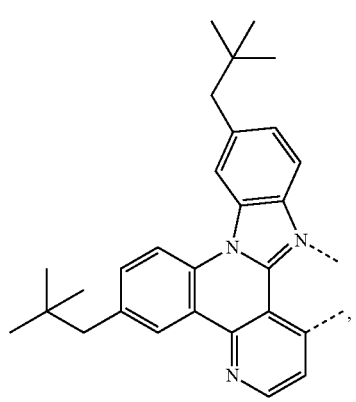
-continued
L<sub>A250</sub>
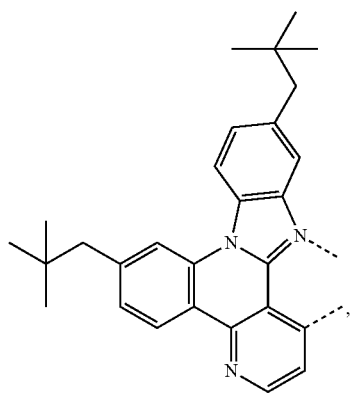
L<sub>A251</sub>
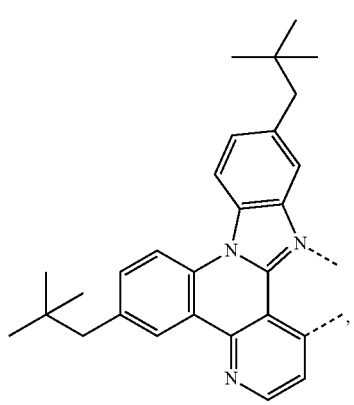
L<sub>A252</sub>
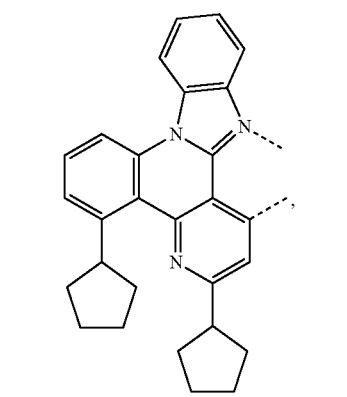
L<sub>A253</sub>
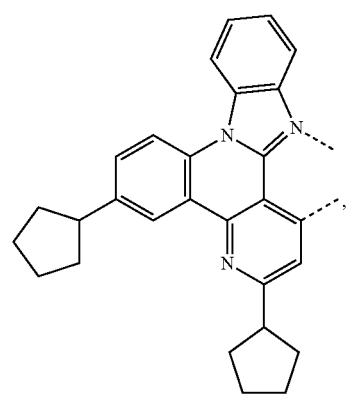

-continued
L<sub>A254</sub>
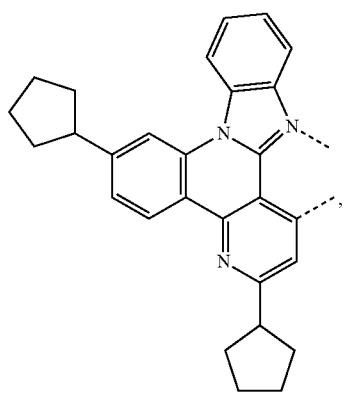
L<sub>A255</sub>
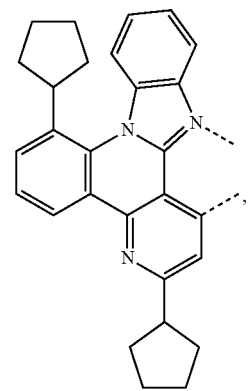
L<sub>A256</sub>
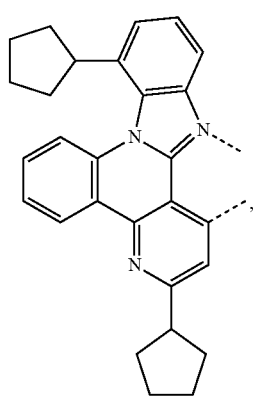
-continued
L<sub>A257</sub>
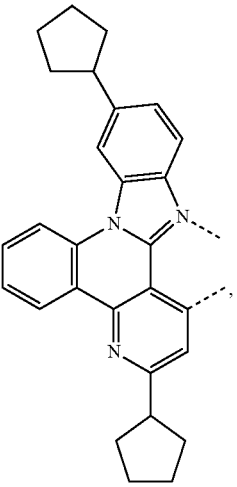
L<sub>A258</sub>
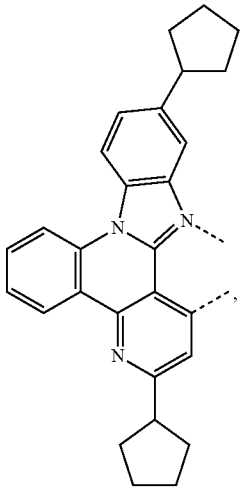
L<sub>A259</sub>
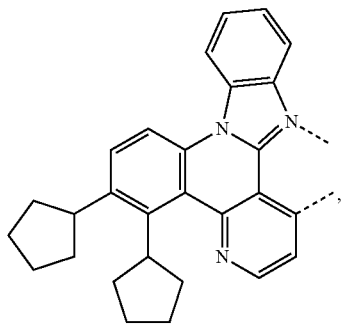
L<sub>A260</sub>
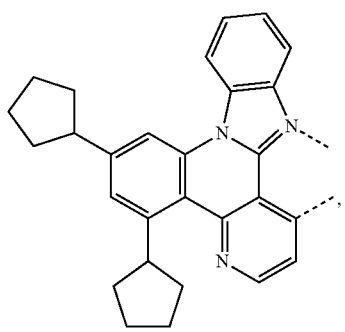

369
-continued
L<sub>A261</sub> 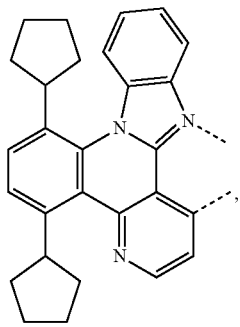
L<sub>A262</sub> 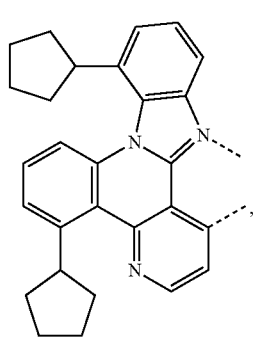
L<sub>A263</sub> 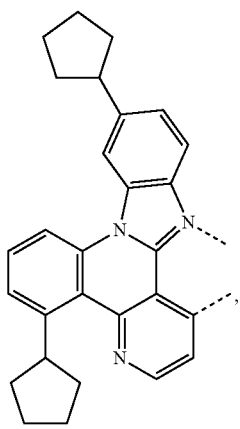
L<sub>A264</sub> 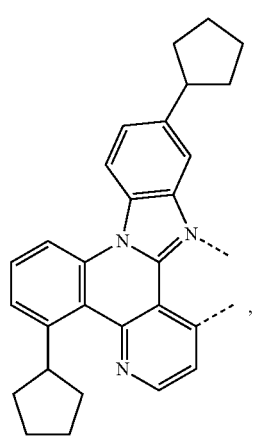
370
-continued
L<sub>A265</sub> 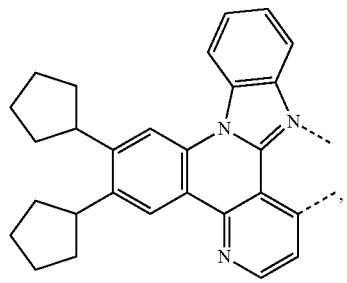
L<sub>A266</sub> 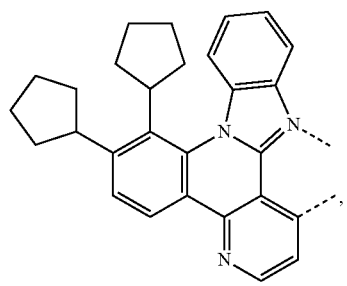
L<sub>A267</sub> 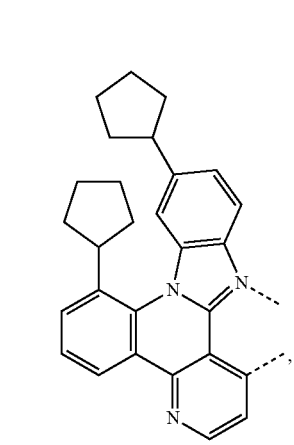
L<sub>A268</sub> 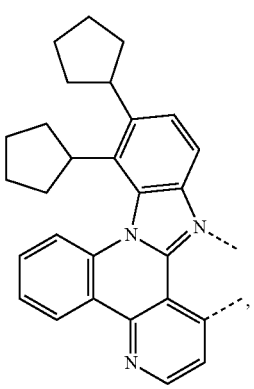

-continued
L$_{A269}$
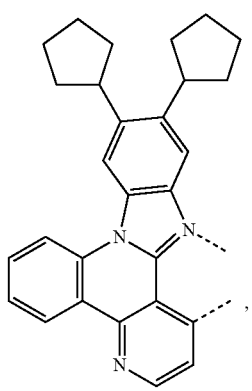
L$_{A270}$
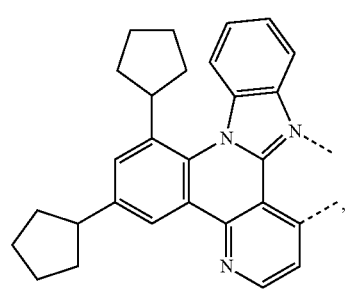
L$_{A271}$
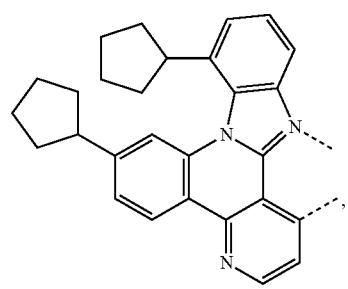
L$_{A272}$
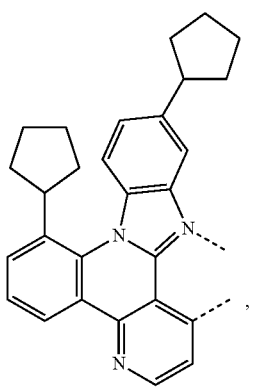
-continued
L$_{A273}$
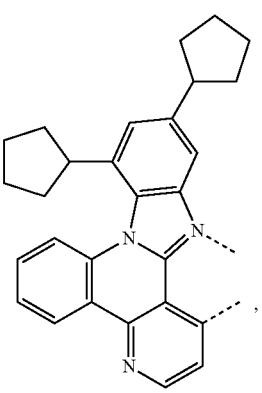
L$_{A274}$
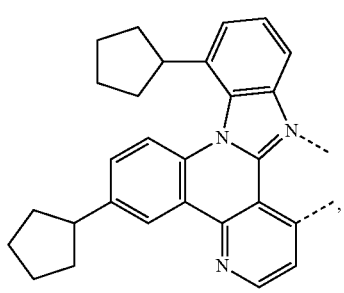
L$_{A275}$
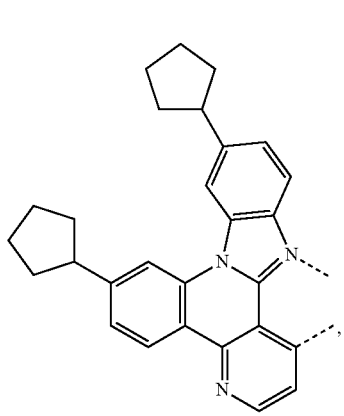
L$_{A276}$
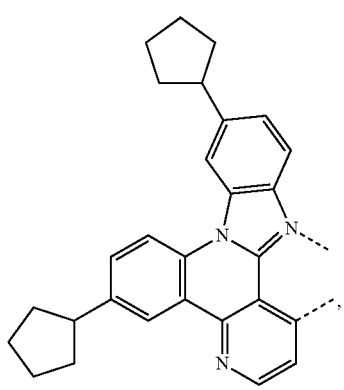

L<sub>A277</sub>
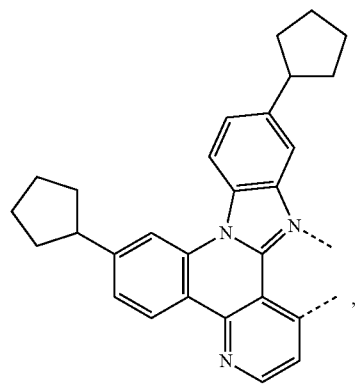
L<sub>A278</sub>
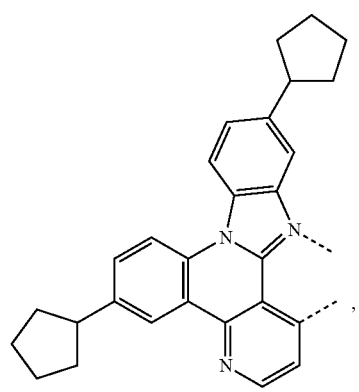
L<sub>A279</sub>
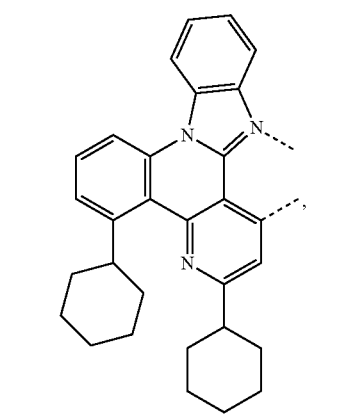
L<sub>A280</sub>
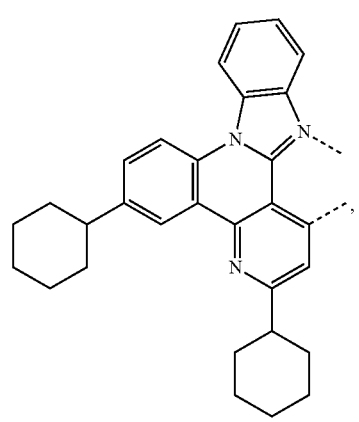
L<sub>A281</sub>
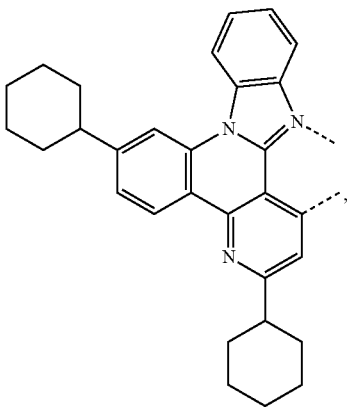
L<sub>A282</sub>
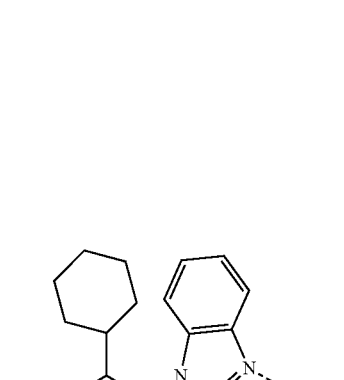
L<sub>A283</sub>
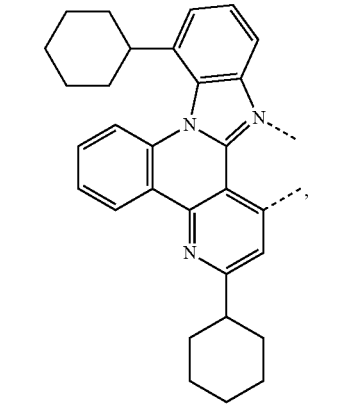

-continued
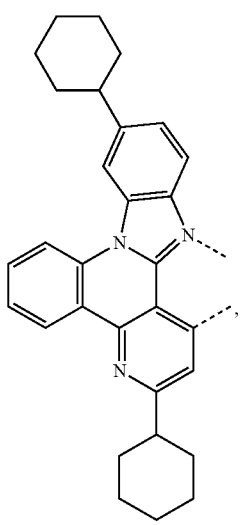
L_{A284}
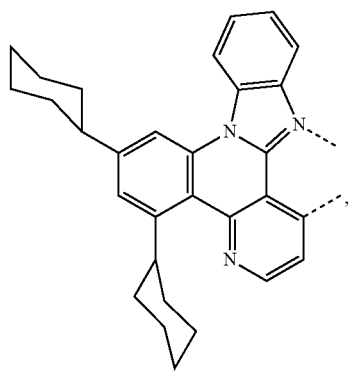
L_{A287}
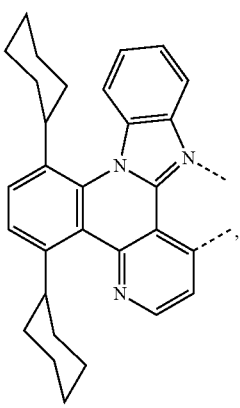
L_{A288}
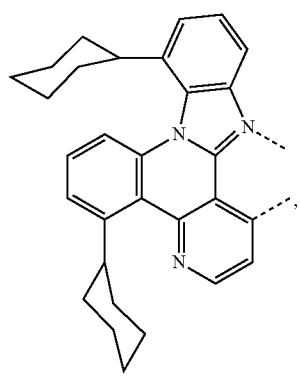
L_{A289}
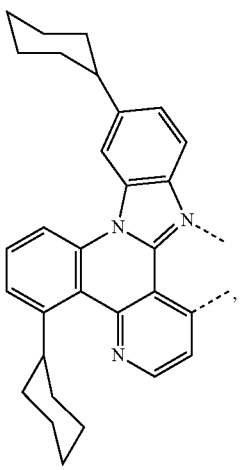
L_{A290}

L<sub>A291</sub>
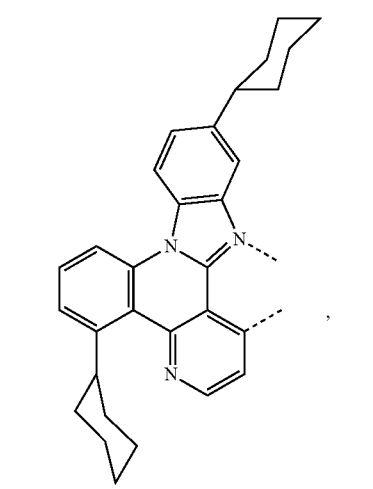
L<sub>A292</sub>
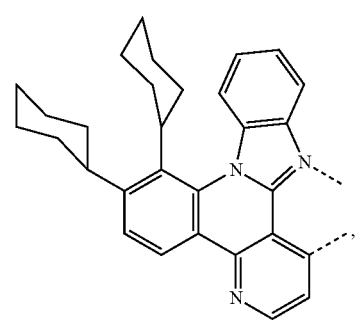
L<sub>A293</sub>
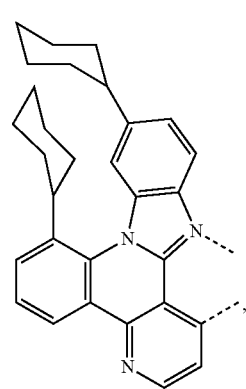
L<sub>A295</sub>
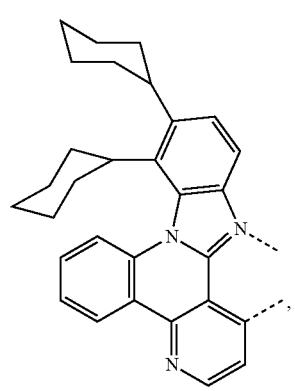
L<sub>A296</sub>
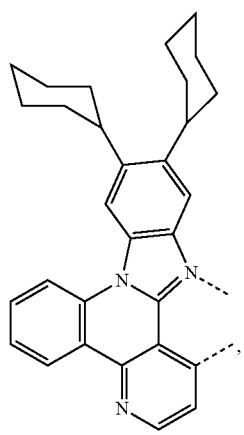
L<sub>A297</sub>
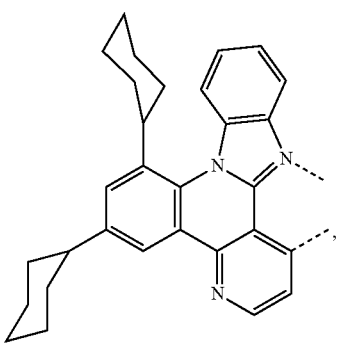
L<sub>A298</sub>
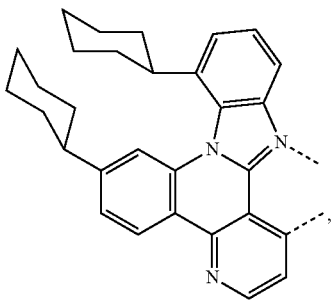

-continued
L_{A299}
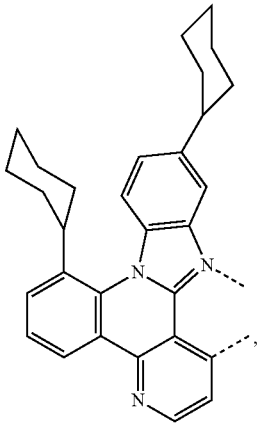
L_{A300}
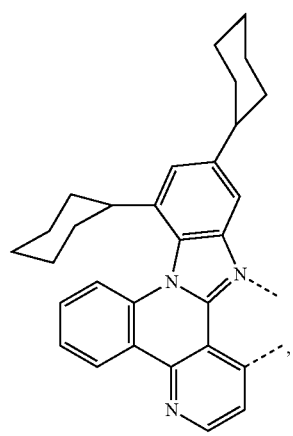
L_{A301}
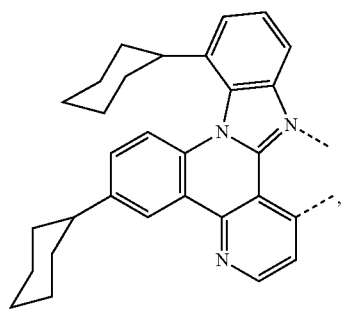
L_{A302}
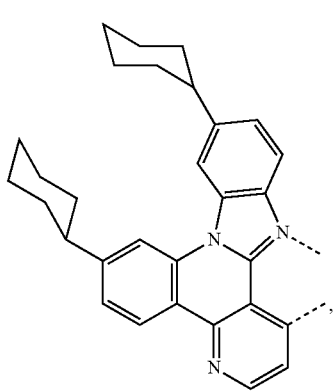
-continued
L_{A303}
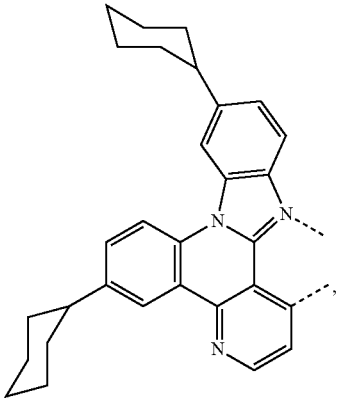
L_{A304}
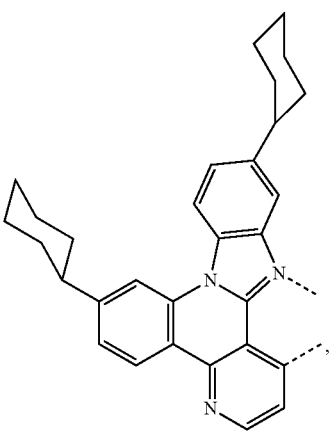
L_{A305}
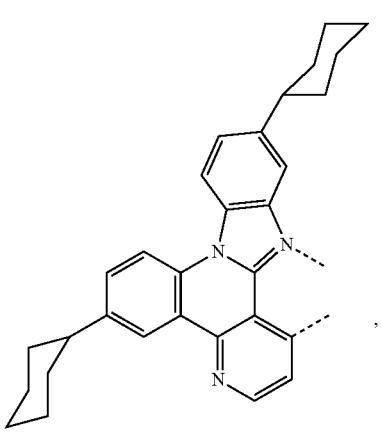

L_{A306}
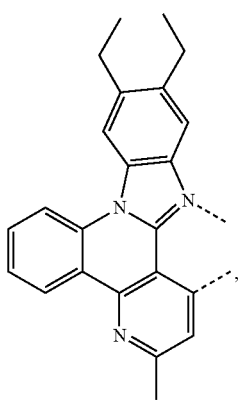
L_{A307}
L_{A308}
L_{A309}
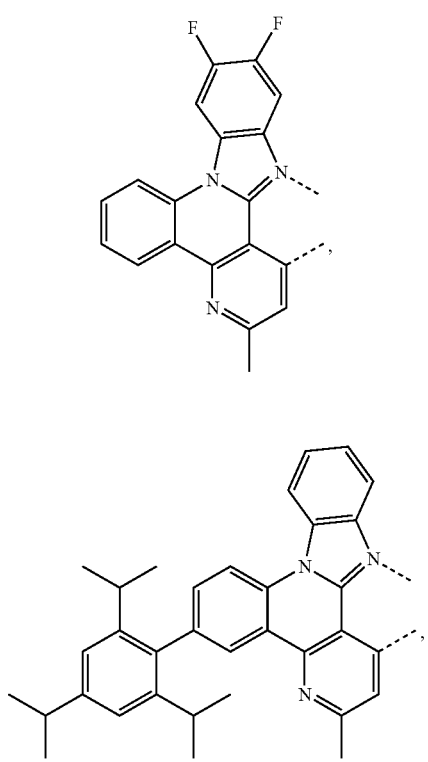
L_{A310}
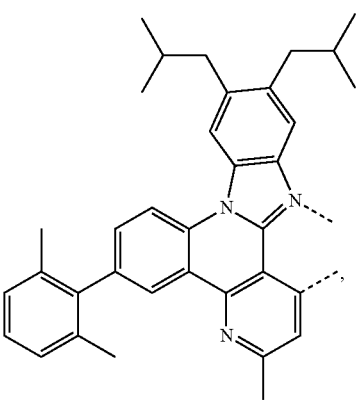
L_{A311}
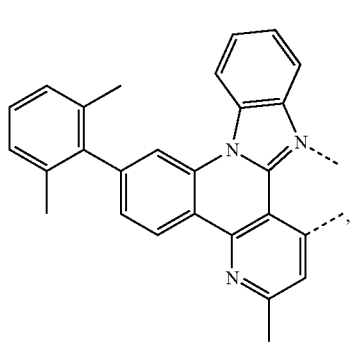
L_{A312}
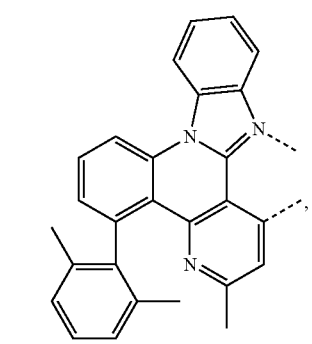
L_{A313}
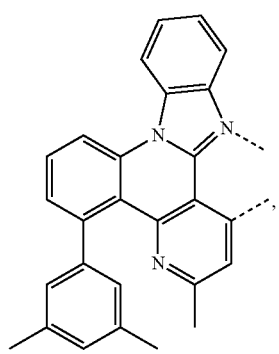

-continued $L_{A314}$

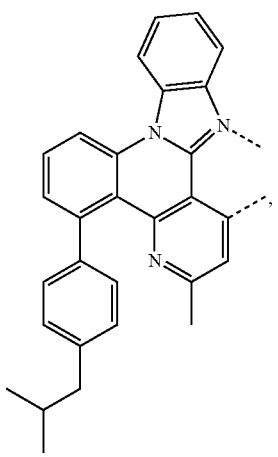

$L_{A315}$

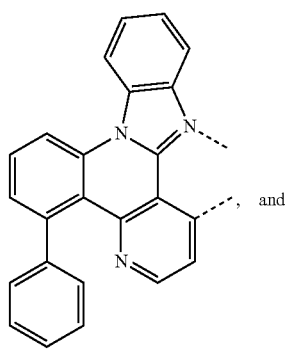, and $L_{A316}$

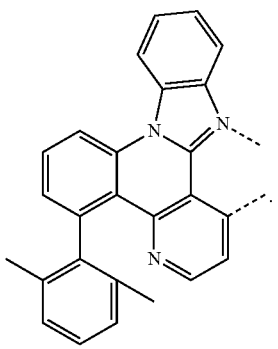.

11. The compound of claim 10, wherein the compound is selected from the group consisting of Compound 1 through Compound 316;

wherein each Compound x has the formula $Ir(L_{Ai})_3$; and wherein x=i; i is an integer from 1 to 316.

12. The compound of claim 1, wherein the compound has the formula $Ir(L_A)_m(L_B)_{3-m}$, having the structure:

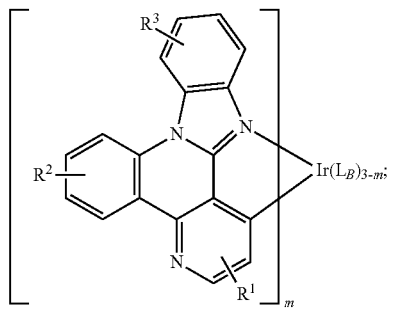

wherein $L_B$ is a different ligand from $L_A$;
wherein m is 1 or 2;
wherein $L_B$ is selected from the group consisting of:

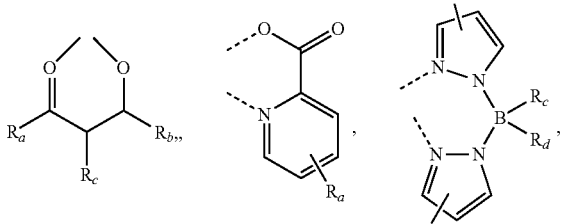

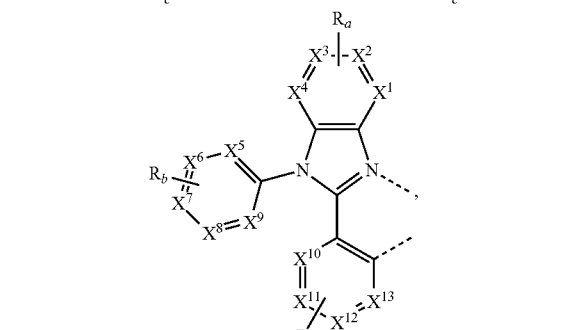

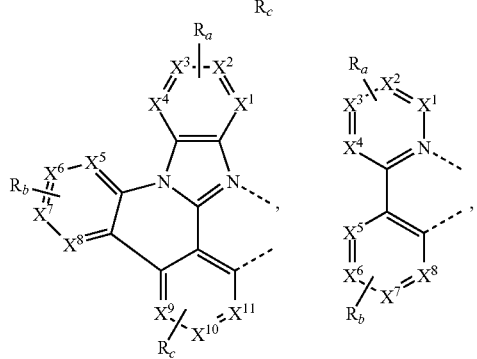

-continued

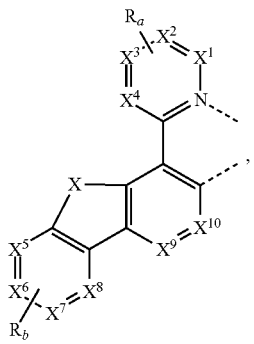
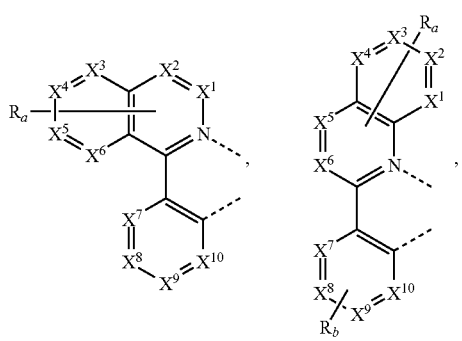
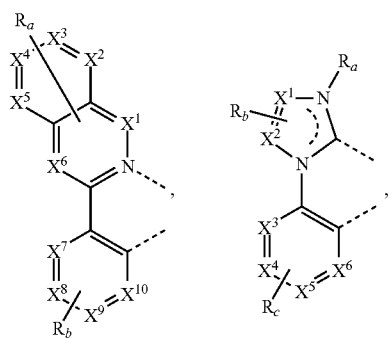
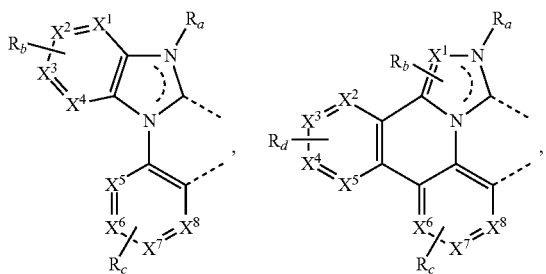
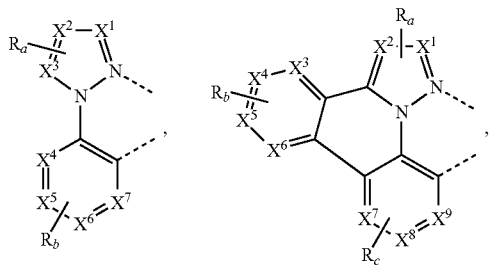

-continued

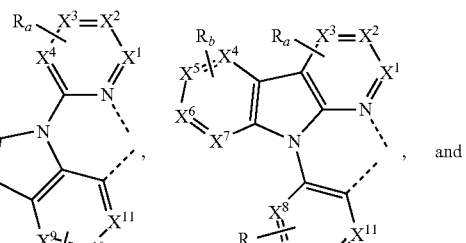
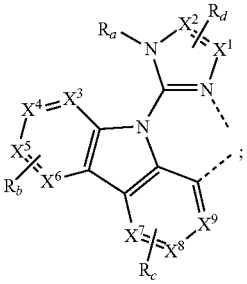

wherein each $X^1$ to $X^{13}$ is independently selected from the group consisting of carbon and nitrogen;

wherein X is selected from the group consisting of BR', NR', PR', O, S, Se, C=O, S=O, $SO_2$, CR'R", SiR'R", and GeR'R";

wherein R' and R" are optionally fused or joined to form a ring;

wherein each $R_a$, $R_b$, $R_c$, and $R_d$ may represent from mono substitution to the possible maximum number of substitution, or no substitution;

wherein $R_a$, $R_b$, $R_c$, and $R_d$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, carboxylic acids, ester, nitrile, and isonitrile; and wherein when $R_a$, $R_b$, $R_c$, and $R_d$ represent at least di substitution, each of the two adjacent $R_a$, two adjacent $R_b$, two adjacent $R_c$, and two adjacent $R_d$ are optionally fused or joined to form a ring or form a multidentate ligand.

13. The compound of claim 12, wherein $L_B$ is selected from the group consisting of:

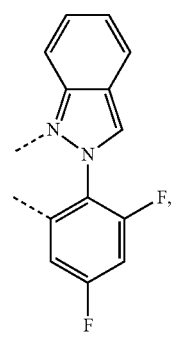

$L_{B1}$

L<sub>B2</sub> 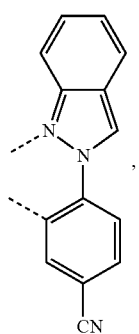
L<sub>B3</sub> 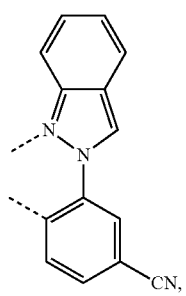
L<sub>B4</sub> 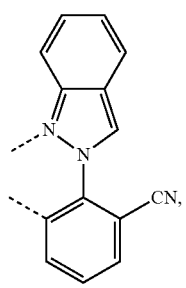
L<sub>B5</sub> 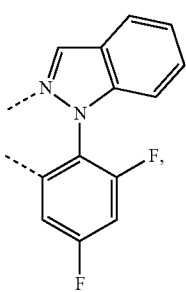
L<sub>B6</sub> 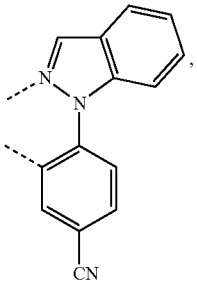
L<sub>B7</sub> 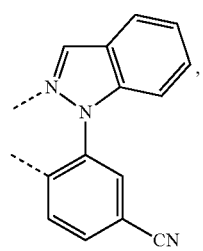
L<sub>B8</sub> 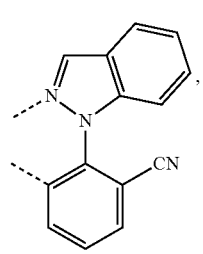
L<sub>B9</sub> 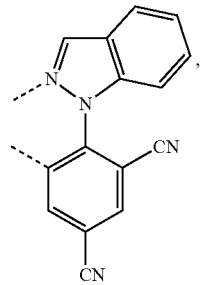
L<sub>B10</sub> 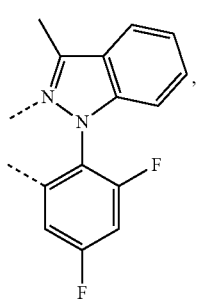
L<sub>B11</sub> 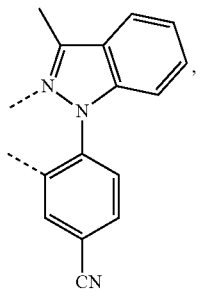

-continued
L_{B12}
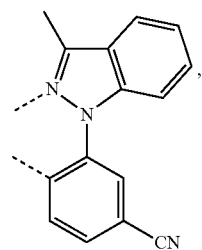
L_{B13}
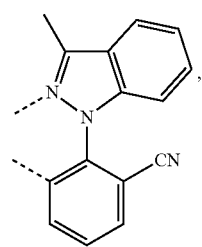
L_{B14}
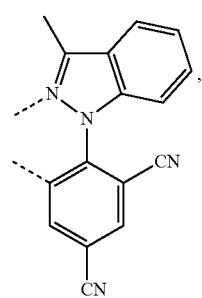
L_{B15}
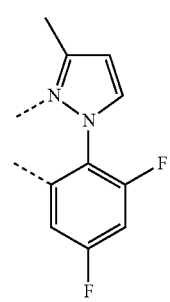
L_{B16}
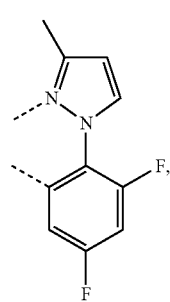
-continued
L_{B17}
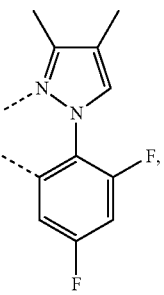
L_{B18}
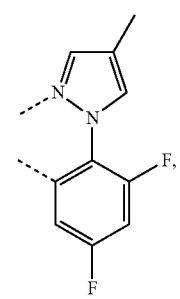
L_{B19}
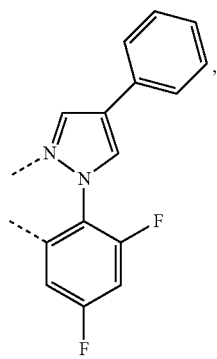
L_{B20}
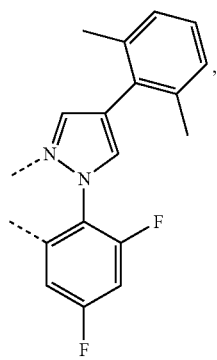

L_{B21} 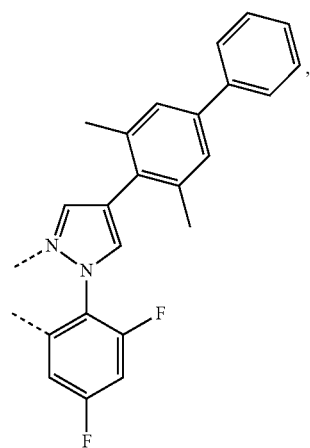
L_{B22} 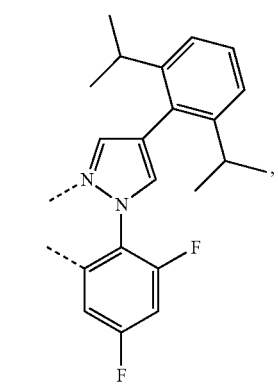
L_{B23} 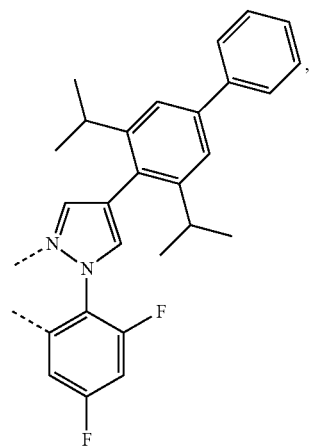
L_{B24} 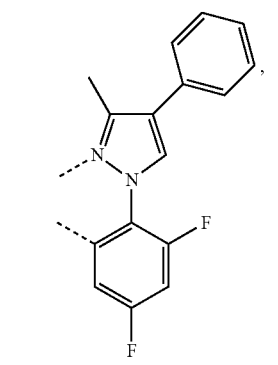
L_{B25} 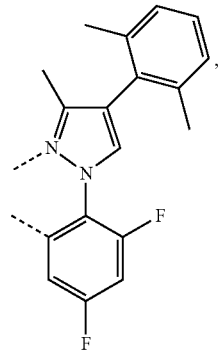
L_{B26} 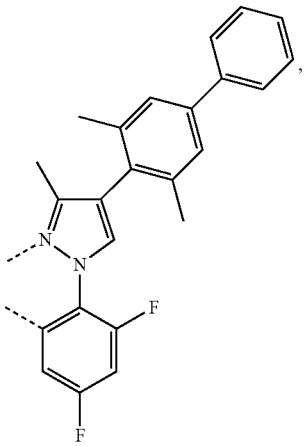
L_{B27} 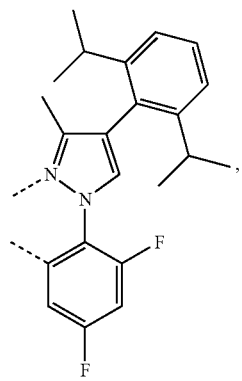
L_{B28} 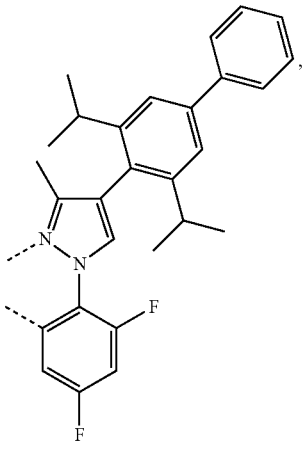

L<sub>B29</sub> 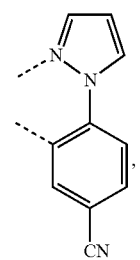
L<sub>B30</sub> 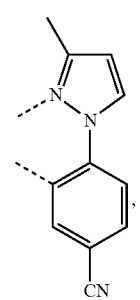
L<sub>B31</sub> 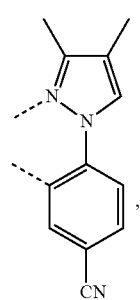
L<sub>B32</sub> 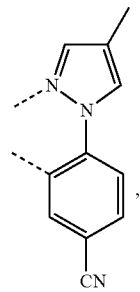
L<sub>B33</sub> 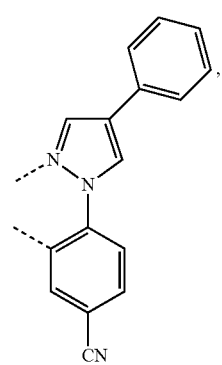
L<sub>B34</sub> 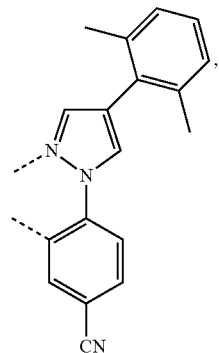
L<sub>B35</sub> 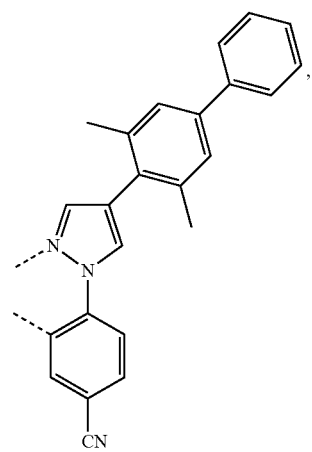
L<sub>B36</sub> 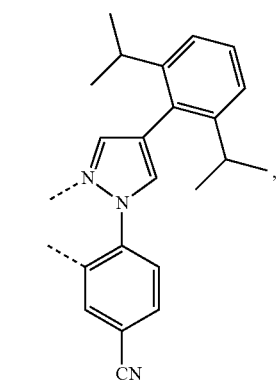
L<sub>B37</sub> 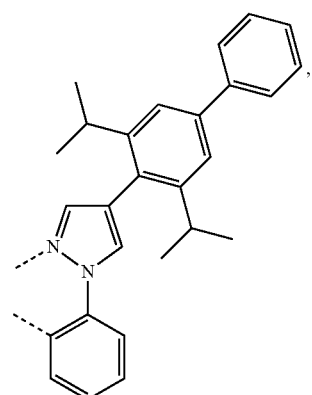

395
-continued
L_{B38}
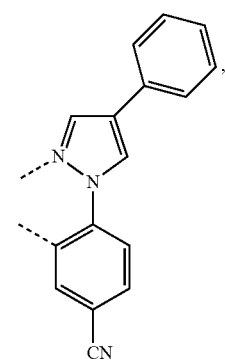
L_{B39}
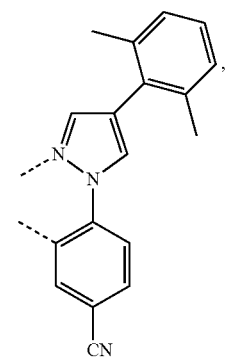
L_{B40}
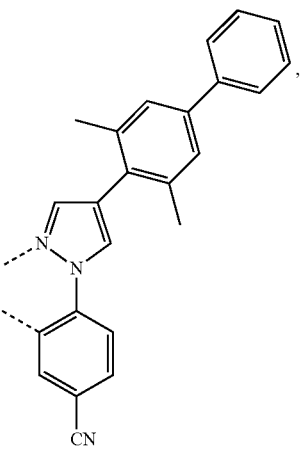
L_{B41}
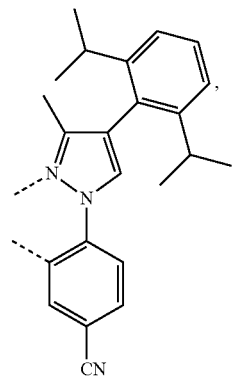
396
-continued
L_{B42}
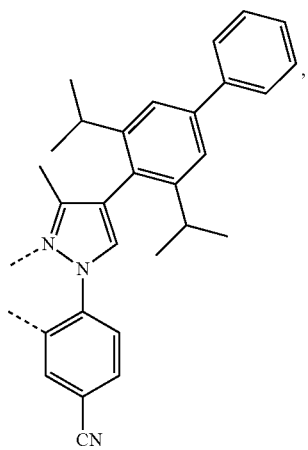
L_{B43}
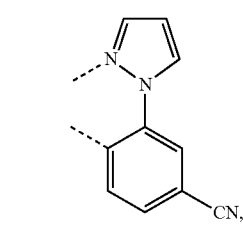
L_{B44}
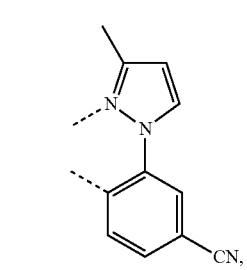
L_{B45}
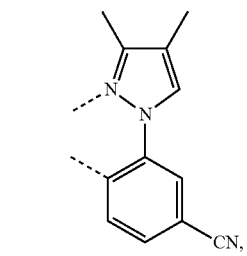
L_{B46}
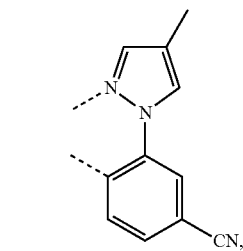

L_{B47}
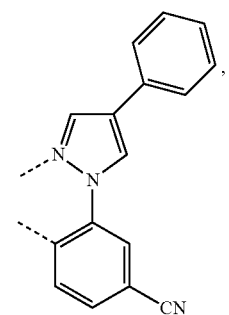
L_{B48}
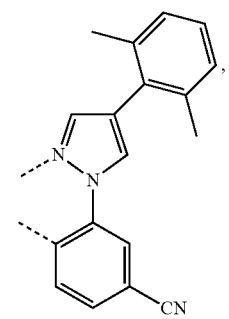
L_{B49}
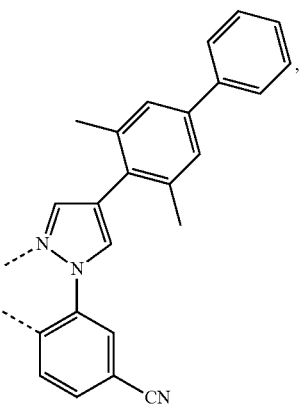
L_{B50}
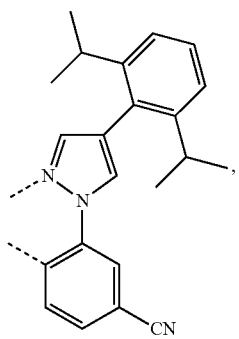
L_{B51}
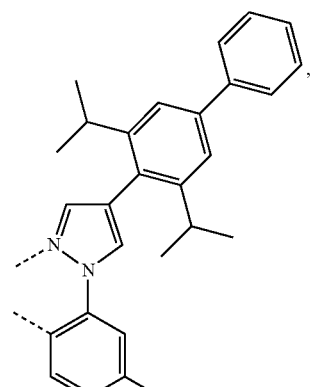
L_{B52}
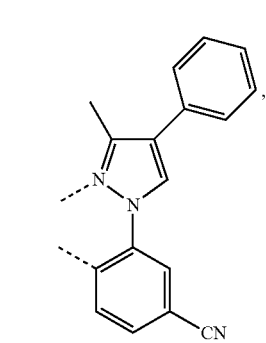
L_{B53}
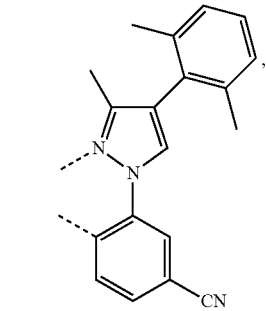
L_{B54}
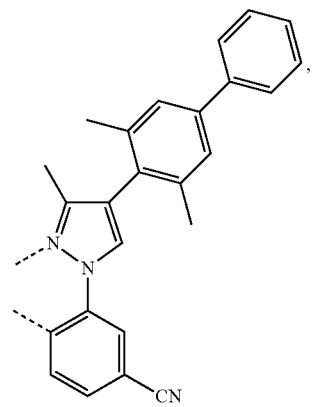

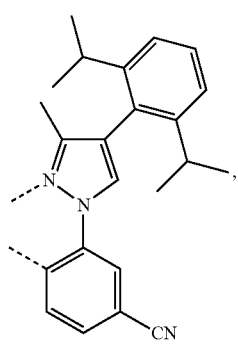 L<sub>B55</sub>
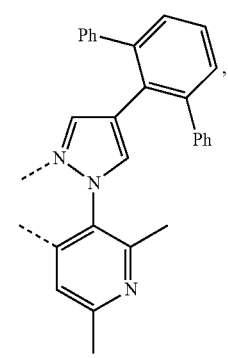 L<sub>B56</sub>
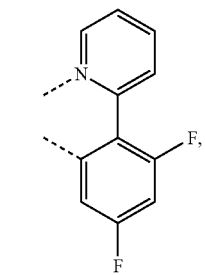 L<sub>B57</sub>
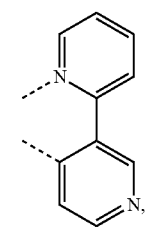 L<sub>B58</sub>
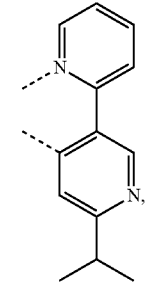 L<sub>B59</sub>
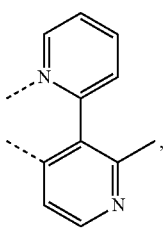 L<sub>B60</sub>
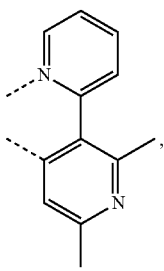 L<sub>B61</sub>
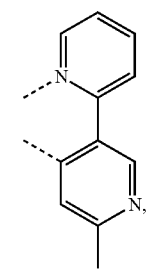 L<sub>B62</sub>
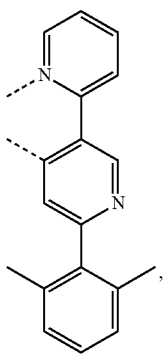 L<sub>B63</sub>
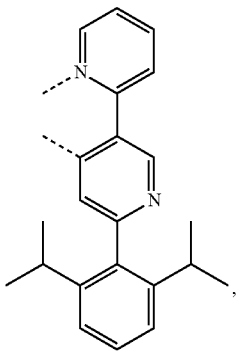 L<sub>B64</sub>

L_{B65}
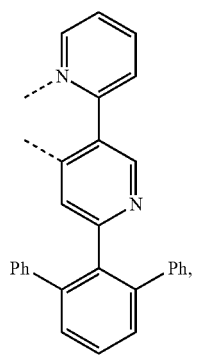
L_{B66}
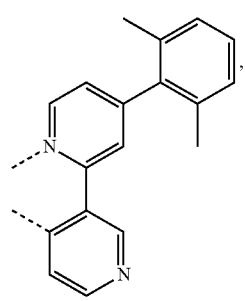
L_{B67}
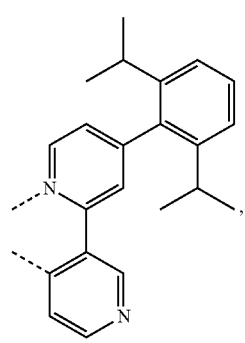
L_{B68}
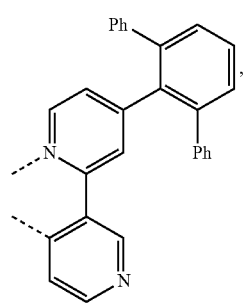
L_{B69}
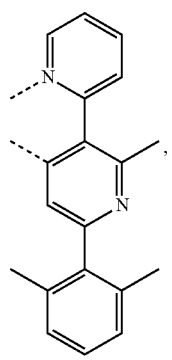
L_{B70}
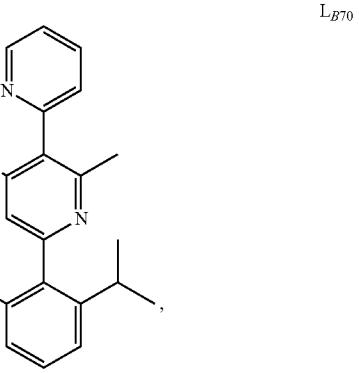
L_{B71}
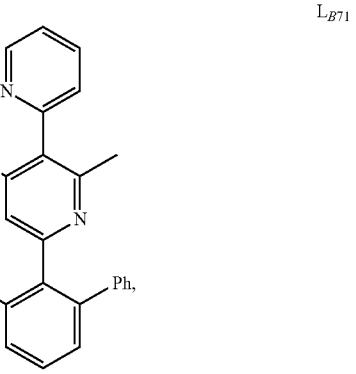
L_{B72}
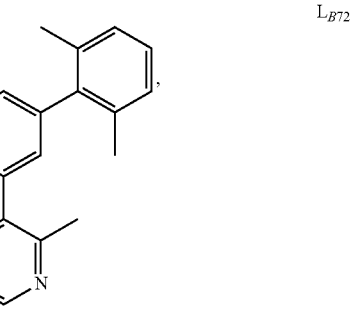

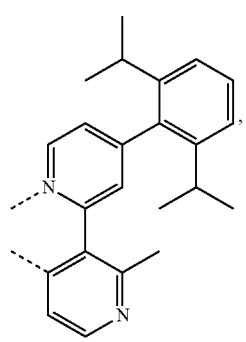 L_{B73}
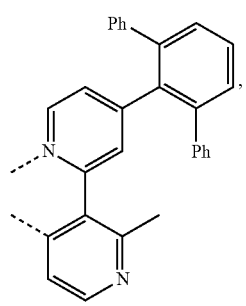 L_{B74}
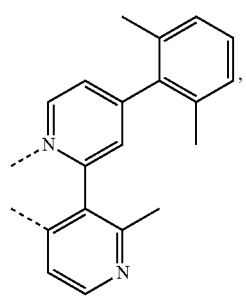 L_{B75}
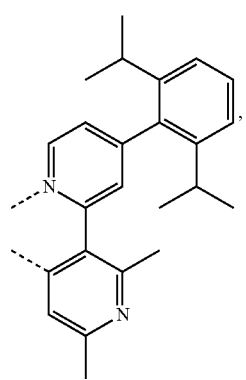 L_{B76}
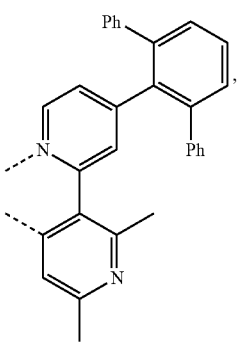 L_{B77}
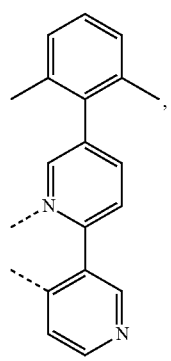 L_{B78}
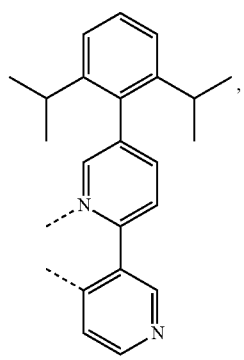 L_{B79}
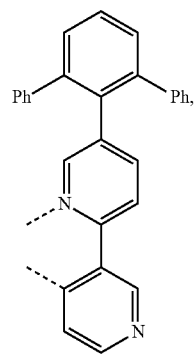 L_{B80}

| | |
|---|---|
| 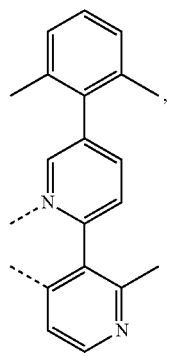 | $L_{B81}$ |
| 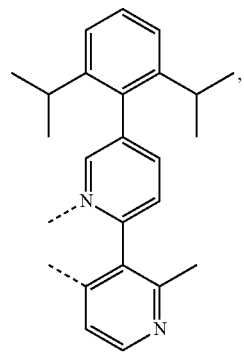 | $L_{B82}$ |
| 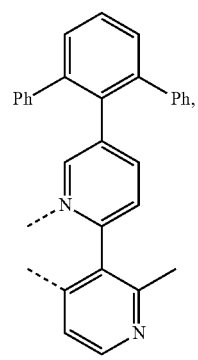 | $L_{B83}$ |
| 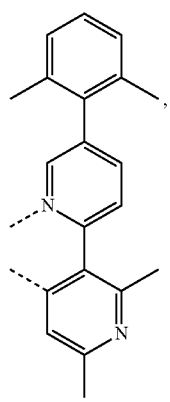 | $L_{B84}$ |
| 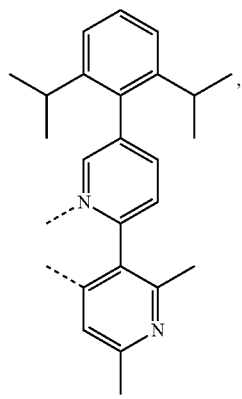 | $L_{B85}$ |
| 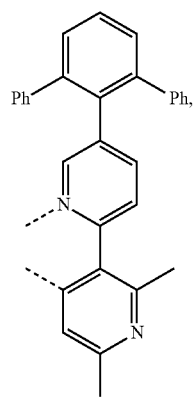 | $L_{B86}$ |
| 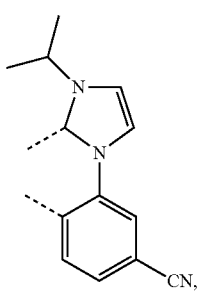 | $L_{B87}$ |
| 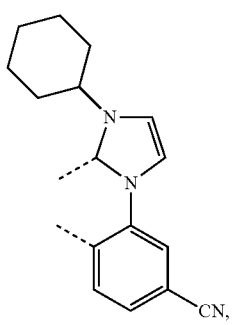 | $L_{B88}$ |

L_{B89} 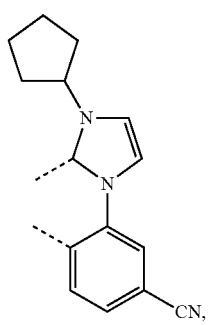
L_{B90} 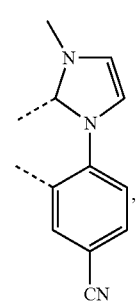
L_{B91} 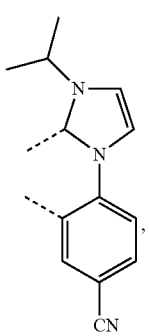
L_{B92} 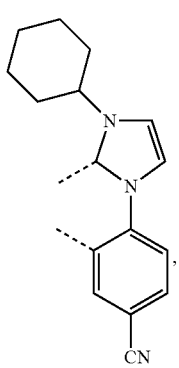
L_{B93} 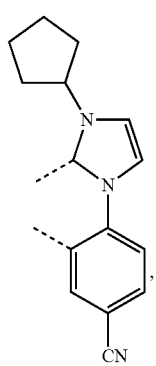
L_{B94} 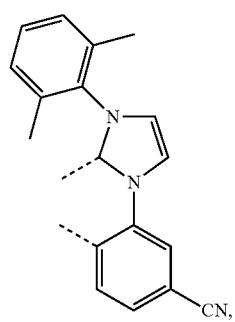
L_{B95} 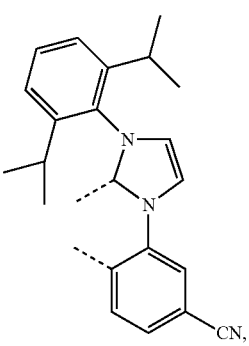
L_{B96} 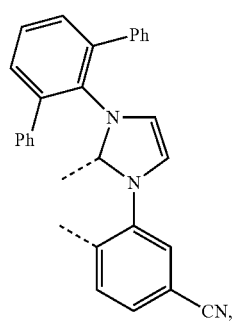

| 409 -continued | 410 -continued |
|---|---|
| 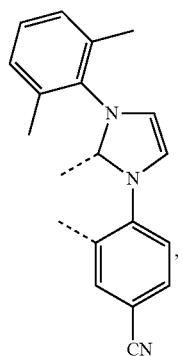 L<sub>B97</sub> | 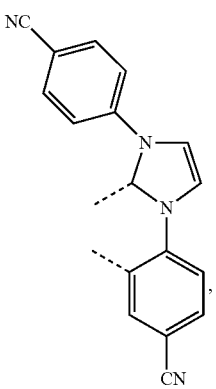 L$_{B101}$ |
| L$_{B98}$ | |
| L$_{B99}$ | 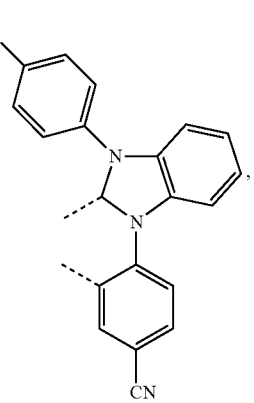 L$_{B102}$ |
| | 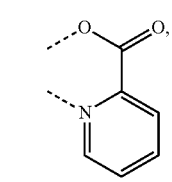 L$_{B103}$ |
| | 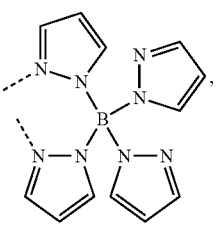 L$_{B104}$ |
| 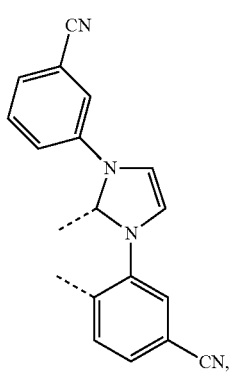 L$_{B100}$ | 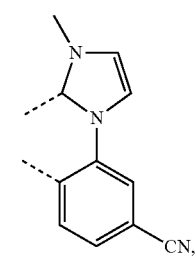 L$_{B105}$ |

411
-continued
L<sub>B106</sub>
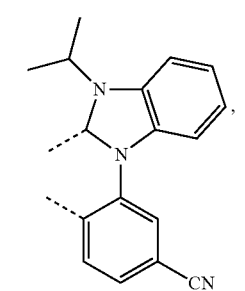
L<sub>B107</sub>
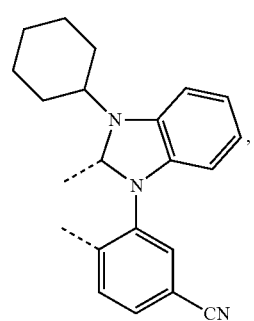
L<sub>B108</sub>
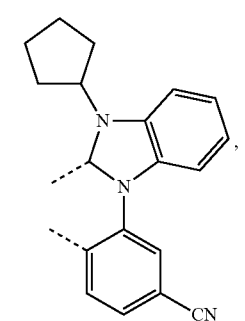
L<sub>B109</sub>
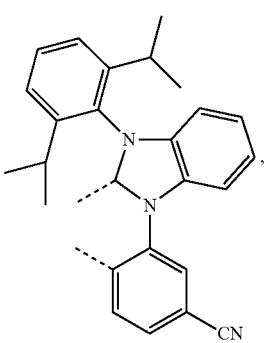
L<sub>B110</sub>
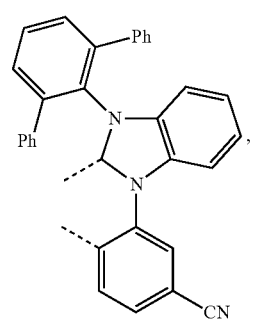
412
-continued
L<sub>B111</sub>
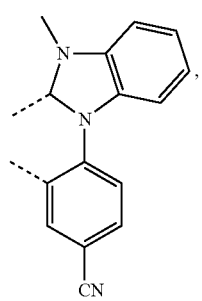
L<sub>B112</sub>
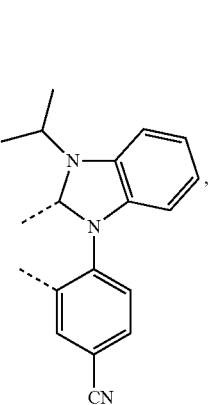
L<sub>B113</sub>
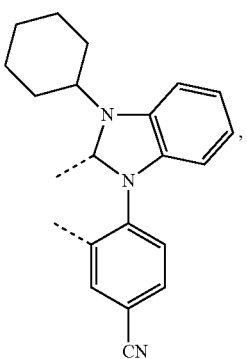
L<sub>B114</sub>
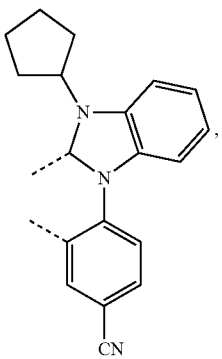

-continued
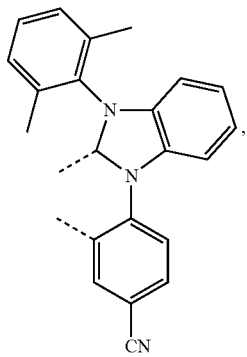
L<sub>B115</sub>
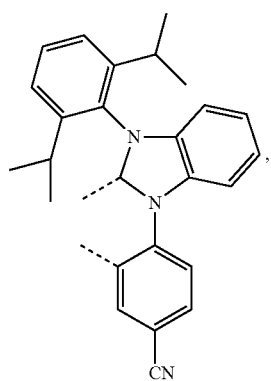
L<sub>B116</sub>
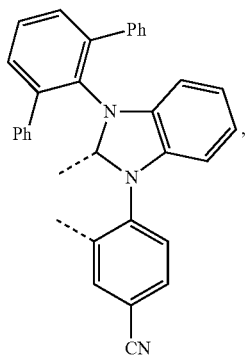
L<sub>B117</sub>
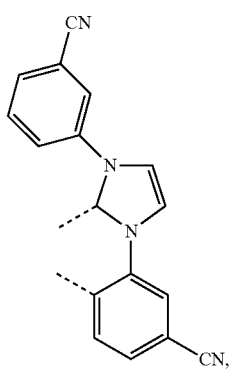
L<sub>B118</sub>
-continued
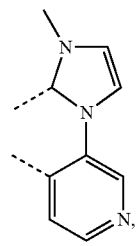
L<sub>B119</sub>
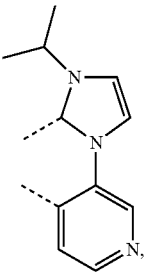
L<sub>B120</sub>
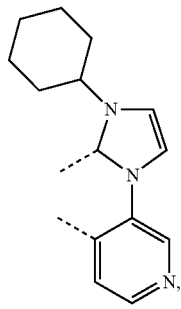
L<sub>B121</sub>
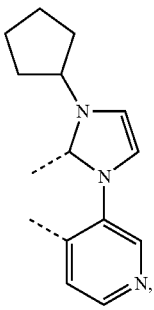
L<sub>B122</sub>
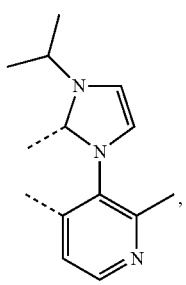
L<sub>B123</sub>

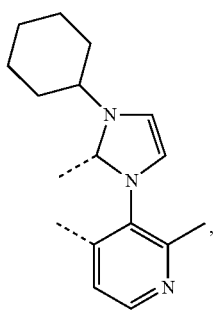
$L_{B124}$
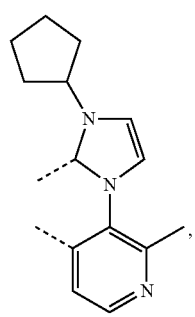
$L_{B125}$
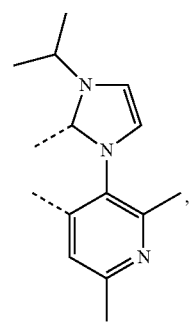
$L_{B126}$
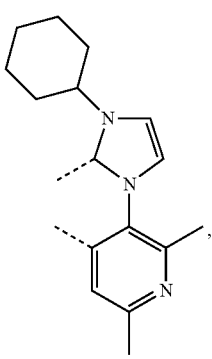
$L_{B127}$
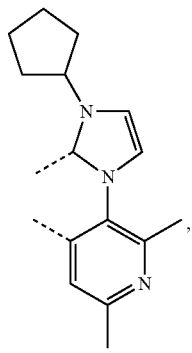
$L_{B128}$
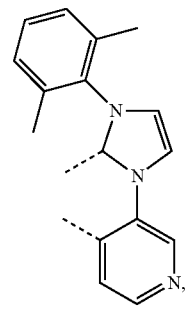
$L_{B129}$
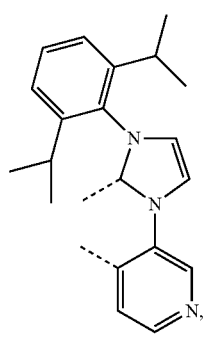
$L_{B130}$
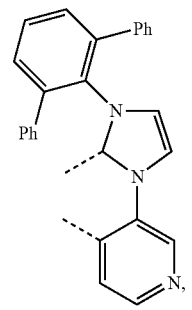
$L_{B131}$
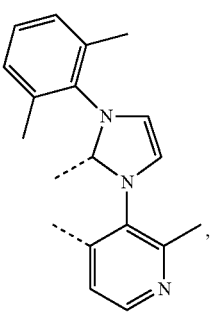
$L_{B132}$ -continued
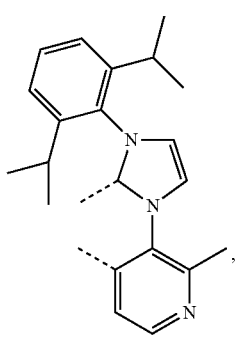
L_{B133}
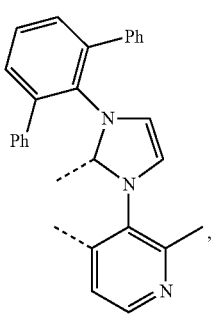
L_{B134}
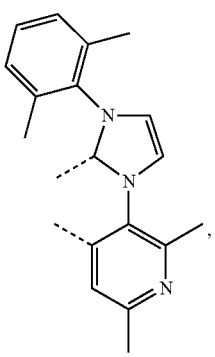
L_{B135}
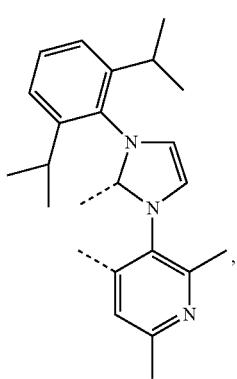
L_{B136}
-continued
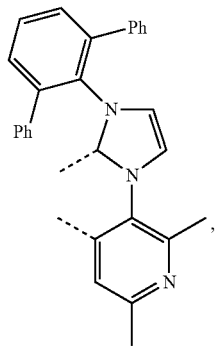
L_{B137}
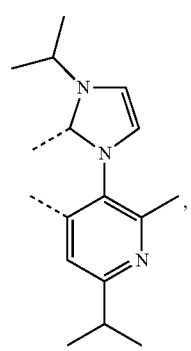
L_{B138}
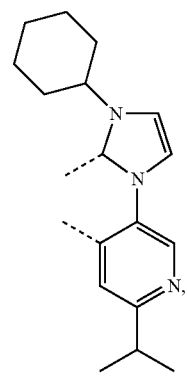
L_{B139}
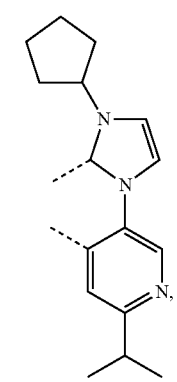
L_{B140}

419
-continued
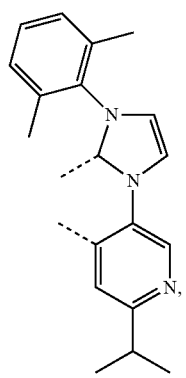 L_{B141}
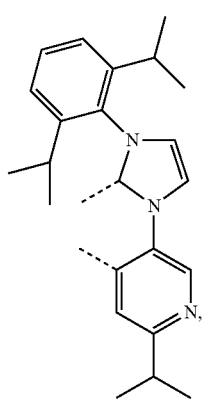 L_{B142}
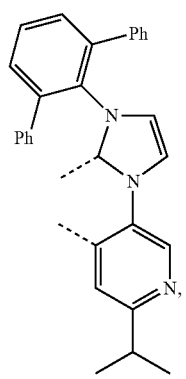 L_{B143}
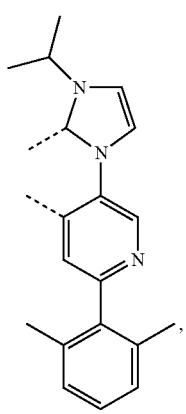 L_{B144}
420
-continued
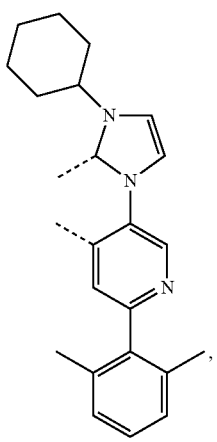 L_{B145}
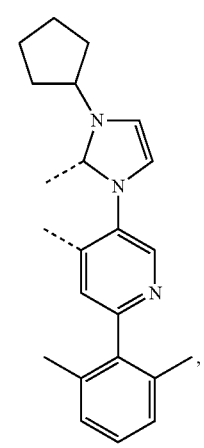 L_{B146}
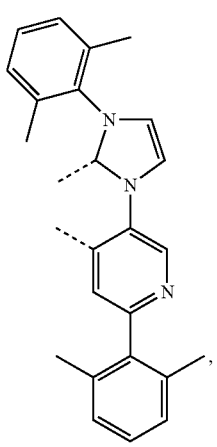 L_{B147}

421
-continued
L<sub>B148</sub>
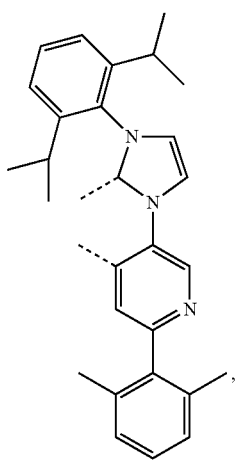
L<sub>B149</sub>
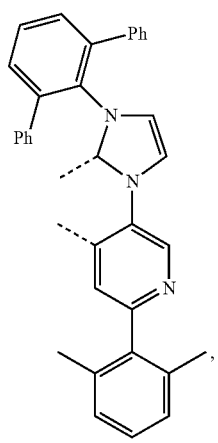
L<sub>B150</sub>
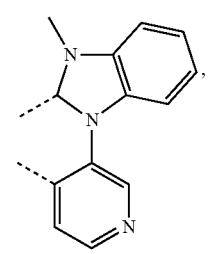
L<sub>B151</sub>
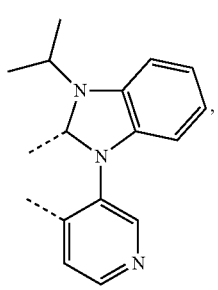
422
-continued
L<sub>B152</sub>
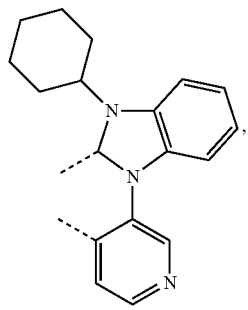
L<sub>B153</sub>
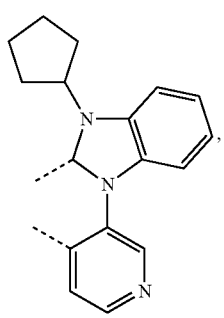
L<sub>B154</sub>
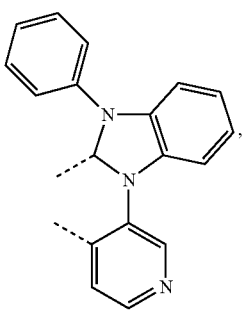
L<sub>B155</sub>
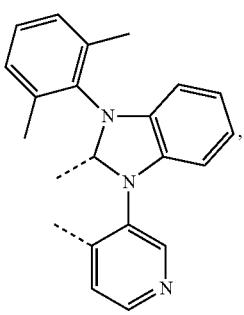
L<sub>B156</sub>
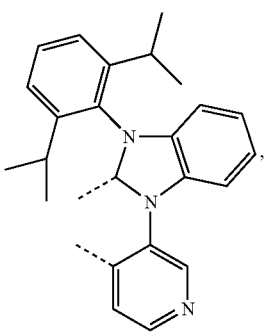

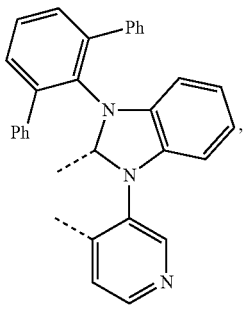 L_{B157}
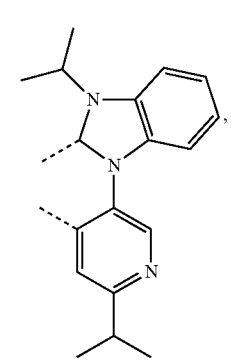 L_{B158}
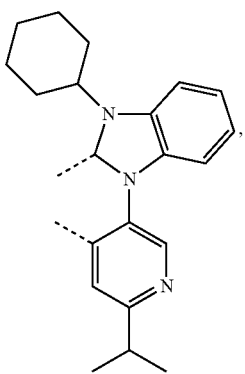 L_{B159}
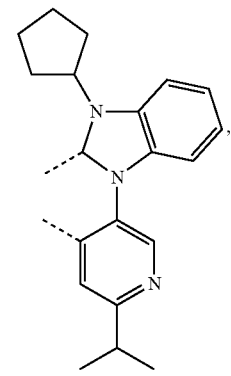 L_{B160}
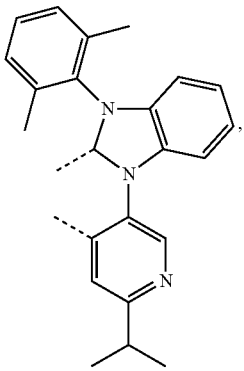 L_{B161}
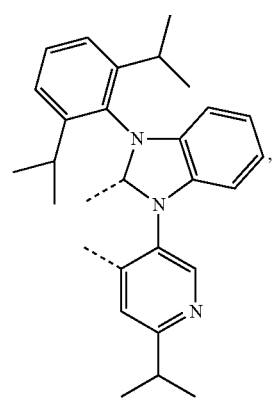 L_{B162}
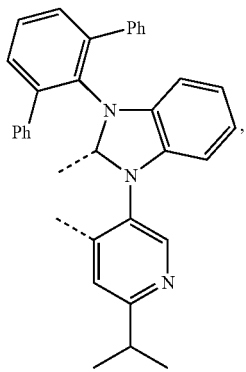 L_{B163}
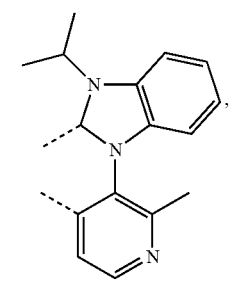 L_{B164}

-continued
L$_{B165}$ 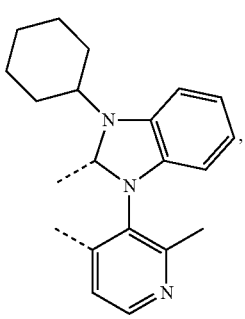
L$_{B166}$ 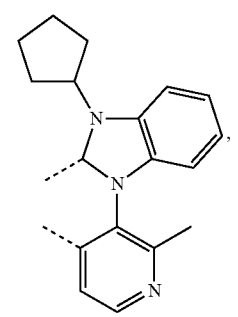
L$_{B167}$ 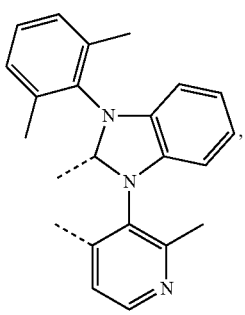
L$_{B168}$ 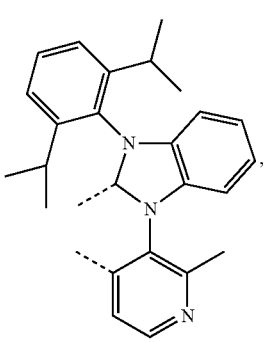
L$_{B169}$ 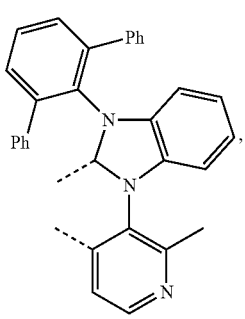
-continued
L$_{B170}$ 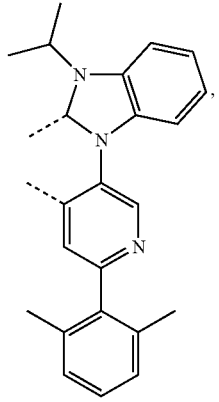
L$_{B171}$ 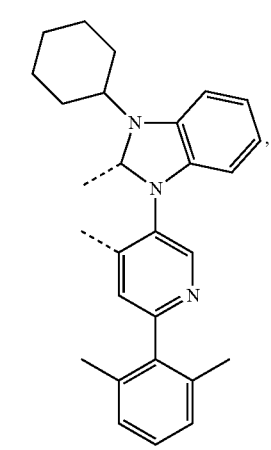
L$_{B172}$ 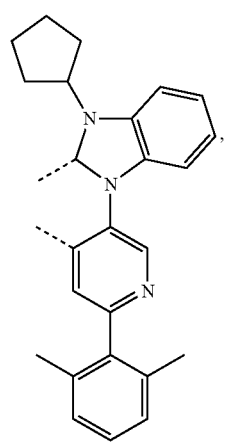

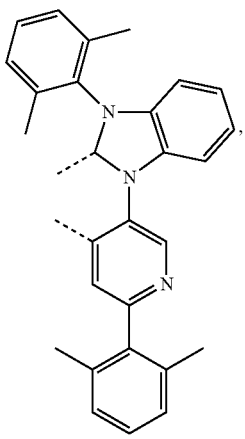
L<sub>B173</sub>
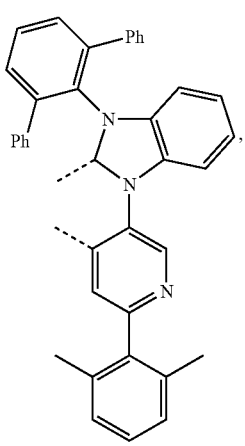
L<sub>B175</sub>
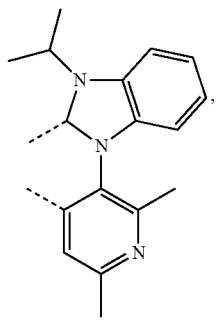
L<sub>B176</sub>
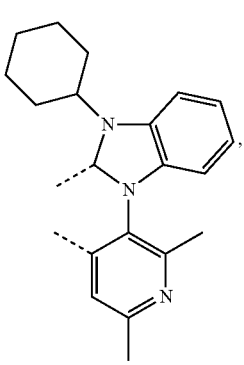
L<sub>B177</sub>
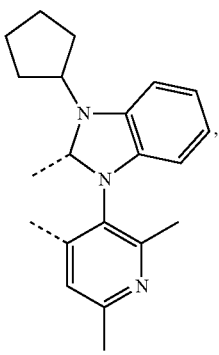
L<sub>B178</sub>
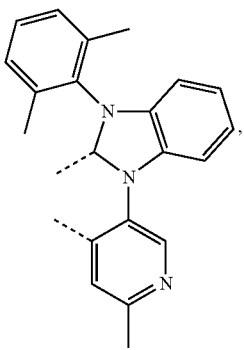
L<sub>B179</sub>

L_B180 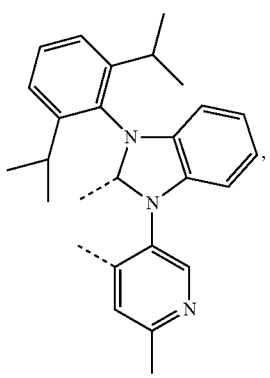
L_B181 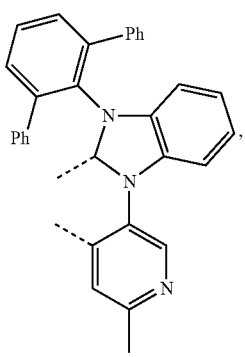
L_B182 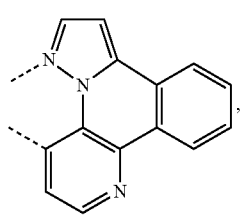
L_B183 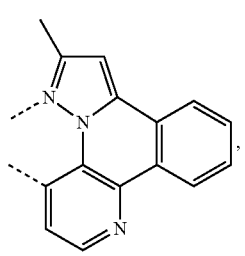
L_B184 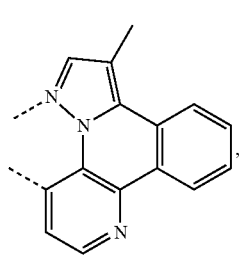
L_B185 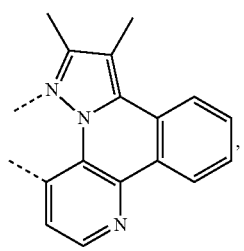
L_B186 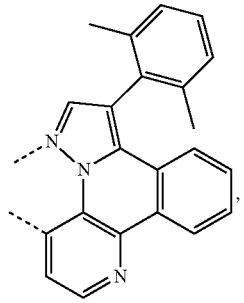
L_B187 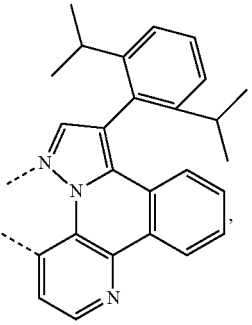
L_B188 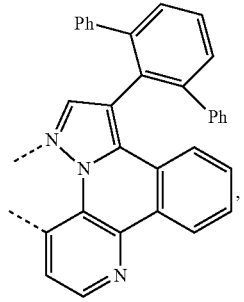
L_B189 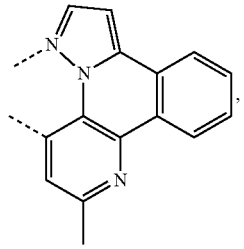

431
-continued
L<sub>B190</sub>
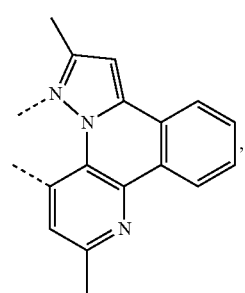
L<sub>B191</sub>
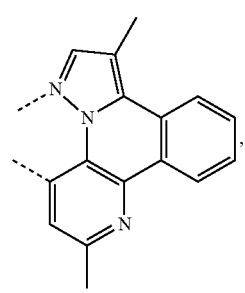
L<sub>B192</sub>
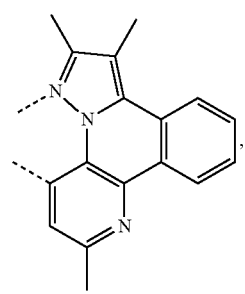
L<sub>B193</sub>
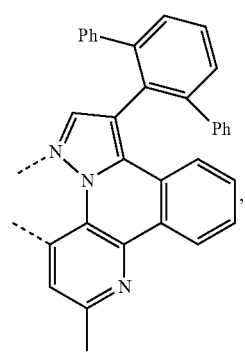
L<sub>B194</sub>
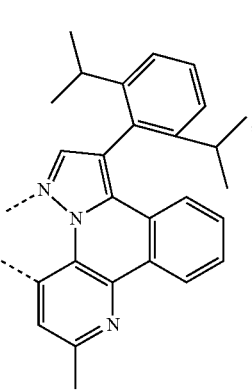
432
-continued
L<sub>B195</sub>
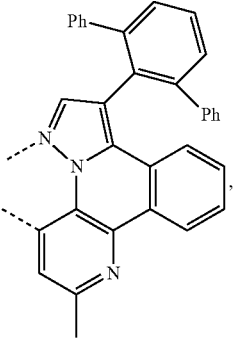
L<sub>B196</sub>
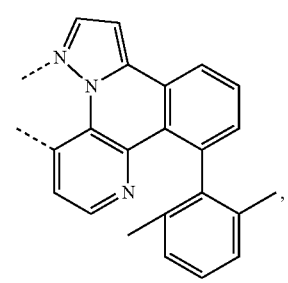
L<sub>B197</sub>
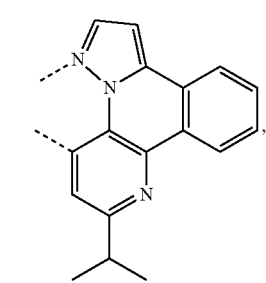
L<sub>B198</sub>
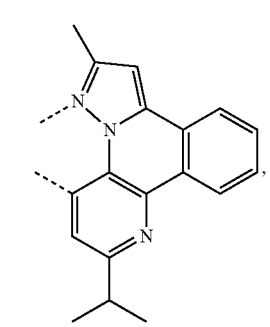
L<sub>B199</sub>
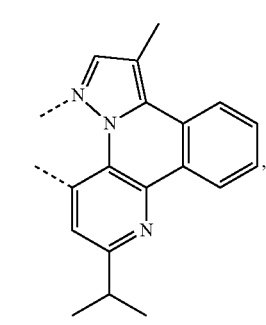

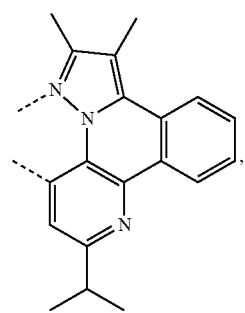
$L_{B200}$
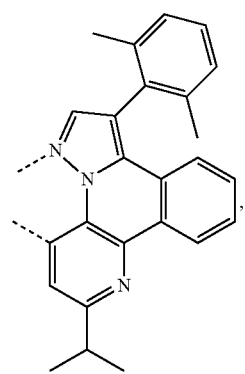
$L_{B201}$
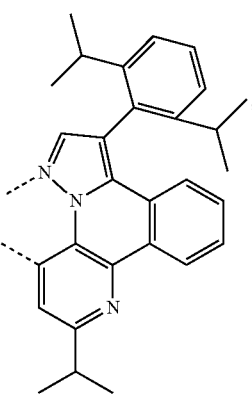
$L_{B202}$
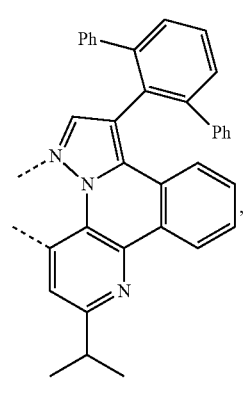
$L_{B203}$
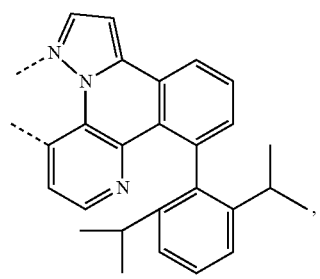
$L_{B204}$
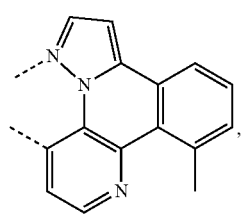
$L_{B205}$
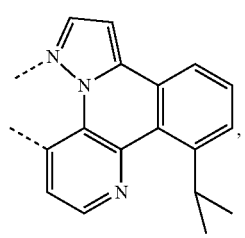
$L_{B206}$
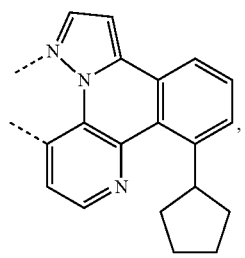
$L_{B207}$
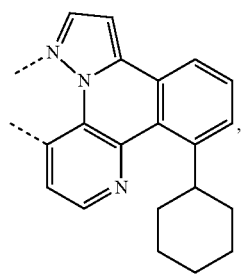
$L_{B208}$
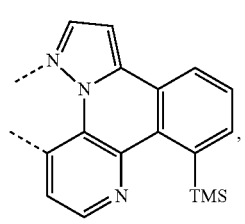
$L_{B209}$ 435
-continued
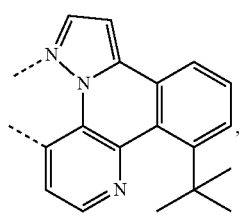
L_{B210}
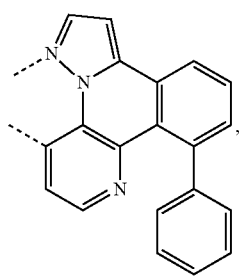
L_{B211}
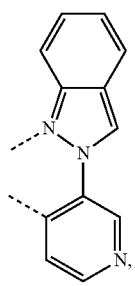
L_{B212}
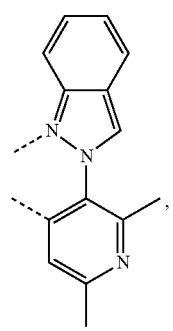
L_{B213}
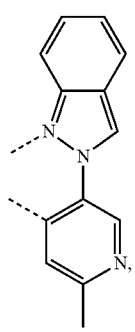
L_{B214}
436
-continued
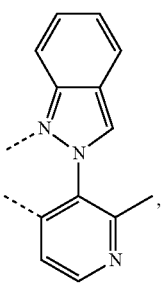
L_{B215}
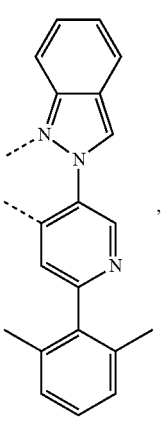
L_{B216}
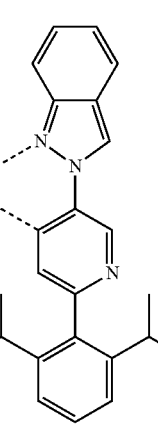
L_{B217}
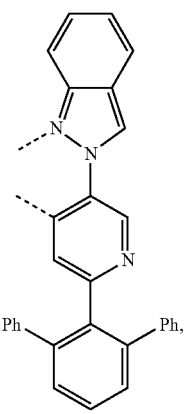
L_{B218}

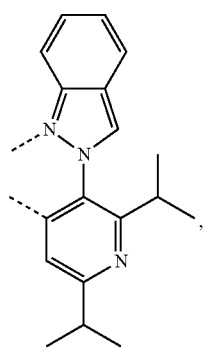
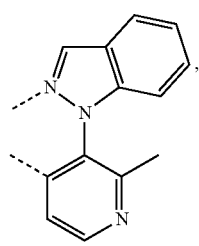
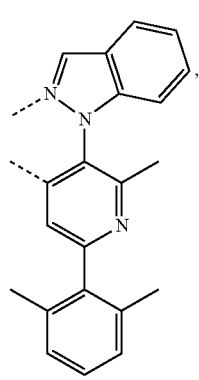
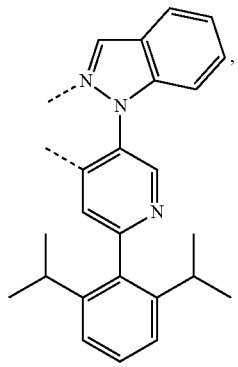
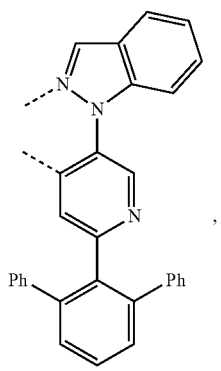

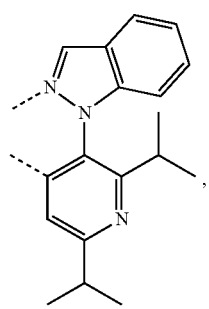 $L_{B228}$
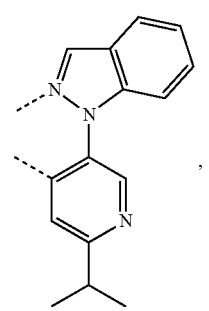 $L_{B229}$
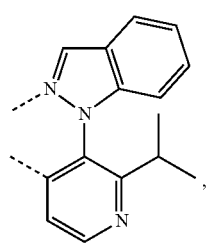 $L_{B230}$
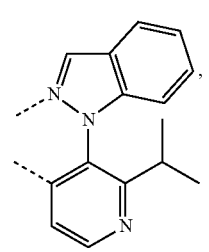 $L_{B231}$
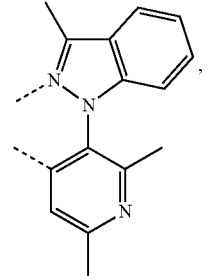 $L_{B232}$

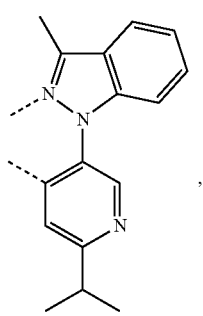 L_{B238}
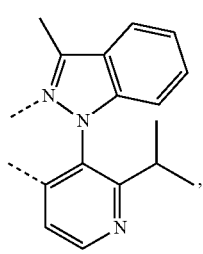 L_{B239}
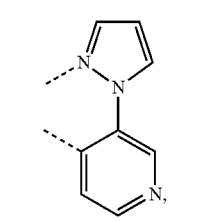 L_{B240}
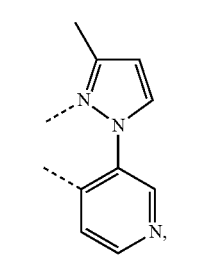 L_{B241}
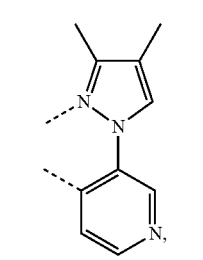 L_{B242}
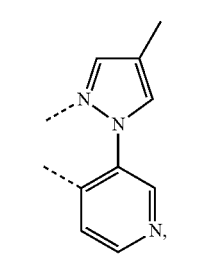 L_{B243}
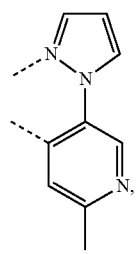 L_{B244}
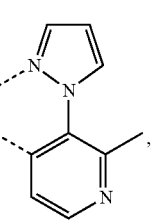 L_{B245}
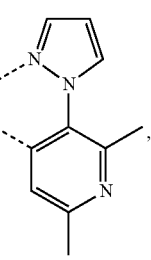 L_{B246}
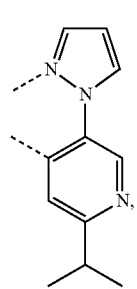 L_{B247}
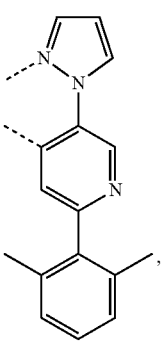 L_{B248}

-continued
$L_{B249}$
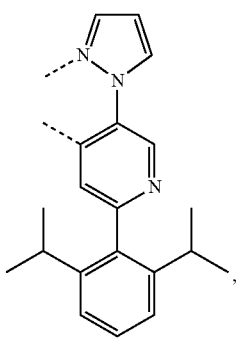
$L_{B250}$
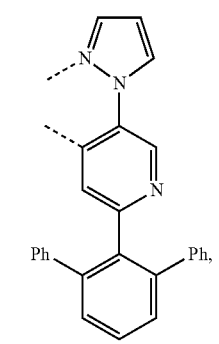
$L_{B251}$
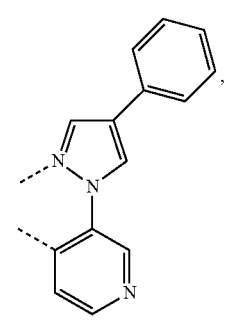
$L_{B252}$
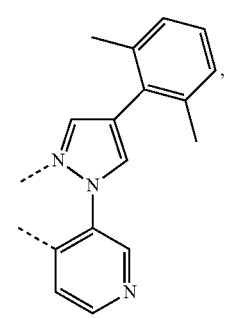
$L_{B253}$
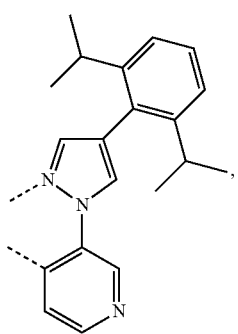
-continued
$L_{B254}$
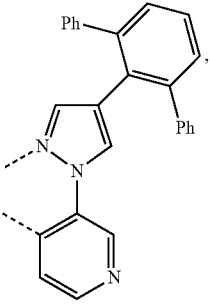
$L_{B255}$
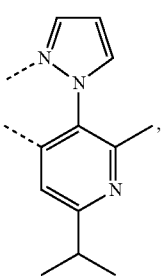
$L_{B256}$
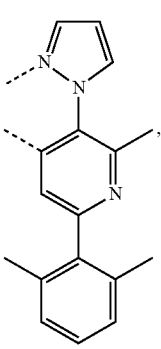
$L_{B257}$
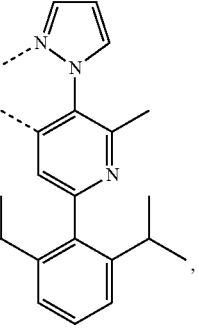
$L_{B258}$
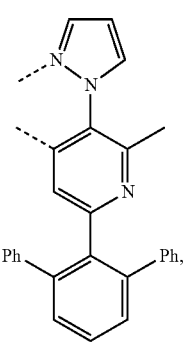

$L_{B259}$ 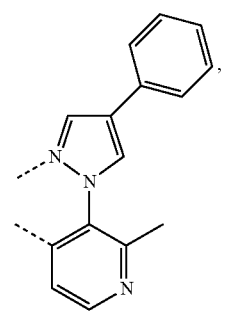
$L_{B260}$ 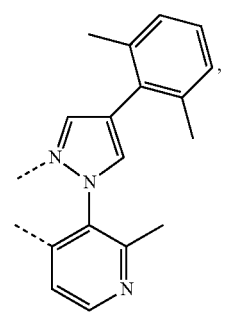
$L_{B261}$ 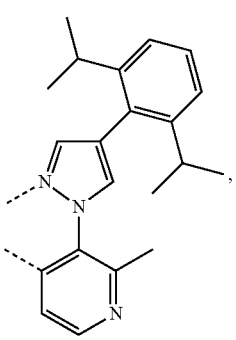
$L_{B262}$ 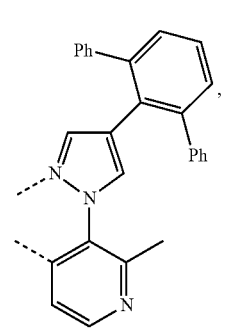
$L_{B263}$ 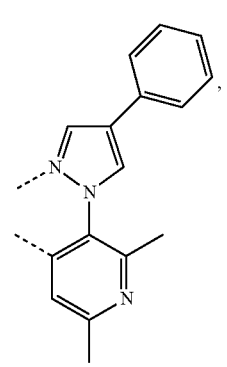
$L_{B264}$ 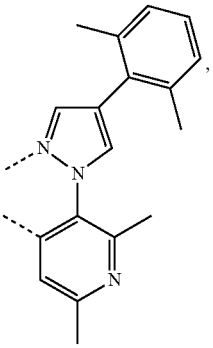
$L_{B265}$ 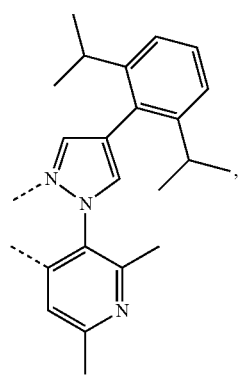
$L_{B266}$ 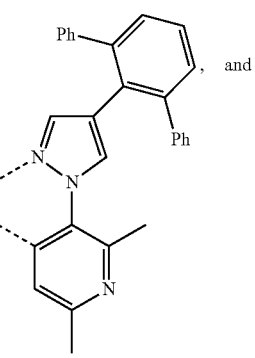, and
$L_{B267}$ 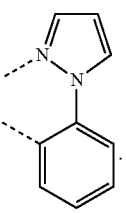.
14. The compound of claim 10, wherein the compound is selected from the group consisting of Compound 317 through Compound 84,688;
wherein each Compound x has the formula $\text{Ir}(L_{Ai})(L_{Bj})_2$;

wherein L$_{Bi}$ is selected from the group consisting of:
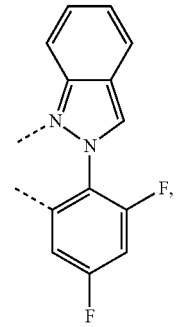
L$_{B1}$
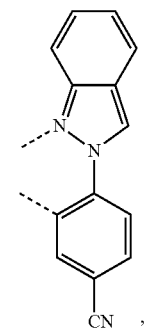
L$_{B2}$
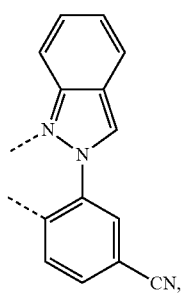
L$_{B3}$
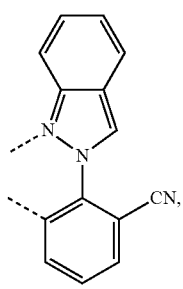
L$_{B4}$
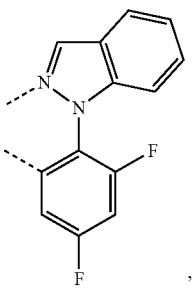
L$_{B5}$
-continued
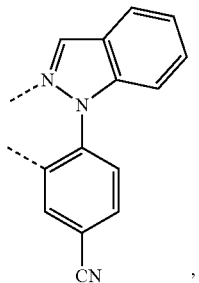
L$_{B6}$
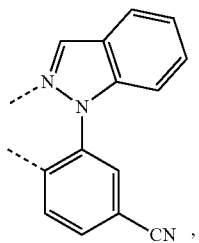
L$_{B7}$
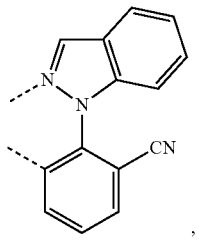
L$_{B8}$
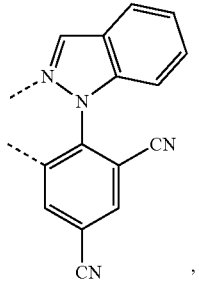
L$_{B9}$
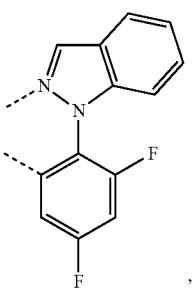
L$_{B10}$ 449
-continued
L_{B11}
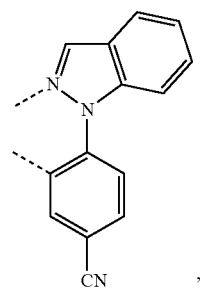,
L_{B12}
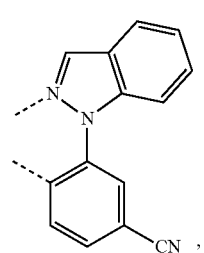,
L_{B13}
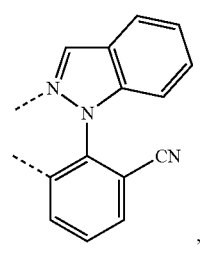,
L_{B14}
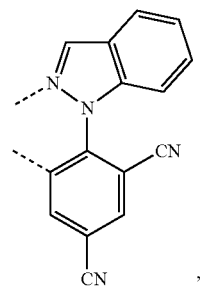,
L_{B15}
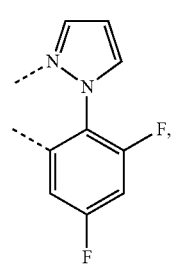,
450
-continued
L_{B16}
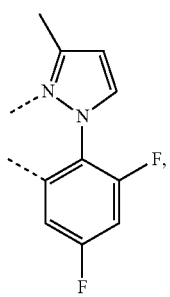,
L_{B17}
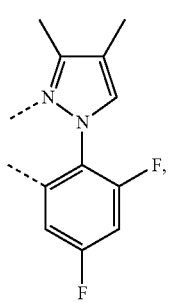,
L_{B18}
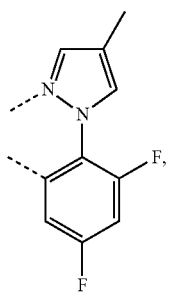,
L_{B19}
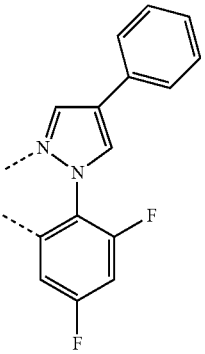,
L_{B20}
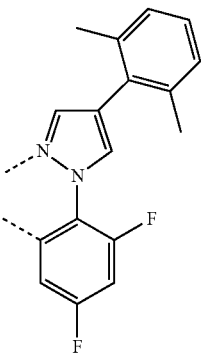, -continued
L_{B21}
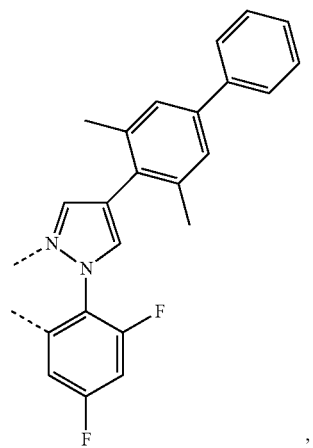
L_{B22}
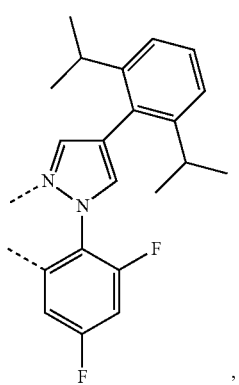
L_{B23}
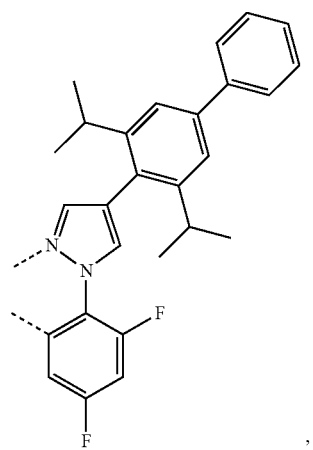
L_{B24}
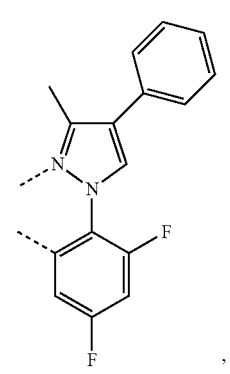
-continued
L_{B25}
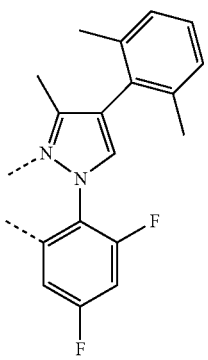
L_{B26}
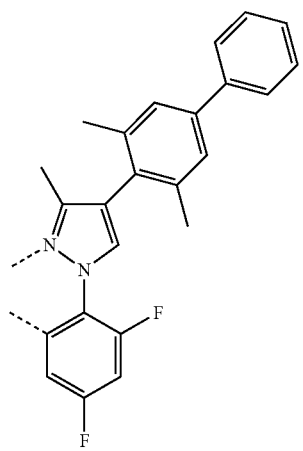
L_{B27}
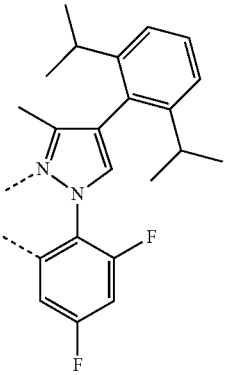
L_{B28}
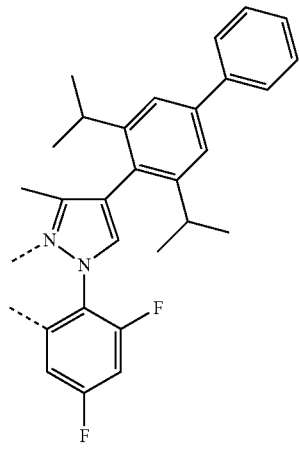

L_{B29} 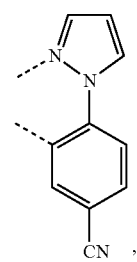
L_{B30} 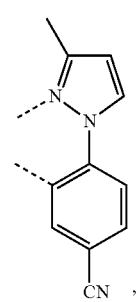
L_{B31} 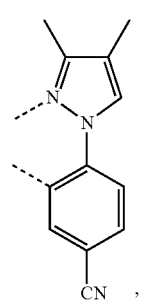
L_{B32} 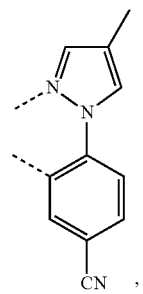
L_{B33} 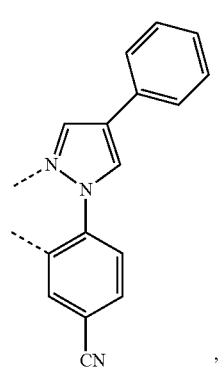
L_{B34} 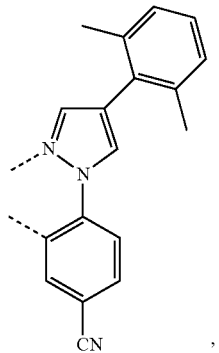
L_{B35} 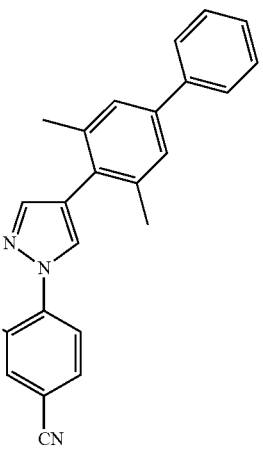
L_{B36} 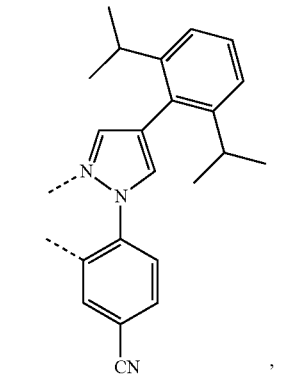
L_{B37} 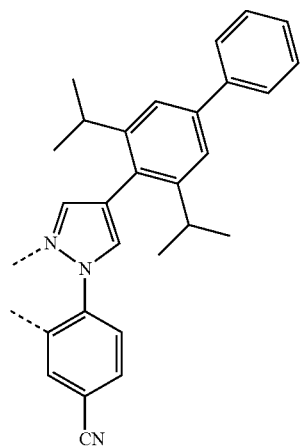

455
-continued
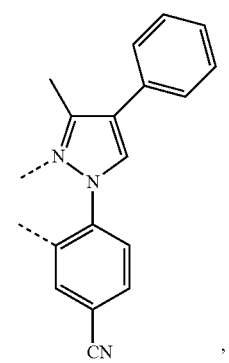
L_{B38}
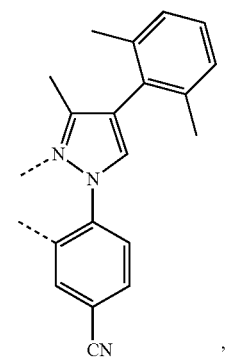
L_{B39}
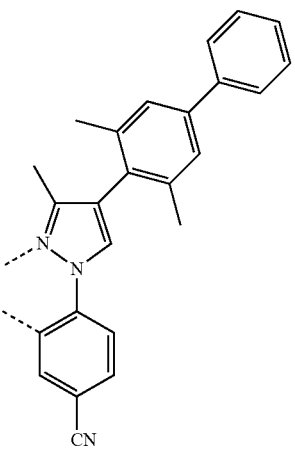
L_{B40}
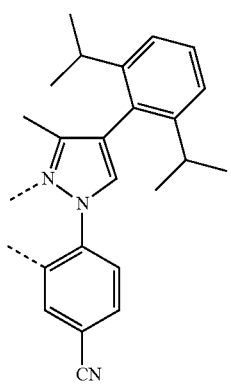
L_{B41}
456
-continued
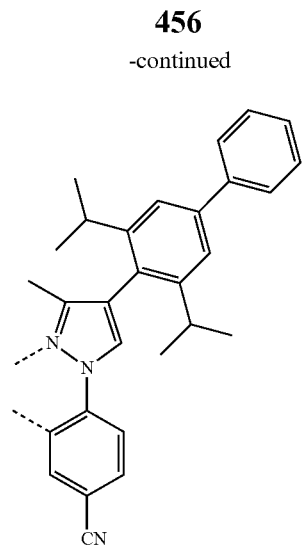
L_{B42}
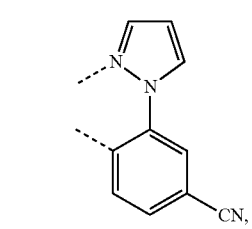
L_{B43}
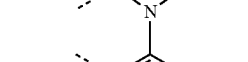
L_{B44}
L_{B45}
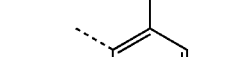
L_{B46}

-continued
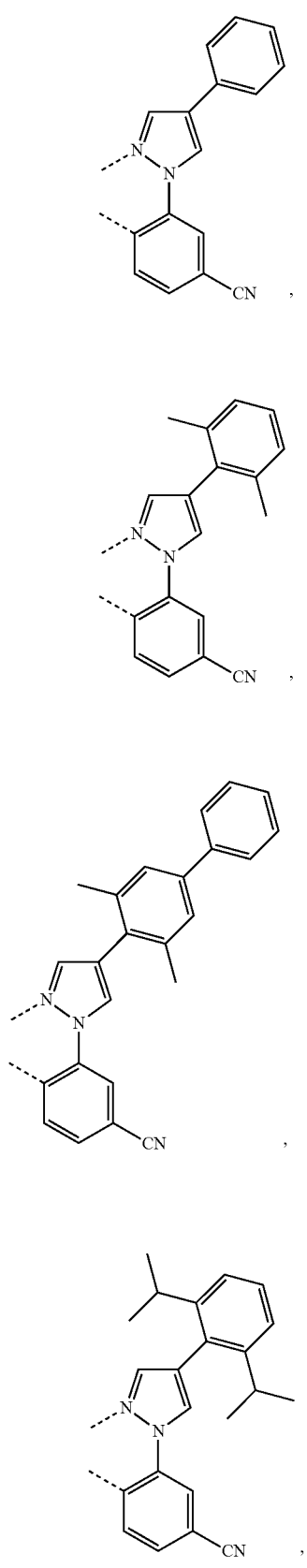
L<sub>B47</sub>
L<sub>B48</sub>
L<sub>B49</sub>
L<sub>B50</sub>
-continued
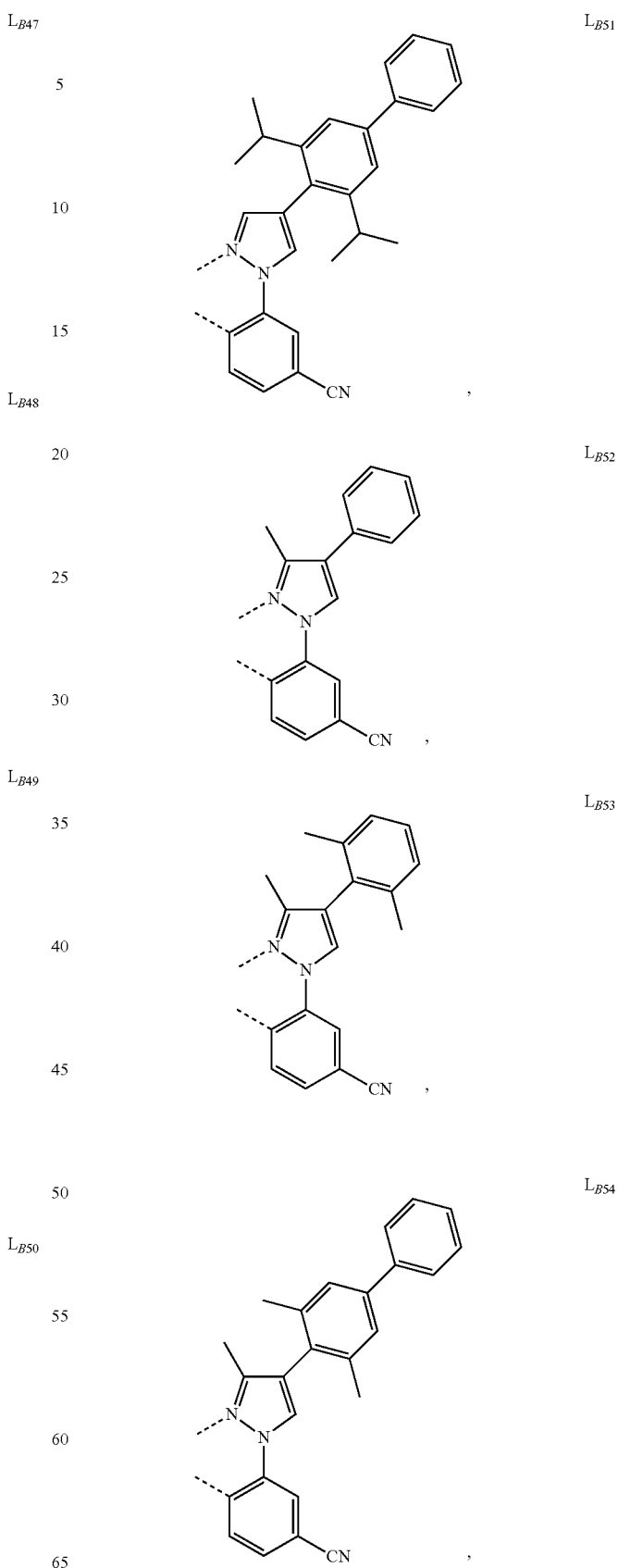
L<sub>B51</sub>
L<sub>B52</sub>
L<sub>B53</sub>
L<sub>B54</sub>

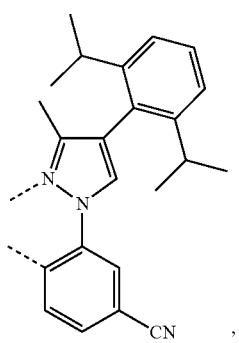
L_{B55}
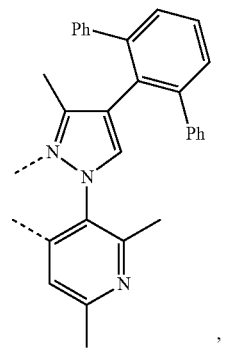
L_{B56}
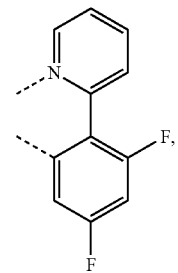
L_{B57}
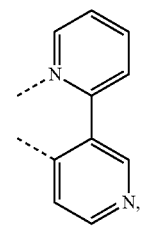
L_{B58}
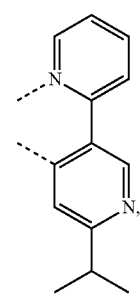
L_{B59}
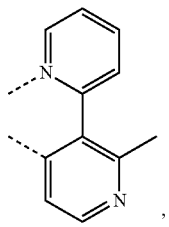
L_{B60}
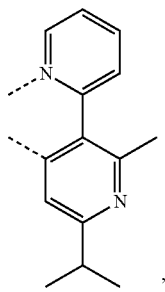
L_{B61}
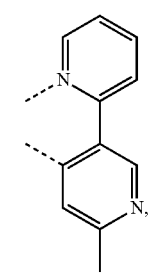
L_{B62}
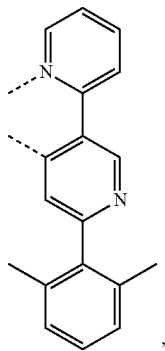
L_{B63}
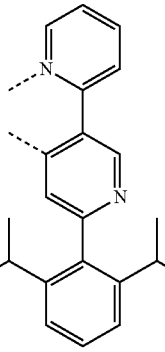
L_{B64}

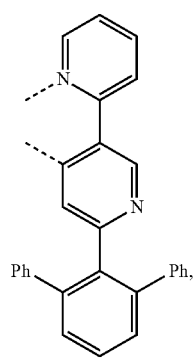 L_{B65}
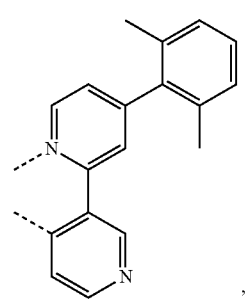 L_{B66}
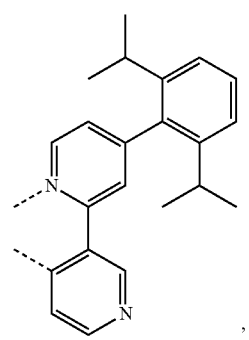 L_{B67}
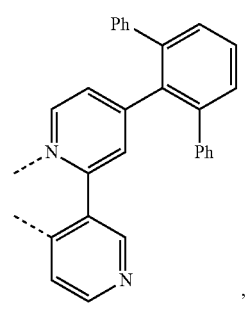 L_{B68}
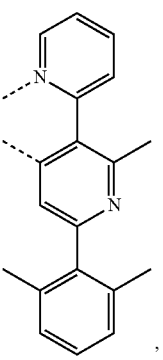 L_{B69}
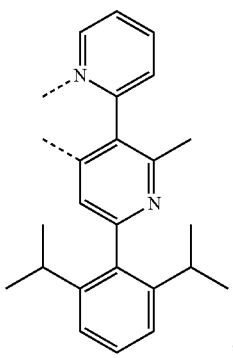 L_{B70}
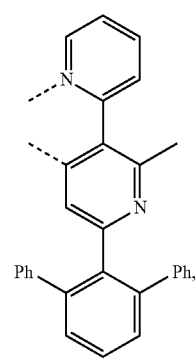 L_{B71}
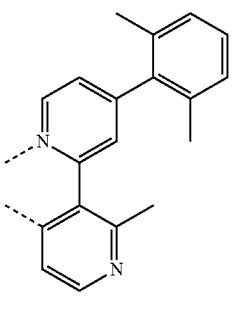 L_{B72}

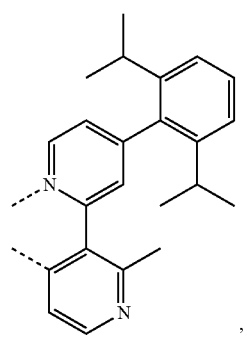 L_{B73}
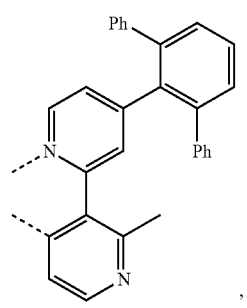 L_{B74}
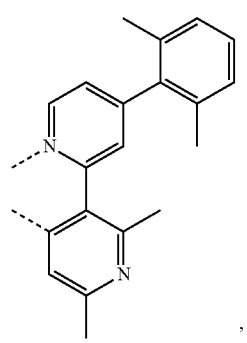 L_{B75}
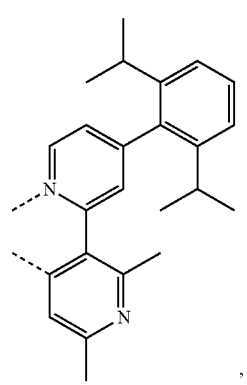 L_{B76}
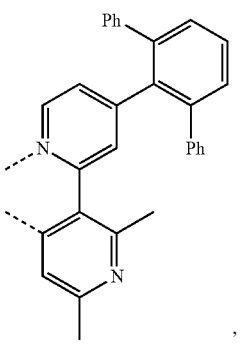 L_{B77}
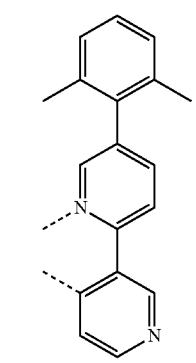 L_{B78}
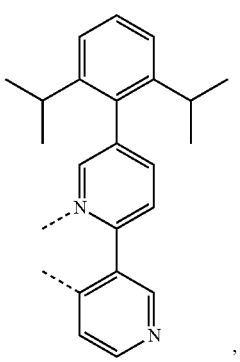 L_{B79}
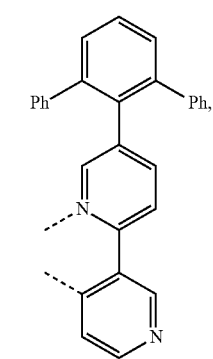 L_{B80}

L_{B81} 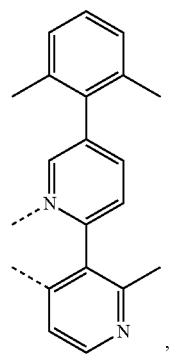
L_{B82} 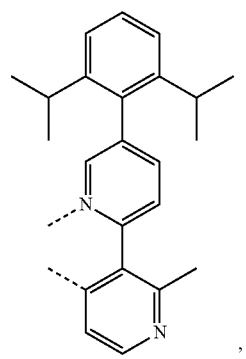
L_{B83} 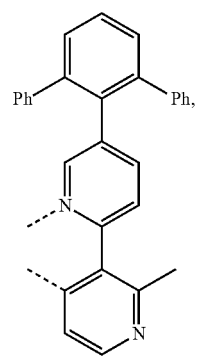
L_{B84} 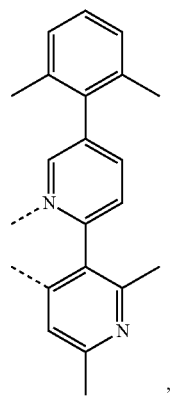
L_{B85} 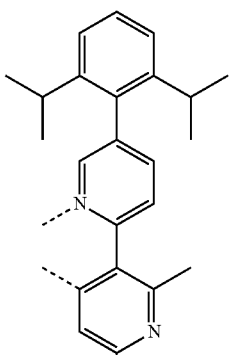
L_{B86} 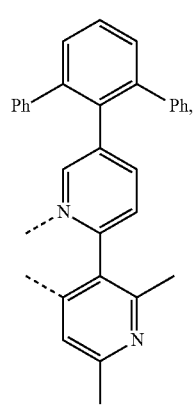
L_{B87} 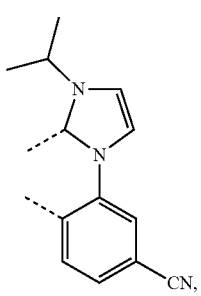
L_{B88} 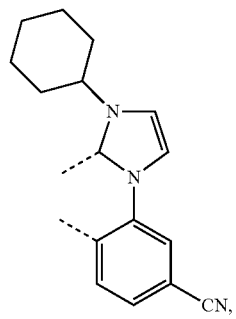

-continued
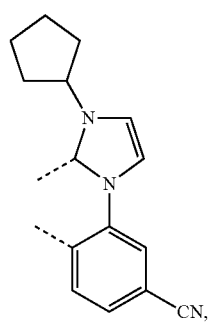 L<sub>B89</sub>
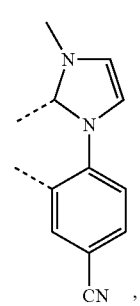 L<sub>B90</sub>
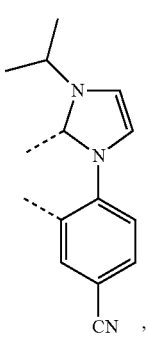 L<sub>B91</sub>
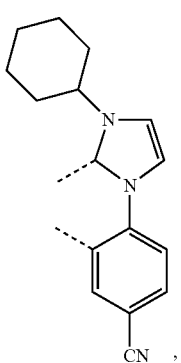 L<sub>B92</sub>
-continued
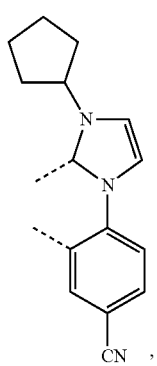 L<sub>B93</sub>
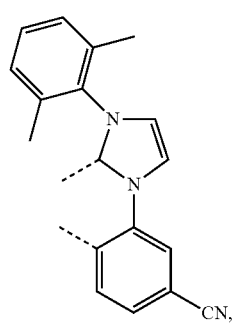 L<sub>B94</sub>
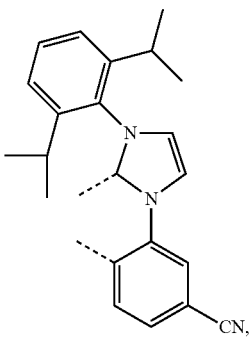 L<sub>B95</sub>
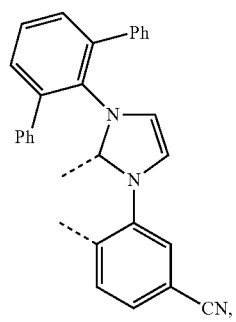 L<sub>B96</sub>

469
-continued
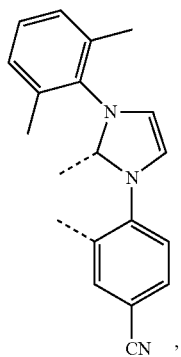 L_{B97}
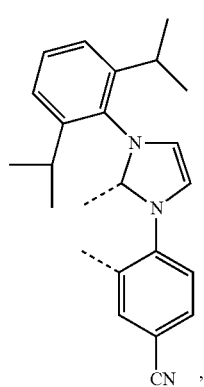 L_{B98}
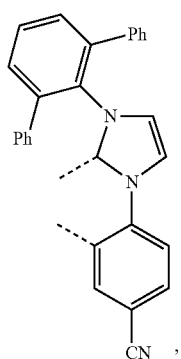 L_{B99}
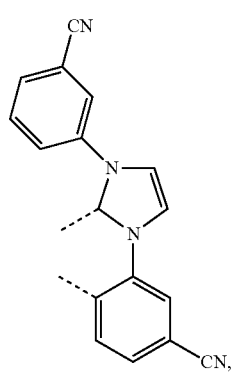 L_{B100}
470
-continued
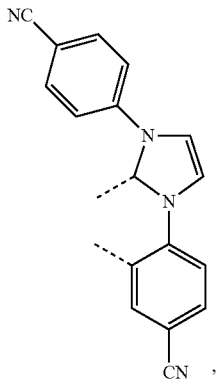 L_{B101}
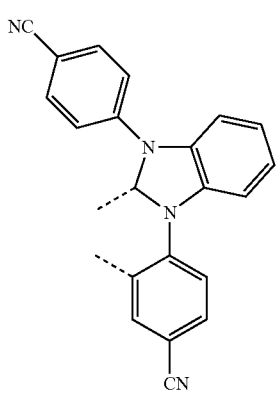 L_{B102}
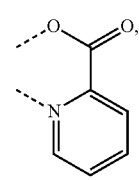 L_{B103}
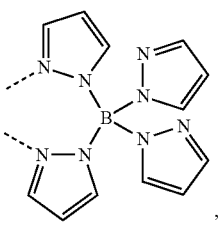 L_{B104}
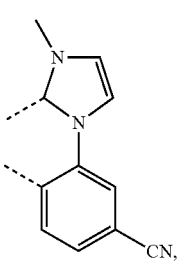 L_{B105}

L<sub>B106</sub>
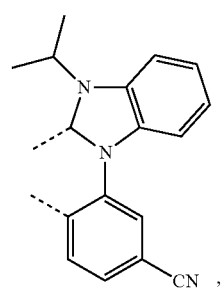
L<sub>B107</sub>
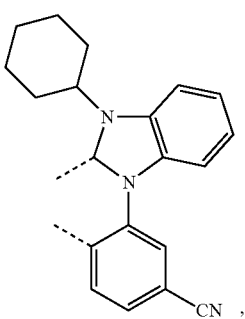
L<sub>B108</sub>
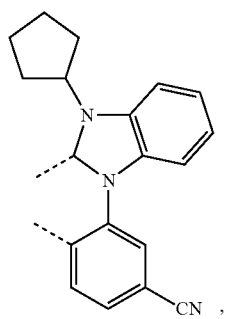
L<sub>B109</sub>
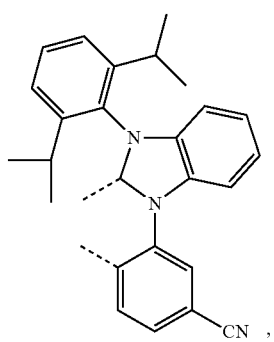
L<sub>B110</sub>
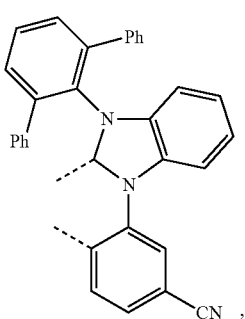
L<sub>B111</sub>
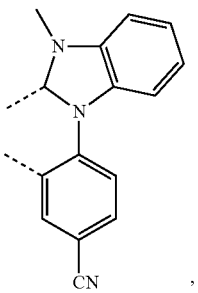
L<sub>B112</sub>
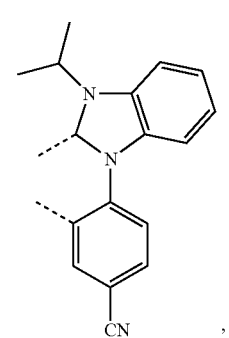
L<sub>B113</sub>
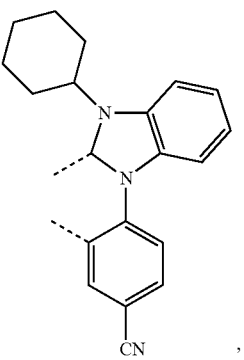
L<sub>B114</sub>
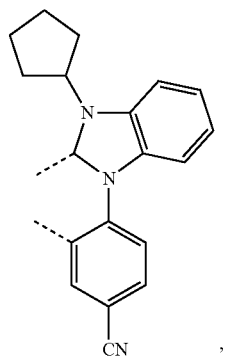

| 473 -continued | | 474 -continued | |
|---|---|---|---|
| 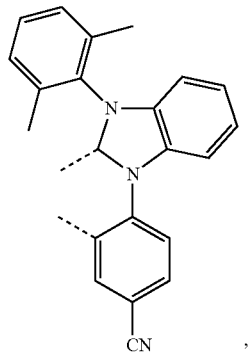 | L<sub>B115</sub> | 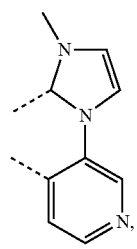 | L<sub>B119</sub> |
| 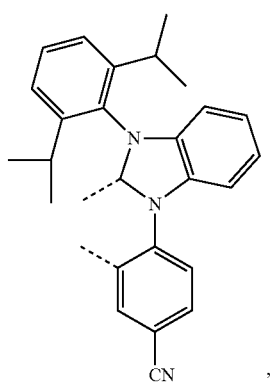 | L<sub>B116</sub> | 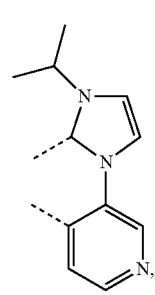 | L<sub>B120</sub> |
| 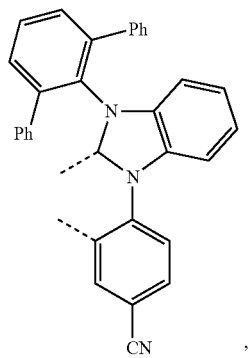 | L<sub>B117</sub> | 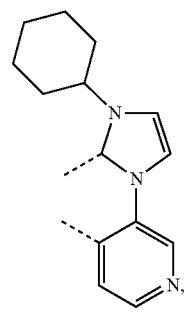 | L<sub>B121</sub> |
| 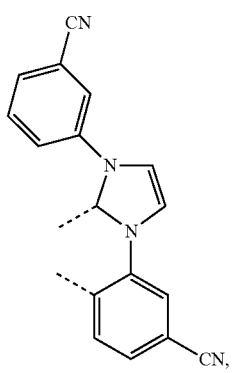 | L<sub>B118</sub> | 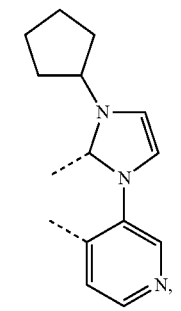 | L<sub>B122</sub> |
| | | 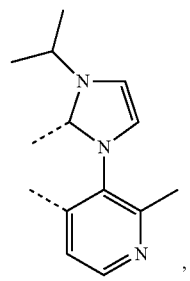 | L<sub>B123</sub> |

-continued
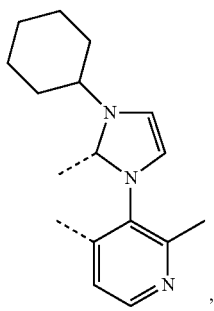
L$_{B124}$
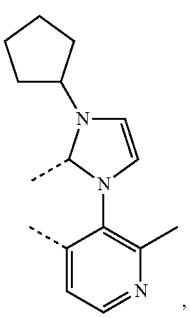
L$_{B125}$
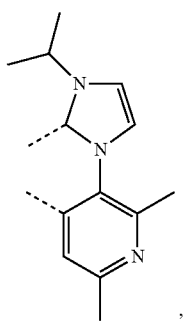
L$_{B126}$
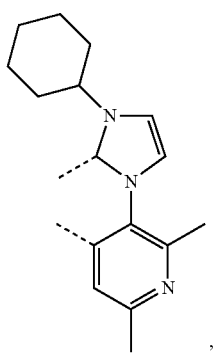
L$_{B127}$
-continued
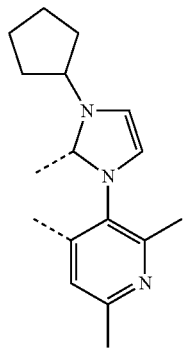
L$_{B128}$
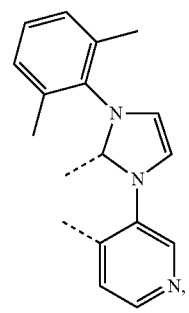
L$_{B129}$
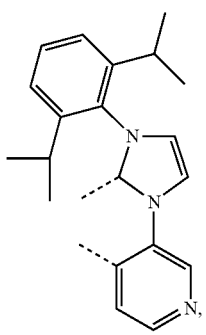
L$_{B130}$
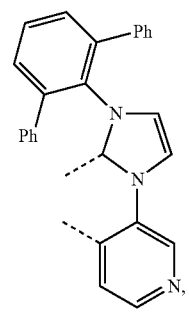
L$_{B131}$
L$_{B132}$ L<sub>B133</sub> 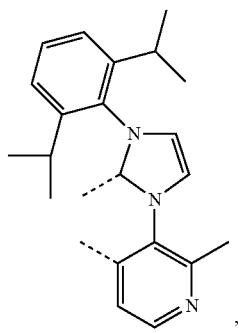
L<sub>B134</sub> 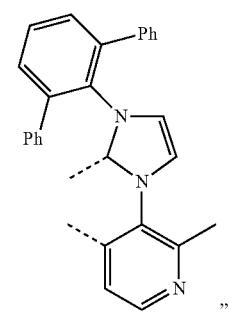
L<sub>B135</sub> 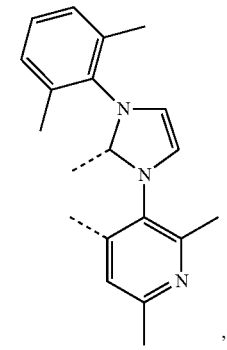
L<sub>B136</sub> 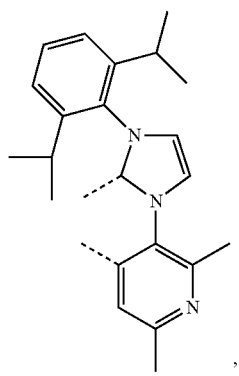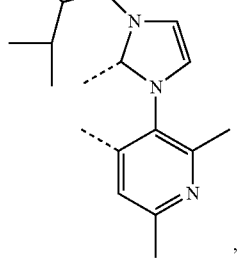
L<sub>B137</sub> 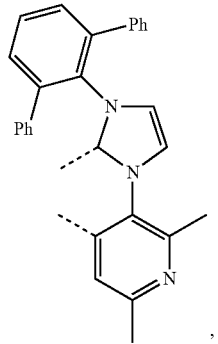
L<sub>B138</sub> 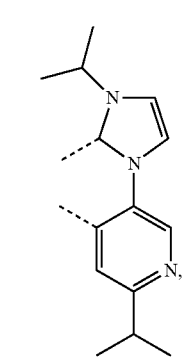
L<sub>B139</sub> 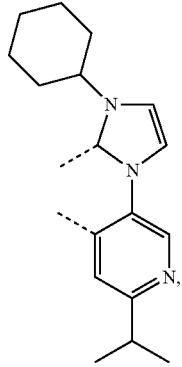
L<sub>B140</sub> 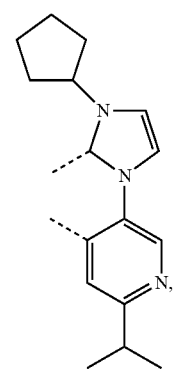

L_{B141}
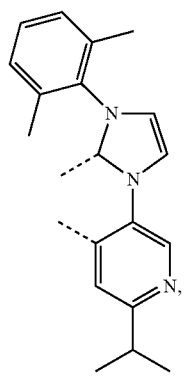
L_{B142}
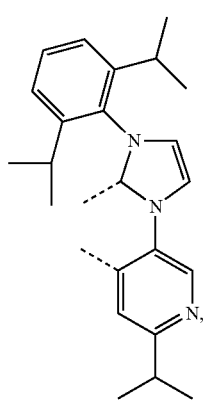
L_{B143}
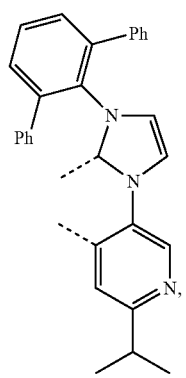
L_{B144}
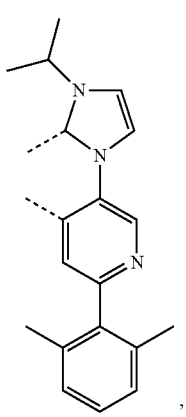
L_{B145}
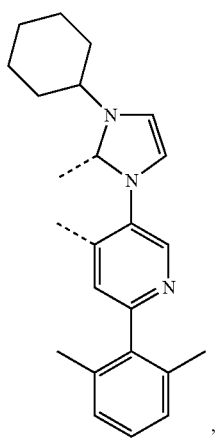
L_{B146}
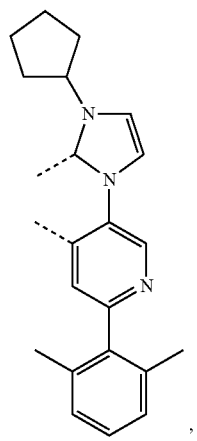
L_{B147}
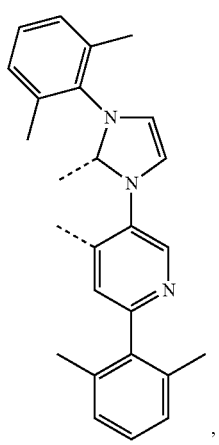

-continued
L_{B148}
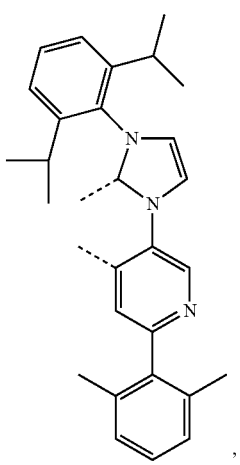
L_{B149}
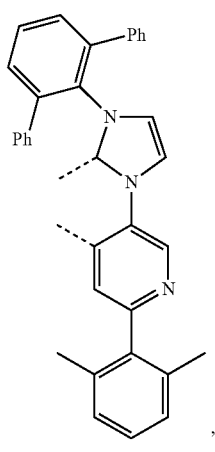
L_{B150}
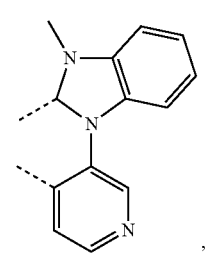
L_{B151}
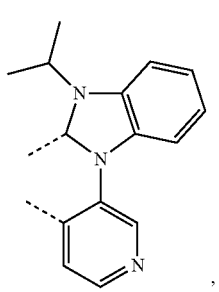
-continued
L_{B152}
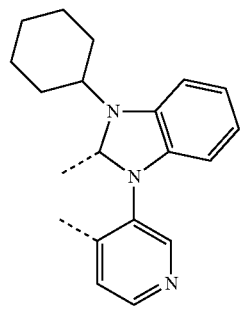
L_{B153}
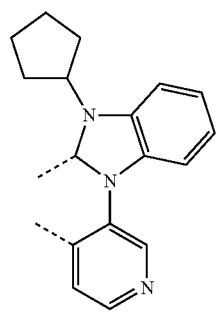
L_{B154}
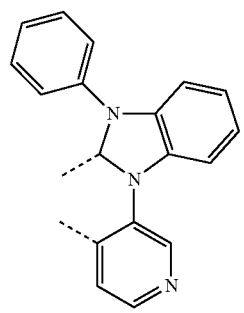
L_{B155}
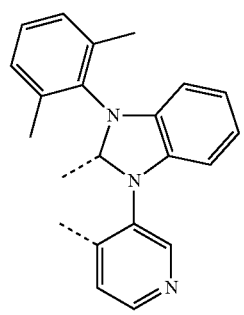
L_{B156}
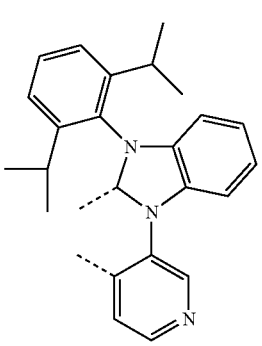

L_{B157}
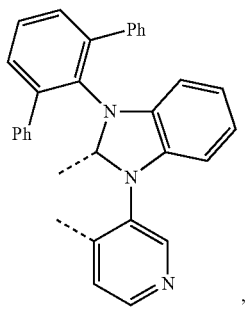
L_{B158}
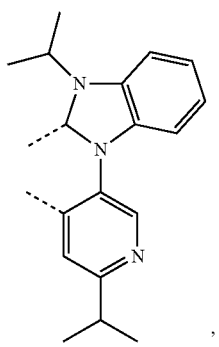
L_{B159}
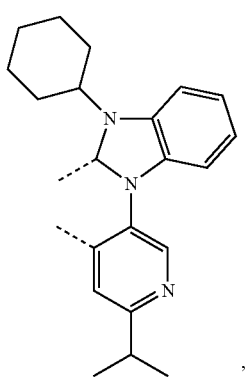
L_{B160}
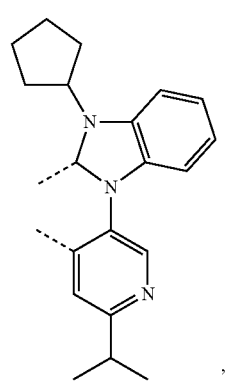
L_{B161}
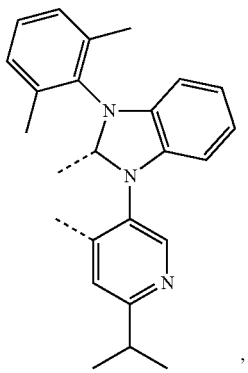
L_{B162}
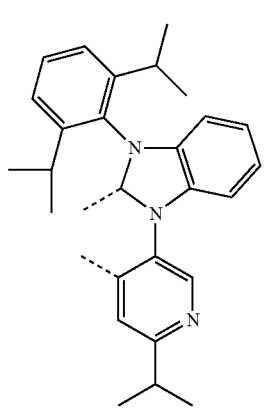
L_{B163}
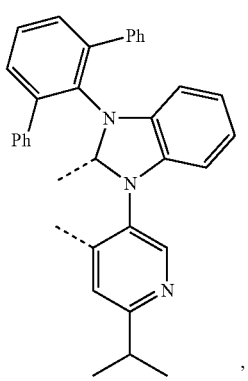
L_{B164}
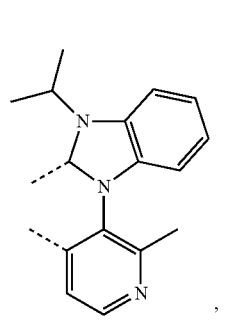

-continued
L_{B165}
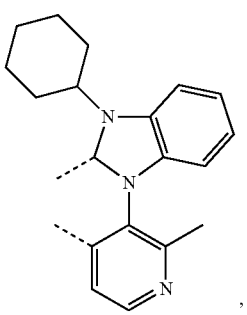
L_{B166}
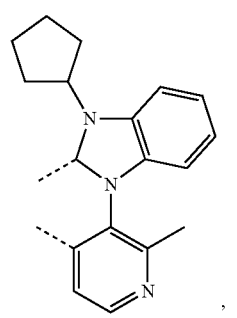
L_{B167}
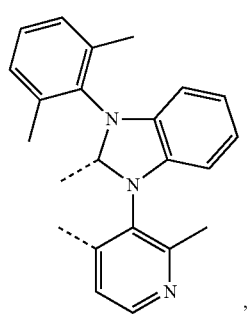
L_{B168}
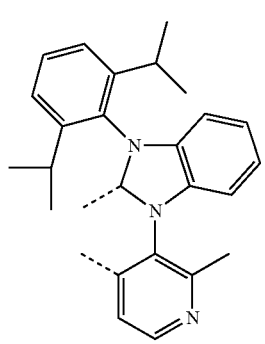
L_{B169}
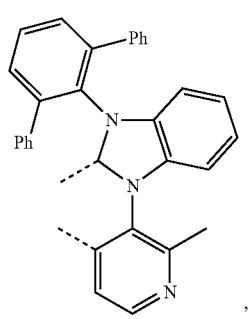
-continued
L_{B170}
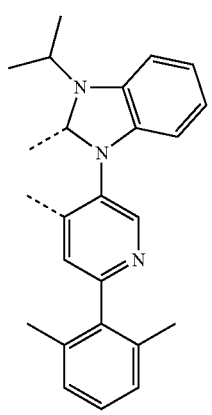
L_{B171}
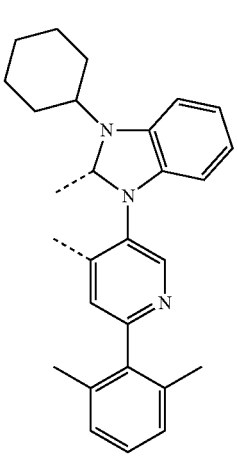
L_{B172}
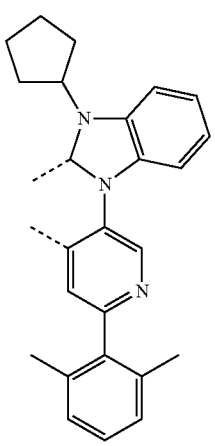

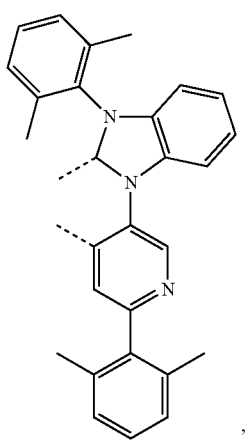 L_{B173}
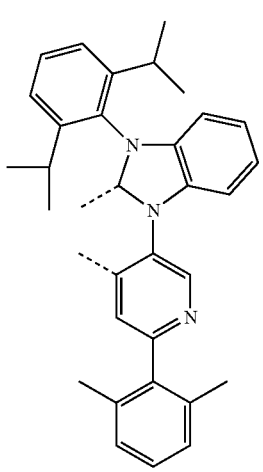 L_{B174}
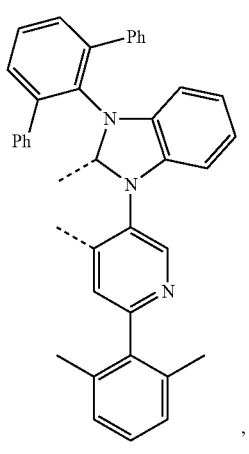 L_{B175}
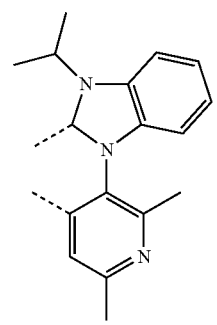 L_{B176}
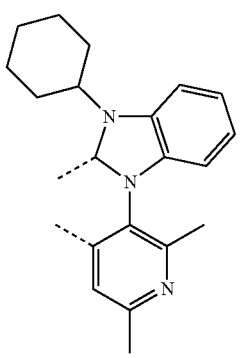 L_{B177}
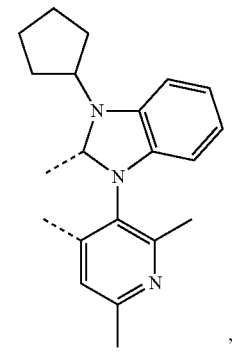 L_{B178}
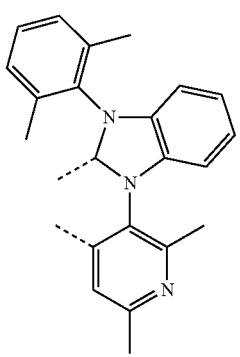 L_{B179}

489
-continued
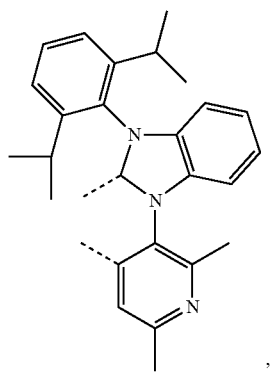
L<sub>B180</sub>
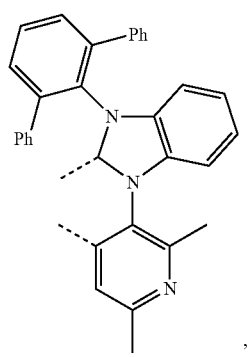
L<sub>B181</sub>
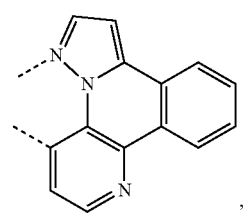
L<sub>B182</sub>
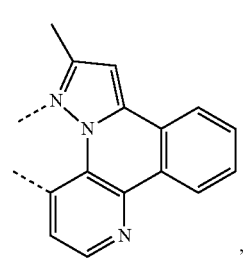
L<sub>B183</sub>
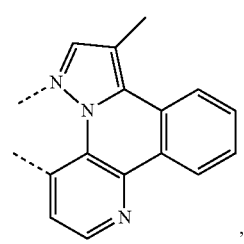
L<sub>B184</sub>
490
-continued
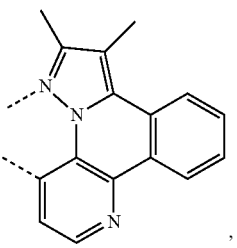
L<sub>B185</sub>
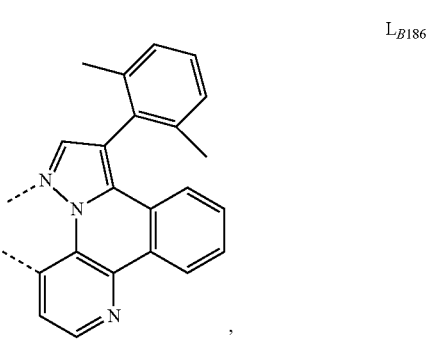
L<sub>B186</sub>
L<sub>B187</sub>
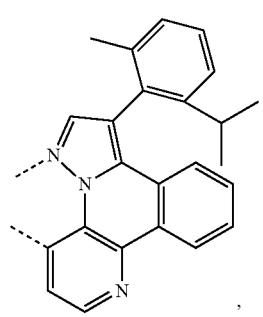
L<sub>B188</sub>
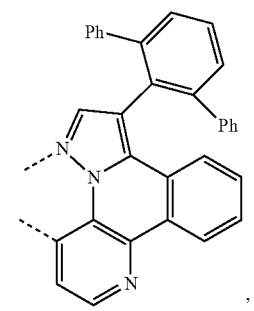
L<sub>B189</sub>
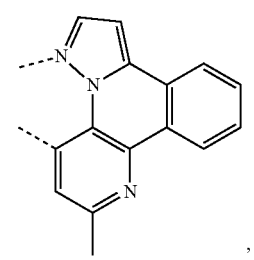

L<sub>B190</sub>
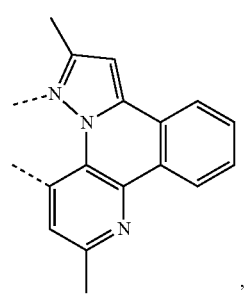
L<sub>B191</sub>
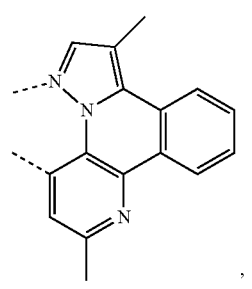
L<sub>B192</sub>
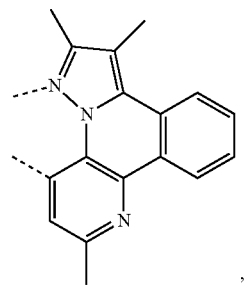
L<sub>B193</sub>
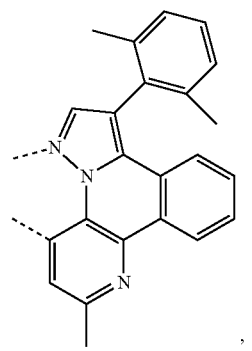
L<sub>B194</sub>
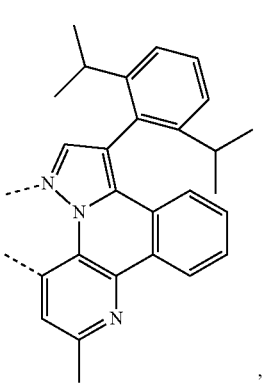
L<sub>B195</sub>
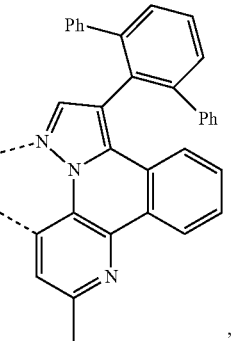
L<sub>B196</sub>
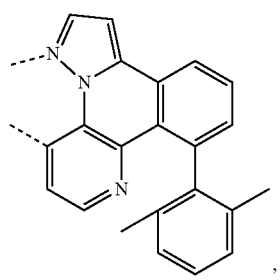
L<sub>B197</sub>
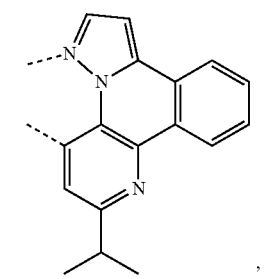
L<sub>B198</sub>
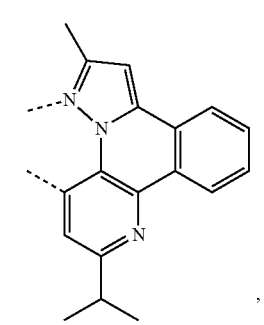
L<sub>B199</sub>
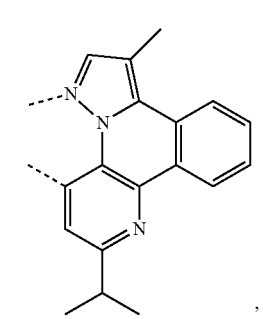

493
-continued
L_{B200}
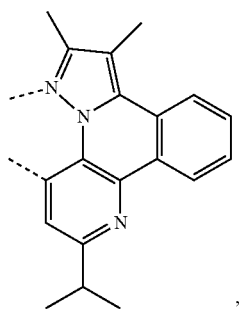
L_{B201}
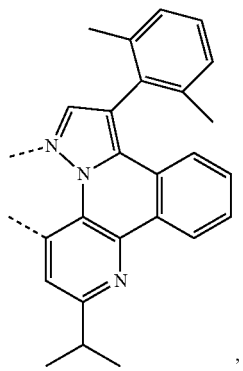
L_{B202}
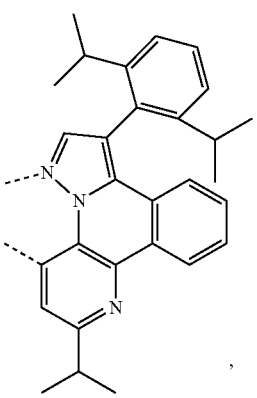
L_{B203}
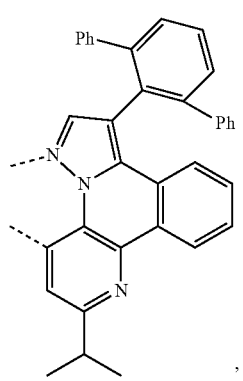
494
-continued
L_{B204}
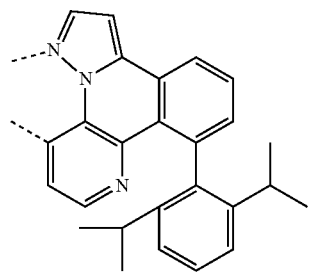
L_{B205}
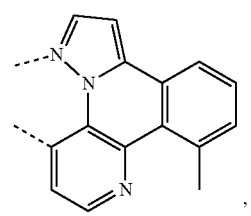
L_{B206}
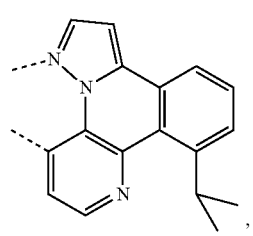
L_{B207}
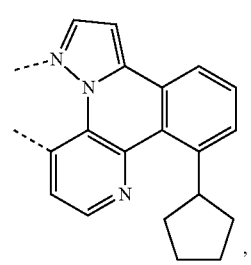
L_{B208}
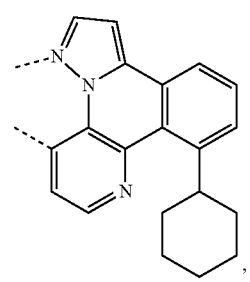
L_{B209}
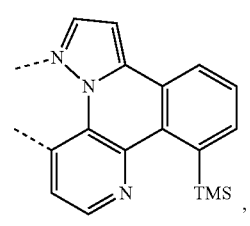

-continued
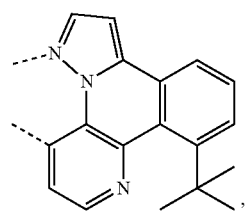
L_{B210}
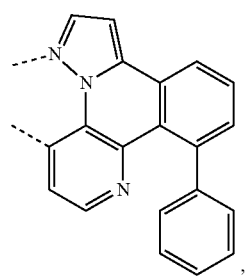
L_{B211}
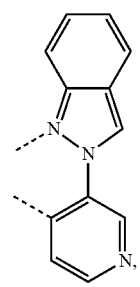
L_{B212}
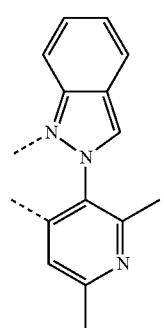
L_{B213}
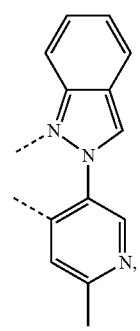
L_{B214}
-continued
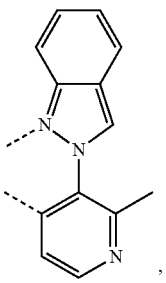
L_{B215}
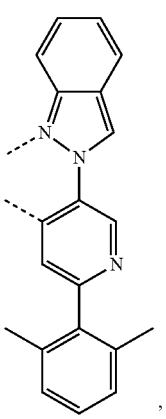
L_{B216}
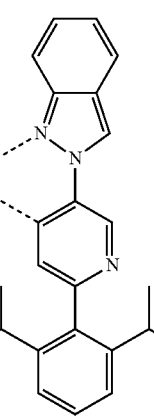
L_{B217}
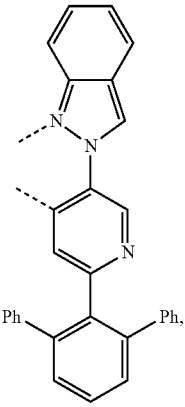
L_{B218}

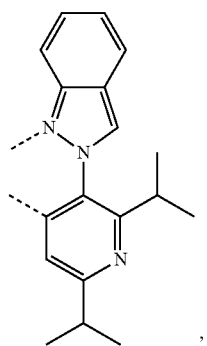 L_{B219},
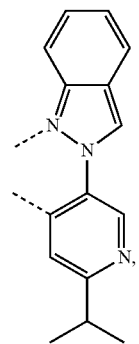 L_{B220},
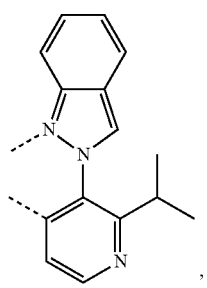 L_{B221},
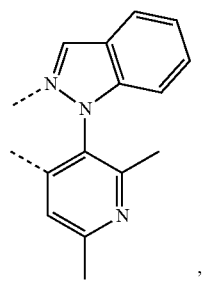 L_{B222},
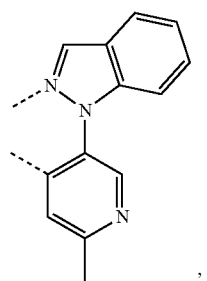 L_{B223},
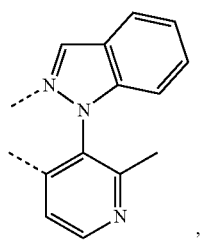 L_{B224},
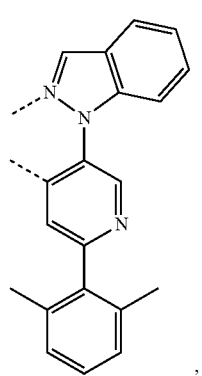 L_{B225},
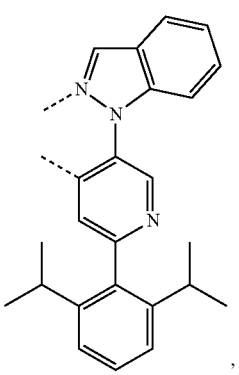 L_{B226},
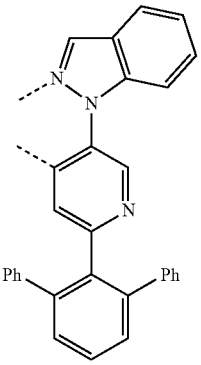 L_{B227},

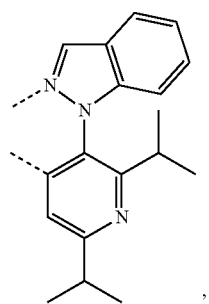 L_{B228}
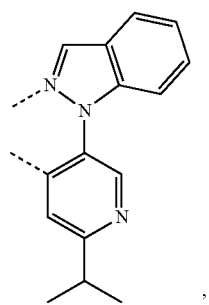 L_{B229}
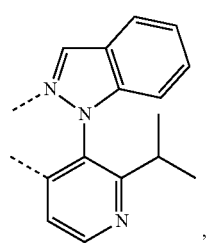 L_{B230}
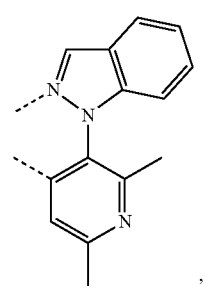 L_{B231}
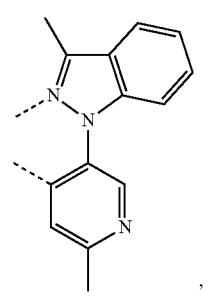 L_{B232}
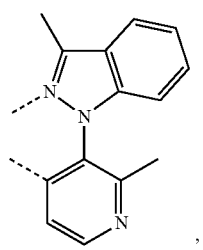 L_{B233}
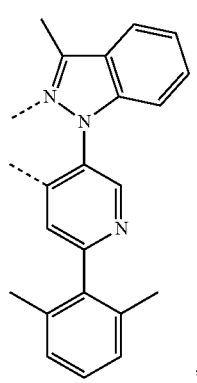 L_{B234}
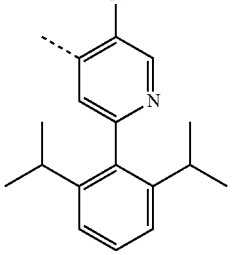 L_{B235}
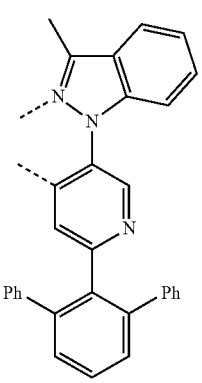 L_{B236}

-continued
L_{B237}
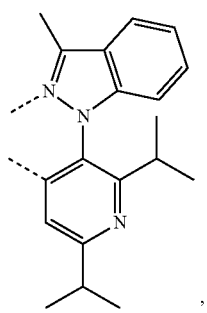
L_{B238}
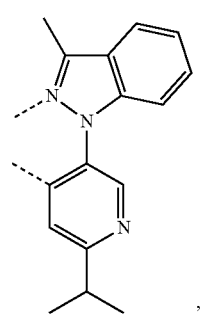
L_{B139}
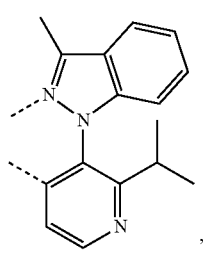
L_{B140}
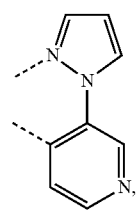
and wherein x=316j+i; i is an integer from 1 to 316, and j is an integer from 1 to 267.
15. The compound of claim 12, wherein the $L_B$ is chosen such that the HOMO energy in $Ir(L_B)_3$ is deeper than that in $Ir(L_A)_3$.
16. The compound of claim 1, wherein the compound is selected from the group consisting of:
Compound 306
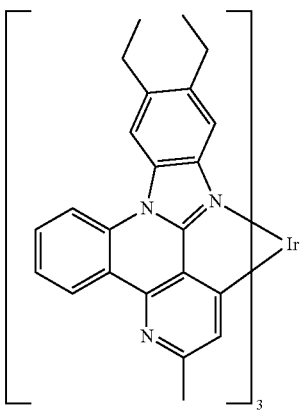
Compound 307
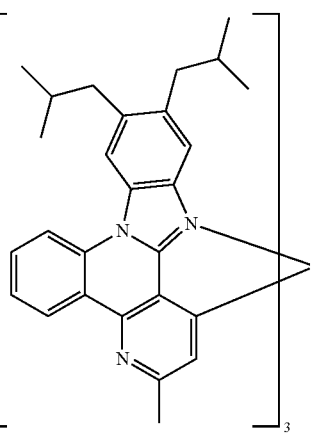
Compound 308
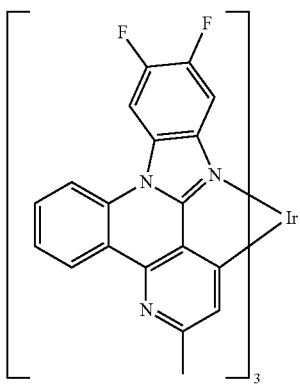
Compound 110
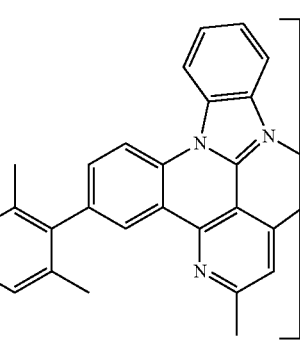

503
-continued
Compound 309
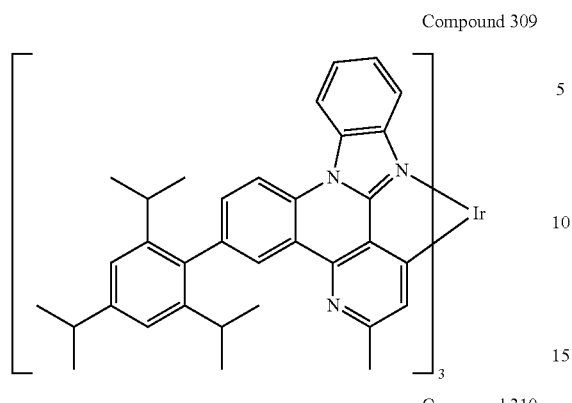
Compound 310
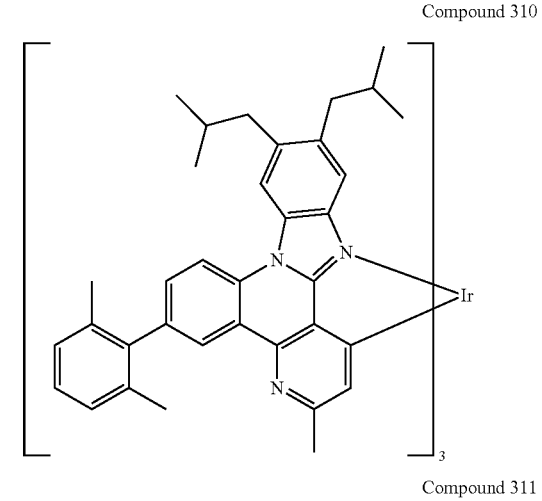
Compound 311
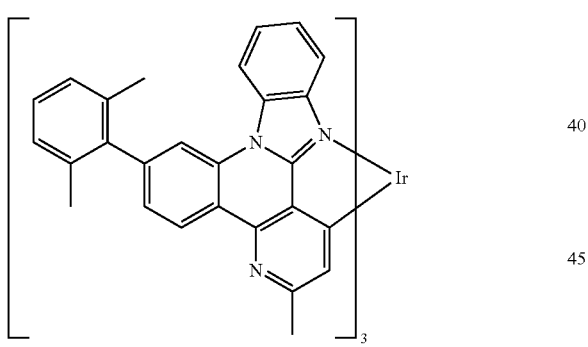
Compound 4
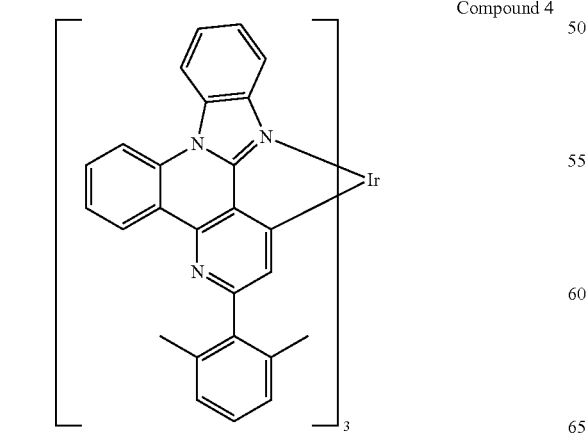
504
-continued
Compound 7
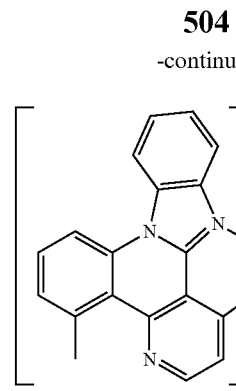
Compound 312
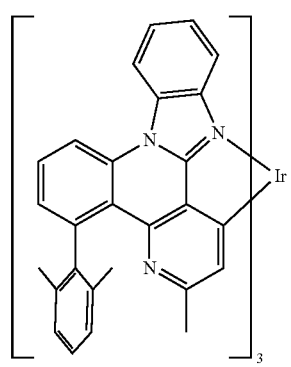
Compound 313
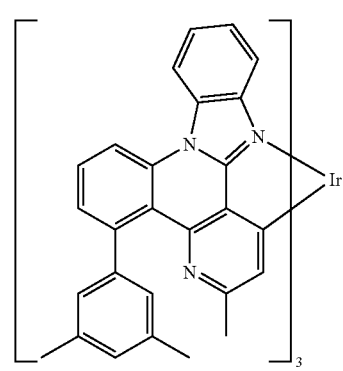
Compound 314
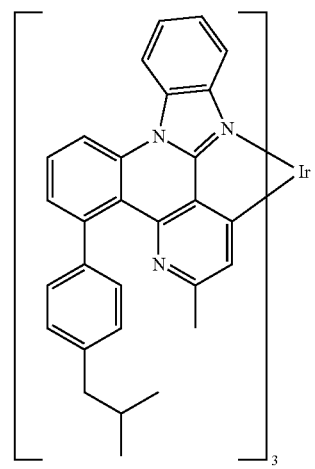

Compound 84678

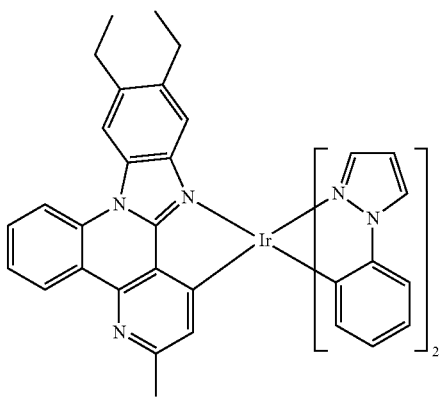

Compound 5046

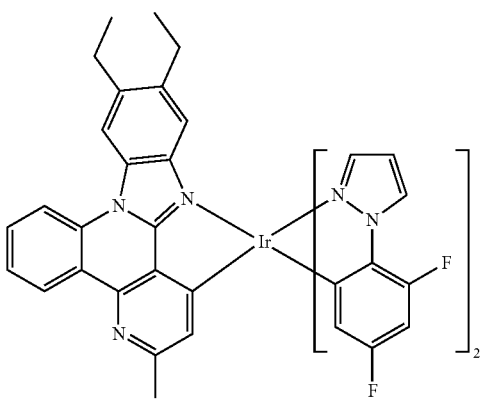

and
Compound 18318

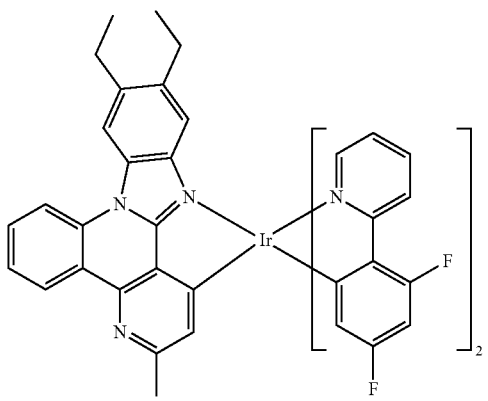

17. A first device comprising a first organic light emitting device, the first organic light emitting device comprising:
an anode;
a cathode; and
an organic layer, disposed between the anode and the cathode, comprising a compound comprising a ligand $L_A$ of Formula I:

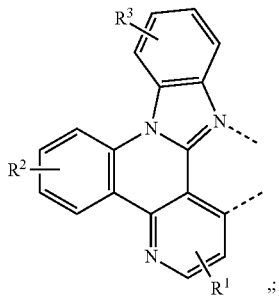

Formula I wherein $R^1$ represents mono, or di-substitution, or no substitution;
wherein $R^2$ and $R^3$ each independently represent mono, di, tri, or tetra-substitution, or no substitution;
wherein any adjacent substitutions in $R^1$, $R^2$ and $R^3$ are optionally linked together to form a ring;
wherein $R^1$, $R^2$ and $R^3$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, and isonitrile;
wherein the ligand $L_A$ is coordinated to a metal M; and
wherein the ligand $L_A$ is optionally linked with other ligands to form a tridentate, tetradentate, pentadentate or hexadentate ligand.

18. The first device of claim 17, wherein the first device is selected from the group consisting of a consumer product, an electronic component module, an organic light-emitting device, and a lighting panel.

19. The first device of claim 17, wherein the organic layer is an emissive layer and the compound is an emissive dopant or a non-emissive dopant.

20. The first device of claim 17, wherein the organic layer further comprises a host, wherein the host comprises at least one chemical group selected from the group consisting of triphenylene, carbazole, dibenzothiphene, dibenzofuran, dibenzoselenophene, azatriphenylene, azacarbazole, aza-dibenzothiophene, aza-dibenzofuran, and aza-dibenzoselenophene.

21. The compound of claim 1, wherein the compound has a calculated triplet energy between 469 nm and 474 nm.

* * * * *